(12) United States Patent
Keller et al.

(10) Patent No.: US 9,611,511 B2
(45) Date of Patent: Apr. 4, 2017

(54) COMPLEX MIRNA SETS AS NOVEL BIOMARKERS FOR AN ACUTE CORONARY SYNDROME

(75) Inventors: Andreas Keller, Püttlingen (DE); Peer F. Stähler, Mannheim (DE); Markus Beier, Weinheim (DE); Benjamin Meder, Dossenheim (DE); Hugo A. Katus, Heidelberg (DE); Wolfgang Rottbauer, Ulm (DE)

(73) Assignee: COMPREHENSIVE BIOMARKER CENTER GMBH, Heidelberg (DE)

( * ) Notice: Subject to any disclaimer, the term of this patent is extended or adjusted under 35 U.S.C. 154(b) by 0 days.

(21) Appl. No.: 13/642,321

(22) PCT Filed: Apr. 19, 2011

(86) PCT No.: PCT/EP2011/001999
§ 371 (c)(1),
(2), (4) Date: Mar. 6, 2013

(87) PCT Pub. No.: WO2011/131354
PCT Pub. Date: Oct. 27, 2011

(65) Prior Publication Data
US 2013/0157883 A1 Jun. 20, 2013

Related U.S. Application Data

(60) Provisional application No. 61/326,043, filed on Apr. 20, 2010.

(30) Foreign Application Priority Data

Apr. 20, 2010 (EP) ..................................... 10004190
Oct. 1, 2010 (EP) ..................................... 10185136

(51) Int. Cl.
C12Q 1/68 (2006.01)

(52) U.S. Cl.
CPC ......... *C12Q 1/6876* (2013.01); *C12Q 1/6883* (2013.01); *C12Q 2600/158* (2013.01); *C12Q 2600/178* (2013.01)

(58) Field of Classification Search
USPC ..... 435/6.1, 6.11, 91.1, 91.31, 6.12; 514/44; 536/23.1, 24.5, 24.31; 506/9, 16
See application file for complete search history.

(56) References Cited

U.S. PATENT DOCUMENTS

| 2007/0050146 A1* | 3/2007 | Bentwich et al. .............. 702/19 |
| 2007/0072204 A1* | 3/2007 | Hannon .............. C12N 15/1135 435/6.14 |
| 2009/0004668 A1* | 1/2009 | Chen ..................... C12N 15/111 435/6.14 |
| 2009/0010908 A1* | 1/2009 | Gow ..................... C12Q 1/6883 424/94.1 |
| 2009/0143326 A1* | 6/2009 | Obad et al. ..................... 514/44 |
| 2011/0144914 A1* | 6/2011 | Harrington et al. ............ 702/19 |
| 2012/0165392 A1* | 6/2012 | Olson et al. ................. 514/44 A |
| 2012/0190730 A1* | 7/2012 | Michael ................. H04B 3/548 514/44 R |
| 2014/0220580 A1* | 8/2014 | Brown ............. G01N 33/57434 435/6.12 |

FOREIGN PATENT DOCUMENTS

| WO | 2009/043353 | 4/2009 |
| WO | WO2009070653 A1 | 6/2009 |
| WO | 2009/149182 | 12/2009 |

OTHER PUBLICATIONS

Xi et al., Biomarker Insights, 2006, pp. 113-121.*
Hammerle-Fickinger et al. (Biotechnology Letters, Jul. 21, 2009, pp. 1-10).*
Kruhøffer et al.( Journal of Molecular Diagnostics, Sep. 2007, vol. 9, No. 4, pp. 452-458).*
Yusuf et al. (European Heart Journal, 1996, 17, Supplement F, pp. 16-29).*
Hoekstra et al, BBRC, vol. 394, pp. 792-797 (2010).*
Tijsen et al, Circulation Res., vol. 106, No. 6 (2010), pp. 1035-1039 and Suppl. Material, pp. 10-28.*
Dimmeler, et al., (2010) "Circulating microRNAs: novel biomarkers for cardiovascular diseases?" European Hearth Journal, 31:2705-2707.
Corsten, et al., (2010) "Circulating Micro-RNA-208b and MicroRNA-499 Reflect Myocardial Damage in Cardiovascular Disease," Circ Cardiovasc Genet, published online Oct. 4, 2010.
Guo, et al., (2010) "miR-146a in PBMCs modulates Th1 function in patients with acute coronary syndrome," Immunology and Cell Biology, 88:555-564.
Fichtlscherer, et al., (2010) "Circulating MicroRNAs in patients with Coronary Artery Disease," Circ Res, 107:677-684.
Ji, et al., (2009) "Plasma miR-208 as a Biomarker of Mycardial Injury," Clinical Chemistry, 55(11):1944-1949.
Bostjancic, et al., (2010) "MicroRNA miR-1 is Up-regulated in Remote Myocardium in Patients with Myocardial Infarction," Folia Biologica, 56:27-31.

(Continued)

*Primary Examiner* — Jane Zara
(74) *Attorney, Agent, or Firm* — MacMillan, Sobanski & Todd, LLC

(57) ABSTRACT

The present invention relates to single polynucleotides or sets of polynucleotides for detecting single miRNAs or sets of miRNAs for diagnosing and/or prognosing of an acute coronary syndrome in a blood sample from a human. Further, the present invention relates to means for diagnosing and/or prognosing of an acute coronary syndrome comprising said polynucleotides or sets of polynucleotides. Furthermore, the present invention relates to a method for diagnosing and/or prognosing of an acute coronary syndrome based on the determination of expression profiles of single miRNAs or sets of miRNAs representative for an acute coronary syndrome compared to a reference. In addition, the present invention relates to a kit for diagnosing and/or prognosing of an acute coronary syndrome comprising means for determining expression profiles of single miRNAs or sets of miRNAs representative for an acute coronary syndrome and at least one reference.

7 Claims, 63 Drawing Sheets

(56) References Cited

OTHER PUBLICATIONS

Ai, et al., (2010) "Circulating micro-RNA-1 as a potential novel biomarker for acute myocardial infarction," Biochemical and Biophysical Research Communications, 391(1):73-77.
Keller, et al. (2009) "miRNAs in lung cancer-Studying complex fingerprints in patient's blood cells by microarray experiments," BMC Cancer, 9(1): 353.
Wang, et al. (2010) "Circulating micro RNA: a novel potential biomarker for early diagnosis of acute myocardial infarction in humans," European Heart Journal, 31(6): 659-666.
Hoekstra, et al., (2010), "The peripheral blood mononuclear cell microRNA signature of coronary artery disease," Biochemical and Biophysical Research Communications, 394(3): 792-797.
Tijsen, et al, (2010) "MiR423-5p as a circulating biomarker for heart failure," Circulation Research, 106(6): 1035-1039.
Written Opinion for PCT/EP2011/001999, mailed Oct. 23, 2012.
International Search Report for PCT/EP2011/001999, mailed Sep. 22, 2011.
Calin, et al. MicroRNAs and leukemias: how strong is the connection? Leuk Res. 2006; 30:653-5.
Calin, et al. A MicroRNA signature associated with prognosis and progression in chronic lymphocytic leukemia. N Engl J Med. 2005; 353:1793-801.
(1983) Risk stratification and survival after myocardial infarction. N Engl J Med 309:331-336.
Adachi, et al. (2010) Plasma microRNA 499 as a biomarker of acute myocardial infarction. Clin Chem 56:1183-1185.
Aliferis, et al. (2009) Factors influencing the statistical power of complex data analysis protocols for molecular signature development from microarray data. PLoS ONE 4:e4922.
Benjamini, et al. (1995) Controlling the false discovery rate: A practical and powerful approach to multiple testing. J R Statist Soc B 57:289-300.
Bose, et al. (2008) Impact of atherosclerotic plaque composition on coronary microembolization during percutaneous coronary interventions. Basic Res Cardiol 103:587-597.
Cai, et al. (2010) The roles of microRNAs in heart diseases: a novel important regulator. Curr Med Chem 17:407-411.
Chen, et al. (2008) Characterization of microRNAs in serum: a novel class of biomarkers for diagnosis of cancer and other diseases. Cell Res 18:997-1006.
Cimmino, et al. (2005) miR-15 and miR-16 induce apoptosis by targeting BCL2. Proc Natl Acad Sci USA 102:13944-13949.
D'Alessandra, et al. (2010) Circulating microRNAs are new and sensitive biomarkers of myocardial infarction. Eur Heart J published online Jun. 9, 2010 doi:I0.I093/eurheartj/ehql67.
Dong, et al. (2009) MicroRNA expression signature and the role of microRNA-21 in the early phase of acute myocardial infarction. J Biol Chem 284:29514-29525.
Dresios, et al. (2005) Cold stress-induced protein Rbm3 binds 60S ribosomal subunits, alters microRNA levels, and enhances global protein synthesis. Proc Natl Acad Sci USA 102:1865-1870.
Duisters, et al. (2009) miR-133 and miR-30 regulate connective tissue growth factor: implications for a role of microRNAs in myocardial matrix remodeling. Circ Res 104: 170-178.
Fleissner, et al. (2010) Short communication: asymmetric dimethyl arginine impairs angiogenic progenitor cell function in patients with coronary artery disease through a microRNA-21-dependent mechanism. Circ Res 107:138-14344.
Gallego-Delgado, et al. (2005) Proteomic approach in the search of new cardiovascular biomarkers. Kidney Int Suppl: S 103-107.
Gerszten, et al. (2008) The search for new cardiovascular biomarkers. Nature 451:949-952.
Giannitsis, et al. (2009) New highly sensitivity assay used to measure cardiac troponin T concentration changes during a continuous 216-km marathon. Clin Chem 55:590-592.
Griffiths-Jones (2006) miRBase: the microRNA sequence database. Methods Mol Biol 42:129-138.
Hochberg (1988) A sharper bonferroni procedure for multiple tests of significance. Biometrica 75:185-193.
Jennewein, et al. (2010) MicroRNA-27b contributes to lipopolysaccharide-mediated peroxisome proliferator-activated receptor gamma (PPARgamma) mRNA destabilization. J Biol Chem 285:11846-11853.
Katus, et al. (1989) Enzyme linked immunoassay of cardiac troponin T for the detection of acute myocardial infarction in patients. J Mol Cell Cardiol 21:1349-1353.
Konstandin, et al. (2009) Beta2-integrin activation on T cell subsets is an independent prognostic factor in unstable angina pectoris. Basic Res Cardiol 104:341-351.
Kurz, et al. (2009) Serial and single time-point measurements of cardiac troponin T for prediction of clinical outcomes in patients with acute ST-segment elevation myocardial infarction. Clin Res Cardiol 98:94-100.
Lainscak, et al. (2009) Biomarkers for chronic heart failure: diagnostic, prognostic, and therapeutic challenges. Herz 34:589-593.
Lee, et al. (1993) The C. elegans heterochronic gene lin-4 encodes small RNAs with antisense complementarity to lin-14. Cell 75:843-854.
Leidinger, et al. (2010) High-throughput miRNA profiling of human melanoma blood samples. BMC Cancer 10:26257.
Manzano-Fernandez, et al. (2009) Complementary prognostic value of cystatin C, N-terminal pro-B-type natriuretic Peptide and cardiac troponin T in patients with acute heart failure. Am J Cardiol 103: 1753-1759.
Meder, et al. (2008) Right into the heart of microRNA-133a. Genes Dev 22:3227-3231.
Meredith, et al. (2009) Dominant-negative loss of PPARgamma function enhances smooth muscle cell proliferation, migration, and vascular remodeling. Arterioscler Thromb Vasc Biol 29:465-471.
Mukoyama, et al. (1990) Increased human brain natriuretic peptide in congestive heart failure. N Engl J Med 323:757-758.
Newton, et al. (2009) The role of b-type natriuretic peptide in heart failure management. Aust Crit Care 22:117-123.
Porela, et al. (2000) Level of circulating phospholipase A2 in prediction of the prognosis of patients with suspected myocardial infarction. Basic Res Cardiol 95:413-417.
Rottbauer, et al. (1996) Troponin T: a diagnostic marker for myocardial infarction and minor cardiac cell damage. Eur Heart J 17 Suppl F:3-8.
Team-RDC (2008) R: A Language and Environment for Statistical Computing. R Foundation for Statistical Computing, Vienna, Austria.
Thurn, et al. (2008) MicroRNA-21 contributes to myocardial disease by stimulating MAP kinase signalling in fibroblasts. Nature 456:980-984.
Tzivoni, et al. (2008) Comparison of Troponin T to creatine kinase and to radionuclide cardiac imaging infarct size in patients with ST elevation myocardial infarction undergoing primary angioplasty. Am J Cardiol 101:753-757.
Voellenkle, et al. (2010) MicroRNA signatures in peripheral blood mononuclear cells of chronic heart failure patients. Physiol Genomics 42:420-426.
Vorwerk, et al. (2008) Microfluidic-based enzymatic on-chip labeling ofmiRNAs. N Biotechnol 25:142-149.
Xin, et al. (2009) MicroRNAs miR-143 and miR-145 modulate cytoskeletal dynamics and responsiveness of smooth muscle cells to injury. Genes Dev 23:2166-2178.
Xu, et al. (2003) The *Drosophila* microRNA Mir-14 suppresses cell death and is required for normal fat metabolism. Curr Biol 13:790-795.
Zhao, et al (2005) Serum response factor regulates a muscle-specific microRNA that targets Hand2 during cardiogenesis. Nature 436:214-220.
Meder, et al., (2011) "MicroRNA signatures in total peripheral blood as novel biomarkers for acute myocardial infarction," Basic Res Cardiol, 106:13-23.

\* cited by examiner

| SEQ ID NO | miRNA | median g1 | median g2 | qmedian | logqmedian | ttest_rawp | ttest_adjp | limma_rawp | limma_adjp | AUC |
|---|---|---|---|---|---|---|---|---|---|---|
| SEQ ID NO: 1 | hsa-miR-1291 | 9.487E-01 | 2.765E+01 | 3.431E+00 | 1.233E+00 | 8.869E-08 | 1.093E-05 | 2.343E-09 | 3.816E-07 | 0.8393 |
| SEQ ID NO: 2 | hsa-miR-1283 | 1.098E+02 | 1.000E+00 | 1.059E-02 | 4.689E+00 | 5.899E-08 | 8.480E-06 | 1.368E-12 | 1.172E-12 | 0.8864 |
| SEQ ID NO: 3 | hsa-miR-1201 | 5.995E-01 | 1.006E+00 | 5.959E-01 | 4.097E-00 | 2.677E-04 | 5.877E-06 | 1.602E-06 | 2.798E-05 | 0.8182 |
| SEQ ID NO: 4 | hsa-miR-1245 | 4.458E-01 | 3.351E+00 | 1.331E+00 | 2.588E-00 | 2.831E-06 | 1.426E-04 | 1.184E-05 | 2.171E-04 | 0.7936 |
| SEQ ID NO: 5 | hsa-miR-208b | 6.046E-01 | 2.760E+01 | 2.191E+00 | 7.844E-01 | 5.209E-07 | 5.816E-05 | 1.059E-03 | 6.275E-03 | 0.7336 |
| SEQ ID NO: 6 | hsa-miR-1912 | 1.539E+02 | 3.334E+01 | 4.615E-01 | 1.539E-03 | 4.278E-05 | 9.321E-04 | 4.184E-08 | 2.777E-06 | 0.8089 |
| SEQ ID NO: 7 | hsa-miR-1275 | 5.447E-01 | 1.245E-01 | 4.376E-01 | 1.476E+00 | 7.899E-06 | 2.224E-04 | 1.027E-08 | 8.869E-07 | 0.8125 |
| SEQ ID NO: 8 | hsa-miR-548p | 1.145E+02 | 5.322E+01 | 2.152E-03 | 7.959E-01 | 1.245E-05 | 3.344E-04 | 4.516E-05 | 6.720E-04 | 0.7793 |
| SEQ ID NO: 9 | hsa-miR-1305 | 9.061E-01 | 4.675E-01 | 1.939E+01 | 6.622E-03 | 3.809E-05 | 7.077E-04 | 8.862E-05 | 1.034E-03 | 0.8036 |
| SEQ ID NO: 10 | hsa-miR-1256 | 6.665E-01 | 2.613E-01 | 2.528E+00 | 9.275E-01 | 4.829E-05 | 7.716E-04 | 2.093E-05 | 3.273E-04 | 0.7829 |
| SEQ ID NO: 11 | hsa-miR-1226* | 1.900E-02 | 1.105E-02 | 1.726E-02 | 5.461E-01 | 6.129E-05 | 1.017E-03 | 1.556E-02 | 4.727E-04 | 0.7479 |
| SEQ ID NO: 12 | hsa-miR-128 | 6.222E+02 | 4.198E+02 | 1.496E+00 | 4.030E-01 | 2.211E-05 | 5.198E-04 | 1.285E-02 | 4.012E-03 | 0.7754 |
| SEQ ID NO: 13 | hsa-miR-300 | 4.865E-01 | 2.011E-01 | 2.419E+00 | 8.834E-01 | 1.497E-05 | 3.799E-04 | 7.589E-03 | 2.684E-02 | 0.7489 |
| SEQ ID NO: 14 | hsa-miR-541 | 1.051E+02 | 2.600E+01 | 4.041E-01 | 1.397E+00 | 3.591E-05 | 7.077E-04 | 3.323E-05 | 5.208E-04 | 0.7871 |
| SEQ ID NO: 15 | hsa-miR-892b | 2.729E-01 | 9.774E-01 | 2.762E-01 | -1.278E+00 | 6.971E-05 | 1.114E-03 | 3.874E-05 | 5.869E-04 | 0.1518 |
| SEQ ID NO: 16 | hsa-miR-455-3p | 1.706E+02 | 6.141E-01 | 2.778E+00 | 1.022E+00 | 2.724E-08 | 5.877E-06 | 1.466E-05 | 2.528E-04 | 0.8625 |
| SEQ ID NO: 17 | hsa-miR-31* | 1.722E-02 | 3.703E-01 | 4.659E+01 | 1.537E-00 | 1.283E-08 | 5.877E-06 | 2.357E-10 | 1.017E-07 | 0.8575 |
| SEQ ID NO: 18 | hsa-miR-192* | 1.141E-02 | 5.953E-01 | 1.918E+00 | 6.514E-01 | 2.344E-08 | 5.877E-06 | 1.613E-07 | 6.466E-06 | 0.8564 |
| SEQ ID NO: 19 | hsa-miR-767-5p | 1.590E+02 | 5.744E+01 | 2.769E+00 | 1.018E+00 | 8.409E-07 | 7.249E-05 | 4.822E-06 | 1.015E-04 | 0.8154 |
| SEQ ID NO: 20 | hsa-miR-993* | 1.308E+02 | 7.051E+02 | 1.891E+00 | 6.318E-01 | 1.287E-06 | 1.009E-04 | 2.863E-04 | 2.446E-03 | 0.7867 |
| SEQ ID NO: 21 | hsa-miR-155 | 5.910E+01 | 1.548E+01 | 3.581E+00 | 1.276E+00 | 1.537E-06 | 1.109E-04 | 3.874E-06 | 6.360E-05 | 0.8098 |
| SEQ ID NO: 22 | hsa-miR-20b* | 6.151E+01 | 2.571E+01 | 2.303E+00 | 8.340E-01 | 2.844E-08 | 1.428E-04 | 9.016E-08 | 4.494E-06 | 0.8200 |
| SEQ ID NO: 23 | hsa-miR-451-3p | 7.799E-01 | 6.687E+00 | 1.164E-01 | 2.455E-00 | 2.422E-06 | 1.428E-04 | 8.068E-07 | 2.487E-05 | 0.8123 |
| SEQ ID NO: 24 | hsa-miR-338-3p | 3.784E+02 | 1.533E+02 | 2.458E-03 | 8.995E-03 | 3.098E-08 | 1.463E-04 | 3.573E-08 | 4.434E-08 | 0.8479 |
| SEQ ID NO: 25 | hsa-miR-146b-5p | 1.016E-02 | 2.223E+02 | 4.549E-01 | -7.876E-01 | 3.143E-08 | 1.463E-03 | 6.001E-05 | 8.439E-04 | 0.1415 |
| SEQ ID NO: 26 | hsa-miR-556-5p | 1.811E-02 | 4.825E-01 | 2.447E-03 | 8.950E-01 | 3.847E-05 | 1.572E-04 | 2.052E-06 | 4.789E-05 | 0.7862 |
| SEQ ID NO: 27 | hsa-miR-423-5p | 2.877E+03 | 1.839E+03 | 1.565E+00 | 4.478E-01 | 4.278E-06 | 1.572E-04 | 8.222E-04 | 4.055E-03 | 0.7496 |
| SEQ ID NO: 28 | hsa-miR-186* | 5.144E-01 | 1.430E+01 | 3.597E+01 | 3.563E+00 | 4.371E-06 | 1.572E-04 | 2.140E-07 | 8.002E-06 | 0.8189 |
| SEQ ID NO: 29 | hsa-miR-99a | 1.027E+02 | 4.515E+01 | 2.274E+00 | 8.215E-01 | 4.795E-06 | 1.650E-04 | 2.555E-06 | 2.317E-03 | 0.7939 |
| SEQ ID NO: 30 | hsa-miR-508-5p | 1.135E+02 | 5.855E+01 | 2.157E+00 | 7.848E-01 | 5.179E-06 | 1.711E-04 | 9.353E-08 | 4.494E-06 | 0.8229 |
| SEQ ID NO: 31 | hsa-miR-199-5p | 1.249E+02 | 4.744E+01 | 2.534E+00 | 9.696E-03 | 5.431E-06 | 1.736E-04 | 1.658E-07 | 6.466E-06 | 0.7921 |
| SEQ ID NO: 32 | hsa-miR-345* | 7.294E-01 | 3.963E-01 | 1.940E-01 | 6.100E-03 | 7.403E-06 | 2.133E-04 | 1.653E-04 | 1.761E-03 | 0.7864 |
| SEQ ID NO: 33 | hsa-miR-96* | 1.152E-02 | 5.943E-01 | 1.938E+00 | 6.616E-01 | 1.489E-05 | 3.799E-04 | 2.286E-03 | 1.081E-02 | 0.7529 |
| SEQ ID NO: 34 | hsa-miR-518a-3p | 5.339E+01 | 3.630E+00 | 1.394E+01 | 2.635E-03 | 1.889E-05 | 4.660E-04 | 2.683E-09 | 3.816E-07 | 0.8346 |
| SEQ ID NO: 35 | hsa-miR-188-3p | 1.312E+02 | 9.397E+01 | 2.187E+01 | 7.827E-01 | 2.111E-05 | 5.060E-04 | 1.532E-05 | 2.593E-04 | 0.7831 |
| SEQ ID NO: 36 | hsa-miR-20a* | 1.407E+02 | 7.555E+01 | 1.863E-00 | 6.246E-01 | 2.663E-05 | 5.605E-04 | 1.083E-04 | 1.291E-03 | 0.7700 |

Figure 7

| SEQ ID NO | miRNA | median g1 | median g2 | qpmedian | logqpmedian | ttest.rawp | ttest.adjp | limma.rawp | limma.adjp | AUC |
|---|---|---|---|---|---|---|---|---|---|---|
| SEQ ID NO: 37 | hsa-miR-500a-5p | 5.975E-01 | 1.306E-01 | 4.568E-00 | 1.519E+00 | 3.123E-05 | 6.416E-04 | 4.234E-06 | 2.699E-06 | 0.7946 |
| SEQ ID NO: 38 | hsa-miR-136* | 5.083E-01 | 1.366E-01 | 2.598E-00 | 9.515E-01 | 4.768E-06 | 8.754E-04 | 1.371E-03 | 7.168E-03 | 0.7543 |
| SEQ ID NO: 39 | hsa-miR-216a | 1.423E-02 | 5.109E-02 | 2.780E-00 | 1.023E+00 | 3.992E-05 | 1.014E-03 | 1.572E-03 | 7.980E-03 | 0.7637 |
| SEQ ID NO: 40 | hsa-miR-532-3p | 4.401E-03 | 2.200E-03 | 1.996E-00 | 6.908E-01 | 7.119E-05 | 1.117E-03 | 7.830E-05 | 1.024E-03 | 0.7943 |
| SEQ ID NO: 41 | hsa-miR-654-5p | 1.823E-02 | 1.086E-02 | 1.663E+00 | 5.087E-01 | 7.933E-05 | 1.219E-03 | 5.185E-04 | 3.638E-03 | 0.7695 |
| SEQ ID NO: 42 | hsa-let-7i-1* | 3.466E-01 | 2.963E-00 | 1.168E+01 | 2.451E+00 | 8.257E-05 | 1.229E-03 | 3.285E-01 | 1.411E-02 | 0.7171 |
| SEQ ID NO: 43 | hsa-miR-145* | 6.006E-01 | 6.278E-00 | 9.567E+00 | 2.258E+00 | 8.512E-05 | 1.236E-03 | 8.494E-05 | 9.048E-04 | 0.7821 |
| SEQ ID NO: 44 | hsa-miR-342-3p | 4.401E-03 | 2.787E-03 | 1.579E+00 | 4.571E-01 | 8.393E-05 | 1.253E-03 | 8.924E-03 | 3.081E-03 | 0.7414 |
| SEQ ID NO: 45 | hsa-miR-488* | 7.382E-01 | 1.427E-01 | 5.175E-00 | 1.641E+00 | 8.996E-05 | 1.255E-03 | 4.165E-03 | 3.549E-07 | 0.8114 |
| SEQ ID NO: 46 | hsa-miR-509-5p | 2.165E-02 | 9.090E-01 | 2.391E+00 | 8.677E-01 | 9.379E-05 | 1.296E-03 | 2.175E-04 | 2.131E-03 | 0.7946 |
| SEQ ID NO: 47 | hsa-miR-519b-5p | 1.290E-02 | 3.558E-01 | 3.498E-00 | 1.253E+00 | 1.089E-04 | 1.424E-03 | 9.868E-07 | 2.789E-05 | 0.8007 |
| SEQ ID NO: 48 | hsa-miR-513b | 4.703E-01 | 5.888E-00 | 7.982E-01 | 2.077E-03 | 1.127E-04 | 1.452E-03 | 1.351E-04 | 1.514E-03 | 0.7645 |
| SEQ ID NO: 49 | hsa-miR-550* | 6.883E-02 | 5.056E-02 | 1.361E+00 | 3.083E-01 | 1.298E-04 | 1.588E-03 | 1.198E-01 | 2.292E-01 | 0.6589 |
| SEQ ID NO: 50 | hsa-miR-196a* | 1.469E-02 | 9.250E-01 | 1.513E+00 | 4.141E-01 | 1.259E-04 | 1.575E-03 | 2.198E-04 | 2.131E-03 | 0.7000 |
| SEQ ID NO: 51 | hsa-miR-1826 | 1.952E-02 | 1.067E-02 | 1.530E-00 | 5.042E-01 | 1.536E-04 | 1.586E-03 | 2.579E-03 | 1.157E-02 | 0.7421 |
| SEQ ID NO: 52 | hsa-miR-602 | 5.375E-01 | 5.434E-01 | 1.106E+01 | 2.398E+00 | 1.620E-04 | 2.161E-03 | 1.208E-05 | 2.171E-04 | 0.7875 |
| SEQ ID NO: 53 | hsa-miR-1272 | 1.319E-02 | 9.220E-01 | 1.423E-00 | 3.526E-01 | 2.109E-04 | 2.496E-03 | 1.616E-02 | 4.876E-02 | 0.7204 |
| SEQ ID NO: 54 | hsa-miR-320c | 1.097E-02 | 6.782E-03 | 1.528E-00 | 4.242E-01 | 2.371E-04 | 2.722E-03 | 8.721E-05 | 1.094E-03 | 0.7357 |
| SEQ ID NO: 55 | hsa-miR-30e* | 3.944E-01 | 1.359E-02 | 2.941E-01 | -1.224E+00 | 2.477E-04 | 2.813E-03 | 5.427E-04 | 3.738E-03 | 0.2036 |
| SEQ ID NO: 56 | hsa-miR-455-5p | 1.322E-01 | 6.981E-01 | 1.893E-01 | -1.964E+00 | 2.526E-04 | 2.824E-03 | 1.186E-04 | 1.326E-03 | 0.1796 |
| SEQ ID NO: 57 | hsa-miR-24-2* | 1.506E-02 | 1.143E-02 | 1.319E+00 | 2.757E-01 | 2.853E-04 | 2.884E-03 | 8.491E-03 | 2.367E-02 | 0.6682 |
| SEQ ID NO: 58 | hsa-miR-181c* | 6.030E-01 | 2.118E-01 | 2.847E+00 | 1.046E+00 | 2.693E-04 | 2.854E-03 | 2.742E-04 | 2.399E-03 | 0.7300 |
| SEQ ID NO: 59 | hsa-miR-1301 | 2.019E-02 | 1.144E-02 | 1.766E-00 | 5.676E-01 | 2.823E-04 | 2.954E-03 | 1.252E-02 | 4.012E-02 | 0.7293 |
| SEQ ID NO: 60 | hsa-miR-1302 | 3.119E-01 | 1.300E-00 | 3.199E-01 | 3.440E+00 | 3.477E-04 | 3.530E-03 | 2.170E-03 | 1.023E-02 | 0.7114 |
| SEQ ID NO: 61 | hsa-miR-933 | 1.768E-02 | 6.931E-01 | 5.555E-01 | 9.380E-01 | 3.820E-04 | 3.633E-03 | 9.324E-05 | 1.150E-03 | 0.7486 |
| SEQ ID NO: 62 | hsa-miR-1281 | 8.314E-01 | 1.386E-02 | 3.331E-01 | -1.076E+00 | 3.851E-04 | 3.757E-03 | 4.331E-04 | 1.763E-02 | 0.2036 |
| SEQ ID NO: 63 | hsa-miR-1247 | 5.339E-01 | 1.025E-02 | 5.209E-01 | -6.522E-01 | 3.874E-04 | 3.766E-03 | 1.564E-03 | 7.980E-03 | 0.2020 |
| SEQ ID NO: 64 | hsa-miR-28-5p | 3.633E-02 | 4.953E-02 | 7.339E-01 | -3.094E-01 | 4.147E-04 | 3.886E-03 | 2.974E-04 | 2.491E-03 | 0.1994 |
| SEQ ID NO: 65 | hsa-miR-876-3p | 1.015E-01 | 7.211E-01 | 1.407E-01 | -1.961E+00 | 4.593E-04 | 4.219E-03 | 2.690E-04 | 2.396E-03 | 0.2063 |
| SEQ ID NO: 66 | hsa-miR-1295 | 1.115E-02 | 6.598E-01 | 1.684E-00 | 5.210E-01 | 5.027E-04 | 4.406E-03 | 2.596E-02 | 7.112E-02 | 0.7292 |
| SEQ ID NO: 67 | hsa-miR-199* | 6.193E-01 | 1.894E-01 | 3.656E-00 | 1.296E+00 | 5.108E-04 | 4.406E-03 | 5.482E-05 | 8.019E-04 | 0.7814 |
| SEQ ID NO: 68 | hsa-miR-23b* | 2.851E-01 | 7.707E-01 | 3.599E-01 | -9.844E-01 | 4.391E-04 | 4.508E-03 | 2.929E-03 | 1.233E-02 | 0.2071 |
| SEQ ID NO: 69 | hsa-miR-2a-1* | 8.704E-01 | 4.370E-01 | 1.991E-00 | 6.891E-01 | 5.365E-04 | 4.584E-03 | 3.535E-04 | 2.317E-03 | 0.7575 |
| SEQ ID NO: 70 | hsa-miR-1250 | 3.689E-01 | 1.051E-02 | 3.504E-01 | -1.049E+00 | 5.579E-04 | 4.675E-03 | 3.794E-04 | 2.890E-03 | 0.2300 |
| SEQ ID NO: 71 | hsa-miR-30e | 2.331E-02 | 4.375E-02 | 5.327E-01 | -6.297E-01 | 5.765E-04 | 4.784E-03 | 7.057E-04 | 4.445E-03 | 0.2314 |
| SEQ ID NO: 72 | hsa-miR-216b | 1.384E-02 | 8.169E-01 | 1.443E-02 | 3.797E-02 | 6.201E-04 | 5.048E-03 | 1.976E-02 | 5.724E-02 | 0.6946 |

Figure 7 cont.

| SEQ ID NO | miRNA | median g1 | median g2 | upmedian | logupmedian | ttest.rawp | ttest.adjp | limma.rawp | limma.adjp | AUC |
|---|---|---|---|---|---|---|---|---|---|---|
| SEQ ID NO: 73 | hsa-miR-146b | 1.000E-01 | 3.498E-01 | 2.841E-02 | -3.528E+00 | 6.502E-04 | 5.24E-03 | 7.381E-06 | 1.498E-04 | 0.7214 |
| SEQ ID NO: 74 | hsa-miR-548o | 9.987E-01 | 4.628E-01 | 2.161E+00 | 7.705E-01 | 6.599E-04 | 5.273E-03 | 7.461E-03 | 2.656E-02 | 0.7446 |
| SEQ ID NO: 75 | hsa-miR-1296 | 4.723E-01 | 9.664E-01 | 4.887E-01 | 7.161E-01 | 7.078E-04 | 5.692E-03 | 7.086E-03 | 2.548E-02 | 0.2118 |
| SEQ ID NO: 76 | hsa-miR-942 | 1.576E-01 | 8.562E-01 | 1.840E-01 | -1.693E+00 | 7.489E-04 | 5.971E-03 | 3.862E-04 | 2.737E-03 | 0.2168 |
| SEQ ID NO: 77 | hsa-miR-34a* | 9.081E-01 | 5.350E-01 | 1.694E+00 | 5.288E-01 | 7.632E-04 | 5.933E-03 | 3.609E-02 | 9.135E-02 | 0.7386 |
| SEQ ID NO: 78 | hsa-miR-518e* | 1.407E-02 | 7.506E-01 | 1.875E-02 | -8.285E+00 | 8.499E-04 | 6.548E-03 | 1.347E-02 | 4.211E-02 | 0.7014 |
| SEQ ID NO: 79 | hsa-miR-624 | 1.816E-01 | 1.329E-01 | 1.366E-01 | -1.391E+00 | 9.163E-04 | 6.879E-03 | 1.035E-03 | 6.120E-03 | 0.2171 |
| SEQ ID NO: 80 | hsa-miR-520* | 1.329E-02 | 6.244E-01 | 2.122E+00 | 7.526E-01 | 9.865E-04 | 7.154E-03 | 3.401E-04 | 2.743E-03 | 0.7386 |
| SEQ ID NO: 81 | hsa-miR-1290 | 1.000E+00 | 2.760E-01 | 3.634E-02 | -3.318E+00 | 1.138E-03 | 7.918E-03 | 6.489E-10 | 1.870E-07 | 0.1211 |
| SEQ ID NO: 82 | hsa-miR-1274b | 7.558E-02 | 1.376E-03 | 5.424E-01 | 5.969E-01 | 1.157E-03 | 7.985E-03 | 4.149E-04 | 3.034E-03 | 0.2207 |
| SEQ ID NO: 83 | hsa-miR-518a-5p | 1.900E-02 | 7.791E-01 | 2.439E+00 | 8.914E-01 | 1.191E-03 | 8.166E-03 | 7.748E-07 | 2.476E-05 | 0.7857 |
| SEQ ID NO: 84 | hsa-miR-1303 | 3.010E-01 | 9.537E-01 | 3.156E-01 | -1.153E+00 | 1.259E-03 | 8.510E-03 | 5.072E-03 | 1.981E-02 | 0.2543 |
| SEQ ID NO: 85 | hsa-miR-140-5p | 2.904E-01 | 8.628E-01 | 3.366E-01 | -1.089E+00 | 1.579E-03 | 1.089E-02 | 5.718E-03 | 2.136E-02 | 0.2464 |
| SEQ ID NO: 86 | hsa-miR-218-1* | 6.586E-01 | 3.778E-01 | 1.779E+00 | 5.703E-01 | 1.629E-03 | 1.061E-02 | 9.457E-04 | 3.738E-03 | 0.7175 |
| SEQ ID NO: 87 | hsa-miR-1271 | 1.509E-02 | 1.227E-02 | 1.280E+00 | 2.070E-01 | 1.687E-03 | 1.195E-02 | 2.315E-01 | 4.387E-01 | 0.5982 |
| SEQ ID NO: 88 | hsa-miR-890 | 3.674E-01 | 9.398E-01 | 3.910E-01 | 1.361E+00 | 1.949E-03 | 1.236E-02 | 1.098E-02 | 5.559E-02 | 0.6643 |
| SEQ ID NO: 89 | hsa-miR-190b | 1.000E+00 | 7.506E-01 | 1.332E-02 | -4.316E+00 | 1.996E-03 | 1.268E-02 | 9.748E-05 | 1.185E-03 | 0.2318 |
| SEQ ID NO: 90 | hsa-miR-938 | 8.635E-01 | 2.168E-01 | 3.880E+00 | 1.381E+00 | 2.220E-03 | 1.378E-02 | 5.029E-06 | 2.859E-05 | 0.7314 |
| SEQ ID NO: 91 | hsa-miR-1066* | 1.318E-02 | 7.972E-01 | 1.653E-02 | 5.026E-01 | 2.248E-03 | 1.361E-02 | 2.818E-06 | 1.241E-03 | 0.7190 |
| SEQ ID NO: 92 | hsa-miR-30c-1* | 3.915E-01 | 1.498E-02 | 2.741E+00 | 1.003E+00 | 2.407E-03 | 1.475E-02 | 7.709E-02 | 1.650E-01 | 0.6743 |
| SEQ ID NO: 93 | hsa-miR-891a | 1.082E-02 | 6.313E-02 | 1.564E-01 | 4.478E-01 | 2.445E-03 | 1.475E-02 | 1.369E-02 | 6.920E-03 | 0.7071 |
| SEQ ID NO: 94 | hsa-miR-1266 | 1.199E-02 | 5.984E-01 | 1.918E+00 | 6.512E-01 | 2.511E-03 | 1.505E-02 | 5.284E-03 | 2.026E-02 | 0.7218 |
| SEQ ID NO: 95 | hsa-miR-135b* | 5.332E-01 | 9.006E-01 | 5.907E-01 | -5.284E-01 | 2.566E-03 | 1.527E-02 | 6.569E-03 | 2.389E-02 | 0.2229 |
| SEQ ID NO: 96 | hsa-miR-223* | 2.889E-01 | 5.244E-01 | 5.507E-01 | -5.966E-01 | 2.657E-03 | 1.568E-02 | 5.932E-03 | 2.117E-02 | 0.2539 |
| SEQ ID NO: 97 | hsa-miR-127-5p | 1.264E-02 | 5.807E-01 | 2.345E+00 | 3.129E-01 | 2.670E-03 | 1.568E-02 | 9.359E-03 | 2.037E-02 | 0.7039 |
| SEQ ID NO: 98 | hsa-miR-1258 | 1.000E+00 | 5.874E-01 | 1.702E-02 | 4.073E+00 | 2.919E-03 | 1.679E-02 | 7.756E-06 | 1.557E-04 | 0.2188 |
| SEQ ID NO: 99 | hsa-let-7f* | 2.893E-02 | 1.208E-02 | 1.896E+00 | 6.398E-01 | 2.913E-03 | 1.679E-02 | 5.194E-03 | 2.010E-02 | 0.7471 |
| SEQ ID NO: 100 | hsa-miR-124 | 1.045E-02 | 5.123E-01 | 2.039E+00 | 7.127E-01 | 3.133E-03 | 1.790E-02 | 3.032E-04 | 2.516E-03 | 0.7950 |
| SEQ ID NO: 101 | hsa-miR-922 | 1.266E-02 | 3.493E-01 | 3.857E+00 | 1.287E+00 | 3.157E-03 | 1.792E-02 | 1.267E-03 | 8.868E-03 | 0.7346 |
| SEQ ID NO: 102 | hsa-miR-454 | 1.154E-02 | 2.368E-02 | 4.874E-01 | -7.193E-01 | 3.205E-03 | 1.808E-02 | 8.976E-03 | 3.086E-02 | 0.2613 |
| SEQ ID NO: 103 | hsa-miR-934 | 3.572E-01 | 4.189E-01 | 1.715E+00 | 5.398E-01 | 3.251E-03 | 1.822E-02 | 1.859E-06 | 4.582E-05 | 0.7186 |
| SEQ ID NO: 104 | hsa-miR-339-5p | 6.883E-02 | 3.950E-02 | 1.748E+00 | 5.552E-01 | 3.382E-03 | 1.883E-02 | 4.455E-03 | 1.072E-02 | 0.6807 |
| SEQ ID NO: 105 | hsa-miR-450b-5p | 6.384E-01 | 2.498E-01 | 2.496E+00 | 3.144E-01 | 3.499E-03 | 1.932E-02 | 4.268E-07 | 1.493E-05 | 0.7418 |
| SEQ ID NO: 106 | hsa-miR-618* | 5.447E-01 | 7.590E+00 | 7.177E-01 | 1.971E+00 | 3.685E-03 | 1.987E-02 | 1.188E-05 | 2.121E-04 | 0.7988 |
| SEQ ID NO: 107 | hsa-miR-593* | 2.365E-02 | 1.390E-02 | 1.498E+00 | 4.040E-01 | 3.695E-03 | 1.987E-02 | 3.935E-02 | 9.657E-02 | 0.7204 |
| SEQ ID NO: 108 | hsa-miR-320a | 1.763E-04 | 9.898E-03 | 1.798E+00 | 5.867E-01 | 3.725E-03 | 1.987E-02 | 3.648E-04 | 2.811E-03 | 0.7361 |

Figure 7 cont.

| SEQ ID NO | miRNA | median_g1 | median_g2 | qmedian | logqmedian | ttest_rawp | ttest_adjp | limma_rawp | limma_adjp | AUC |
|---|---|---|---|---|---|---|---|---|---|---|
| SEQ ID NO: 109 | hsa-miR-379 | 5.397E+01 | 2.249E+01 | 2.403E+00 | 8.769E-01 | 3.961E-03 | 2.057E-02 | 2.097E-03 | 9.967E-03 | 0.7136 |
| SEQ ID NO: 110 | hsa-miR-1270 | 2.086E+01 | 1.060E+01 | 2.086E+00 | 3.023E+00 | 4.029E-03 | 2.126E-02 | 1.220E-02 | 3.544E-02 | 0.6809 |
| SEQ ID NO: 111 | hsa-miR-526-3p | 1.300E+00 | 4.732E-01 | 2.118E-02 | -3.855E+00 | 4.294E-03 | 2.277E-02 | 5.359E-04 | 3.901E-03 | 0.2664 |
| SEQ ID NO: 112 | hsa-miR-17 | 5.591E+02 | 4.617E+02 | 1.211E+00 | 1.914E-01 | 4.461E-03 | 2.293E-02 | 6.484E-01 | 7.695E-01 | 0.5958 |
| SEQ ID NO: 113 | hsa-miR-340* | 4.482E+01 | 7.649E+02 | 5.996E-00 | -5.345E-00 | 4.526E-03 | 2.298E-02 | 4.663E-03 | 1.849E-02 | 0.2432 |
| SEQ ID NO: 114 | hsa-miR-1915 | 2.795E+01 | 8.861E+00 | 3.121E+00 | 1.198E+00 | 4.486E-03 | 2.298E-02 | 3.890E-02 | 9.594E-02 | 0.6933 |
| SEQ ID NO: 115 | hsa-miR-509-3-5p | 2.106E+02 | 1.312E+02 | 1.593E+00 | 4.875E-01 | 4.630E-03 | 2.336E-02 | 1.203E-03 | 6.652E-03 | 0.7187 |
| SEQ ID NO: 116 | hsa-miR-339-3p | 2.723E+02 | 2.059E+02 | 1.299E+00 | 2.619E-00 | 4.885E-03 | 2.339E-02 | 1.363E-01 | 2.489E-01 | 0.6809 |
| SEQ ID NO: 117 | hsa-miR-3200 | 8.346E+02 | 5.591E+02 | 1.693E+00 | 4.765E-01 | 4.832E-03 | 2.339E-02 | 9.864E-02 | 1.984E-01 | 0.6436 |
| SEQ ID NO: 118 | hsa-miR-340* | 1.586E+01 | 7.699E+02 | 2.061E-01 | -1.580E+00 | 4.799E-03 | 2.370E-02 | 9.283E-03 | 3.137E-02 | 0.2775 |
| SEQ ID NO: 119 | hsa-miR-424* | 1.110E+02 | 2.199E+02 | 5.045E-01 | -6.843E-01 | 4.991E-03 | 2.437E-02 | 4.061E-03 | 1.669E-02 | 0.2539 |
| SEQ ID NO: 120 | hsa-miR-1204 | 3.395E+01 | 8.286E+01 | 3.241E-01 | -1.452E+00 | 5.397E-03 | 2.610E-02 | 4.499E-03 | 1.809E-02 | 0.2575 |
| SEQ ID NO: 121 | hsa-miR-518a-3p | 6.795E-00 | 4.394E-01 | 1.569E-01 | -1.399E+00 | 5.419E-03 | 2.619E-02 | 3.459E-04 | 2.794E-03 | 0.2414 |
| SEQ ID NO: 122 | hsa-miR-590 | 2.513E+02 | 1.906E+02 | 1.319E+00 | 2.785E-01 | 5.583E-03 | 2.655E-02 | 1.310E-01 | 3.118E-01 | 0.6911 |
| SEQ ID NO: 123 | hsa-miR-148b-3p | 5.447E+01 | 3.736E+01 | 1.450E+00 | 3.718E-01 | 5.836E-03 | 2.665E-02 | 1.591E-02 | 4.219E-02 | 0.6625 |
| SEQ ID NO: 124 | hsa-miR-199a-3p | 9.671E+01 | 1.769E+01 | 5.467E+00 | -6.338E-01 | 5.694E-03 | 2.719E-02 | 8.502E-02 | 1.782E-01 | 0.2686 |
| SEQ ID NO: 125 | hsa-miR-1285 | 2.654E+02 | 1.801E+01 | 1.444E+00 | 3.673E-01 | 5.811E-03 | 2.773E-02 | 2.282E-03 | 1.061E-02 | 0.7232 |
| SEQ ID NO: 126 | hsa-miR-371-5p | 4.395E+01 | 8.687E+00 | 6.503E+00 | 1.872E+00 | 5.945E-03 | 2.785E-02 | 1.646E-03 | 8.213E-03 | 0.6953 |
| SEQ ID NO: 127 | hsa-miR-574-3p | 2.110E+03 | 1.668E+03 | 1.276E+00 | 2.439E-01 | 5.970E-03 | 2.785E-02 | 1.367E-01 | 2.489E-01 | 0.6257 |
| SEQ ID NO: 128 | hsa-miR-1282 | 1.300E+00 | 4.795E-00 | 2.085E-02 | -3.870E+00 | 6.174E-03 | 2.865E-02 | 5.206E-04 | 3.541E-03 | 0.2518 |
| SEQ ID NO: 129 | hsa-miR-1537 | 2.723E+01 | 1.034E+01 | 2.638E+00 | 9.790E-01 | 6.499E-03 | 2.983E-02 | 8.599E-03 | 2.977E-02 | 0.7011 |
| SEQ ID NO: 130 | hsa-miR-298 | 1.192E+02 | 6.181E+01 | 1.929E+00 | 6.568E-01 | 6.918E-03 | 3.126E-02 | 7.522E-07 | 2.476E-05 | 0.7359 |
| SEQ ID NO: 131 | hsa-miR-580-3p | 6.319E+01 | 5.041E+01 | 1.194E+00 | 1.772E-01 | 6.873E-03 | 3.129E-02 | 1.500E-01 | 2.663E-01 | 0.6519 |
| SEQ ID NO: 132 | hsa-miR-296-2 | 3.526E+01 | 7.305E+01 | 4.827E-01 | -7.289E-01 | 7.133E-03 | 3.176E-02 | 2.284E-03 | 1.591E-02 | 0.2779 |
| SEQ ID NO: 133 | hsa-miR-548a-3p | 7.070E+01 | 6.059E+01 | 1.168E+00 | 1.553E-01 | 7.266E-03 | 3.255E-02 | 1.216E-01 | 3.063E-01 | 0.6297 |
| SEQ ID NO: 134 | hsa-miR-411* | 5.046E+01 | 9.252E+01 | 5.465E-01 | -6.061E-01 | 7.350E-03 | 3.252E-02 | 1.700E-02 | 5.075E-02 | 0.2921 |
| SEQ ID NO: 135 | hsa-miR-7-1* | 2.547E+02 | 2.102E+02 | 1.492E+00 | 3.360E-01 | 7.442E-03 | 3.260E-02 | 2.705E-02 | 7.263E-02 | 0.6661 |
| SEQ ID NO: 136 | hsa-miR-520a-3p | 1.000E+00 | 3.624E-01 | 2.760E-02 | -3.590E+00 | 7.513E-03 | 3.265E-02 | 2.494E-03 | 1.127E-02 | 0.2986 |
| SEQ ID NO: 137 | hsa-miR-920 | 2.723E+01 | 7.991E+01 | 3.413E-01 | -1.075E+00 | 7.936E-03 | 3.337E-02 | 2.242E-04 | 2.159E-03 | 0.2293 |
| SEQ ID NO: 138 | hsa-miR-132* | 4.681E+01 | 2.461E+01 | 1.979E+00 | 8.834E-01 | 7.936E-03 | 3.374E-02 | 1.061E-02 | 3.468E-02 | 0.6935 |
| SEQ ID NO: 139 | hsa-miR-615-3p | 2.899E+01 | 8.071E+01 | 3.588E-01 | -1.826E-01 | 8.548E-03 | 3.564E-02 | 3.793E-02 | 1.807E-02 | 0.2414 |
| SEQ ID NO: 140 | hsa-miR-744 | 6.104E+02 | 4.720E+02 | 1.293E+00 | 2.571E-01 | 8.978E-03 | 3.655E-02 | 7.259E-01 | 8.290E-01 | 0.6011 |
| SEQ ID NO: 141 | hsa-miR-875-5p | 2.890E+01 | 7.602E+01 | 3.498E-01 | -1.050E+00 | 9.254E-03 | 3.732E-02 | 1.070E-01 | 2.104E-01 | 0.2954 |
| SEQ ID NO: 142 | hsa-miR-454* | 1.253E+01 | 3.475E+01 | 3.601E-01 | -1.021E+00 | 9.747E-03 | 3.854E-02 | 3.624E-03 | 1.810E-02 | 0.2836 |
| SEQ ID NO: 143 | hsa-miR-188-5p | 1.120E+02 | 8.386E+01 | 1.337E+00 | 2.901E-01 | 9.937E-03 | 3.955E-02 | 1.382E-06 | 3.507E-05 | 0.6766 |
| SEQ ID NO: 144 | hsa-miR-22* | 4.639E+01 | 9.474E+01 | 4.896E-01 | -7.141E-01 | 1.053E-02 | 4.061E-02 | 2.393E-02 | 1.190E-02 | 0.2597 |

Figure 7 cont.

| SEQ ID NO | miRNA | median g1 | median g2 | qmedian | logqmedian | ttest rawp | ttest adjp | limma rawp | limma adjp | AUC |
|---|---|---|---|---|---|---|---|---|---|---|
| SEQ ID NO: 145 | hsa-miR-125a-5p | 1.500E-02 | 2.844E-02 | 5.294E-01 | -6.361E-01 | 1.029E-03 | 4.961E-02 | 3.899E-03 | 1.629E-02 | 0.2911 |
| SEQ ID NO: 146 | hsa-let-7f-2* | 4.779E+00 | 4.113E-01 | 1.162E-01 | -2.152E+00 | 1.042E-02 | 4.068E-02 | 6.561E-03 | 2.367E-02 | 0.3011 |
| SEQ ID NO: 147 | hsa-miR-483-3p | 1.899E+01 | 4.855E-01 | 3.909E-01 | -9.394E-01 | 1.052E-02 | 4.088E-02 | 5.967E-04 | 3.901E-03 | 0.2904 |
| SEQ ID NO: 148 | hsa-miR-1304 | 4.944E+03 | 7.608E-01 | 6.498E-01 | -4.311E-01 | 1.154E-02 | 4.428E-02 | 1.302E-02 | 4.125E-02 | 0.2425 |
| SEQ ID NO: 149 | hsa-miR-548f | 2.384E+01 | 1.000E+00 | 2.384E-01 | -3.171E+00 | 1.162E-02 | 4.437E-02 | 1.524E-03 | 7.831E-03 | 0.6690 |
| SEQ ID NO: 150 | hsa-miR-1264 | 3.129E+02 | 8.673E-01 | 1.301E+00 | 2.633E-01 | 1.304E-02 | 4.518E-02 | 6.375E-01 | 7.852E-01 | 0.6498 |
| SEQ ID NO: 151 | hsa-miR-92a-1* | 1.408E+03 | 8.587E-01 | 1.669E-01 | -1.819E+00 | 1.211E-02 | 4.532E-02 | 5.429E-04 | 3.739E-03 | 0.2333 |
| SEQ ID NO: 152 | hsa-miR-744* | 3.894E+03 | 1.118E+00 | 3.571E+00 | 1.273E+00 | 1.231E-02 | 4.578E-02 | 1.836E-03 | 9.054E-03 | 0.7057 |
| SEQ ID NO: 153 | hsa-miR-519d-5p | 1.569E+02 | 6.141E-01 | 2.556E+00 | 9.379E-01 | 1.321E-02 | 4.827E-02 | 1.771E-04 | 1.856E-03 | 0.6911 |
| SEQ ID NO: 154 | hsa-miR-25a | 8.572E+03 | 8.333E-03 | 7.336E-01 | -3.068E-01 | 3.661E-03 | 6.319E-06 | 1.293E-03 | 6.887E-03 | 0.1332 |
| SEQ ID NO: 155 | hsa-miR-484 | 7.714E+03 | 5.379E+03 | 1.434E+00 | 3.835E-01 | 6.998E-07 | 6.317E-05 | 2.012E-03 | 9.757E-03 | 0.7779 |
| SEQ ID NO: 156 | hsa-miR-217 | 1.417E+02 | 3.709E+01 | 3.821E-01 | 1.341E+00 | 1.801E-06 | 1.198E-04 | 1.937E-07 | 6.466E-06 | 0.8525 |
| SEQ ID NO: 157 | hsa-miR-566 | 8.653E+01 | 2.365E+02 | 3.820E+00 | 1.340E+00 | 3.222E-06 | 1.463E-04 | 4.216E-09 | 4.548E-07 | 0.8418 |
| SEQ ID NO: 158 | hsa-miR-515-5p | 1.609E+02 | 5.121E+01 | 3.142E+00 | 1.149E+00 | 4.021E-06 | 1.572E-04 | 5.174E-09 | 4.961E-07 | 0.8575 |
| SEQ ID NO: 159 | hsa-miR-126* | 2.133E+00 | 5.093E+01 | 3.553E-02 | -3.387E+00 | 4.160E-06 | 1.522E-04 | 1.009E-07 | 4.584E-06 | 0.1229 |
| SEQ ID NO: 160 | hsa-miR-200a | 9.031E-01 | 3.289E+01 | 2.755E+00 | 1.013E+00 | 6.329E-06 | 1.849E-04 | 1.186E-05 | 2.171E-04 | 0.8139 |
| SEQ ID NO: 161 | hsa-miR-302b* | 6.695E+00 | 1.000E+00 | 6.895E+00 | 1.909E+00 | 6.549E-06 | 1.949E-04 | 1.218E-03 | 6.693E-03 | 0.7964 |
| SEQ ID NO: 162 | hsa-miR-142-5p | 7.478E+02 | 1.183E+03 | 6.319E-01 | -4.590E-01 | 2.440E-05 | 5.540E-04 | 1.285E-03 | 6.887E-03 | 0.2214 |
| SEQ ID NO: 163 | hsa-miR-519e* | 6.006E+01 | 2.626E+00 | 2.297E-01 | 3.130E+00 | 2.603E-05 | 5.605E-04 | 2.362E-09 | 3.816E-07 | 0.7943 |
| SEQ ID NO: 164 | hsa-miR-512-5p | 5.361E+01 | 1.776E+02 | 3.018E+00 | 1.105E+00 | 2.642E-05 | 5.605E-04 | 1.376E-06 | 3.507E-05 | 0.8964 |
| SEQ ID NO: 165 | hsa-miR-101 | 5.865E+02 | 9.093E+02 | 5.895E-01 | -5.189E-01 | 4.910E-05 | 8.827E-04 | 1.634E-03 | 8.198E-03 | 0.1729 |
| SEQ ID NO: 166 | hsa-miR-493 | 1.562E+02 | 7.534E+01 | 2.073E+00 | 7.299E-01 | 5.885E-05 | 9.422E-04 | 5.645E-04 | 3.602E-03 | 0.7661 |
| SEQ ID NO: 167 | hsa-miR-627 | 1.538E+02 | 7.978E+01 | 1.924E+00 | 6.346E-01 | 5.459E-05 | 9.422E-04 | 8.199E-06 | 1.745E-04 | 0.7779 |
| SEQ ID NO: 168 | hsa-let-7g | 2.994E+02 | 8.553E+02 | 3.149E-01 | -1.158E+00 | 6.659E-05 | 1.190E-03 | 7.499E-04 | 4.589E-03 | 0.2286 |
| SEQ ID NO: 169 | hsa-miR-324-3p | 8.192E+02 | 5.322E+02 | 1.537E+00 | 4.301E-01 | 8.049E-05 | 1.213E-03 | 4.113E-03 | 1.709E-02 | 0.7188 |
| SEQ ID NO: 170 | hsa-miR-568 | 7.147E+01 | 2.864E+01 | 2.496E+00 | 9.146E-01 | 8.665E-05 | 1.238E-03 | 8.461E-07 | 2.513E-05 | 0.7829 |
| SEQ ID NO: 171 | hsa-miR-646 | 2.063E+02 | 7.714E+01 | 2.675E+00 | 9.899E-01 | 1.011E-04 | 1.342E-03 | 1.784E-05 | 2.961E-04 | 0.7746 |
| SEQ ID NO: 172 | hsa-miR-27a | 2.728E+02 | 6.418E+01 | 4.262E-01 | -9.552E-01 | 1.011E-04 | 1.342E-03 | 2.955E-06 | 5.376E-05 | 0.1246 |
| SEQ ID NO: 173 | hsa-miR-891 | 5.361E+01 | 9.653E+00 | 5.553E+00 | 1.714E+00 | 1.744E-04 | 2.120E-03 | 3.990E-09 | 2.777E-06 | 0.7819 |
| SEQ ID NO: 174 | hsa-miR-636 | 1.577E+02 | 9.203E+01 | 1.711E+00 | 5.371E-01 | 1.869E-04 | 2.206E-03 | 3.912E-04 | 2.961E-03 | 0.7579 |
| SEQ ID NO: 175 | hsa-miR-126 | 1.620E+03 | 2.953E+03 | 5.513E-01 | -5.954E-01 | 2.679E-04 | 2.884E-03 | 1.098E-03 | 6.275E-03 | 0.2369 |
| SEQ ID NO: 176 | hsa-miR-298 | 3.229E+02 | 6.814E+02 | 4.739E-01 | -7.467E-01 | 2.721E-04 | 2.884E-03 | 1.171E-03 | 6.556E-03 | 0.2229 |
| SEQ ID NO: 177 | hsa-miR-621 | 3.404E+02 | 1.320E+02 | 2.579E+00 | 9.473E-01 | 2.735E-04 | 2.884E-03 | 1.088E-03 | 6.275E-03 | 0.8590 |
| SEQ ID NO: 178 | hsa-miR-598 | 1.162E+02 | 8.189E+01 | 4.474E-01 | -2.043E-01 | 3.379E-04 | 3.471E-03 | 2.452E-03 | 1.120E-02 | 0.2032 |
| SEQ ID NO: 179 | hsa-miR-603 | 3.009E+02 | 1.587E+02 | 1.408E+00 | 5.470E-01 | 3.829E-04 | 3.787E-03 | 7.884E-04 | 4.825E-03 | 0.7057 |
| SEQ ID NO: 180 | hsa-miR-214 | 3.009E+02 | 1.587E+02 | 1.895E+00 | 6.391E-01 | 3.913E-04 | 3.787E-03 | 1.603E-03 | 8.091E-03 | 0.7436 |

Figure 7 cont.

| SEQ ID NO | miRNA | median_gt1 | median_gt2 | qtmedian | logpmedian | ttest_rawp | ttest_adjp | limma_rawp | limma_adjp | AUC |
|---|---|---|---|---|---|---|---|---|---|---|
| SEQ ID NO: 181 | hsa-miR-145 | 1.263E-02 | 3.052E-02 | 4.142E-01 | 8.814E-01 | 3.918E-04 | 3.757E-03 | 3.279E-03 | 5.208E-04 | 0.1950 |
| SEQ ID NO: 182 | hsa-miR-185 | 8.508E-01 | 1.548E-02 | 5.495E-01 | 5.988E-01 | 4.190E-04 | 3.888E-03 | 2.981E-03 | 1.293E-02 | 0.2294 |
| SEQ ID NO: 183 | hsa-miR-452* | 2.947E-02 | 1.457E-02 | 2.023E+00 | 7.946E-01 | 4.750E-04 | 4.315E-03 | 2.434E-03 | 1.118E-02 | 0.7414 |
| SEQ ID NO: 184 | hsa-miR-492 | 7.192E-01 | 2.129E-01 | 3.379E-01 | 1.218E+00 | 4.973E-04 | 4.408E-03 | 2.128E-04 | 2.131E-03 | 0.7468 |
| SEQ ID NO: 185 | hsa-miR-221 | 8.143E-01 | 1.679E-02 | 4.849E-01 | 7.239E-01 | 5.076E-04 | 4.408E-03 | 2.493E-03 | 1.127E-02 | 0.2150 |
| SEQ ID NO: 186 | hsa-miR-16 | 1.574E-04 | 2.047E-04 | 7.819E-01 | 2.626E-01 | 5.567E-04 | 4.676E-03 | 1.043E-02 | 3.421E-02 | 0.2850 |
| SEQ ID NO: 187 | hsa-miR-222 | 4.499E-02 | 6.363E-02 | 7.032E-01 | 3.520E-01 | 6.098E-04 | 4.999E-03 | 4.196E-03 | 1.733E-02 | 0.2393 |
| SEQ ID NO: 188 | hsa-miR-302b | 1.000E+00 | 5.271E-01 | 1.897E-02 | -3.965E+00 | 6.735E-04 | 6.671E-03 | 2.316E-06 | 1.519E-06 | 0.1379 |
| SEQ ID NO: 189 | hsa-miR-564 | 1.565E-02 | 8.677E-01 | 1.804E+00 | 5.899E-01 | 9.318E-04 | 6.879E-03 | 1.106E-03 | 6.275E-03 | 0.7425 |
| SEQ ID NO: 190 | hsa-let-7d | 2.008E-03 | 3.153E-03 | 6.345E-01 | -4.547E-01 | 9.326E-04 | 6.879E-03 | 1.448E-02 | 4.464E-02 | 0.2407 |
| SEQ ID NO: 191 | hsa-miR-596 | 7.255E-02 | 1.193E-02 | 6.097E-01 | -4.948E-01 | 9.326E-04 | 8.961E-03 | 3.527E-03 | 1.511E-02 | 0.2289 |
| SEQ ID NO: 192 | hsa-miR-338 | 1.729E-02 | 1.314E-02 | 1.315E+00 | 2.737E-01 | 9.519E-04 | 8.961E-03 | 1.309E-01 | 2.419E-01 | 0.6757 |
| SEQ ID NO: 193 | hsa-miR-422a | 1.385E-01 | 2.740E-02 | 5.056E-01 | -6.861E-01 | 1.038E-03 | 7.408E-03 | 1.118E-04 | 1.298E-03 | 0.2168 |
| SEQ ID NO: 194 | hsa-miR-519 | 6.030E-01 | 2.536E-01 | 2.379E+00 | 6.861E-01 | 1.059E-03 | 7.408E-03 | 1.349E-03 | 7.099E-03 | 0.7336 |
| SEQ ID NO: 195 | hsa-miR-142-3p | 1.784E-01 | 9.595E-01 | 1.919E-01 | -1.651E+00 | 1.098E-03 | 7.844E-03 | 2.970E-04 | 2.491E-03 | 0.2357 |
| SEQ ID NO: 196 | hsa-miR-447b | 5.423E-01 | 2.125E-01 | 2.552E+00 | 3.371E-01 | 1.127E-03 | 7.908E-03 | 3.319E-07 | 1.193E-06 | 0.7475 |
| SEQ ID NO: 197 | hsa-miR-153 | 3.027E-02 | 5.219E-01 | 1.957E+00 | 6.769E-01 | 1.345E-03 | 9.066E-03 | 1.583E-04 | 2.793E-01 | 0.7343 |
| SEQ ID NO: 198 | hsa-miR-148 | 1.711E-01 | 3.220E-02 | 5.282E-01 | 6.384E-01 | 1.436E-03 | 9.605E-03 | 5.779E-03 | 2.150E-02 | 0.2182 |
| SEQ ID NO: 199 | hsa-miR-497 | 1.672E-02 | 9.698E-01 | 1.729E+00 | 5.512E-01 | 1.561E-03 | 1.036E-02 | 3.359E-04 | 2.737E-03 | 0.6950 |
| SEQ ID NO: 200 | hsa-miR-554 | 8.815E-01 | 5.057E-01 | 1.746E+00 | 5.557E-01 | 1.729E-03 | 1.114E-02 | 6.801E-04 | 4.189E-03 | 0.7207 |
| SEQ ID NO: 201 | hsa-miR-514 | 3.902E-01 | 7.482E+00 | 5.213E+00 | 1.852E+00 | 2.034E-03 | 1.281E-02 | 1.983E-03 | 9.664E-03 | 0.7099 |
| SEQ ID NO: 202 | hsa-miR-375 | 8.713E+00 | 7.071E+00 | 1.222E+00 | -2.064E+00 | 2.145E-03 | 1.341E-02 | 1.093E-04 | 1.291E-03 | 0.2057 |
| SEQ ID NO: 203 | hsa-miR-425 | 1.198E-04 | 1.574E-04 | 7.608E-01 | -2.739E-01 | 2.257E-03 | 1.391E-02 | 3.649E-02 | 9.265E-02 | 0.2804 |
| SEQ ID NO: 204 | hsa-miR-543 | 5.144E-01 | 2.291E-01 | 2.437E+00 | 8.491E-01 | 2.664E-03 | 1.664E-02 | 3.034E-03 | 1.369E-02 | 0.7186 |
| SEQ ID NO: 205 | hsa-miR-521 | 4.709E-01 | 1.192E-02 | 3.943E+00 | -9.291E-01 | 3.497E-03 | 1.922E-02 | 2.330E-03 | 2.197E-03 | 0.2311 |
| SEQ ID NO: 206 | hsa-miR-509 | 7.396E-01 | 3.475E-01 | 2.129E+00 | 7.554E-01 | 3.716E-03 | 1.987E-02 | 4.670E-03 | 1.848E-02 | 0.6929 |
| SEQ ID NO: 207 | hsa-miR-32 | 1.417E-02 | 1.194E-02 | 1.167E+00 | 1.714E-01 | 3.939E-03 | 2.098E-02 | 4.529E-02 | 1.077E-01 | 0.6908 |
| SEQ ID NO: 208 | hsa-miR-520g | 4.935E-01 | 2.453E-01 | 1.971E+00 | 6.782E-01 | 4.138E-03 | 2.146E-02 | 8.722E-02 | 1.796E-01 | 0.6725 |
| SEQ ID NO: 209 | hsa-miR-183 | 3.814E-02 | 6.513E-02 | 5.072E-01 | -6.789E-01 | 4.527E-03 | 2.298E-02 | 2.963E-02 | 1.293E-02 | 0.2746 |
| SEQ ID NO: 210 | hsa-miR-22b | 3.149E-03 | 3.998E-03 | 7.655E-01 | -2.404E-01 | 4.858E-03 | 2.396E-02 | 1.015E-02 | 3.227E-02 | 0.2882 |
| SEQ ID NO: 211 | hsa-miR-203 | 8.438E+00 | 3.266E-03 | 2.567E-01 | -1.366E+00 | 4.928E-03 | 2.437E-02 | 1.273E-03 | 6.866E-03 | 0.2657 |
| SEQ ID NO: 212 | hsa-miR-15a | 4.897E-01 | 8.281E-03 | 5.673E-01 | -5.869E-01 | 6.257E-03 | 2.862E-02 | 1.233E-01 | 2.338E-01 | 0.2757 |
| SEQ ID NO: 213 | hsa-miR-346 | 5.397E-01 | 3.646E-01 | 1.480E+00 | 3.922E-01 | 6.913E-03 | 3.125E-02 | 5.195E-03 | 2.019E-02 | 0.6829 |
| SEQ ID NO: 214 | hsa-miR-200a* | 6.273E-01 | 2.833E-01 | 2.137E+00 | 7.395E-01 | 7.034E-03 | 3.182E-02 | 2.329E-03 | 1.167E-02 | 0.6793 |
| SEQ ID NO: 215 | hsa-miR-409-5p | 7.844E-01 | 4.099E-01 | 1.915E+00 | 6.497E-01 | 7.140E-03 | 3.176E-02 | 6.008E-05 | 8.499E-04 | 0.7193 |
| SEQ ID NO: 216 | hsa-miR-656 | 4.881E-01 | 8.978E-01 | 5.826E-01 | 5.403E-01 | 7.390E-03 | 3.268E-02 | 1.003E-02 | 3.316E-02 | 0.3011 |

Figure 7 cont.

| SEQ ID NO | miRNA | median g1 | median g2 | gpmedian | logqmedian | ttest_rawp | ttest_adjp | limma_rawp | limma_adjp | AUC |
|---|---|---|---|---|---|---|---|---|---|---|
| SEQ ID NO: 217 | hsa-miR-148b | 5.277E-02 | 4.704E-02 | 1.122E+00 | 1.150E-01 | 7.619E-03 | 3.239E-02 | 3.997E-02 | 4.439E-01 | 0.6275 |
| SEQ ID NO: 218 | hsa-miR-363* | 6.193E-01 | 4.759E-01 | 1.301E+00 | 2.635E-01 | 7.860E-03 | 3.384E-02 | 4.192E-04 | 3.034E-03 | 0.6764 |
| SEQ ID NO: 219 | hsa-miR-34a | 2.191E-01 | 5.659E-01 | 3.871E-01 | -9.490E-01 | 8.026E-03 | 3.385E-02 | 1.191E-03 | 6.631E-03 | 0.2643 |
| SEQ ID NO: 220 | hsa-miR-375a* | 1.010E+00 | 4.664E-01 | 2.144E-02 | -3.643E+00 | 8.155E-03 | 3.434E-02 | 2.637E-04 | 2.370E-03 | 0.2636 |
| SEQ ID NO: 221 | hsa-miR-605 | 1.030E+00 | 4.561E-01 | 2.192E-02 | -3.820E+00 | 8.353E-03 | 3.502E-02 | 1.272E-05 | 2.333E-04 | 0.2192 |
| SEQ ID NO: 222 | hsa-miR-361-3p | 1.450E-01 | 5.212E-01 | 2.781E-01 | -1.280E+00 | 8.606E-03 | 3.571E-02 | 1.198E-03 | 6.275E-03 | 0.2618 |
| SEQ ID NO: 223 | hsa-miR-542-5p | 8.383E-01 | 1.237E-01 | 8.777E-01 | 3.891E-01 | 8.962E-03 | 3.577E-02 | 1.373E-02 | 4.279E-02 | 0.2364 |
| SEQ ID NO: 224 | hsa-miR-550 | 1.137E-02 | 7.423E-01 | 1.532E+00 | 4.264E-01 | 8.842E-03 | 3.621E-02 | 1.723E-02 | 5.128E-02 | 0.6829 |
| SEQ ID NO: 225 | hsa-miR-575 | 1.273E-02 | 7.442E-01 | 1.710E+00 | 5.365E-01 | 8.853E-03 | 3.627E-02 | 1.002E-02 | 3.316E-02 | 0.6675 |
| SEQ ID NO: 226 | hsa-miR-625 | 5.447E-03 | 1.574E-02 | 3.461E-01 | -1.061E+00 | 9.178E-03 | 3.672E-02 | 6.283E-03 | 2.300E-02 | 0.2393 |
| SEQ ID NO: 227 | hsa-miR-22 | 7.714E-03 | 1.041E-04 | 7.410E-01 | -2.998E-01 | 9.637E-03 | 3.868E-02 | 3.869E-02 | 9.594E-02 | 0.2950 |
| SEQ ID NO: 228 | hsa-miR-149 | 2.190E-01 | 6.099E-01 | 3.495E-01 | -1.061E+00 | 1.035E-02 | 4.061E-02 | 3.719E-03 | 1.581E-02 | 0.3283 |
| SEQ ID NO: 229 | hsa-miR-451 | 1.585E-03 | 9.886E-02 | 1.603E+00 | 4.720E-01 | 1.118E-02 | 4.315E-02 | 2.809E-01 | 4.229E-01 | 0.6561 |
| SEQ ID NO: 230 | hsa-miR-520h | 3.648E-01 | 1.009E+00 | 3.845E-01 | -3.597E+00 | 1.120E-02 | 4.315E-02 | 2.876E-05 | 4.568E-04 | 0.7229 |
| SEQ ID NO: 231 | hsa-miR-9 | 3.450E-03 | 4.161E-03 | 7.087E-01 | -3.439E-01 | 1.341E-02 | 4.419E-02 | 1.229E-02 | 3.856E-02 | 0.2293 |
| SEQ ID NO: 232 | hsa-miR-624 | 5.144E-01 | 8.092E-01 | 6.357E-01 | -4.539E-01 | 1.173E-02 | 4.446E-02 | 8.957E-02 | 1.754E-01 | 0.2858 |
| SEQ ID NO: 233 | hsa-miR-493 | 6.273E-01 | 2.769E-01 | 2.273E+00 | 8.211E-01 | 1.194E-02 | 4.468E-02 | 2.034E-02 | 5.613E-02 | 0.7029 |
| SEQ ID NO: 234 | hsa-miR-498 | 2.797E-01 | 5.017E-01 | 5.586E-01 | -5.877E-01 | 1.235E-02 | 4.576E-02 | 1.099E-03 | 3.094E-02 | 0.2886 |
| SEQ ID NO: 235 | hsa-miR-518b | 9.390E-01 | 5.652E-01 | 1.697E+00 | 5.288E-01 | 1.266E-02 | 4.689E-02 | 7.709E-03 | 2.718E-02 | 0.6989 |
| SEQ ID NO: 236 | hsa-miR-448 | 8.557E-01 | 3.480E-01 | 2.459E+00 | 6.897E-01 | 1.283E-02 | 4.710E-02 | 7.227E-03 | 2.559E-02 | 0.7095 |
| SEQ ID NO: 237 | hsa-miR-639 | 6.105E-01 | 4.194E-01 | 1.468E+00 | 3.826E-01 | 1.341E-02 | 4.884E-02 | 2.572E-04 | 2.301E-02 | 0.7054 |
| SEQ ID NO: 238 | hsa-miR-21 | 8.391E-02 | 1.252E-03 | 6.703E-01 | -4.002E-01 | 2.048E-02 | 6.522E-02 | 2.172E-02 | 6.171E-02 | 0.2875 |
| SEQ ID NO: 239 | hsa-miR-1 | 1.322E-01 | 3.352E-01 | 3.943E-01 | -9.309E-01 | 2.907E-02 | 8.385E-02 | 5.219E-02 | 1.213E-01 | 0.3475 |
| SEQ ID NO: 240 | hsa-miR-223 | 2.206E-03 | 1.962E-03 | 1.129E+00 | 1.758E-01 | 7.866E-02 | 8.668E-01 | 6.539E-01 | 7.714E-01 | 0.5246 |
| SEQ ID NO: 241 | hsa-miR-30c | 2.158E-03 | 2.357E-03 | 3.153E-01 | -8.853E-02 | 9.123E-01 | 9.537E-01 | 3.260E-01 | 4.720E-01 | 0.4454 |
| SEQ ID NO: 242 | hsa-let-7i | 0.0955E-04 | 0.085E-04 | 0.644E-03 | -0.439E+00 | 0.320E+00 | 0.472E+00 | 0.031E+01 | 0.082E+00 | |
| SEQ ID NO: 243 | hsa-miR-191-5p | 0.440E-04 | 0.430E-04 | 1.024E+00 | 0.024E+00 | 0.355E+00 | 0.519E+00 | 1.000E+00 | 1.010E+00 | |
| SEQ ID NO: 244 | hsa-miR-87-1 | 0.015E-04 | 0.015E-04 | 1.063E+01 | 0.061E+00 | 0.077E+00 | 0.174E+00 | 0.085E+00 | 0.126E+00 | |
| SEQ ID NO: 245 | hsa-miR-106a | 0.392E-04 | 0.771E-04 | 1.798E-01 | -0.254E+00 | 0.297E+00 | 0.459E+00 | 0.097E+00 | 0.193E+00 | |
| SEQ ID NO: 246 | hsa-miR-26a | 0.382E-04 | 0.354E-04 | 1.092E-01 | 0.024E+00 | 0.224E+00 | 0.739E+00 | 0.267E+00 | 0.404E+00 | |
| SEQ ID NO: 247 | hsa-miR-143a | 0.096E-04 | 0.091E-04 | 1.047E-01 | 0.046E+00 | 0.044E+00 | 0.115E+00 | 0.056E+00 | 0.771E+00 | |
| SEQ ID NO: 248 | hsa-let-7b | 0.391E-04 | 0.091E-04 | 0.883E-01 | -0.115E-01 | 0.819E+00 | 0.738E+00 | 0.116E+00 | 0.215E+00 | |
| SEQ ID NO: 249 | hsa-miR-30b* | 0.014E-04 | 0.102E-04 | 1.115E-01 | 0.199E+00 | 0.063E+00 | 0.144E+00 | 4.503E-04 | 0.003E+00 | |
| SEQ ID NO: 250 | hsa-miR-374a | 0.025E-04 | 0.045E-04 | 0.565E+00 | -0.544E-05 | 0.015E+00 | 0.061E+00 | 0.052E+00 | 0.082E+00 | |
| SEQ ID NO: 251 | hsa-miR-182 | 0.492E-04 | 0.512E-04 | 0.919E+00 | -0.159E+00 | 0.089E+00 | 0.179E+00 | 0.169E+00 | 0.329E+00 | |
| SEQ ID NO: 252 | hsa-miR-497* | 0.010E-04 | 0.027E-04 | 1.555E+00 | 0.442E+00 | 0.067E+00 | 0.135E+00 | 0.029E+00 | 0.088E+00 | |

Figure 7 cont.

| SEQ ID NO | miRNA | median g1 | median g2 | qmedian | logqmedian | ttest_rawp | ttest_adjp | limma_rawp | limma_adjp | AUC |
|---|---|---|---|---|---|---|---|---|---|---|
| SEQ ID NO: 253 | hsa-miR-345 | 0.011E+04 | 0.010E+04 | 1.072E+00 | 0.169E+00 | 0.669E+00 | 0.773E+00 | 0.417E+00 | 0.555E+00 | |
| SEQ ID NO: 254 | hsa-miR-323-3p | 0.003E+04 | 0.002E+04 | 1.534E+00 | 0.428E+00 | 0.213E+00 | 0.357E+00 | 0.238E+00 | 0.368E+00 | |
| SEQ ID NO: 255 | hsa-miR-193a-3p | 0.012E+04 | 0.009E+04 | 1.477E+00 | 0.390E+00 | 0.017E+00 | 0.055E+00 | 0.331E+00 | 0.478E+00 | |
| SEQ ID NO: 256 | hsa-miR-134 | 0.008E+04 | 0.011E+04 | 0.519E+00 | -0.667E+00 | 0.068E+00 | 0.142E+00 | 0.149E+00 | 0.265E+00 | |
| SEQ ID NO: 257 | hsa-miR-663b | 0.005E+04 | 0.005E+04 | 1.168E+00 | 0.155E+00 | 0.122E+00 | 0.244E+00 | 0.090E+00 | 0.169E+00 | |
| SEQ ID NO: 258 | hsa-miR-489-3p | 0.006E+04 | 0.004E+04 | 1.305E+00 | 0.266E+00 | 0.029E+00 | 0.084E+00 | 0.345E+00 | 0.488E+00 | |
| SEQ ID NO: 259 | hsa-miR-531 | 0.013E+04 | 0.010E+04 | 1.261E+00 | 0.232E+00 | 0.019E+00 | 0.062E+00 | 0.101E+00 | 0.202E+00 | |
| SEQ ID NO: 260 | hsa-miR-544 | 0.004E+04 | 0.006E+04 | 0.629E+00 | -0.463E+00 | 0.098E+00 | 0.208E+00 | 0.363E+00 | 0.505E+00 | |
| SEQ ID NO: 261 | hsa-miR-1006* | 0.007E+04 | 0.009E+04 | 0.793E+00 | -0.308E+00 | 0.278E+00 | 0.427E+00 | 0.393E+00 | 0.534E+00 | |
| SEQ ID NO: 262 | hsa-miR-126 | 0.009E+04 | 0.005E+04 | 1.897E+00 | 0.640E+00 | 0.019E+00 | 0.060E+00 | 0.065E+00 | 0.143E+00 | |
| SEQ ID NO: 263 | hsa-miR-409-3p | 0.004E+04 | 0.007E+04 | 0.492E+00 | -0.710E+00 | 0.051E+00 | 0.128E+00 | 0.044E+00 | 0.107E+00 | |
| SEQ ID NO: 264 | hsa-miR-513a-5p | 0.005E+04 | 0.002E+04 | 2.230E+00 | 0.799E+00 | 0.019E+00 | 0.060E+00 | 0.095E+00 | 0.199E+00 | |
| SEQ ID NO: 265 | hsa-miR-129-5p | 0.005E+04 | 0.006E+04 | 0.644E+00 | -0.446E+00 | 0.030E+00 | 0.084E+00 | 0.062E+00 | 0.139E+00 | |
| SEQ ID NO: 266 | hsa-miR-615-5p | 0.005E+04 | 0.006E+04 | 0.628E+00 | -0.465E+00 | 0.016E+00 | 0.057E+00 | 0.019E+00 | 0.056E+00 | |
| SEQ ID NO: 267 | hsa-miR-193b | 0.006E+04 | 0.009E+04 | 0.641E+00 | -0.445E+00 | 0.024E+00 | 0.071E+00 | 0.042E+00 | 0.102E+00 | |
| SEQ ID NO: 268 | hsa-miR-677* | 0.017E+04 | 0.009E+04 | 0.920E+00 | -0.198E+00 | 0.586E+00 | 0.719E+00 | 0.196E+00 | 0.319E+00 | |
| SEQ ID NO: 269 | hsa-miR-195 | 0.005E+04 | 0.008E+04 | 0.857E+00 | -0.154E+00 | 0.308E+00 | 0.456E+00 | 0.353E+00 | 0.479E+00 | |
| SEQ ID NO: 270 | hsa-miR-296-3p | 0.005E+04 | 0.007E+04 | 0.734E+00 | -0.308E+00 | 0.570E+00 | 0.702E+00 | 0.194E+00 | 0.306E+00 | |
| SEQ ID NO: 271 | hsa-miR-27a* | 0.008E+04 | 0.008E+04 | 0.548E+00 | -0.589E+00 | 0.071E+00 | 0.163E+00 | 0.158E+00 | 0.277E+00 | |
| SEQ ID NO: 272 | hsa-miR-99b* | 0.005E+04 | 0.007E+04 | 0.748E+00 | -0.289E+00 | 0.483E+00 | 0.631E+00 | 0.358E+00 | 0.501E+00 | |
| SEQ ID NO: 273 | hsa-miR-194* | 0.004E+04 | 0.008E+04 | 0.552E+00 | -0.595E+00 | 0.081E+00 | 0.173E+00 | 0.866E+00 | 0.918E+00 | |
| SEQ ID NO: 274 | hsa-miR-653 | 0.002E+04 | 0.002E+04 | 1.185E+00 | 0.170E+00 | 0.491E+00 | 0.637E+00 | 0.903E+00 | 0.934E+00 | |
| SEQ ID NO: 275 | hsa-miR-608 | 0.005E+04 | 0.005E+04 | 0.993E+00 | -0.008E+00 | 0.509E+00 | 0.652E+00 | 0.333E+00 | 0.479E+00 | |
| SEQ ID NO: 276 | hsa-miR-337-3p | 0.004E+04 | 0.003E+04 | 1.542E+00 | 0.433E+00 | 0.126E+00 | 0.244E+00 | 0.026E+00 | 0.076E+00 | |
| SEQ ID NO: 277 | hsa-miR-1207-3p | 0.003E+04 | 0.001E+04 | 3.301E+00 | 1.194E+00 | 0.086E+00 | 0.189E+00 | 0.067E+00 | 0.145E+00 | |
| SEQ ID NO: 278 | hsa-miR-579 | 0.003E+03 | 0.003E+04 | 1.097E+00 | 0.092E+00 | 0.847E+00 | 0.904E+00 | 0.428E+00 | 0.564E+00 | |
| SEQ ID NO: 279 | hsa-miR-323-3p | 0.005E+04 | 0.010E+04 | 0.499E+00 | -0.788E+00 | 0.017E+00 | 0.059E+00 | 0.032E+00 | 0.010E+00 | |
| SEQ ID NO: 280 | hsa-miR-634 | 0.010E+03 | 0.003E+04 | 3.869E+00 | 1.351E+00 | 0.027E+00 | 0.079E+00 | 0.715E-04 | 9.645E-04 | |
| SEQ ID NO: 281 | hsa-miR-144* | 0.055E+03 | 0.065E+04 | 0.999E+00 | -0.001E+00 | 0.891E+00 | 0.990E+00 | 0.202E+00 | 0.325E+00 | |
| SEQ ID NO: 282 | hsa-miR-519d | 0.006E+04 | 0.007E+04 | 0.799E+00 | -0.224E+00 | 0.154E+00 | 0.263E+00 | 0.116E+00 | 0.222E+00 | |
| SEQ ID NO: 283 | hsa-miR-191* | 0.005E+04 | 0.003E+04 | 1.728E+00 | 0.548E+00 | 0.606E+00 | 0.732E+00 | 0.333E+00 | 0.485E+00 | |

Figure 7 cont.

| SEQ ID NO: | miRNA | Sequences 5'—3' |
|---|---|---|
| SEQ ID NO: 1 | hsa-miR-1291 | UGGCCCUGACUGAAGACCAGCAGU |
| SEQ ID NO: 2 | hsa-miR-1283 | UCUACAAAGGAAAGCGCUUUCU |
| SEQ ID NO: 3 | hsa-miR-1201 | AGCCUGAUUAAACACAUGCUCUGA |
| SEQ ID NO: 4 | hsa-miR-1245 | AAGUGAUCUAAAGGCCUACAU |
| SEQ ID NO: 5 | hsa-miR-208b | AUAAGACGAACAAAAGGUUUGU |
| SEQ ID NO: 6 | hsa-miR-1912 | UACCCAGAGCAUGCAGUGUGAA |
| SEQ ID NO: 7 | hsa-miR-1278 | UAGUACUGUGCAUAUCAUCUAU |
| SEQ ID NO: 8 | hsa-miR-548p | UAGCAAAAACUGCAGUUACUUU |
| SEQ ID NO: 9 | hsa-miR-1305 | UUUUCAACUCUAAUGGGAGAGA |
| SEQ ID NO: 10 | hsa-miR-1256 | AGGCAUUGACUUCUCACUAGCU |
| SEQ ID NO: 11 | hsa-miR-1226* | GUGAGGGCAUGCAGGCCUGGAUGGGG |
| SEQ ID NO: 12 | hsa-miR-128 | UCACAGUGAACCGGUCUCUUU |
| SEQ ID NO: 13 | hsa-miR-300 | UAUACAAGGGCAGACUCUCUCU |
| SEQ ID NO: 14 | hsa-miR-541 | UGGUGGGCACAGAAUCUGGACU |
| SEQ ID NO: 15 | hsa-miR-892b | CACUGGCUCCUUUCUGGGUAGA |
| SEQ ID NO: 16 | hsa-miR-455-3p | GCAGUCCAUGGGCAUAUACAC |
| SEQ ID NO: 17 | hsa-miR-31* | UGCUAUGCCAACAUAUUGCCAU |
| SEQ ID NO: 18 | hsa-miR-192* | CUGCCAAUUCCAUAGGUCACAG |
| SEQ ID NO: 19 | hsa-miR-767-5p | UGCACCAUGGUUGUCUGAGCAUG |
| SEQ ID NO: 20 | hsa-miR-93* | ACUGCUGAGCUAGCACUUCCCG |
| SEQ ID NO: 21 | hsa-miR-155* | CUCCUACAUAUUAGCAUUAACA |
| SEQ ID NO: 22 | hsa-miR-20b* | ACUGUAGUAUGGGCACUUCCAG |
| SEQ ID NO: 23 | hsa-miR-491-3p | CUUAUGCAAGAUUCCCUUCUAC |
| SEQ ID NO: 24 | hsa-miR-330-3p | GCAAAGCACACGGCCUGCAGAGA |
| SEQ ID NO: 25 | hsa-miR-148b-5p | UGAGAACUGAAUUCCAUAGGCU |
| SEQ ID NO: 26 | hsa-miR-556-5p | GAUGAGCUCAUUGUAAUAUGAG |
| SEQ ID NO: 27 | hsa-miR-423-5p | UGAGGGGCAGAGAGCGAGACUUU |
| SEQ ID NO: 28 | hsa-miR-10b* | ACAGAUUCGAUUCUAGGGGAAU |
| SEQ ID NO: 29 | hsa-miR-33a | GUGCAUUGUAGUUGCAUUGCA |
| SEQ ID NO: 30 | hsa-miR-508-5p | UACUCCAGAGGGCGUCACUCAUG |
| SEQ ID NO: 31 | hsa-miR-139-5p | UCUACAGUGCACGUGUCUCCAG |
| SEQ ID NO: 32 | hsa-miR-380* | UGGUUGACCAUAGAACAUGCGC |
| SEQ ID NO: 33 | hsa-miR-96* | AAUCAUGUGCAGUGCCAAUAUG |
| SEQ ID NO: 34 | hsa-miR-518a-3p | GAAAGCGCUUCCCUUUGCUGGA |
| SEQ ID NO: 35 | hsa-miR-188-3p | CUCCCACAUGCAGGGUUUGCA |
| SEQ ID NO: 36 | hsa-miR-20a* | ACUGCAUUAUGAGCACUUAAAG |
| SEQ ID NO: 37 | hsa-miR-520d-5p | CUACAAAGGGAAGCCCUUUC |
| SEQ ID NO: 38 | hsa-miR-136* | CAUCAUCGUCUCAAAUGAGUCU |
| SEQ ID NO: 39 | hsa-miR-216a | UAAUCUCAGCUGGCAACUGUGA |
| SEQ ID NO: 40 | hsa-miR-532-3p | CCUCCCACACCCAAGGCUUGCA |
| SEQ ID NO: 41 | hsa-miR-654-5p | UGGUGGGCCGCAGAACAUGUGC |
| SEQ ID NO: 42 | hsa-let-7f-1* | CUAUACAAUCUAUUGCCUUCCC |
| SEQ ID NO: 43 | hsa-miR-145* | GGAUUCCUGGAAAUACUGUUCU |
| SEQ ID NO: 44 | hsa-miR-342-3p | UCUCACACAGAAAUCGCACCCGU |
| SEQ ID NO: 45 | hsa-miR-488* | CCCAGAUAAUGGCACUCUCAA |
| SEQ ID NO: 46 | hsa-miR-509-5p | UACUGCAGACAGUGGCAAUCA |
| SEQ ID NO: 47 | hsa-miR-519b-5p | CUCUAGAGGGAAGCGCUUUCUG |
| SEQ ID NO: 48 | hsa-miR-513b | UUCACAAGGAGGUGUCAUUUAU |
| SEQ ID NO: 49 | hsa-miR-550* | UGUCUUACUCCCUCAGGCACAU |
| SEQ ID NO: 50 | hsa-miR-196a* | CGGCAACAAGAAACUGCCUGAG |
| SEQ ID NO: 51 | hsa-miR-1826 | AUUGAUCAUCGACACUUCGAACGCAAU |

Figure 12

| SEQ ID NO: | miRNA | Sequences 5'---3' |
|---|---|---|
| SEQ ID NO: 52 | hsa-miR-802 | CAGUAACAAAGAUUCAUCCUUGU |
| SEQ ID NO: 53 | hsa-miR-1272 | GAUGAUGAUGGCAGCAAAUUCUGAAA |
| SEQ ID NO: 54 | hsa-miR-220c | ACACAGGGCUGUUGUGAAGACU |
| SEQ ID NO: 55 | hsa-miR-30e* | CUUUCAGUCGGAUGUUUACAGC |
| SEQ ID NO: 56 | hsa-miR-455-5p | UAUGUGCCUUUGGACUACAUCG |
| SEQ ID NO: 57 | hsa-miR-24-2* | UGCCUACUGAGCUGAAACACAG |
| SEQ ID NO: 58 | hsa-miR-181c* | AACCAUCGACCGUUGAGUGGAC |
| SEQ ID NO: 59 | hsa-miR-1301 | UUGCAGCUGCCUGGGAGUGACUUC |
| SEQ ID NO: 60 | hsa-miR-1302 | UUGGGACAUACUUAUGCUAAA |
| SEQ ID NO: 61 | hsa-miR-933 | UGUGCGCAGGGAGACCUCUCCC |
| SEQ ID NO: 62 | hsa-miR-1281 | UCGCCUCCUCCUCUCCC |
| SEQ ID NO: 63 | hsa-miR-1247 | ACCCGUCCCGUUCGUCCCGGA |
| SEQ ID NO: 64 | hsa-miR-28-5p | AAGGAGCUCACAGUCUAUUGAG |
| SEQ ID NO: 65 | hsa-miR-876-3p | UGGUGGUUUACAAAGUAAUUCA |
| SEQ ID NO: 66 | hsa-miR-1295 | UUAGGCCGCAGAUCUGGGUGA |
| SEQ ID NO: 67 | hsa-miR-100* | CAAGCUUGUAUCUAUAGGUAUG |
| SEQ ID NO: 68 | hsa-miR-23b* | UGGGUUCCUGGCAUGCUGAUUU |
| SEQ ID NO: 69 | hsa-miR-24-1* | UGCCUACUGAGCUGAUAUCAGU |
| SEQ ID NO: 70 | hsa-miR-1250 | ACGGUGCUGGAUGUGGCCUUU |
| SEQ ID NO: 71 | hsa-miR-30e | UGUAAACAUCCUUGACUGGAAG |
| SEQ ID NO: 72 | hsa-miR-216b | AAAUCUCUGCAGGCAAAUGUGA |
| SEQ ID NO: 73 | hsa-miR-1468 | CUCCGUUUGCCUGUUUCGCUG |
| SEQ ID NO: 74 | hsa-miR-548o | CCAAAACUGCAGUUACUUUUGC |
| SEQ ID NO: 75 | hsa-miR-1296 | UUAGGGCCCUGGCUCCAUCUCC |
| SEQ ID NO: 76 | hsa-miR-942 | UCUUCUCUGUUUUGGCCAUGUG |
| SEQ ID NO: 77 | hsa-miR-34a* | CAAUCAGCAAGUAUACUGCCCU |
| SEQ ID NO: 78 | hsa-miR-518e* | CUCUAGAGGGAAGCGCUUUCUG |
| SEQ ID NO: 79 | hsa-miR-924 | AGAGUCUUGUGAUGUCUUGC |
| SEQ ID NO: 80 | hsa-miR-522* | CUCUAGAGGGAAGCGCUUUCUG |
| SEQ ID NO: 81 | hsa-miR-1290 | UGGAUUUUUGGAUCAGGGA |
| SEQ ID NO: 82 | hsa-miR-1274b | UCCCUGUUCGGGCGCCA |
| SEQ ID NO: 83 | hsa-miR-516a-5p | UUCUCGAGGAAAGAAGCACUUUC |
| SEQ ID NO: 84 | hsa-miR-1303 | UUUAGAGACGGGGUCUUGCUCU |
| SEQ ID NO: 85 | hsa-miR-140-5p | CAGUGGUUUUACCCUAUGGUAG |
| SEQ ID NO: 86 | hsa-miR-218-1* | AUGGUUCCGUCAAGCACCAUGG |
| SEQ ID NO: 87 | hsa-miR-1271 | CUUGGCACCUAGCAAGCACUCA |
| SEQ ID NO: 88 | hsa-miR-890 | UACUUGGAAAGGCAUCAGUUG |
| SEQ ID NO: 89 | hsa-miR-190b | UGAUAUGUUUGAUAUUGGGUU |
| SEQ ID NO: 90 | hsa-miR-938 | UGCCCUUAAAGGUGAACCCAGU |
| SEQ ID NO: 91 | hsa-miR-106a* | CUGCAAUGUAAGCACUUCUUAC |
| SEQ ID NO: 92 | hsa-miR-30c-1* | CUGGGAGAGGGUUGUUUACUCC |
| SEQ ID NO: 93 | hsa-miR-891a | UGCAACGAACCUGAGCCACUGA |
| SEQ ID NO: 94 | hsa-miR-1266 | CCUCAGGGCUGUAGAACAGGGCU |
| SEQ ID NO: 95 | hsa-miR-135b* | AUGUAGGGCUAAAAGCCAUGGG |
| SEQ ID NO: 96 | hsa-miR-223* | CGUGUAUUUGACAAGCUGAGUU |
| SEQ ID NO: 97 | hsa-miR-127-5p | CUGAAGCUCAGAGGGCUCUGAU |
| SEQ ID NO: 98 | hsa-miR-1258 | AGUUAGGAUUAGGUCGUGGAA |
| SEQ ID NO: 99 | hsa-let-7i* | CUGCGCAAGCUACUGCCUUGCU |
| SEQ ID NO: 100 | hsa-miR-124 | UAAGGCACGCGGUGAAUGCC |
| SEQ ID NO: 101 | hsa-miR-922 | GCAGCAGAGAAUAGGACUACGUC |
| SEQ ID NO: 102 | hsa-miR-454 | UAGUGCAAUAUUGCUUAUAGGGU |
| SEQ ID NO: 103 | hsa-miR-934 | UGUCUACUACUGGAGACACUGG |

Figure 12 cont.

| SEQ ID NO: | miRNA | Sequences 5'→3' |
|---|---|---|
| SEQ ID NO: 104 | hsa-miR-339-5p | UCCCUGUCCUCCAGGAGCUCACG |
| SEQ ID NO: 105 | hsa-miR-450b-5p | UUUUGCAAUAUGUUCCUGAAUA |
| SEQ ID NO: 106 | hsa-miR-616* | ACUCAAAACCCUUCAGUGACUU |
| SEQ ID NO: 107 | hsa-miR-593* | AGGCACCAGCCAGGCAUUGCUCAGC |
| SEQ ID NO: 108 | hsa-miR-320a | AAAAGCUGGGUUGAGAGGGCGA |
| SEQ ID NO: 109 | hsa-miR-379* | UAUGUAACAUGGUCCACUAACU |
| SEQ ID NO: 110 | hsa-miR-1270 | CUGGAGAUAUGGAAGAGCUGUGU |
| SEQ ID NO: 111 | hsa-miR-556-3p | AUAUUACCAUUAGCUCAUCUUU |
| SEQ ID NO: 112 | hsa-miR-17* | ACUGCAGUGAAGGCACUUGUAG |
| SEQ ID NO: 113 | hsa-miR-34b* | UAGGCAGUGUCAUUAGCUGAUUG |
| SEQ ID NO: 114 | hsa-miR-1915* | ACCUUGCCUUGCUGCCCGGGCC |
| SEQ ID NO: 115 | hsa-miR-509-3-5p | UACUGCAGACGUGGCAAUCAUG |
| SEQ ID NO: 116 | hsa-miR-339-3p | UGAGCGCCUCGACGACAGAGCCG |
| SEQ ID NO: 117 | hsa-miR-320d | AAAAGCUGGGUUGAGAGGA |
| SEQ ID NO: 118 | hsa-miR-340* | UCCGUCUCAGUUACUUUAUAGC |
| SEQ ID NO: 119 | hsa-miR-424* | CAAAACGUGAGGCGCUGCUAU |
| SEQ ID NO: 120 | hsa-miR-1204 | UCGUGGCCUGGUCUCCAUUAU |
| SEQ ID NO: 121 | hsa-miR-516a-3p | UGCUUCCUUUCAGAGGGU |
| SEQ ID NO: 122 | hsa-miR-500* | AUGCACCUGGGCAAGGAUUCUG |
| SEQ ID NO: 123 | hsa-miR-146b-3p | UGCCCUGUGGACUCAGUUCUGG |
| SEQ ID NO: 124 | hsa-miR-199a-3p | ACAGUAGUCUGCACAUUGGUUA |
| SEQ ID NO: 125 | hsa-miR-1285 | UCUGGGCAACAAAGUGAGACCU |
| SEQ ID NO: 126 | hsa-miR-371-5p | ACUCAAACUGUGGGGGCACU |
| SEQ ID NO: 127 | hsa-miR-574-3p | CACGCUCAUGCACACACCCACA |
| SEQ ID NO: 128 | hsa-miR-1262 | AUGGGUGAAUUUGUAGAAGGAU |
| SEQ ID NO: 129 | hsa-miR-1537 | AAAACCGUCUAGUUACAGUUGU |
| SEQ ID NO: 130 | hsa-miR-298 | AGCAGAAGCAGGGAGGUUCUCCCA |
| SEQ ID NO: 131 | hsa-miR-582-3p | UAACUGGUUGAACAACUGAACC |
| SEQ ID NO: 132 | hsa-miR-29b-2* | CUGGUUUCACAUGGUGGCUUAG |
| SEQ ID NO: 133 | hsa-miR-548a-3p | CAAAACUGGCAAUUACUUUUGC |
| SEQ ID NO: 134 | hsa-miR-411* | UAUGUAACACGGUCCACUAACC |
| SEQ ID NO: 135 | hsa-miR-7-1* | CAACAAAUCACAGUCUGCCAUA |
| SEQ ID NO: 136 | hsa-miR-520a-3p | AAAGUGCUUCCCUUUGGACUGU |
| SEQ ID NO: 137 | hsa-miR-920 | GGGGAGCUGUGGAAGCAGUA |
| SEQ ID NO: 138 | hsa-miR-122* | AACGCCAUUAUCACACUAAAUA |
| SEQ ID NO: 139 | hsa-miR-615-3p | UCCGAGCCUGGGUCUCCCUCUU |
| SEQ ID NO: 140 | hsa-miR-744 | UGCGGGGCUAGGGCUAACAGCA |
| SEQ ID NO: 141 | hsa-miR-875-5p | UAUACCUCAGUUUUAUCAGGUG |
| SEQ ID NO: 142 | hsa-miR-454* | ACCCUAUCAAUAUUGUCUCUGC |
| SEQ ID NO: 143 | hsa-miR-188-5p | CAUCCCUUGCAUGGUGGAGGG |
| SEQ ID NO: 144 | hsa-miR-22* | AGUUCUUCAGUGGCAAGCUUUA |
| SEQ ID NO: 145 | hsa-miR-125a-5p | UCCCUGAGACCCUUUAACCUGUGA |
| SEQ ID NO: 146 | hsa-let-7f-2* | CUAUACAGUCUACUGUCUUUCC |
| SEQ ID NO: 147 | hsa-miR-483-3p | UCACUCCUCUCCUCCCGUCUU |
| SEQ ID NO: 148 | hsa-miR-1304 | UUUGAGGCUACAGUGAGAUGUG |
| SEQ ID NO: 149 | hsa-miR-545* | UCAGUAAAUGUUUAUUAGAUGA |
| SEQ ID NO: 150 | hsa-miR-1254 | AGCCUGGAAGCUGGAGCCUGCAGU |
| SEQ ID NO: 151 | hsa-miR-92a-1* | AGGUUGGGAUCGGUUGCAAUGCU |
| SEQ ID NO: 152 | hsa-miR-744* | CUGUUGCCACUAACCUCAACCU |
| SEQ ID NO: 153 | hsa-miR-518d-5p | CUCUAGAGGGAAGCACUUUCUG |
| SEQ ID NO: 154 | hsa-miR-26a | UUCAAGUAAUCCAGGAUAGGCU |
| SEQ ID NO: 155 | hsa-miR-484 | UCAGGCUCAGUCCCCUCCCGAU |

Figure 12 cont.

| SEQ ID NO: | miRNA | Sequences 5'---3' |
|---|---|---|
| SEQ ID NO: 156 | hsa-miR-217 | UACUGCAUCAGGAACUGAUUGGA |
| SEQ ID NO: 157 | hsa-miR-566 | GGGCGCCUGUGAUCCCAAC |
| SEQ ID NO: 158 | hsa-miR-515-5p | UUCUCCAAAAGAAAGCACUUUCUG |
| SEQ ID NO: 159 | hsa-miR-126* | CAUUAUUACUUUUGGUACGCG |
| SEQ ID NO: 160 | hsa-miR-200a | UAACACUGUCUGGUAACGAUGU |
| SEQ ID NO: 161 | hsa-miR-302b* | ACUUUAACAUGGAAGUGCUUUC |
| SEQ ID NO: 162 | hsa-miR-142-5p | CAUAAAGUAGAAAGCACUACU |
| SEQ ID NO: 163 | hsa-miR-519e* | UUCUCCAAAAGGGAGCACUUUC |
| SEQ ID NO: 164 | hsa-miR-512-5p | CACUCAGCCUUGAGGGCACUUUC |
| SEQ ID NO: 165 | hsa-miR-101 | UACAGUACUGUGAUAACUGAA |
| SEQ ID NO: 166 | hsa-miR-489 | GUGACAUCACAUAUACGGCAGC |
| SEQ ID NO: 167 | hsa-miR-627 | GUGAGUCUCAAGAAAAGAGGA |
| SEQ ID NO: 168 | hsa-let-7g | UGAGGUAGUAGUUUGUACAGUU |
| SEQ ID NO: 169 | hsa-miR-324-3p | ACUGCCCCAGGUGCUGCUGG |
| SEQ ID NO: 170 | hsa-miR-568 | AUGUAUAAAUGUAUACACAC |
| SEQ ID NO: 171 | hsa-miR-646 | AAGCAGCUGCCUCUGAGGC |
| SEQ ID NO: 172 | hsa-miR-27a | UUCACAGUGGCUAAGUUCCGC |
| SEQ ID NO: 173 | hsa-miR-591 | AGACCAUGGGUUCUCAUUGU |
| SEQ ID NO: 174 | hsa-miR-638 | UGUGCUUGCUCGUCCCGCCCGCA |
| SEQ ID NO: 175 | hsa-miR-126 | UCGUACCGUGAGUAAUAAUGCG |
| SEQ ID NO: 176 | hsa-miR-26b | UUCAAGUAAUUCAGGAUAGGU |
| SEQ ID NO: 177 | hsa-miR-621 | GGCUAGCAACAGCGCUUACCU |
| SEQ ID NO: 178 | hsa-miR-598 | UACGUCAUCGUUGUCAUCGUCA |
| SEQ ID NO: 179 | hsa-miR-603 | CACACACUGCAAUUACUUUUGC |
| SEQ ID NO: 180 | hsa-miR-214 | ACAGCAGGCACAGACAGGCAGU |
| SEQ ID NO: 181 | hsa-miR-145 | GUCCAGUUUUCCCAGGAAUCCCU |
| SEQ ID NO: 182 | hsa-miR-155 | UUAAUGCUAAUCGUGAUAGGGGU |
| SEQ ID NO: 183 | hsa-miR-452* | CUCAUCUGCAAAGAAGUAAGUG |
| SEQ ID NO: 184 | hsa-miR-492 | AGGACCUGCGGGACAAGAUUCUU |
| SEQ ID NO: 185 | hsa-miR-221 | AGCUACAUUGUCUGCUGGGUUUC |
| SEQ ID NO: 186 | hsa-miR-16 | UAGCAGCACGUAAAUAUUGGCG |
| SEQ ID NO: 187 | hsa-miR-222 | AGCUACAUCUGGCUACUGGGU |
| SEQ ID NO: 188 | hsa-miR-302b | UAAGUGCUUCCAUGUUUUAGUAG |
| SEQ ID NO: 189 | hsa-miR-564 | AGGCACGGUGUCAGCAGGC |
| SEQ ID NO: 190 | hsa-let-7d | AGAGGUAGUAGGUUGCAUAGUU |
| SEQ ID NO: 191 | hsa-miR-596 | AAGCCUGCCCGGCUCCUCGGG |
| SEQ ID NO: 192 | hsa-miR-33b | GUGCAUUGCUGUUGCAUUGC |
| SEQ ID NO: 193 | hsa-miR-422a | ACUGGACUUAGGGUCAGAAGGC |
| SEQ ID NO: 194 | hsa-miR-510 | UACUCAGGAGAGUGGCAAUCAC |
| SEQ ID NO: 195 | hsa-miR-142-3p | UGUAGUGUUUCCUACUUUAUGGA |
| SEQ ID NO: 196 | hsa-miR-487b | AAUCGUACAGGGUCAUCCACUU |
| SEQ ID NO: 197 | hsa-miR-153 | UUGCAUAGUCACAAAAGUGAUC |
| SEQ ID NO: 198 | hsa-miR-143 | UGAGAUGAAGCACUGUAGCUC |
| SEQ ID NO: 199 | hsa-miR-497 | CAGCAGCACACUGUGGUUUGU |
| SEQ ID NO: 200 | hsa-miR-554 | GCUAGUCCUGACUCAGCCAGU |
| SEQ ID NO: 201 | hsa-miR-514 | AUUGACACUUCUGUGAGUAGA |
| SEQ ID NO: 202 | hsa-miR-375 | UUUGUUCGUUCGGCUCGCGUGA |
| SEQ ID NO: 203 | hsa-miR-425 | AAUGACACGAUCACUCCCGUUGA |
| SEQ ID NO: 204 | hsa-miR-549 | UGACAACUAUGGAUGAGCUCU |
| SEQ ID NO: 205 | hsa-miR-521 | AACGCACUUCCCUUUAGAGUGU |
| SEQ ID NO: 206 | hsa-miR-600 | ACUUACAGACAAGAGCCUUGCUC |
| SEQ ID NO: 207 | hsa-miR-32 | UAUUGCACAUUACUAAGUUGCA |

Figure 12 cont.

| SEQ ID NO: | miRNA | Sequences 5'—3' |
|---|---|---|
| SEQ ID NO: 208 | hsa-miR-520g | ACAAAGUGCUUCCCUUUAGAGUGU |
| SEQ ID NO: 209 | hsa-miR-183 | UAUGGCACUGGUAGAAUUCACU |
| SEQ ID NO: 210 | hsa-miR-23b | AUCACAUUGCCAGGGAUUACC |
| SEQ ID NO: 211 | hsa-miR-203 | GUGAAAUGUUUAGGACCACUAG |
| SEQ ID NO: 212 | hsa-miR-10a | UACCCUGUAGAUCCGAAUUUGUG |
| SEQ ID NO: 213 | hsa-miR-346 | UGUCUGCCCGCAUGCCUGCCUCU |
| SEQ ID NO: 214 | hsa-miR-200a* | CAUCUUACCGGACAGUGCUGGA |
| SEQ ID NO: 215 | hsa-miR-409-5p | AGGUUACCCGAGCAACUUUGCAU |
| SEQ ID NO: 216 | hsa-miR-658 | GGCGGAGGGAAGUAGGUCGUUGGU |
| SEQ ID NO: 217 | hsa-miR-148b | UCAGUGCAUCACAGAACUUUGU |
| SEQ ID NO: 218 | hsa-miR-363* | CGGGUGGAUCACGAUGCAAUUU |
| SEQ ID NO: 219 | hsa-miR-34a | UGGCAGUGUCUUAGCUGGUUGU |
| SEQ ID NO: 220 | hsa-miR-376a* | GUAGAUUCUCCUUCUAUGAGUA |
| SEQ ID NO: 221 | hsa-miR-609 | AGGGUGUUUCUCUCAUCUCU |
| SEQ ID NO: 222 | hsa-miR-299-3p | UAUGUGGGAUGGUAAACCGCUU |
| SEQ ID NO: 223 | hsa-miR-542-5p | UCGGGGAUCAUCAUGUCACGAGA |
| SEQ ID NO: 224 | hsa-miR-550 | AGUGCCUGAGGGAGUAAGAGCCC |
| SEQ ID NO: 225 | hsa-miR-575 | GAGCCAGUUGGACAGGAGC |
| SEQ ID NO: 226 | hsa-miR-629 | UGGGUUUACGUUGGGAGAACU |
| SEQ ID NO: 227 | hsa-miR-22 | AAGCUGCCAGUUGAAGAACUGU |
| SEQ ID NO: 228 | hsa-miR-149 | UCUGGCUCCGUGUCUUCACUCCC |
| SEQ ID NO: 229 | hsa-miR-520h | ACAAAGUGCUUCCCUUUAGAGU |
| SEQ ID NO: 230 | hsa-miR-451 | AAACCGUUACCAUUACUGAGUU |
| SEQ ID NO: 231 | hsa-miR-93 | CAAAGUGCUGUUCGUGCAGGUAG |
| SEQ ID NO: 232 | hsa-miR-624 | CACAAGGUAUUGGUAUUACCU |
| SEQ ID NO: 233 | hsa-miR-433 | AUCAUGAUGGGCUCCUCGGUGU |
| SEQ ID NO: 234 | hsa-miR-498 | UUUCAAGCCAGGGGGCGUUUUC |
| SEQ ID NO: 235 | hsa-miR-518b | CAAAGCGCUCCCCUUUAGAGGU |
| SEQ ID NO: 236 | hsa-miR-448 | UUGCAUAUGUAGGAUGUCCCAU |
| SEQ ID NO: 237 | hsa-miR-639 | AUCGCUGCGGUUGCGAGCGCUGU |
| SEQ ID NO: 238 | hsa-miR-21 | UAGCUUAUCAGACUGAUGUUGA |
| SEQ ID NO: 239 | hsa-miR-1 | UGGAAUGUAAAGAAGUAUGUAU |
| SEQ ID NO: 240 | hsa-miR-223 | UGUCAGUUUGUCAAAUACCCCA |
| SEQ ID NO: 241 | hsa-miR-30c | UGUAAACAUCCUACACUCUCAGC |
| SEQ ID NO: 242 | hsa-let-7i | UGAGGUAGUAGUUUGUGCUGUU |
| SEQ ID NO: 243 | hsa-miR-151-5p | UCGAGGAGCUCACAGUCUAGU |
| SEQ ID NO: 244 | hsa-miR-874 | CUGCCCUGGCCCGAGGGACCGA |
| SEQ ID NO: 245 | hsa-miR-106a | AAAAGUGCUUACAGUGCAGGUAG |
| SEQ ID NO: 246 | hsa-miR-20a | UAAAGUGCUUAUAGUGCAGGUAG |
| SEQ ID NO: 247 | hsa-miR-148a | UCAGUGCACUACAGAACUUUGU |
| SEQ ID NO: 248 | hsa-let-7b | UGAGGUAGUAGGUUGUGUGGUU |
| SEQ ID NO: 249 | hsa-miR-33b* | CAGUGCCUCGGCAGUGCAGCCC |
| SEQ ID NO: 250 | hsa-miR-374a | UUAUAAUACAACCUGAUAAGUG |
| SEQ ID NO: 251 | hsa-miR-182 | UUUGGCAAUGGUAGAACUCACACU |
| SEQ ID NO: 252 | hsa-miR-497* | CAAACCACACUGUGGUGUUAGA |
| SEQ ID NO: 253 | hsa-miR-345 | GCUGACUCCUAGUCCAGGGCUC |
| SEQ ID NO: 254 | hsa-miR-323-3p | CACAUUACACGGUCGACCUCU |
| SEQ ID NO: 255 | hsa-miR-193a-3p | AACUGGCCUACAAAGUCCCAGU |
| SEQ ID NO: 256 | hsa-miR-134 | UGUGACUGGUUGACCAGAGGGG |
| SEQ ID NO: 257 | hsa-miR-663b | GGUGGCCCGGCCGUGCCUGAGG |
| SEQ ID NO: 258 | hsa-miR-499-3p | AACAUCACAGCAAGUCUGUGCU |
| SEQ ID NO: 259 | hsa-miR-631 | AGACCUGGCCCAGACCUCAGC |

Figure 12 cont.

| SEQ ID NO: | miRNA | Sequences 5'---3' |
|---|---|---|
| SEQ ID NO: 260 | hsa-miR-544 | AUUCUGCAUUUUUAGCAAGUUC |
| SEQ ID NO: 261 | hsa-miR-200b* | CAUCUUACUGGGCAGCAUUGGA |
| SEQ ID NO: 262 | hsa-miR-326 | CCUCUGGGCCCUUCCUCCAG |
| SEQ ID NO: 263 | hsa-miR-409-3p | GAAUGUUGCUCGGUGAACCCCU |
| SEQ ID NO: 264 | hsa-miR-513a-5p | UUCACAGGGAGGUGUCAU |
| SEQ ID NO: 265 | hsa-miR-129-5p | CUUUUUGCGGUCUGGGCUUGC |
| SEQ ID NO: 266 | hsa-miR-615-5p | GGGGGUCCCCGGUGCUCGGAUC |
| SEQ ID NO: 267 | hsa-miR-193b | AACUGGCCCUCAAAGUCCCGCU |
| SEQ ID NO: 268 | hsa-miR-877* | UCCUCUUCUCCCUCCUCCCAG |
| SEQ ID NO: 269 | hsa-miR-105 | UCAAAUGCUCAGACUCCUGUGGU |
| SEQ ID NO: 270 | hsa-miR-296-3p | GAGGGUUGGGUGGAGGCUCUCC |
| SEQ ID NO: 271 | hsa-miR-27a* | AGGGCUUAGCUGCUUGUGAGCA |
| SEQ ID NO: 272 | hsa-miR-99b* | CAAGCUCGUGUCUGUGGGUCCG |
| SEQ ID NO: 273 | hsa-miR-194* | CCAGUGGGGCUGCUGUUAUCUG |
| SEQ ID NO: 274 | hsa-miR-653 | GUGUUGAAACAAUCUCUACUG |
| SEQ ID NO: 275 | hsa-miR-608 | AGGGGUGGUGUUGGGACAGCUCCGU |
| SEQ ID NO: 276 | hsa-miR-337-5p | GAACGGCUUCAUACAGGAGUU |
| SEQ ID NO: 277 | hsa-miR-1207-3p | UCAGCUGGCCCUCAUUUC |
| SEQ ID NO: 278 | hsa-miR-579 | UUCAUUUGGUAUAAACCGCGAUU |
| SEQ ID NO: 279 | hsa-miR-323-5p | AGGUGGUCCGUGGCGCGUUCGC |
| SEQ ID NO: 280 | hsa-miR-634 | AACCAGCACCCCAACUUUGGAC |
| SEQ ID NO: 281 | hsa-miR-144* | GGAUAUCAUCAUAUACUGUAAG |
| SEQ ID NO: 282 | hsa-miR-519d | CAAAGUGCCUCCCUUUAGAGUG |
| SEQ ID NO: 283 | hsa-miR-191* | GCUGCGCUUGGAUUUCGUCCCC |

Figure 12 cont.

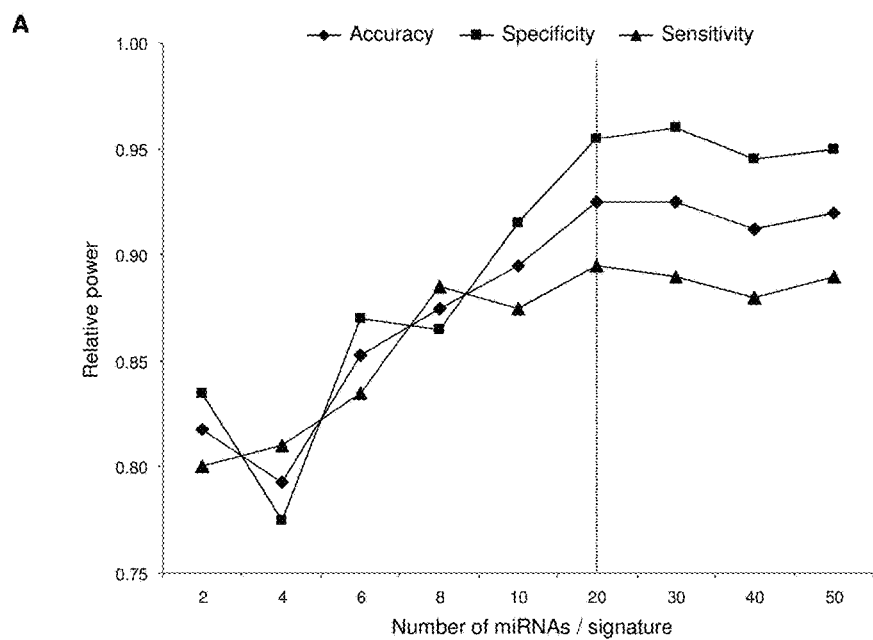
Figure 27A
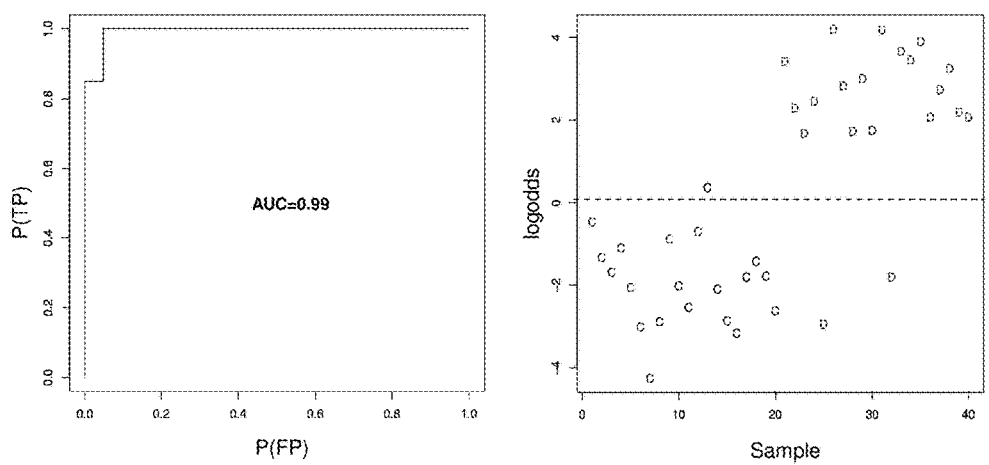
Figure 27B
Figure 27C

| Set No. | SEQ-ID NO: | miRNAs | Acc | Spec | Sens |
|---|---|---|---|---|---|
| 1 | SEQ ID NO: 162, 16 | hsa-miR-142-5p, hsa-miR-455-3p | 97.5% | 100.0% | 95.0% |
| 2 | SEQ ID NO: 150, 174 | hsa-miR-1254, hsa-miR-636 | 96.8% | 99.2% | 93.4% |
| 3 | SEQ ID NO: 243, 244 | hsa-miR-151-5p, hsa-miR-874 | 94.8% | 89.6% | 100.0% |
| 4 | SEQ ID NO: 243, 123 | hsa-miR-151-5p, hsa-miR-146b-3p | 94.6% | 89.2% | 100.0% |
| 5 | SEQ ID NO: 24, 243 | hsa-miR-330-3p, hsa-miR-151-5p | 94.4% | 94.2% | 94.6% |
| 6 | SEQ ID NO: 243, 16 | hsa-miR-151-5p, hsa-miR-455-3p | 94.3% | 89.8% | 98.8% |
| 7 | SEQ ID NO: 234, 52 | hsa-miR-493, hsa-miR-802 | 93.4% | 90.8% | 96.0% |
| 8 | SEQ ID NO: 62, 52 | hsa-miR-1281, hsa-miR-802 | 92.9% | 100.0% | 85.8% |
| 9 | SEQ ID NO: 234, 62 | hsa-miR-493, hsa-miR-1281 | 92.6% | 91.0% | 94.2% |
| 10 | SEQ ID NO: 137, 162 | hsa-miR-920, hsa-miR-142-5p | 92.6% | 95.0% | 90.2% |
| 11 | SEQ ID NO: 137, 243 | hsa-miR-920, hsa-miR-151-5p | 92.5% | 94.8% | 90.2% |
| 12 | SEQ ID NO: 52, 62 | hsa-miR-802, hsa-miR-1281 | 92.4% | 99.2% | 85.6% |
| 13 | SEQ ID NO: 162, 252 | hsa-miR-142-5p, hsa-miR-497* | 92.3% | 90.6% | 94.0% |
| 14 | SEQ ID NO: 243, 231 | hsa-miR-151-5p, hsa-miR-93 | 92.3% | 93.0% | 91.6% |
| 15 | SEQ ID NO: 62, 253 | hsa-miR-1281, hsa-miR-345 | 92.2% | 94.4% | 90.0% |
| 16 | SEQ ID NO: 15, 243 | hsa-miR-892b, hsa-miR-151-5p | 92.0% | 95.2% | 88.8% |
| 17 | SEQ ID NO: 197, 137 | hsa-miR-566, hsa-miR-920 | 92.0% | 94.8% | 89.2% |
| 18 | SEQ ID NO: 243, 19 | hsa-miR-151-5p, hsa-miR-767-5p | 92.0% | 90.8% | 93.2% |
| 19 | SEQ ID NO: 162, 24 | hsa-miR-142-5p, hsa-miR-330-3p | 91.9% | 89.3% | 94.6% |
| 20 | SEQ ID NO: 62, 150 | hsa-miR-1281, hsa-miR-1254 | 91.7% | 98.6% | 84.8% |
| 21 | SEQ ID NO: 184, 162 | hsa-miR-492, hsa-miR-142-5p | 91.7% | 94.8% | 88.8% |
| 22 | SEQ ID NO: 52, 68 | hsa-miR-802, hsa-miR-23b* | 91.6% | 98.0% | 85.2% |
| 23 | SEQ ID NO: 68, 52 | hsa-miR-23b*, hsa-miR-802 | 91.5% | 98.0% | 85.0% |
| 24 | SEQ ID NO: 162, 184 | hsa-miR-142-5p, hsa-miR-492 | 91.4% | 94.0% | 88.8% |
| 25 | SEQ ID NO: 151, 257 | hsa-miR-1254, hsa-miR-663b | 91.4% | 95.0% | 87.8% |
| 26 | SEQ ID NO: 234, 68 | hsa-miR-493, hsa-miR-23b* | 91.3% | 90.2% | 92.4% |
| 27 | SEQ ID NO: 15, 32 | hsa-miR-892b, hsa-miR-23b* | 91.1% | 94.2% | 88.0% |
| 28 | SEQ ID NO: 137, 52 | hsa-miR-920, hsa-miR-802 | 91.1% | 97.0% | 85.2% |
| 29 | SEQ ID NO: 162, 70 | hsa-miR-142-5p, hsa-miR-1250 | 91.0% | 94.0% | 88.0% |
| 30 | SEQ ID NO: 243, 62 | hsa-miR-151-5p, hsa-miR-1281 | 90.9% | 94.8% | 87.0% |
| 31 | SEQ ID NO: 52, 184 | hsa-miR-802, hsa-miR-492 | 90.7% | 99.2% | 82.2% |
| 32 | SEQ ID NO: 162, 62 | hsa-miR-142-5p, hsa-miR-1281 | 90.6% | 95.0% | 86.2% |
| 33 | SEQ ID NO: 62, 243 | hsa-miR-1281, hsa-miR-151-5p | 90.6% | 94.6% | 86.6% |
| 34 | SEQ ID NO: 184, 52 | hsa-miR-492, hsa-miR-802 | 90.5% | 100.0% | 81.0% |
| 35 | SEQ ID NO: 257, 162 | hsa-miR-663b, hsa-miR-142-5p | 90.3% | 90.8% | 89.8% |
| 36 | SEQ ID NO: 68, 137 | hsa-miR-23b*, hsa-miR-920 | 90.3% | 99.3% | 80.3% |
| 37 | SEQ ID NO: 234, 252 | hsa-miR-493, hsa-miR-497* | 90.2% | 90.0% | 90.4% |
| 38 | SEQ ID NO: 252, 184 | hsa-miR-497*, hsa-miR-492 | 90.2% | 96.0% | 84.4% |
| 39 | SEQ ID NO: 197, 184 | hsa-miR-566, hsa-miR-492 | 90.2% | 99.8% | 80.8% |
| 40 | SEQ ID NO: 52, 137 | hsa-miR-802, hsa-miR-920 | 90.2% | 95.8% | 84.6% |
| 41 | SEQ ID NO: 52, 16 | hsa-miR-802, hsa-miR-455-3p | 90.0% | 97.2% | 82.8% |
| 42 | SEQ ID NO: 257, 234 | hsa-miR-663b, hsa-miR-493 | 90.0% | 85.0% | 95.0% |
| 43 | SEQ ID NO: 62, 95 | hsa-miR-1281, hsa-miR-135b* | 89.8% | 95.6% | 84.0% |
| 44 | SEQ ID NO: 62, 123 | hsa-miR-1281, hsa-miR-146b-3p | 89.7% | 98.4% | 81.0% |
| 45 | SEQ ID NO: 234, 184 | hsa-miR-493, hsa-miR-492 | 89.6% | 85.2% | 94.0% |
| 46 | SEQ ID NO: 253, 123 | hsa-miR-345, hsa-miR-146b-3p | 89.6% | 94.2% | 85.0% |
| 47 | SEQ ID NO: 123, 156 | hsa-miR-146b-3p, hsa-miR-217 | 89.5% | 99.4% | 79.6% |
| 48 | SEQ ID NO: 257, 197 | hsa-miR-663b, hsa-miR-566 | 89.4% | 95.0% | 83.8% |
| 49 | SEQ ID NO: 243, 70 | hsa-miR-151-5p, hsa-miR-1250 | 89.3% | 80.4% | 98.2% |
| 50 | SEQ ID NO: 162, 197 | hsa-miR-142-5p, hsa-miR-566 | 89.2% | 93.8% | 84.8% |
| 51 | SEQ ID NO: 31, 252 | hsa-miR-380*, hsa-miR-497* | 89.2% | 89.6% | 88.8% |
| 52 | SEQ ID NO: 197, 162 | hsa-miR-566, hsa-miR-142-5p | 89.1% | 93.2% | 85.0% |
| 53 | SEQ ID NO: 95, 197 | hsa-miR-135b*, hsa-miR-566 | 89.0% | 99.6% | 78.4% |

Figure 28

| Set No. | SEQ-ID NO: | miRNAs | Acc | Spec | Sens |
|---|---|---|---|---|---|
| 54 | SEQ ID NO: 68, 252 | hsa-miR-23b*, hsa-miR-497* | 89.0% | 93.2% | 79.8% |
| 55 | SEQ ID NO: 135, 19 | hsa-miR-7-1*, hsa-miR-767-5p | 88.3% | 83.4% | 94.2% |
| 56 | SEQ ID NO: 244, 254 | hsa-miR-874, hsa-miR-323-3p | 88.6% | 81.6% | 95.6% |
| 57 | SEQ ID NO: 158, 157 | hsa-miR-1254, hsa-miR-566 | 88.5% | 92.8% | 84.2% |
| 58 | SEQ ID NO: 162, 265 | hsa-miR-142-5p, hsa-miR-129-3p | 88.4% | 89.2% | 87.6% |
| 59 | SEQ ID NO: 15, 62 | hsa-miR-892b, hsa-miR-1281 | 88.3% | 96.4% | 80.0% |
| 60 | SEQ ID NO: 68, 16 | hsa-miR-23b*, hsa-miR-455-3p | 88.1% | 96.4% | 79.8% |
| 61 | SEQ ID NO: 62, 16 | hsa-miR-1281, hsa-miR-455-3p | 88.0% | 95.0% | 81.0% |
| 62 | SEQ ID NO: 158, 253 | hsa-miR-1254, hsa-miR-345 | 87.9% | 89.8% | 86.0% |
| 63 | SEQ ID NO: 162, 135 | hsa-miR-142-5p, hsa-miR-7-1* | 87.8% | 88.2% | 87.6% |
| 64 | SEQ ID NO: 266, 24 | hsa-miR-615-5p, hsa-miR-330-3p | 87.9% | 95.8% | 80.0% |
| 65 | SEQ ID NO: 95, 269 | hsa-miR-135b*, hsa-miR-105 | 87.8% | 90.0% | 85.3% |
| 66 | SEQ ID NO: 184, 70 | hsa-miR-492, hsa-miR-1250 | 87.8% | 90.2% | 85.4% |
| 67 | SEQ ID NO: 162, 234 | hsa-miR-142-5p, hsa-miR-498 | 87.7% | 85.4% | 90.0% |
| 68 | SEQ ID NO: 253, 31 | hsa-miR-345, hsa-miR-139-5p | 87.7% | 90.4% | 85.0% |
| 69 | SEQ ID NO: 252, 52 | hsa-miR-497*, hsa-miR-802 | 87.5% | 100.0% | 75.0% |
| 70 | SEQ ID NO: 269, 135 | hsa-miR-105, hsa-miR-7-1* | 87.5% | 95.0% | 80.0% |
| 71 | SEQ ID NO: 52, 157 | hsa-miR-802, hsa-miR-566 | 87.5% | 100.0% | 75.0% |
| 72 | SEQ ID NO: 70, 266 | hsa-miR-1250, hsa-miR-615-5p | 87.5% | 94.6% | 80.4% |
| 73 | SEQ ID NO: 252, 15 | hsa-miR-497*, hsa-miR-892b | 87.4% | 99.6% | 75.2% |
| 74 | SEQ ID NO: 265, 257 | hsa-miR-129-3p, hsa-miR-663b | 87.4% | 86.4% | 88.4% |
| 75 | SEQ ID NO: 116, 62 | hsa-miR-339-3p, hsa-miR-1281 | 87.1% | 93.2% | 81.0% |
| 76 | SEQ ID NO: 68, 157 | hsa-miR-23b*, hsa-miR-566 | 87.0% | 95.2% | 78.8% |
| 77 | SEQ ID NO: 157, 234 | hsa-miR-566, hsa-miR-498 | 86.9% | 83.6% | 90.2% |
| 78 | SEQ ID NO: 232, 71 | hsa-miR-624, hsa-miR-30e | 86.9% | 94.4% | 79.4% |
| 79 | SEQ ID NO: 15, 95 | hsa-miR-892b, hsa-miR-135b* | 86.8% | 99.8% | 73.8% |
| 80 | SEQ ID NO: 52, 15 | hsa-miR-802, hsa-miR-892b | 86.7% | 100.0% | 73.4% |
| 81 | SEQ ID NO: 157, 68 | hsa-miR-566, hsa-miR-23b* | 86.7% | 95.0% | 78.4% |
| 82 | SEQ ID NO: 257, 95 | hsa-miR-663b, hsa-miR-135b* | 86.5% | 88.8% | 84.2% |
| 83 | SEQ ID NO: 184, 243 | hsa-miR-492, hsa-miR-151-5p | 86.4% | 87.4% | 85.4% |
| 84 | SEQ ID NO: 16, 253 | hsa-miR-455-3p, hsa-miR-345 | 86.3% | 87.0% | 85.6% |
| 85 | SEQ ID NO: 234, 157 | hsa-miR-498, hsa-miR-566 | 86.3% | 82.6% | 90.0% |
| 86 | SEQ ID NO: 62, 184 | hsa-miR-1281, hsa-miR-492 | 86.1% | 91.8% | 80.4% |
| 87 | SEQ ID NO: 157, 253 | hsa-miR-566, hsa-miR-345 | 86.1% | 89.6% | 82.6% |
| 88 | SEQ ID NO: 253, 174 | hsa-miR-345, hsa-miR-636 | 86.1% | 84.4% | 87.8% |
| 89 | SEQ ID NO: 162, 71 | hsa-miR-142-5p, hsa-miR-30e | 86.0% | 93.4% | 78.8% |
| 90 | SEQ ID NO: 162, 266 | hsa-miR-142-5p, hsa-miR-615-5p | 85.7% | 79.2% | 92.2% |
| 91 | SEQ ID NO: 123, 269 | hsa-miR-146b-3p, hsa-miR-105 | 85.7% | 90.4% | 81.0% |
| 92 | SEQ ID NO: 157, 15 | hsa-miR-566, hsa-miR-892b | 85.6% | 91.4% | 79.8% |
| 93 | SEQ ID NO: 167, 243 | hsa-miR-627, hsa-miR-151-5p | 85.6% | 83.2% | 88.0% |
| 94 | SEQ ID NO: 184, 16 | hsa-miR-492, hsa-miR-455-3p | 85.6% | 87.0% | 84.2% |
| 95 | SEQ ID NO: 253, 15 | hsa-miR-345, hsa-miR-892b | 85.5% | 90.8% | 80.2% |
| 96 | SEQ ID NO: 137, 70 | hsa-miR-920, hsa-miR-1250 | 85.5% | 85.6% | 85.4% |
| 97 | SEQ ID NO: 70, 137 | hsa-miR-1250, hsa-miR-920 | 85.4% | 85.4% | 85.4% |
| 98 | SEQ ID NO: 252, 62 | hsa-miR-497*, hsa-miR-1281 | 85.3% | 90.6% | 80.0% |
| 99 | SEQ ID NO: 137, 15 | hsa-miR-920, hsa-miR-892b | 85.3% | 95.0% | 75.6% |
| 100 | SEQ ID NO: 234, 16 | hsa-miR-498, hsa-miR-455-3p | 85.3% | 90.0% | 80.6% |
| 101 | SEQ ID NO: 24, 269 | hsa-miR-330-3p, hsa-miR-105 | 85.2% | 86.6% | 83.8% |
| 102 | SEQ ID NO: 184, 266 | hsa-miR-492, hsa-miR-615-5p | 85.2% | 92.8% | 77.6% |
| 103 | SEQ ID NO: 16, 32 | hsa-miR-455-3p, hsa-miR-380* | 85.1% | 79.4% | 90.8% |
| 104 | SEQ ID NO: 255, 24 | hsa-miR-193a-3p, hsa-miR-330-3p | 85.1% | 90.2% | 80.0% |
| 105 | SEQ ID NO: 156, 24 | hsa-miR-217, hsa-miR-330-3p | 84.9% | 89.8% | 80.0% |
| 106 | SEQ ID NO: 24, 32 | hsa-miR-330-3p, hsa-miR-208b* | 84.9% | 89.6% | 80.2% |
| 107 | SEQ ID NO: 137, 184 | hsa-miR-920, hsa-miR-492 | 84.9% | 95.2% | 74.6% |

Figure 28 cont.

| Set No. | SEQ ID NO: | miRNAs | Acc | Spec | Sens |
|---|---|---|---|---|---|
| 108 | SEQ ID NO: 243, 85 | hsa-miR-151-5p, hsa-miR-135b* | 84.8% | 75.2% | 94.4% |
| 109 | SEQ ID NO: 174, 254 | hsa-miR-636, hsa-miR-323-3p | 84.7% | 75.4% | 94.0% |
| 110 | SEQ ID NO: 254, 255 | hsa-miR-323-3p, hsa-miR-193a-3p | 84.7% | 85.0% | 84.4% |
| 111 | SEQ ID NO: 71, 35 | hsa-miR-30e, hsa-miR-183-3p | 84.7% | 89.4% | 80.0% |
| 112 | SEQ ID NO: 22, 32 | hsa-miR-20b*, hsa-miR-380* | 84.7% | 84.0% | 85.4% |
| 113 | SEQ ID NO: 15, 174 | hsa-miR-892b, hsa-miR-636 | 84.6% | 89.8% | 79.4% |
| 114 | SEQ ID NO: 273, 252 | hsa-miR-194*, hsa-miR-497* | 84.5% | 89.4% | 89.6% |
| 115 | SEQ ID NO: 242, 244 | hsa-let-7i, hsa-miR-874 | 84.4% | 78.6% | 90.2% |
| 116 | SEQ ID NO: 123, 265 | hsa-miR-146b-3p, hsa-miR-129-5p | 84.4% | 83.8% | 85.0% |
| 117 | SEQ ID NO: 184, 68 | hsa-miR-492, hsa-miR-23b* | 84.3% | 89.8% | 78.8% |
| 118 | SEQ ID NO: 35, 242 | hsa-miR-183-3p, hsa-let-7i | 84.3% | 79.0% | 89.6% |
| 119 | SEQ ID NO: 243, 68 | hsa-miR-151-5p, hsa-miR-23b* | 84.2% | 84.0% | 84.4% |
| 120 | SEQ ID NO: 19, 32 | hsa-miR-767-5p, hsa-miR-380* | 84.2% | 79.2% | 89.2% |
| 121 | SEQ ID NO: 22, 232 | hsa-miR-20b*, hsa-miR-624 | 84.1% | 85.0% | 83.2% |
| 122 | SEQ ID NO: 35, 243 | hsa-miR-135b*, hsa-miR-151-5p | 84.0% | 74.0% | 94.0% |
| 123 | SEQ ID NO: 32, 273 | hsa-miR-380*, hsa-miR-194* | 83.9% | 87.6% | 80.2% |
| 124 | SEQ ID NO: 68, 32 | hsa-miR-23b*, hsa-miR-380* | 83.9% | 88.0% | 79.8% |
| 125 | SEQ ID NO: 265, 24 | hsa-miR-129-5p, hsa-miR-330-3p | 83.7% | 78.4% | 89.0% |
| 126 | SEQ ID NO: 156, 22 | hsa-miR-217, hsa-miR-20b* | 83.7% | 79.0% | 88.4% |
| 127 | SEQ ID NO: 217, 62 | hsa-miR-143b, hsa-miR-1281 | 83.6% | 84.6% | 82.6% |
| 128 | SEQ ID NO: 15, 156 | hsa-miR-892b, hsa-miR-217 | 83.6% | 88.8% | 78.4% |
| 129 | SEQ ID NO: 123, 174 | hsa-miR-146b-3p, hsa-miR-636 | 83.5% | 92.2% | 74.8% |
| 130 | SEQ ID NO: 68, 70 | hsa-miR-23b*, hsa-miR-1250 | 83.3% | 86.4% | 80.2% |
| 131 | SEQ ID NO: 266, 231 | hsa-miR-615-5p, hsa-miR-93 | 83.3% | 85.0% | 81.6% |
| 132 | SEQ ID NO: 157, 31 | hsa-miR-566, hsa-miR-139-5p | 83.2% | 94.2% | 72.2% |
| 133 | SEQ ID NO: 70, 32 | hsa-miR-1250, hsa-miR-380* | 83.0% | 82.0% | 84.0% |
| 134 | SEQ ID NO: 243, 259 | hsa-miR-151-3p, hsa-miR-631 | 83.0% | 81.4% | 84.6% |
| 135 | SEQ ID NO: 31, 18 | hsa-miR-139-5p, hsa-miR-455-3p | 83.0% | 87.8% | 78.2% |
| 136 | SEQ ID NO: 32, 159 | hsa-miR-380*, hsa-miR-1254 | 82.9% | 80.4% | 85.4% |
| 137 | SEQ ID NO: 71, 255 | hsa-miR-30e, hsa-miR-193a-3p | 82.9% | 79.4% | 86.4% |
| 138 | SEQ ID NO: 70, 52 | hsa-miR-1250, hsa-miR-802 | 82.9% | 90.4% | 75.4% |
| 139 | SEQ ID NO: 135, 85 | hsa-miR-7-1*, hsa-miR-140-5p | 82.8% | 81.2% | 84.4% |
| 140 | SEQ ID NO: 252, 137 | hsa-miR-497*, hsa-miR-900 | 82.7% | 93.6% | 71.8% |
| 141 | SEQ ID NO: 135, 255 | hsa-miR-7-1*, hsa-miR-193a-3p | 82.6% | 80.6% | 84.6% |
| 142 | SEQ ID NO: 70, 252 | hsa-miR-1250, hsa-miR-497* | 82.6% | 91.8% | 73.4% |
| 143 | SEQ ID NO: 231, 32 | hsa-miR-93, hsa-miR-380* | 82.5% | 80.0% | 85.0% |
| 144 | SEQ ID NO: 269, 22 | hsa-miR-105, hsa-miR-20b* | 82.5% | 80.8% | 84.2% |
| 145 | SEQ ID NO: 18, 159 | hsa-miR-455-3p, hsa-miR-1254 | 82.4% | 78.2% | 86.6% |
| 146 | SEQ ID NO: 123, 159 | hsa-miR-146b-3p, hsa-miR-1254 | 82.4% | 89.8% | 75.0% |
| 147 | SEQ ID NO: 259, 157 | hsa-miR-631, hsa-miR-566 | 82.3% | 91.0% | 73.6% |
| 148 | SEQ ID NO: 15, 123 | hsa-miR-892b, hsa-miR-146b-3p | 82.2% | 94.4% | 70.0% |
| 149 | SEQ ID NO: 31, 30 | hsa-miR-139-5p, hsa-miR-330* | 82.2% | 83.8% | 80.6% |
| 150 | SEQ ID NO: 259, 231 | hsa-miR-631, hsa-miR-93 | 82.1% | 76.8% | 87.4% |
| 151 | SEQ ID NO: 252, 24 | hsa-miR-497*, hsa-miR-330-3p | 82.1% | 89.2% | 75.0% |
| 152 | SEQ ID NO: 24, 242 | hsa-miR-330-3p, hsa-let-7i | 82.0% | 74.0% | 90.0% |
| 153 | SEQ ID NO: 116, 252 | hsa-miR-339-3p, hsa-miR-497* | 82.0% | 88.6% | 75.4% |
| 154 | SEQ ID NO: 243, 159 | hsa-miR-151-5p, hsa-miR-1285 | 82.0% | 74.8% | 89.2% |
| 155 | SEQ ID NO: 252, 159 | hsa-miR-497*, hsa-miR-1254 | 82.0% | 84.4% | 79.6% |
| 156 | SEQ ID NO: 237, 15 | hsa-miR-663b, hsa-miR-892b | 82.0% | 88.8% | 75.2% |
| 157 | SEQ ID NO: 123, 244 | hsa-miR-146b-3p, hsa-miR-874 | 81.9% | 79.2% | 84.6% |
| 158 | SEQ ID NO: 259, 159 | hsa-miR-631, hsa-miR-1285 | 81.9% | 90.2% | 73.6% |
| 159 | SEQ ID NO: 18, 70 | hsa-miR-455-3p, hsa-miR-1250 | 81.7% | 79.8% | 83.6% |
| 160 | SEQ ID NO: 259, 85 | hsa-miR-631, hsa-miR-135b* | 81.7% | 83.4% | 80.0% |
| 161 | SEQ ID NO: 71, 24 | hsa-miR-30e, hsa-miR-330-3p | 81.7% | 77.4% | 86.0% |

Figure 28 cont.

| Set No. | SEQ-ID NO: | miRNAs | Acc | Spec | Sens |
|---|---|---|---|---|---|
| 162 | SEQ ID NO: 150, 123 | hsa-miR-1254, hsa-miR-146b-3p | 81.6% | 88.2% | 75.0% |
| 163 | SEQ ID NO: 22, 269 | hsa-miR-20b*, hsa-miR-105 | 81.5% | 80.2% | 82.8% |
| 164 | SEQ ID NO: 16, 174 | hsa-miR-455-3p, hsa-miR-636 | 81.3% | 75.8% | 86.8% |
| 165 | SEQ ID NO: 95, 156 | hsa-miR-135b*, hsa-miR-217 | 81.2% | 84.2% | 78.2% |
| 166 | SEQ ID NO: 246, 181 | hsa-miR-20a, hsa-miR-143 | 81.0% | 82.0% | 80.0% |
| 167 | SEQ ID NO: 243, 22 | hsa-miR-151-5p, hsa-miR-20b* | 81.0% | 69.0% | 93.0% |
| 168 | SEQ ID NO: 135, 35 | hsa-miR-7-1*, hsa-miR-188-3p | 80.9% | 79.0% | 82.8% |
| 169 | SEQ ID NO: 150, 135 | hsa-miR-1254, hsa-miR-7-1* | 80.8% | 78.3% | 83.3% |
| 170 | SEQ ID NO: 269, 243 | hsa-miR-105, hsa-miR-151-5p | 80.8% | 85.6% | 76.0% |
| 171 | SEQ ID NO: 88, 169 | hsa-miR-1295, hsa-miR-324-3p | 80.6% | 82.4% | 78.8% |
| 172 | SEQ ID NO: 150, 19 | hsa-miR-1254, hsa-miR-892b | 80.6% | 82.8% | 78.4% |
| 173 | SEQ ID NO: 31, 123 | hsa-miR-139-5p, hsa-miR-146b-3p | 80.3% | 92.2% | 68.4% |
| 174 | SEQ ID NO: 217, 252 | hsa-miR-148b, hsa-miR-497* | 80.2% | 84.8% | 75.6% |
| 175 | SEQ ID NO: 88, 245 | hsa-miR-1295, hsa-miR-106a | 80.2% | 81.8% | 78.6% |
| 176 | SEQ ID NO: 266, 257 | hsa-miR-615-5p, hsa-miR-663b | 80.2% | 76.2% | 84.2% |
| 177 | SEQ ID NO: 269, 232 | hsa-miR-105, hsa-miR-624 | 79.9% | 83.8% | 76.0% |
| 178 | SEQ ID NO: 265, 150 | hsa-miR-129-5p, hsa-miR-1254 | 79.9% | 82.4% | 77.4% |
| 179 | SEQ ID NO: 156, 269 | hsa-miR-217, hsa-miR-105 | 79.9% | 89.8% | 70.0% |
| 180 | SEQ ID NO: 22, 174 | hsa-miR-20b*, hsa-miR-636 | 79.8% | 81.0% | 78.6% |
| 181 | SEQ ID NO: 70, 265 | hsa-miR-1250, hsa-miR-129-5p | 79.8% | 79.6% | 80.0% |
| 182 | SEQ ID NO: 32, 23 | hsa-miR-380*, hsa-miR-491-3p | 79.8% | 75.0% | 84.6% |
| 183 | SEQ ID NO: 22, 19 | hsa-miR-20b*, hsa-miR-767-5p | 79.7% | 88.2% | 71.2% |
| 184 | SEQ ID NO: 283, 71 | hsa-miR-345, hsa-miR-30e | 79.6% | 79.2% | 80.0% |
| 185 | SEQ ID NO: 244, 125 | hsa-miR-874, hsa-miR-1285 | 79.5% | 84.6% | 74.4% |
| 186 | SEQ ID NO: 70, 259 | hsa-miR-1250, hsa-miR-631 | 79.4% | 79.4% | 79.4% |
| 187 | SEQ ID NO: 174, 135 | hsa-miR-636, hsa-miR-7-1* | 79.4% | 81.6% | 77.2% |
| 188 | SEQ ID NO: 135, 24 | hsa-miR-7-1*, hsa-miR-330-3p | 79.4% | 78.2% | 80.6% |
| 189 | SEQ ID NO: 283, 135 | hsa-miR-345, hsa-miR-7-1* | 79.4% | 88.8% | 70.0% |
| 190 | SEQ ID NO: 30, 259 | hsa-miR-380*, hsa-miR-631 | 79.3% | 78.0% | 80.6% |
| 191 | SEQ ID NO: 123, 22 | hsa-miR-146b-3p, hsa-miR-20b* | 79.2% | 78.0% | 80.4% |
| 192 | SEQ ID NO: 150, 265 | hsa-miR-1254, hsa-miR-129-5p | 79.2% | 82.2% | 76.2% |
| 193 | SEQ ID NO: 135, 31 | hsa-miR-7-1*, hsa-miR-139-5p | 79.2% | 81.6% | 76.8% |
| 194 | SEQ ID NO: 16, 252 | hsa-miR-455-3p, hsa-miR-497* | 79.1% | 82.6% | 75.6% |
| 195 | SEQ ID NO: 254, 85 | hsa-miR-323-3p, hsa-miR-140-5p | 78.9% | 83.6% | 94.2% |
| 196 | SEQ ID NO: 174, 71 | hsa-miR-636, hsa-miR-30e | 78.9% | 80.2% | 77.6% |
| 197 | SEQ ID NO: 242, 259 | hsa-let-7i, hsa-miR-631 | 78.9% | 75.0% | 82.8% |
| 198 | SEQ ID NO: 24, 231 | hsa-miR-330-3p, hsa-miR-93 | 78.9% | 76.4% | 81.4% |
| 199 | SEQ ID NO: 27, 252 | hsa-miR-423-5p, hsa-miR-497* | 78.8% | 81.8% | 85.8% |
| 200 | SEQ ID NO: 242, 243 | hsa-let-7i, hsa-miR-151-5p | 78.7% | 87.4% | 70.0% |
| 201 | SEQ ID NO: 22, 244 | hsa-miR-20b*, hsa-miR-874 | 78.6% | 77.0% | 80.2% |
| 202 | SEQ ID NO: 135, 16 | hsa-miR-7-1*, hsa-miR-455-3p | 78.6% | 73.2% | 84.0% |
| 203 | SEQ ID NO: 95, 283 | hsa-miR-135b*, hsa-miR-345 | 78.5% | 76.8% | 80.2% |
| 204 | SEQ ID NO: 252, 16 | hsa-miR-497*, hsa-miR-455-3p | 78.5% | 82.0% | 75.0% |
| 205 | SEQ ID NO: 250, 217 | hsa-miR-374a, hsa-miR-148b | 78.5% | 77.4% | 79.6% |
| 206 | SEQ ID NO: 31, 19 | hsa-miR-139-5p, hsa-miR-892b | 78.4% | 88.8% | 68.0% |
| 207 | SEQ ID NO: 244, 231 | hsa-miR-874, hsa-miR-93 | 78.4% | 78.4% | 78.4% |
| 208 | SEQ ID NO: 123, 95 | hsa-miR-146b-3p, hsa-miR-135b* | 78.4% | 82.4% | 74.4% |
| 209 | SEQ ID NO: 71, 85 | hsa-miR-30e, hsa-miR-140-5p | 78.3% | 75.4% | 81.2% |
| 210 | SEQ ID NO: 253, 35 | hsa-miR-193a-3p, hsa-miR-188-3p | 78.3% | 91.6% | 65.0% |
| 211 | SEQ ID NO: 156, 266 | hsa-miR-217, hsa-miR-615-3p | 78.3% | 76.0% | 80.6% |
| 212 | SEQ ID NO: 71, 243 | hsa-miR-30e, hsa-miR-151-5p | 78.2% | 77.4% | 79.0% |
| 213 | SEQ ID NO: 95, 150 | hsa-miR-135b*, hsa-miR-1254 | 78.2% | 74.0% | 82.4% |
| 214 | SEQ ID NO: 231, 22 | hsa-miR-93, hsa-miR-20b* | 78.2% | 86.4% | 70.0% |
| 215 | SEQ ID NO: 254, 71 | hsa-miR-323-3p, hsa-miR-30e | 78.1% | 79.0% | 77.2% |

Figure 28 cont.

| Set No. | SEQ-ID NO: | miRNAs | Acc | Spec | Sens |
|---|---|---|---|---|---|
| 216 | SEQ ID NO: 85, 255 | hsa-miR-140-5p, hsa-miR-193a-3p | 77.8% | 89.4% | 66.4% |
| 217 | SEQ ID NO: 30, 71 | hsa-miR-380*, hsa-miR-30e | 77.8% | 74.6% | 81.2% |
| 218 | SEQ ID NO: 174, 255 | hsa-miR-636, hsa-miR-193a-3p | 77.8% | 79.6% | 76.0% |
| 219 | SEQ ID NO: 230, 135 | hsa-miR-624, hsa-miR-7-1* | 77.8% | 82.0% | 73.6% |
| 220 | SEQ ID NO: 85, 39 | hsa-miR-140-5p, hsa-miR-188-3p | 77.7% | 90.2% | 65.2% |
| 221 | SEQ ID NO: 242, 125 | hsa-let-7i, hsa-miR-1285 | 77.7% | 71.4% | 84.0% |
| 222 | SEQ ID NO: 257, 123 | hsa-miR-663b, hsa-miR-146b-3p | 77.7% | 84.6% | 70.8% |
| 223 | SEQ ID NO: 265, 15 | hsa-miR-129-5p, hsa-miR-892b | 77.7% | 80.0% | 75.4% |
| 224 | SEQ ID NO: 30, 232 | hsa-miR-380*, hsa-miR-514 | 77.6% | 81.6% | 73.6% |
| 225 | SEQ ID NO: 41, 251 | hsa-miR-654-5p, hsa-miR-182 | 77.5% | 91.8% | 63.2% |
| 226 | SEQ ID NO: 158, 266 | hsa-miR-1254, hsa-miR-619-5p | 77.5% | 81.8% | 73.2% |
| 227 | SEQ ID NO: 252, 23 | hsa-miR-497*, hsa-miR-491-3p | 77.5% | 81.8% | 73.2% |
| 228 | SEQ ID NO: 150, 95 | hsa-miR-1254, hsa-miR-135b* | 77.4% | 74.4% | 80.4% |
| 229 | SEQ ID NO: 30, 95 | hsa-miR-380*, hsa-miR-135b* | 77.4% | 79.0% | 75.8% |
| 230 | SEQ ID NO: 153, 247 | hsa-miR-484, hsa-miR-146a | 77.3% | 81.0% | 73.6% |
| 231 | SEQ ID NO: 22, 31 | hsa-miR-20b*, hsa-miR-139-5p | 77.3% | 79.8% | 74.8% |
| 232 | SEQ ID NO: 19, 16 | hsa-miR-767-5p, hsa-miR-455-3p | 77.2% | 75.6% | 78.8% |
| 233 | SEQ ID NO: 244, 135 | hsa-miR-874, hsa-miR-7-1* | 77.1% | 69.4% | 84.8% |
| 234 | SEQ ID NO: 27, 217 | hsa-miR-423-5p, hsa-miR-148b | 77.1% | 74.4% | 79.8% |
| 235 | SEQ ID NO: 125, 66 | hsa-miR-1285, hsa-miR-1295 | 77.0% | 79.2% | 75.0% |
| 236 | SEQ ID NO: 125, 153 | hsa-miR-1285, hsa-miR-484 | 77.0% | 67.0% | 87.0% |
| 237 | SEQ ID NO: 16, 137 | hsa-miR-455-3p, hsa-miR-920 | 77.0% | 78.4% | 75.6% |
| 238 | SEQ ID NO: 31, 22 | hsa-miR-139-5p, hsa-miR-20b* | 76.9% | 79.6% | 74.2% |
| 239 | SEQ ID NO: 116, 16 | hsa-miR-339-3p, hsa-miR-455-3p | 76.9% | 70.0% | 83.8% |
| 240 | SEQ ID NO: 231, 66 | hsa-miR-93, hsa-miR-1295 | 76.9% | 75.0% | 78.8% |
| 241 | SEQ ID NO: 167, 242 | hsa-miR-627, hsa-let-7i | 76.5% | 69.2% | 83.8% |
| 242 | SEQ ID NO: 253, 150 | hsa-miR-631, hsa-miR-1254 | 76.3% | 88.6% | 64.0% |
| 243 | SEQ ID NO: 156, 231 | hsa-miR-217, hsa-miR-93 | 76.2% | 80.2% | 72.2% |
| 244 | SEQ ID NO: 58, 181 | hsa-miR-1301, hsa-miR-145 | 76.0% | 86.8% | 65.2% |
| 245 | SEQ ID NO: 71, 242 | hsa-miR-30e, hsa-let-7i | 76.0% | 72.8% | 79.2% |
| 246 | SEQ ID NO: 125, 231 | hsa-miR-1285, hsa-miR-93 | 75.9% | 73.2% | 78.6% |
| 247 | SEQ ID NO: 24, 244 | hsa-miR-330-3p, hsa-miR-874 | 75.9% | 70.0% | 81.8% |
| 248 | SEQ ID NO: 167, 253 | hsa-miR-627, hsa-miR-631 | 75.8% | 82.2% | 69.4% |
| 249 | SEQ ID NO: 16, 273 | hsa-miR-455-3p, hsa-miR-194* | 75.8% | 77.4% | 74.2% |
| 250 | SEQ ID NO: 95, 31 | hsa-miR-135b*, hsa-miR-139-5p | 75.6% | 82.6% | 68.4% |
| 251 | SEQ ID NO: 289, 32 | hsa-miR-105, hsa-miR-888* | 75.5% | 77.2% | 73.8% |
| 252 | SEQ ID NO: 243, 135 | hsa-miR-151-5p, hsa-miR-7-1* | 75.5% | 69.8% | 81.2% |
| 253 | SEQ ID NO: 244, 71 | hsa-miR-874, hsa-miR-30e | 75.4% | 75.0% | 75.8% |
| 254 | SEQ ID NO: 265, 156 | hsa-miR-129-5p, hsa-miR-217 | 75.4% | 85.4% | 65.4% |
| 255 | SEQ ID NO: 231, 269 | hsa-miR-93, hsa-miR-105 | 75.3% | 79.8% | 70.8% |
| 256 | SEQ ID NO: 266, 150 | hsa-miR-619-5p, hsa-miR-1254 | 75.3% | 78.6% | 71.8% |
| 257 | SEQ ID NO: 22, 135 | hsa-miR-20b*, hsa-miR-7-1* | 75.2% | 70.0% | 80.4% |
| 258 | SEQ ID NO: 244, 66 | hsa-miR-874, hsa-miR-1295 | 75.2% | 80.4% | 70.0% |
| 259 | SEQ ID NO: 150, 156 | hsa-miR-1254, hsa-miR-217 | 74.9% | 71.0% | 78.8% |
| 260 | SEQ ID NO: 156, 243 | hsa-miR-217, hsa-miR-151-5p | 74.9% | 66.2% | 83.6% |
| 261 | SEQ ID NO: 59, 248 | hsa-miR-1301, hsa-let-7b | 74.7% | 91.0% | 58.4% |
| 262 | SEQ ID NO: 19, 31 | hsa-miR-767-5p, hsa-miR-139-5p | 74.7% | 84.6% | 64.8% |
| 263 | SEQ ID NO: 16, 253 | hsa-miR-455-3p, hsa-miR-631 | 74.6% | 66.0% | 83.2% |
| 264 | SEQ ID NO: 24, 167 | hsa-miR-330-3p, hsa-miR-627 | 74.6% | 71.2% | 78.0% |
| 265 | SEQ ID NO: 41, 27 | hsa-miR-654-5p, hsa-miR-423-5p | 74.5% | 72.4% | 76.6% |
| 266 | SEQ ID NO: 255, 167 | hsa-miR-193a-3p, hsa-miR-627 | 74.4% | 77.8% | 71.0% |
| 267 | SEQ ID NO: 189, 59 | hsa-miR-324-3p, hsa-miR-1301 | 74.3% | 85.4% | 63.2% |
| 268 | SEQ ID NO: 32, 243 | hsa-miR-888*, hsa-miR-151-5p | 73.9% | 76.8% | 71.0% |
| 269 | SEQ ID NO: 174, 244 | hsa-miR-636, hsa-miR-874 | 73.9% | 89.8% | 58.0% |

Figure 28 cont.

| Set No. | SEQ ID NO: | miRNAs | Acc | Spec | Sens |
|---|---|---|---|---|---|
| 270 | SEQ ID NO: 35, 24 | hsa-miR-135b*, hsa-miR-330-3p | 73.3% | 72.6% | 75.2% |
| 271 | SEQ ID NO: 32, 135 | hsa-miR-380*, hsa-miR-7-1* | 73.9% | 62.0% | 85.8% |
| 272 | SEQ ID NO: 23, 24 | hsa-miR-491-3p, hsa-miR-330-3p | 73.8% | 69.4% | 78.2% |
| 273 | SEQ ID NO: 169, 246 | hsa-miR-324-3p, hsa-miR-20a | 73.6% | 72.4% | 74.8% |
| 274 | SEQ ID NO: 125, 245 | hsa-miR-1285, hsa-miR-106a | 73.4% | 75.0% | 71.8% |
| 275 | SEQ ID NO: 181, 249 | hsa-miR-145, hsa-miR-33b* | 73.3% | 91.6% | 55.0% |
| 276 | SEQ ID NO: 231, 155 | hsa-miR-93, hsa-miR-484 | 73.2% | 68.4% | 78.0% |
| 277 | SEQ ID NO: 231, 169 | hsa-miR-93, hsa-miR-324-3p | 73.1% | 66.0% | 80.2% |
| 278 | SEQ ID NO: 273, 24 | hsa-miR-194*, hsa-miR-330-3p | 72.8% | 79.2% | 66.4% |
| 279 | SEQ ID NO: 248, 41 | hsa-let-7b, hsa-miR-654-5p | 72.6% | 71.8% | 73.4% |
| 280 | SEQ ID NO: 35, 269 | hsa-miR-135b*, hsa-miR-129-5p | 72.6% | 72.0% | 73.2% |
| 281 | SEQ ID NO: 59, 12 | hsa-miR-1301, hsa-miR-128 | 72.1% | 89.0% | 55.2% |
| 282 | SEQ ID NO: 244, 245 | hsa-miR-874, hsa-miR-106a | 72.0% | 68.4% | 75.6% |
| 283 | SEQ ID NO: 231, 245 | hsa-miR-93, hsa-miR-106a | 71.9% | 81.4% | 62.4% |
| 284 | SEQ ID NO: 265, 266 | hsa-miR-129-5p, hsa-miR-615-5p | 71.9% | 78.4% | 65.4% |
| 285 | SEQ ID NO: 266, 22 | hsa-miR-615-5p, hsa-miR-20b* | 71.8% | 61.2% | 82.6% |
| 286 | SEQ ID NO: 266, 265 | hsa-miR-615-5p, hsa-miR-129-5p | 71.8% | 78.8% | 64.8% |
| 287 | SEQ ID NO: 70, 153 | hsa-miR-1250, hsa-miR-1254 | 71.6% | 70.4% | 72.8% |
| 288 | SEQ ID NO: 247, 59 | hsa-miR-148a, hsa-miR-1301 | 71.6% | 83.8% | 59.4% |
| 289 | SEQ ID NO: 12, 250 | hsa-miR-128, hsa-miR-374a | 71.3% | 77.4% | 65.2% |
| 290 | SEQ ID NO: 251, 217 | hsa-miR-182, hsa-miR-148b | 71.1% | 60.0% | 82.2% |
| 291 | SEQ ID NO: 35, 167 | hsa-miR-135b*, hsa-miR-627 | 71.0% | 77.0% | 65.0% |
| 292 | SEQ ID NO: 31, 273 | hsa-miR-139-5p, hsa-miR-194* | 71.0% | 85.2% | 56.8% |
| 293 | SEQ ID NO: 27, 116 | hsa-miR-423-5p, hsa-miR-339-3p | 70.9% | 69.2% | 72.6% |
| 294 | SEQ ID NO: 135, 254 | hsa-miR-7-1*, hsa-miR-323-3p | 70.5% | 50.8% | 90.2% |
| 295 | SEQ ID NO: 155, 169 | hsa-miR-484, hsa-miR-324-3p | 69.9% | 67.4% | 72.4% |
| 296 | SEQ ID NO: 245, 169 | hsa-miR-106a, hsa-miR-324-3p | 69.9% | 72.0% | 67.8% |
| 297 | SEQ ID NO: 246, 247 | hsa-miR-20a, hsa-miR-148a | 69.7% | 83.0% | 56.4% |
| 298 | SEQ ID NO: 246, 59 | hsa-miR-20a, hsa-miR-1301 | 69.4% | 80.4% | 58.4% |
| 299 | SEQ ID NO: 248, 249 | hsa-let-7b, hsa-miR-33b* | 69.3% | 62.4% | 76.2% |
| 300 | SEQ ID NO: 217, 116 | hsa-miR-148b, hsa-miR-339-3p | 69.0% | 72.0% | 66.0% |
| 301 | SEQ ID NO: 135, 71 | hsa-miR-7-1*, hsa-miR-30a | 68.5% | 62.8% | 74.2% |
| 302 | SEQ ID NO: 181, 12 | hsa-miR-145, hsa-miR-128 | 68.5% | 72.4% | 64.6% |
| 303 | SEQ ID NO: 259, 244 | hsa-miR-631, hsa-miR-874 | 68.2% | 69.4% | 67.0% |
| 304 | SEQ ID NO: 247, 181 | hsa-miR-148a, hsa-miR-145 | 68.0% | 55.4% | 80.6% |
| 305 | SEQ ID NO: 12, 249 | hsa-miR-128, hsa-miR-33b* | 67.8% | 56.8% | 79.0% |
| 306 | SEQ ID NO: 273, 23 | hsa-miR-194*, hsa-miR-491-3p | 67.7% | 75.4% | 60.0% |
| 307 | SEQ ID NO: 169, 247 | hsa-miR-324-3p, hsa-miR-148a | 67.6% | 69.2% | 66.0% |
| 308 | SEQ ID NO: 248, 12 | hsa-let-7b, hsa-miR-128 | 67.4% | 61.6% | 73.2% |
| 309 | SEQ ID NO: 41, 250 | hsa-miR-654-5p, hsa-miR-374a | 67.3% | 58.8% | 75.8% |
| 310 | SEQ ID NO: 66, 155 | hsa-miR-1285, hsa-miR-484 | 67.1% | 68.2% | 66.0% |
| 311 | SEQ ID NO: 135, 242 | hsa-miR-7-1*, hsa-let-7i | 65.8% | 70.2% | 61.4% |
| 312 | SEQ ID NO: 249, 251 | hsa-miR-33b*, hsa-miR-182 | 65.3% | 65.0% | 65.6% |
| 313 | SEQ ID NO: 247, 248 | hsa-miR-148a, hsa-let-7b | 65.2% | 64.0% | 66.4% |
| 314 | SEQ ID NO: 245, 246 | hsa-miR-106a, hsa-miR-20a | 64.7% | 77.6% | 51.8% |
| 315 | SEQ ID NO: 12, 41 | hsa-miR-128, hsa-miR-654-5p | 64.4% | 55.0% | 73.8% |
| 316 | SEQ ID NO: 250, 27 | hsa-miR-374a, hsa-miR-423-5p | 63.4% | 76.2% | 50.6% |
| 317 | SEQ ID NO: 245, 155 | hsa-miR-106a, hsa-miR-484 | 61.3% | 58.8% | 63.8% |
| 318 | SEQ ID NO: 155, 246 | hsa-miR-484, hsa-miR-20a | 61.0% | 54.2% | 67.8% |
| 319 | SEQ ID NO: 249, 41 | hsa-miR-33b*, hsa-miR-654-5p | 60.8% | 56.4% | 65.2% |
| 320 | SEQ ID NO: 251, 27 | hsa-miR-182, hsa-miR-423-5p | 59.7% | 58.2% | 61.2% |
| 321 | SEQ ID NO: 249, 250 | hsa-miR-33b*, hsa-miR-374a | 59.6% | 62.8% | 56.4% |
| 322 | SEQ ID NO: 181, 248 | hsa-miR-145, hsa-let-7b | 57.4% | 55.6% | 59.2% |
| 323 | SEQ ID NO: 251, 116 | hsa-miR-182, hsa-miR-339-3p | 56.8% | 50.4% | 63.2% |

Figure 28 cont.

| Set No. | SEQ-ID NO: | miRNAs | Acc | Spec | Sens |
|---|---|---|---|---|---|
| 324 | SEQ ID NO: 250, 251 | hsa-miR-374a, hsa-miR-182 | 96.3% | 87.2% | 49.4% |
| 325 | SEQ ID NO: 150, 253, 174 | hsa-miR-1254, hsa-miR-345, hsa-miR-636 | 99.8% | 100.0% | 99.6% |
| 326 | SEQ ID NO: 137, 15, 243 | hsa-miR-920, hsa-miR-892b, hsa-miR-151-5p | 99.0% | 99.8% | 98.2% |
| 327 | SEQ ID NO: 16, 253, 174 | hsa-miR-455-3p, hsa-miR-345, hsa-miR-636 | 98.1% | 99.2% | 97.0% |
| 328 | SEQ ID NO: 162, 16, 150 | hsa-miR-142-5p, hsa-miR-455-3p, hsa-miR-1254 | 97.5% | 100.0% | 95.0% |
| 329 | SEQ ID NO: 150, 174, 133 | hsa-miR-1254, hsa-miR-636, hsa-miR-7-1* | 96.5% | 95.6% | 97.4% |
| 330 | SEQ ID NO: 253, 174, 71 | hsa-miR-345, hsa-miR-636, hsa-miR-30e | 96.3% | 97.0% | 95.6% |
| 331 | SEQ ID NO: 123, 269, 243 | hsa-miR-146b-3p, hsa-miR-195, hsa-miR-151-5p | 96.2% | 93.8% | 98.6% |
| 332 | SEQ ID NO: 62, 253, 174 | hsa-miR-1281, hsa-miR-345, hsa-miR-636 | 95.8% | 98.0% | 93.6% |
| 333 | SEQ ID NO: 162, 70, 266 | hsa-miR-142-5p, hsa-miR-1250, hsa-miR-615-5p | 95.5% | 98.8% | 92.2% |
| 334 | SEQ ID NO: 15, 243, 62 | hsa-miR-892b, hsa-miR-151-5p, hsa-miR-1281 | 95.1% | 99.6% | 90.6% |
| 335 | SEQ ID NO: 24, 242, 243 | hsa-miR-330-3p, hsa-let-7i, hsa-miR-151-5p | 95.0% | 95.0% | 95.0% |
| 336 | SEQ ID NO: 242, 243, 244 | hsa-let-7i, hsa-miR-151-5p, hsa-miR-874 | 95.0% | 95.0% | 95.0% |
| 337 | SEQ ID NO: 71, 243, 244 | hsa-miR-30e, hsa-miR-151-5p, hsa-miR-874 | 95.0% | 90.0% | 100.0% |
| 338 | SEQ ID NO: 243, 16, 32 | hsa-miR-151-5p, hsa-miR-455-3p, hsa-miR-383* | 94.9% | 94.8% | 95.0% |
| 339 | SEQ ID NO: 243, 244, 129 | hsa-miR-151-5p, hsa-miR-874, hsa-miR-1289 | 94.9% | 90.0% | 99.8% |
| 340 | SEQ ID NO: 252, 137, 243 | hsa-miR-497*, hsa-miR-920, hsa-miR-151-5p | 94.9% | 89.8% | 100.0% |
| 341 | SEQ ID NO: 174, 254, 71 | hsa-miR-636, hsa-miR-323-3p, hsa-miR-30e | 94.8% | 99.6% | 90.0% |
| 342 | SEQ ID NO: 52, 137, 162 | hsa-miR-802, hsa-miR-920, hsa-miR-142-5p | 94.8% | 95.0% | 94.6% |
| 343 | SEQ ID NO: 71, 24, 243 | hsa-miR-30e, hsa-miR-330-3p, hsa-miR-151-5p | 94.7% | 94.4% | 95.0% |
| 344 | SEQ ID NO: 150, 174, 71 | hsa-miR-1254, hsa-miR-636, hsa-miR-30e | 94.7% | 89.4% | 100.0% |
| 345 | SEQ ID NO: 35, 24, 243 | hsa-miR-188-3p, hsa-miR-330-3p, hsa-miR-151-5p | 94.6% | 94.8% | 94.4% |
| 346 | SEQ ID NO: 231, 21, 232 | hsa-miR-93, hsa-miR-20b*, hsa-miR-624 | 94.6% | 94.2% | 95.0% |
| 347 | SEQ ID NO: 137, 184, 70 | hsa-miR-366, hsa-miR-492, hsa-miR-1250 | 94.6% | 100.0% | 89.2% |
| 348 | SEQ ID NO: 184, 243, 16 | hsa-miR-492, hsa-miR-151-5p, hsa-miR-455-3p | 94.5% | 100.0% | 89.0% |
| 349 | SEQ ID NO: 184, 52, 243 | hsa-miR-492, hsa-miR-802, hsa-miR-151-5p | 94.4% | 96.4% | 92.4% |
| 350 | SEQ ID NO: 243, 244, 231 | hsa-miR-151-5p, hsa-miR-874, hsa-miR-93 | 94.4% | 90.0% | 98.8% |
| 351 | SEQ ID NO: 167, 243, 244 | hsa-miR-627, hsa-miR-151-5p, hsa-miR-874 | 94.2% | 88.4% | 100.0% |
| 352 | SEQ ID NO: 234, 52, 137 | hsa-miR-498, hsa-miR-802, hsa-miR-920 | 94.2% | 95.0% | 93.4% |
| 353 | SEQ ID NO: 254, 71, 255 | hsa-miR-323-3p, hsa-miR-30e, hsa-miR-193a-3p | 94.1% | 95.4% | 92.8% |
| 354 | SEQ ID NO: 35, 242, 243 | hsa-miR-188-3p, hsa-let-7i, hsa-miR-151-5p | 94.1% | 94.6% | 93.6% |
| 355 | SEQ ID NO: 137, 52, 243 | hsa-miR-920, hsa-miR-802, hsa-miR-151-5p | 94.0% | 93.2% | 94.8% |
| 356 | SEQ ID NO: 254, 71, 35 | hsa-miR-323-3p, hsa-miR-30e, hsa-miR-140-5p | 93.9% | 94.4% | 93.4% |
| 357 | SEQ ID NO: 243, 16, 70 | hsa-miR-151-5p, hsa-miR-455-3p, hsa-miR-1250 | 93.9% | 90.4% | 97.4% |
| 358 | SEQ ID NO: 15, 243, 99 | hsa-miR-892b, hsa-miR-151-5p, hsa-miR-138b* | 93.9% | 97.4% | 90.4% |
| 359 | SEQ ID NO: 137, 162, 70 | hsa-miR-920, hsa-miR-142-5p, hsa-miR-1250 | 93.9% | 95.0% | 92.8% |
| 360 | SEQ ID NO: 52, 137, 184 | hsa-miR-802, hsa-miR-366, hsa-miR-492 | 93.3% | 99.8% | 86.8% |
| 361 | SEQ ID NO: 162, 252, 16 | hsa-miR-142-5p, hsa-miR-497*, hsa-miR-455-3p | 93.2% | 91.6% | 94.8% |
| 362 | SEQ ID NO: 15, 123, 269 | hsa-miR-892b, hsa-miR-146b-3p, hsa-miR-195 | 92.9% | 93.8% | 92.0% |
| 363 | SEQ ID NO: 174, 244, 254 | hsa-miR-636, hsa-miR-874, hsa-miR-323-3p | 92.8% | 88.2% | 97.4% |
| 364 | SEQ ID NO: 167, 242, 243 | hsa-miR-627, hsa-let-7i, hsa-miR-151-5p | 92.8% | 94.8% | 90.8% |
| 365 | SEQ ID NO: 243, 123, 150 | hsa-miR-151-5p, hsa-miR-146b-3p, hsa-miR-1254 | 92.8% | 86.2% | 99.4% |
| 366 | SEQ ID NO: 252, 184, 243 | hsa-miR-497*, hsa-miR-492, hsa-miR-151-5p | 92.7% | 99.8% | 85.6% |
| 367 | SEQ ID NO: 162, 234, 68 | hsa-miR-142-5p, hsa-miR-498, hsa-miR-23b* | 92.7% | 90.4% | 95.0% |
| 368 | SEQ ID NO: 234, 68, 70 | hsa-miR-498, hsa-miR-23b*, hsa-miR-1250 | 92.7% | 95.4% | 90.0% |
| 369 | SEQ ID NO: 125, 24, 243 | hsa-miR-7-1*, hsa-miR-330-3p, hsa-miR-151-5p | 92.6% | 93.0% | 92.2% |
| 370 | SEQ ID NO: 24, 167, 243 | hsa-miR-330-3p, hsa-miR-627, hsa-miR-151-5p | 92.6% | 93.0% | 92.2% |
| 371 | SEQ ID NO: 234, 62, 52 | hsa-miR-498, hsa-miR-1281, hsa-miR-802 | 92.5% | 95.0% | 90.0% |

Figure 28 cont.

| Set No. | SEQ ID NO: | miRNAs | Acc | Spec | Sens |
|---|---|---|---|---|---|
| 372 | SEQ ID NO: 162, 135, 24 | hsa-miR-142-5p, hsa-miR-7-1*, hsa-miR-330-3p | 92.5% | 95.0% | 90.0% |
| 373 | SEQ ID NO: 24, 243, 244 | hsa-miR-330-3p, hsa-miR-151-5p, hsa-miR-874 | 92.5% | 90.0% | 95.0% |
| 374 | SEQ ID NO: 162, 62, 150 | hsa-miR-142-5p, hsa-miR-1281, hsa-miR-1254 | 92.5% | 95.0% | 90.0% |
| 375 | SEQ ID NO: 15, 62, 95 | hsa-miR-892b, hsa-miR-1281, hsa-miR-135b* | 92.5% | 100.0% | 85.0% |
| 376 | SEQ ID NO: 234, 68, 52 | hsa-miR-498, hsa-miR-23b*, hsa-miR-802 | 92.5% | 95.0% | 90.0% |
| 377 | SEQ ID NO: 234, 68, 137 | hsa-miR-498, hsa-miR-23b*, hsa-miR-920 | 92.5% | 94.0% | 91.0% |
| 378 | SEQ ID NO: 68, 52, 184 | hsa-miR-23b*, hsa-miR-802, hsa-miR-492 | 92.5% | 95.0% | 90.0% |
| 379 | SEQ ID NO: 162, 234, 252 | hsa-miR-142-5p, hsa-miR-498, hsa-miR-497* | 92.4% | 99.8% | 85.0% |
| 380 | SEQ ID NO: 184, 52, 68 | hsa-miR-492, hsa-miR-802, hsa-miR-23b* | 92.4% | 94.8% | 90.0% |
| 381 | SEQ ID NO: 184, 52, 16 | hsa-miR-492, hsa-miR-802, hsa-miR-455-3p | 92.4% | 99.8% | 85.0% |
| 382 | SEQ ID NO: 243, 244, 245 | hsa-miR-151-5p, hsa-miR-874, hsa-miR-106a | 92.4% | 89.4% | 95.4% |
| 383 | SEQ ID NO: 62, 16, 253 | hsa-miR-1281, hsa-miR-455-3p, hsa-miR-345 | 92.4% | 95.0% | 89.8% |
| 384 | SEQ ID NO: 22, 269, 232 | hsa-miR-20b*, hsa-miR-105, hsa-miR-624 | 92.4% | 99.2% | 85.6% |
| 385 | SEQ ID NO: 268, 24, 269 | hsa-miR-615-5p, hsa-miR-330-3p, hsa-miR-105 | 92.4% | 99.8% | 85.0% |
| 386 | SEQ ID NO: 15, 95, 269 | hsa-miR-892b, hsa-miR-135b*, hsa-miR-105 | 92.4% | 99.8% | 85.0% |
| 387 | SEQ ID NO: 157, 137, 70 | hsa-miR-566, hsa-miR-920, hsa-miR-1258 | 92.4% | 95.2% | 89.6% |
| 388 | SEQ ID NO: 162, 265, 150 | hsa-miR-142-5p, hsa-miR-129-5p, hsa-miR-1254 | 92.4% | 90.2% | 94.6% |
| 389 | SEQ ID NO: 243, 68, 16 | hsa-miR-151-5p, hsa-miR-23b*, hsa-miR-455-3p | 92.3% | 95.6% | 89.0% |
| 390 | SEQ ID NO: 15, 62, 123 | hsa-miR-892b, hsa-miR-1281, hsa-miR-146b-3p | 92.3% | 99.6% | 85.0% |
| 391 | SEQ ID NO: 137, 52, 62 | hsa-miR-920, hsa-miR-802, hsa-miR-1281 | 92.3% | 100.0% | 84.6% |
| 392 | SEQ ID NO: 62, 150, 253 | hsa-miR-1281, hsa-miR-1254, hsa-miR-345 | 92.2% | 95.0% | 89.4% |
| 393 | SEQ ID NO: 52, 62, 123 | hsa-miR-802, hsa-miR-1281, hsa-miR-146b-3p | 92.2% | 99.4% | 85.0% |
| 394 | SEQ ID NO: 52, 137, 184 | hsa-miR-802, hsa-miR-920, hsa-miR-492 | 92.2% | 95.2% | 89.2% |
| 395 | SEQ ID NO: 253, 31, 123 | hsa-miR-345, hsa-miR-139-5p, hsa-miR-146b-3p | 92.1% | 94.2% | 90.0% |
| 396 | SEQ ID NO: 162, 71, 24 | hsa-miR-142-5p, hsa-miR-30e, hsa-miR-330-3p | 92.1% | 91.2% | 93.0% |
| 397 | SEQ ID NO: 16, 150, 174 | hsa-miR-455-3p, hsa-miR-1254, hsa-miR-638 | 92.1% | 85.4% | 98.8% |
| 398 | SEQ ID NO: 62, 123, 95 | hsa-miR-1281, hsa-miR-146b-3p, hsa-miR-135b* | 92.1% | 99.2% | 85.0% |
| 399 | SEQ ID NO: 62, 150, 265 | hsa-miR-1281, hsa-miR-1254, hsa-miR-129-5p | 92.1% | 94.6% | 89.6% |
| 400 | SEQ ID NO: 52, 184, 162 | hsa-miR-802, hsa-miR-492, hsa-miR-142-5p | 92.1% | 94.6% | 89.6% |
| 401 | SEQ ID NO: 24, 243, 125 | hsa-miR-330-3p, hsa-miR-151-5p, hsa-miR-1285 | 92.0% | 93.4% | 90.6% |
| 402 | SEQ ID NO: 68, 16, 137 | hsa-miR-23b*, hsa-miR-455-3p, hsa-miR-920 | 92.0% | 99.0% | 85.0% |
| 403 | SEQ ID NO: 68, 252, 137 | hsa-miR-23b*, hsa-miR-497*, hsa-miR-920 | 92.0% | 99.6% | 84.4% |
| 404 | SEQ ID NO: 234, 184, 16 | hsa-miR-498, hsa-miR-492, hsa-miR-455-3p | 91.9% | 93.2% | 90.6% |
| 405 | SEQ ID NO: 62, 123, 150 | hsa-miR-1281, hsa-miR-146b-3p, hsa-miR-1254 | 91.9% | 98.8% | 85.0% |
| 406 | SEQ ID NO: 234, 68, 16 | hsa-miR-498, hsa-miR-23b*, hsa-miR-455-3p | 91.9% | 93.8% | 90.0% |
| 407 | SEQ ID NO: 62, 184, 52 | hsa-miR-1281, hsa-miR-492, hsa-miR-802 | 91.8% | 95.0% | 88.6% |
| 408 | SEQ ID NO: 162, 252, 62 | hsa-miR-142-5p, hsa-miR-497*, hsa-miR-1281 | 91.8% | 95.2% | 88.4% |
| 409 | SEQ ID NO: 253, 15, 123 | hsa-miR-345, hsa-miR-892b, hsa-miR-146b-3p | 91.8% | 94.6% | 89.0% |
| 410 | SEQ ID NO: 243, 259, 231 | hsa-miR-151-5p, hsa-miR-631, hsa-miR-93 | 91.8% | 89.8% | 93.8% |
| 411 | SEQ ID NO: 265, 150, 257 | hsa-miR-129-5p, hsa-miR-1254, hsa-miR-663b | 91.8% | 93.8% | 89.8% |
| 412 | SEQ ID NO: 157, 184, 68 | hsa-miR-566, hsa-miR-492, hsa-miR-23b* | 91.6% | 98.6% | 84.6% |
| 413 | SEQ ID NO: 243, 135, 19 | hsa-miR-151-5p, hsa-miR-7-1*, hsa-miR-767-5p | 91.6% | 88.8% | 94.4% |
| 414 | SEQ ID NO: 68, 157, 184 | hsa-miR-23b*, hsa-miR-566, hsa-miR-492 | 91.6% | 98.4% | 84.8% |
| 415 | SEQ ID NO: 234, 252, 52 | hsa-miR-498, hsa-miR-497*, hsa-miR-802 | 91.5% | 93.2% | 89.8% |
| 416 | SEQ ID NO: 52, 15, 62 | hsa-miR-802, hsa-miR-892b, hsa-miR-1281 | 91.5% | 100.0% | 83.0% |
| 417 | SEQ ID NO: 68, 52, 137 | hsa-miR-23b*, hsa-miR-802, hsa-miR-920 | 91.5% | 98.6% | 84.4% |
| 418 | SEQ ID NO: 157, 162, 70 | hsa-miR-566, hsa-miR-142-5p, hsa-miR-1258 | 91.5% | 95.4% | 87.6% |
| 419 | SEQ ID NO: 157, 234, 184 | hsa-miR-566, hsa-miR-498, hsa-miR-492 | 91.4% | 93.2% | 89.6% |
| 420 | SEQ ID NO: 252, 184, 52 | hsa-miR-497*, hsa-miR-492, hsa-miR-802 | 91.3% | 98.8% | 83.8% |

Figure 28 cont.

| Set No. | SEQ-ID NO: | miRNAs | Acc | Spec | Sens |
|---|---|---|---|---|---|
| 421 | SEQ ID NO: 162, 62, 16 | hsa-miR-142-5p, hsa-miR-1281, hsa-miR-499-3p | 91.3% | 95.6% | 87.0% |
| 422 | SEQ ID NO: 137, 19, 62 | hsa-miR-920, hsa-miR-892b, hsa-miR-1281 | 91.3% | 99.6% | 83.5% |
| 423 | SEQ ID NO: 137, 243, 62 | hsa-miR-920, hsa-miR-151-5p, hsa-miR-1281 | 91.3% | 95.4% | 87.2% |
| 424 | SEQ ID NO: 217, 62, 16 | hsa-miR-148b, hsa-miR-1281, hsa-miR-455-3p | 91.2% | 97.4% | 85.0% |
| 425 | SEQ ID NO: 259, 150, 157 | hsa-miR-631, hsa-miR-1254, hsa-miR-566 | 91.1% | 97.4% | 84.3% |
| 426 | SEQ ID NO: 24, 243, 259 | hsa-miR-330-3p, hsa-miR-151-5p, hsa-miR-631 | 91.1% | 93.3% | 90.0% |
| 427 | SEQ ID NO: 234, 252, 184 | hsa-miR-498, hsa-miR-497*, hsa-miR-492 | 91.0% | 89.2% | 92.8% |
| 428 | SEQ ID NO: 95, 253, 19 | hsa-miR-133b*, hsa-miR-345, hsa-miR-892b | 91.0% | 94.2% | 87.8% |
| 429 | SEQ ID NO: 157, 68, 16 | hsa-miR-566, hsa-miR-23b*, hsa-miR-455-3p | 91.0% | 99.0% | 82.8% |
| 430 | SEQ ID NO: 266, 265, 257 | hsa-miR-619-5p, hsa-miR-129-5p, hsa-miR-663b | 91.0% | 94.2% | 87.8% |
| 431 | SEQ ID NO: 269, 135, 19 | hsa-miR-103, hsa-miR-7-1*, hsa-miR-767-5p | 91.0% | 89.6% | 92.4% |
| 432 | SEQ ID NO: 257, 157, 184 | hsa-miR-663b, hsa-miR-566, hsa-miR-492 | 90.9% | 98.6% | 83.2% |
| 433 | SEQ ID NO: 243, 62, 150 | hsa-miR-151-5p, hsa-miR-1281, hsa-miR-1254 | 90.7% | 95.2% | 86.2% |
| 434 | SEQ ID NO: 184, 162, 266 | hsa-miR-492, hsa-miR-142-5p, hsa-miR-619-5p | 90.7% | 93.0% | 88.4% |
| 435 | SEQ ID NO: 244, 254, 71 | hsa-miR-874, hsa-miR-323-3p, hsa-miR-30e | 90.6% | 85.2% | 96.0% |
| 436 | SEQ ID NO: 62, 52, 68 | hsa-miR-1281, hsa-miR-802, hsa-miR-23b* | 90.6% | 96.8% | 84.4% |
| 437 | SEQ ID NO: 162, 252, 150 | hsa-miR-142-5p, hsa-miR-497*, hsa-miR-1254 | 90.6% | 91.0% | 90.2% |
| 438 | SEQ ID NO: 243, 62, 123 | hsa-miR-151-5p, hsa-miR-1281, hsa-miR-148b-3p | 90.6% | 94.6% | 86.6% |
| 439 | SEQ ID NO: 68, 16, 252 | hsa-miR-23b*, hsa-miR-455-3p, hsa-miR-497* | 90.6% | 96.2% | 85.0% |
| 440 | SEQ ID NO: 184, 68, 252 | hsa-miR-492, hsa-miR-23b*, hsa-miR-497* | 90.6% | 96.4% | 84.8% |
| 441 | SEQ ID NO: 16, 137, 52 | hsa-miR-455-3p, hsa-miR-920, hsa-miR-802 | 90.6% | 97.4% | 83.8% |
| 442 | SEQ ID NO: 234, 184, 52 | hsa-miR-498, hsa-miR-492, hsa-miR-802 | 90.5% | 91.0% | 90.0% |
| 443 | SEQ ID NO: 243, 70, 32 | hsa-miR-151-5p, hsa-miR-1250, hsa-miR-380* | 90.5% | 96.0% | 85.0% |
| 444 | SEQ ID NO: 243, 259, 244 | hsa-miR-151-5p, hsa-miR-631, hsa-miR-874 | 90.5% | 85.0% | 96.0% |
| 445 | SEQ ID NO: 234, 184, 70 | hsa-miR-498, hsa-miR-492, hsa-miR-1250 | 90.5% | 91.0% | 90.0% |
| 446 | SEQ ID NO: 123, 196, 243 | hsa-miR-148b-3p, hsa-miR-217, hsa-miR-151-5p | 90.5% | 89.6% | 91.4% |
| 447 | SEQ ID NO: 243, 19, 91 | hsa-miR-193-5p, hsa-miR-767-5p, hsa-miR-139-5p | 90.5% | 92.0% | 89.0% |
| 448 | SEQ ID NO: 234, 252, 62 | hsa-miR-498, hsa-miR-497*, hsa-miR-1281 | 90.3% | 90.6% | 90.0% |
| 449 | SEQ ID NO: 162, 157, 184 | hsa-miR-142-5p, hsa-miR-566, hsa-miR-492 | 90.3% | 95.6% | 85.0% |
| 450 | SEQ ID NO: 162, 157, 68 | hsa-miR-142-5p, hsa-miR-566, hsa-miR-23b* | 90.3% | 90.6% | 90.0% |
| 451 | SEQ ID NO: 157, 234, 16 | hsa-miR-566, hsa-miR-498, hsa-miR-455-3p | 90.3% | 95.8% | 84.8% |
| 452 | SEQ ID NO: 234, 62, 157 | hsa-miR-498, hsa-miR-802, hsa-miR-566 | 90.3% | 90.8% | 89.8% |
| 453 | SEQ ID NO: 162, 234, 62 | hsa-miR-142-5p, hsa-miR-498, hsa-miR-1281 | 90.2% | 90.2% | 90.2% |
| 454 | SEQ ID NO: 52, 243, 16 | hsa-miR-802, hsa-miR-151-5p, hsa-miR-455-3p | 90.2% | 91.0% | 89.4% |
| 455 | SEQ ID NO: 62, 52, 243 | hsa-miR-1281, hsa-miR-802, hsa-miR-151-5p | 90.2% | 92.4% | 88.0% |
| 456 | SEQ ID NO: 162, 139, 242 | hsa-miR-142-5p, hsa-miR-7-1*, hsa-let-7i | 90.2% | 93.3% | 86.6% |
| 457 | SEQ ID NO: 68, 70, 137 | hsa-miR-23b*, hsa-miR-1250, hsa-miR-920 | 90.2% | 94.8% | 85.6% |
| 458 | SEQ ID NO: 157, 137, 162 | hsa-miR-566, hsa-miR-920, hsa-miR-142-5p | 90.2% | 90.0% | 90.4% |
| 459 | SEQ ID NO: 157, 184, 162 | hsa-miR-566, hsa-miR-492, hsa-miR-142-5p | 90.2% | 95.4% | 85.0% |
| 460 | SEQ ID NO: 123, 22, 174 | hsa-miR-148b-3p, hsa-miR-20b*, hsa-miR-636 | 90.1% | 91.4% | 88.8% |
| 461 | SEQ ID NO: 266, 150, 257 | hsa-miR-619-5p, hsa-miR-1254, hsa-miR-663b | 90.1% | 93.4% | 86.8% |
| 462 | SEQ ID NO: 123, 196, 269 | hsa-miR-148b-3p, hsa-miR-217, hsa-miR-103 | 90.1% | 99.0% | 81.2% |
| 463 | SEQ ID NO: 22, 139, 16 | hsa-miR-20b*, hsa-miR-7-1*, hsa-miR-455-3p | 90.1% | 90.0% | 90.2% |
| 464 | SEQ ID NO: 68, 16, 259 | hsa-miR-23b*, hsa-miR-455-3p, hsa-miR-631 | 90.0% | 96.4% | 83.6% |
| 465 | SEQ ID NO: 243, 125, 231 | hsa-miR-151-5p, hsa-miR-1265, hsa-miR-93 | 90.0% | 87.6% | 92.4% |
| 466 | SEQ ID NO: 62, 150, 174 | hsa-miR-1281, hsa-miR-1254, hsa-miR-636 | 90.0% | 95.0% | 85.0% |
| 467 | SEQ ID NO: 252, 62, 253 | hsa-miR-497*, hsa-miR-1281, hsa-miR-345 | 90.0% | 90.2% | 89.8% |
| 468 | SEQ ID NO: 252, 150, 253 | hsa-miR-497*, hsa-miR-1254, hsa-miR-345 | 90.0% | 95.0% | 85.0% |
| 469 | SEQ ID NO: 68, 157, 137 | hsa-miR-23b*, hsa-miR-566, hsa-miR-920 | 90.0% | 95.0% | 85.0% |
| 470 | SEQ ID NO: 162, 70, 150 | hsa-miR-142-5p, hsa-miR-1250, hsa-miR-1254 | 90.0% | 95.4% | 84.6% |

Figure 28 cont.

| Set No. | SEQ ID NO: | miRNAs | Acc | Spec | Sens |
|---|---|---|---|---|---|
| 471 | SEQ ID NO: 150, 95, 157 | hsa-miR-1254, hsa-miR-135b*, hsa-miR-566 | 89.9% | 100.0% | 79.8% |
| 472 | SEQ ID NO: 62, 184, 243 | hsa-miR-1281, hsa-miR-492, hsa-miR-151-5p | 89.9% | 94.6% | 85.2% |
| 473 | SEQ ID NO: 15, 22, 174 | hsa-miR-892b, hsa-miR-206*, hsa-miR-636 | 89.9% | 94.0% | 85.8% |
| 474 | SEQ ID NO: 157, 184, 16 | hsa-miR-566, hsa-miR-492, hsa-miR-455-3p | 89.9% | 95.0% | 84.8% |
| 475 | SEQ ID NO: 137, 70, 266 | hsa-miR-920, hsa-miR-1250, hsa-miR-615-5p | 89.9% | 94.8% | 85.0% |
| 476 | SEQ ID NO: 150, 15, 123 | hsa-miR-1254, hsa-miR-892b, hsa-miR-146b-3p | 89.8% | 99.6% | 80.0% |
| 477 | SEQ ID NO: 22, 174, 254 | hsa-miR-206*, hsa-miR-636, hsa-miR-323-3p | 89.7% | 94.8% | 84.6% |
| 478 | SEQ ID NO: 62, 95, 150 | hsa-miR-1281, hsa-miR-135b*, hsa-miR-1254 | 89.7% | 98.4% | 81.0% |
| 479 | SEQ ID NO: 52, 15, 123 | hsa-miR-802, hsa-miR-892b, hsa-miR-146b-3p | 89.7% | 100.0% | 79.4% |
| 480 | SEQ ID NO: 184, 162, 70 | hsa-miR-492, hsa-miR-142-5p, hsa-miR-1250 | 89.7% | 94.4% | 85.0% |
| 481 | SEQ ID NO: 234, 157, 137 | hsa-miR-498, hsa-miR-566, hsa-miR-920 | 89.7% | 89.4% | 90.0% |
| 482 | SEQ ID NO: 259, 95, 157 | hsa-miR-631, hsa-miR-135b*, hsa-miR-566 | 89.6% | 99.2% | 80.0% |
| 483 | SEQ ID NO: 162, 252, 184 | hsa-miR-142-5p, hsa-miR-497*, hsa-miR-492 | 89.6% | 94.2% | 85.0% |
| 484 | SEQ ID NO: 150, 253, 31 | hsa-miR-1254, hsa-miR-345, hsa-miR-139-5p | 89.6% | 94.2% | 85.0% |
| 485 | SEQ ID NO: 243, 123, 246 | hsa-miR-151-5p, hsa-miR-1285, hsa-miR-106a | 89.6% | 85.4% | 93.8% |
| 486 | SEQ ID NO: 41, 27, 217 | hsa-miR-654-5p, hsa-miR-423-5p, hsa-miR-148b | 89.6% | 89.4% | 89.8% |
| 487 | SEQ ID NO: 252, 16, 253 | hsa-miR-497*, hsa-miR-455-3p, hsa-miR-345 | 89.6% | 89.4% | 89.8% |
| 488 | SEQ ID NO: 157, 184, 68 | hsa-miR-566, hsa-miR-492, hsa-miR-23b* | 89.6% | 89.0% | 90.2% |
| 489 | SEQ ID NO: 62, 95, 269 | hsa-miR-1281, hsa-miR-135b*, hsa-miR-129-5p | 89.6% | 94.8% | 84.4% |
| 490 | SEQ ID NO: 234, 62, 184 | hsa-miR-498, hsa-miR-1281, hsa-miR-492 | 89.5% | 89.0% | 90.2% |
| 491 | SEQ ID NO: 252, 62, 243 | hsa-miR-497*, hsa-miR-1281, hsa-miR-151-5p | 89.5% | 94.4% | 84.6% |
| 492 | SEQ ID NO: 253, 123, 22 | hsa-miR-345, hsa-miR-146b-3p, hsa-miR-206* | 89.5% | 88.6% | 90.4% |
| 493 | SEQ ID NO: 52, 243, 62 | hsa-miR-802, hsa-miR-151-5p, hsa-miR-1281 | 89.5% | 91.6% | 87.4% |
| 494 | SEQ ID NO: 257, 234, 184 | hsa-miR-663b, hsa-miR-498, hsa-miR-492 | 89.5% | 84.8% | 94.2% |
| 495 | SEQ ID NO: 234, 68, 157 | hsa-miR-498, hsa-miR-23b*, hsa-miR-566 | 89.5% | 89.0% | 90.0% |
| 496 | SEQ ID NO: 15, 156, 269 | hsa-miR-892b, hsa-miR-317, hsa-miR-105 | 89.5% | 89.8% | 89.2% |
| 497 | SEQ ID NO: 253, 15, 22 | hsa-miR-345, hsa-miR-892b, hsa-miR-206* | 89.4% | 90.0% | 89.8% |
| 498 | SEQ ID NO: 162, 24, 242 | hsa-miR-142-5p, hsa-miR-330-3p, hsa-let-7i | 89.4% | 85.8% | 93.0% |
| 499 | SEQ ID NO: 62, 16, 174 | hsa-miR-1281, hsa-miR-455-3p, hsa-miR-636 | 89.4% | 94.4% | 84.4% |
| 500 | SEQ ID NO: 184, 68, 70 | hsa-miR-492, hsa-miR-23b*, hsa-miR-1250 | 89.4% | 89.4% | 89.4% |
| 501 | SEQ ID NO: 137, 162, 266 | hsa-miR-920, hsa-miR-142-5p, hsa-miR-615-5p | 89.4% | 88.6% | 90.2% |
| 502 | SEQ ID NO: 68, 137, 184 | hsa-miR-23b*, hsa-miR-920, hsa-miR-492 | 89.4% | 94.4% | 84.4% |
| 503 | SEQ ID NO: 253, 31, 15 | hsa-miR-345, hsa-miR-139-5p, hsa-miR-892b | 89.3% | 88.6% | 89.8% |
| 504 | SEQ ID NO: 52, 15, 243 | hsa-miR-802, hsa-miR-892b, hsa-miR-151-5p | 89.3% | 95.4% | 83.2% |
| 505 | SEQ ID NO: 22, 269, 135 | hsa-miR-206*, hsa-miR-105, hsa-miR-7-1* | 89.3% | 89.6% | 89.0% |
| 506 | SEQ ID NO: 68, 52, 157 | hsa-miR-23b*, hsa-miR-802, hsa-miR-566 | 89.3% | 98.4% | 80.2% |
| 507 | SEQ ID NO: 41, 250, 217 | hsa-miR-654-5p, hsa-miR-374a, hsa-miR-148b | 89.2% | 86.2% | 92.2% |
| 508 | SEQ ID NO: 184, 70, 252 | hsa-miR-492, hsa-miR-1250, hsa-miR-497* | 89.2% | 94.8% | 83.6% |
| 509 | SEQ ID NO: 137, 184, 162 | hsa-miR-920, hsa-miR-492, hsa-miR-142-5p | 89.2% | 90.4% | 88.0% |
| 510 | SEQ ID NO: 123, 95, 269 | hsa-miR-146b-3p, hsa-miR-135b*, hsa-miR-105 | 89.2% | 93.8% | 84.6% |
| 511 | SEQ ID NO: 269, 22, 135 | hsa-miR-105, hsa-miR-206*, hsa-miR-7-1* | 89.2% | 89.0% | 89.4% |
| 512 | SEQ ID NO: 15, 123, 156 | hsa-miR-892b, hsa-miR-146b-3p, hsa-miR-317 | 89.1% | 99.4% | 78.8% |
| 513 | SEQ ID NO: 243, 68, 70 | hsa-miR-151-5p, hsa-miR-23b*, hsa-miR-1250 | 89.0% | 88.8% | 89.2% |
| 514 | SEQ ID NO: 52, 68, 16 | hsa-miR-802, hsa-miR-23b*, hsa-miR-455-3p | 89.0% | 99.2% | 78.8% |
| 515 | SEQ ID NO: 62, 16, 150 | hsa-miR-1281, hsa-miR-455-3p, hsa-miR-1254 | 89.0% | 98.0% | 80.0% |
| 516 | SEQ ID NO: 32, 273, 252 | hsa-miR-380*, hsa-miR-194*, hsa-miR-497* | 89.0% | 89.8% | 88.2% |
| 517 | SEQ ID NO: 253, 174, 135 | hsa-miR-345, hsa-miR-636, hsa-miR-7-1* | 88.9% | 93.4% | 84.4% |
| 518 | SEQ ID NO: 259, 123, 231 | hsa-miR-631, hsa-miR-1285, hsa-miR-93 | 88.9% | 89.8% | 88.0% |
| 519 | SEQ ID NO: 231, 22, 269 | hsa-miR-93, hsa-miR-206*, hsa-miR-105 | 88.9% | 93.0% | 84.8% |
| 520 | SEQ ID NO: 265, 266, 24 | hsa-miR-129-5p, hsa-miR-615-5p, hsa-miR-330-3p | 88.9% | 93.8% | 84.0% |
| 521 | SEQ ID NO: 70, 252, 15 | hsa-miR-1250, hsa-miR-497*, hsa-miR-892b | 88.9% | 99.8% | 78.0% |

Figure 28 cont.

| Set No. | SEQ-ID NO: | miRNAs | Acc | Spec | Sens |
|---|---|---|---|---|---|
| 522 | SEQ ID NO: 174, 71, 35 | hsa-miR-636, hsa-miR-30e, hsa-miR-183-3p | 88.8% | 90.0% | 87.6% |
| 523 | SEQ ID NO: 243, 123, 98 | hsa-miR-151-5p, hsa-miR-146b-3p, hsa-miR-135b* | 88.8% | 81.8% | 94.8% |
| 524 | SEQ ID NO: 123, 98, 243 | hsa-miR-146b-3p, hsa-miR-135b*, hsa-miR-151-5p | 88.8% | 83.8% | 93.8% |
| 525 | SEQ ID NO: 157, 233, 123 | hsa-miR-566, hsa-miR-345, hsa-miR-146b-3p | 88.7% | 91.8% | 85.6% |
| 526 | SEQ ID NO: 135, 35, 24 | hsa-miR-7-1*, hsa-miR-183-3p, hsa-miR-330-3p | 88.7% | 86.2% | 91.2% |
| 527 | SEQ ID NO: 32, 232, 71 | hsa-miR-380*, hsa-miR-624, hsa-miR-30e | 88.7% | 93.2% | 84.2% |
| 528 | SEQ ID NO: 162, 184, 68 | hsa-miR-142-5p, hsa-miR-492, hsa-miR-23b* | 88.7% | 90.0% | 87.4% |
| 529 | SEQ ID NO: 157, 137, 184 | hsa-miR-566, hsa-miR-920, hsa-miR-492 | 88.7% | 98.4% | 79.0% |
| 530 | SEQ ID NO: 162, 70, 265 | hsa-miR-142-5p, hsa-miR-1250, hsa-miR-129-5p | 88.7% | 85.4% | 91.0% |
| 531 | SEQ ID NO: 98, 269, 22 | hsa-miR-135b*, hsa-miR-105, hsa-miR-20b* | 88.7% | 92.4% | 85.6% |
| 532 | SEQ ID NO: 232, 13, 243 | hsa-miR-497*, hsa-miR-892b, hsa-miR-151-5p | 88.6% | 99.8% | 77.4% |
| 533 | SEQ ID NO: 22, 19, 16 | hsa-miR-20b*, hsa-miR-767-5p, hsa-miR-455-3p | 88.6% | 87.2% | 90.0% |
| 534 | SEQ ID NO: 243, 231, 245 | hsa-miR-151-5p, hsa-miR-93, hsa-miR-106a | 88.5% | 88.6% | 88.4% |
| 535 | SEQ ID NO: 68, 70, 232 | hsa-miR-23b*, hsa-miR-1250, hsa-miR-497* | 88.5% | 94.8% | 82.2% |
| 536 | SEQ ID NO: 123, 265, 196 | hsa-miR-146b-3p, hsa-miR-129-5p, hsa-miR-217 | 88.5% | 92.2% | 84.8% |
| 537 | SEQ ID NO: 70, 266, 150 | hsa-miR-1250, hsa-miR-615-5p, hsa-miR-1254 | 88.4% | 99.8% | 77.0% |
| 538 | SEQ ID NO: 150, 257, 123 | hsa-miR-1254, hsa-miR-663b, hsa-miR-146b-3p | 88.4% | 95.0% | 81.8% |
| 539 | SEQ ID NO: 52, 16, 70 | hsa-miR-302, hsa-miR-455-3p, hsa-miR-1250 | 88.3% | 96.6% | 80.0% |
| 540 | SEQ ID NO: 150, 257, 98 | hsa-miR-1254, hsa-miR-663b, hsa-miR-135b* | 88.3% | 95.4% | 81.2% |
| 541 | SEQ ID NO: 22, 244, 254 | hsa-miR-20b*, hsa-miR-874, hsa-miR-323-3p | 88.2% | 86.4% | 90.0% |
| 542 | SEQ ID NO: 135, 88, 255 | hsa-miR-7-1*, hsa-miR-140-5p, hsa-miR-193a-3p | 88.2% | 85.0% | 91.4% |
| 543 | SEQ ID NO: 116, 62, 16 | hsa-miR-339-3p, hsa-miR-1281, hsa-miR-455-3p | 88.2% | 94.2% | 82.2% |
| 544 | SEQ ID NO: 257, 162, 157 | hsa-miR-663b, hsa-miR-142-5p, hsa-miR-566 | 88.2% | 89.6% | 86.8% |
| 545 | SEQ ID NO: 257, 162, 184 | hsa-miR-663b, hsa-miR-142-5p, hsa-miR-492 | 88.2% | 92.8% | 83.6% |
| 546 | SEQ ID NO: 62, 123, 265 | hsa-miR-1281, hsa-miR-146b-3p, hsa-miR-129-5p | 88.2% | 91.4% | 85.0% |
| 547 | SEQ ID NO: 98, 269, 243 | hsa-miR-135b*, hsa-miR-105, hsa-miR-151-5p | 88.2% | 89.6% | 86.8% |
| 548 | SEQ ID NO: 232, 62, 52 | hsa-miR-497*, hsa-miR-1281, hsa-miR-302 | 88.1% | 95.6% | 80.6% |
| 549 | SEQ ID NO: 162, 62, 184 | hsa-miR-142-5p, hsa-miR-1281, hsa-miR-492 | 88.1% | 90.8% | 85.4% |
| 550 | SEQ ID NO: 232, 62, 150 | hsa-miR-497*, hsa-miR-1281, hsa-miR-1254 | 88.1% | 97.8% | 78.4% |
| 551 | SEQ ID NO: 68, 16, 70 | hsa-miR-23b*, hsa-miR-455-3p, hsa-miR-1250 | 88.0% | 92.0% | 84.0% |
| 552 | SEQ ID NO: 123, 174, 135 | hsa-miR-146b-3p, hsa-miR-636, hsa-miR-7-1* | 88.0% | 94.4% | 81.6% |
| 553 | SEQ ID NO: 162, 266, 265 | hsa-miR-142-5p, hsa-miR-615-5p, hsa-miR-129-5p | 88.0% | 87.4% | 88.6% |
| 554 | SEQ ID NO: 135, 31, 16 | hsa-miR-7-1*, hsa-miR-139-3p, hsa-miR-455-3p | 88.0% | 85.6% | 90.4% |
| 555 | SEQ ID NO: 98, 157, 31 | hsa-miR-135b*, hsa-miR-566, hsa-miR-139-3p | 87.9% | 100.0% | 75.8% |
| 556 | SEQ ID NO: 16, 150, 135 | hsa-miR-455-3p, hsa-miR-1254, hsa-miR-7-1* | 87.9% | 83.0% | 92.8% |
| 557 | SEQ ID NO: 162, 157, 234 | hsa-miR-142-5p, hsa-miR-566, hsa-miR-498 | 87.9% | 86.2% | 89.6% |
| 558 | SEQ ID NO: 70, 52, 19 | hsa-miR-1250, hsa-miR-302, hsa-miR-092b | 87.9% | 96.6% | 79.2% |
| 559 | SEQ ID NO: 52, 157, 137 | hsa-miR-302, hsa-miR-566, hsa-miR-920 | 87.9% | 95.4% | 80.4% |
| 560 | SEQ ID NO: 52, 243, 68 | hsa-miR-302, hsa-miR-151-5p, hsa-miR-23b* | 87.9% | 86.0% | 89.8% |
| 561 | SEQ ID NO: 244, 135, 254 | hsa-miR-874, hsa-miR-7-1*, hsa-miR-323-3p | 87.8% | 85.6% | 90.0% |
| 562 | SEQ ID NO: 254, 71, 35 | hsa-miR-323-3p, hsa-miR-30e, hsa-miR-183-3p | 87.8% | 93.8% | 81.8% |
| 563 | SEQ ID NO: 184, 68, 16 | hsa-miR-492, hsa-miR-23b*, hsa-miR-455-3p | 87.8% | 85.2% | 90.4% |
| 564 | SEQ ID NO: 137, 52, 13 | hsa-miR-920, hsa-miR-302, hsa-miR-892b | 87.8% | 99.8% | 75.8% |
| 565 | SEQ ID NO: 13, 243, 123 | hsa-miR-892b, hsa-miR-151-5p, hsa-miR-146b-3p | 87.8% | 94.0% | 81.6% |
| 566 | SEQ ID NO: 184, 16, 70 | hsa-miR-492, hsa-miR-455-3p, hsa-miR-1250 | 87.8% | 90.0% | 85.6% |
| 567 | SEQ ID NO: 184, 16, 232 | hsa-miR-492, hsa-miR-455-3p, hsa-miR-497* | 87.8% | 95.0% | 80.6% |
| 568 | SEQ ID NO: 266, 231, 269 | hsa-miR-615-5p, hsa-miR-93, hsa-miR-105 | 87.8% | 86.8% | 88.8% |
| 569 | SEQ ID NO: 16, 70, 52 | hsa-miR-455-3p, hsa-miR-1250, hsa-miR-302 | 87.8% | 95.6% | 80.0% |

Figure 28 cont.

| Set No. | SEQ-ID NO: | miRNAs | Acc | Spec | Sens |
|---|---|---|---|---|---|
| 570 | SEQ ID NO: 162, 135, 71 | hsa-miR-142-5p, hsa-miR-7-1*, hsa-miR-30e | 87.7% | 93.0% | 82.4% |
| 571 | SEQ ID NO: 280, 52, 15 | hsa-miR-497*, hsa-miR-302, hsa-miR-892b | 87.7% | 100.0% | 75.4% |
| 572 | SEQ ID NO: 263, 243, 19 | hsa-miR-105, hsa-miR-151-5p, hsa-miR-767-5p | 87.7% | 94.0% | 81.4% |
| 573 | SEQ ID NO: 135, 254, 255 | hsa-miR-7-1*, hsa-miR-323-3p, hsa-miR-193a-3p | 87.6% | 90.2% | 85.0% |
| 574 | SEQ ID NO: 242, 243, 239 | hsa-let-7i, hsa-miR-151-5p, hsa-miR-631 | 87.6% | 90.0% | 85.2% |
| 575 | SEQ ID NO: 234, 184, 68 | hsa-miR-498, hsa-miR-492, hsa-miR-23b* | 87.6% | 85.6% | 89.6% |
| 576 | SEQ ID NO: 297, 157, 234 | hsa-miR-663b, hsa-miR-566, hsa-miR-498 | 87.6% | 84.4% | 90.8% |
| 577 | SEQ ID NO: 268, 22, 269 | hsa-miR-615-5p, hsa-miR-20b*, hsa-miR-105 | 87.6% | 93.6% | 81.6% |
| 578 | SEQ ID NO: 184, 70, 268 | hsa-miR-492, hsa-miR-1250, hsa-miR-615-5p | 87.6% | 94.0% | 81.2% |
| 579 | SEQ ID NO: 167, 242, 239 | hsa-miR-627, hsa-let-7i, hsa-miR-631 | 87.5% | 85.0% | 90.0% |
| 580 | SEQ ID NO: 243, 62, 95 | hsa-miR-151-5p, hsa-miR-1281, hsa-miR-135b* | 87.5% | 89.0% | 86.0% |
| 581 | SEQ ID NO: 52, 243, 123 | hsa-miR-302, hsa-miR-151-5p, hsa-miR-146b-3p | 87.5% | 90.0% | 85.0% |
| 582 | SEQ ID NO: 137, 184, 70 | hsa-miR-920, hsa-miR-492, hsa-miR-1250 | 87.5% | 89.8% | 85.2% |
| 583 | SEQ ID NO: 263, 243, 135 | hsa-miR-105, hsa-miR-151-5p, hsa-miR-7-1* | 87.5% | 95.0% | 80.0% |
| 584 | SEQ ID NO: 62, 184, 68 | hsa-miR-1281, hsa-miR-492, hsa-miR-23b* | 87.4% | 94.8% | 80.0% |
| 585 | SEQ ID NO: 157, 15, 123 | hsa-miR-566, hsa-miR-892b, hsa-miR-146b-3p | 87.4% | 99.6% | 75.2% |
| 586 | SEQ ID NO: 280, 62, 16 | hsa-miR-497*, hsa-miR-1281, hsa-miR-455-3p | 87.4% | 94.8% | 80.0% |
| 587 | SEQ ID NO: 242, 239, 105 | hsa-let-7i, hsa-miR-631, hsa-miR-1283 | 87.4% | 85.0% | 89.8% |
| 588 | SEQ ID NO: 253, 71, 255 | hsa-miR-345, hsa-miR-30e, hsa-miR-193a-3p | 87.4% | 90.4% | 84.4% |
| 589 | SEQ ID NO: 297, 162, 234 | hsa-miR-663b, hsa-miR-142-5p, hsa-miR-498 | 87.4% | 86.6% | 88.2% |
| 590 | SEQ ID NO: 70, 137, 15 | hsa-miR-1250, hsa-miR-920, hsa-miR-892b | 87.4% | 98.8% | 76.0% |
| 591 | SEQ ID NO: 184, 70, 265 | hsa-miR-492, hsa-miR-1250, hsa-miR-129-5p | 87.4% | 89.8% | 85.0% |
| 592 | SEQ ID NO: 280, 62, 184 | hsa-miR-497*, hsa-miR-1281, hsa-miR-492 | 87.3% | 90.8% | 83.8% |
| 593 | SEQ ID NO: 71, 85, 255 | hsa-miR-30e, hsa-miR-146-5p, hsa-miR-193a-3p | 87.3% | 86.4% | 88.2% |
| 594 | SEQ ID NO: 70, 32, 150 | hsa-miR-1250, hsa-miR-380*, hsa-miR-1254 | 87.3% | 87.8% | 86.8% |
| 595 | SEQ ID NO: 135, 19, 16 | hsa-miR-7-1*, hsa-miR-767-5p, hsa-miR-455-3p | 87.3% | 81.2% | 93.4% |
| 596 | SEQ ID NO: 297, 123, 156 | hsa-miR-663b, hsa-miR-146b-3p, hsa-miR-217 | 87.3% | 96.8% | 77.8% |
| 597 | SEQ ID NO: 242, 243, 105 | hsa-let-7i, hsa-miR-151-5p, hsa-miR-1283 | 87.2% | 90.0% | 84.4% |
| 598 | SEQ ID NO: 268, 24, 22 | hsa-miR-615-5p, hsa-miR-330-3p, hsa-miR-20b* | 87.2% | 91.0% | 83.4% |
| 599 | SEQ ID NO: 243, 95, 150 | hsa-miR-151-5p, hsa-miR-135b*, hsa-miR-1254 | 87.2% | 79.2% | 95.2% |
| 600 | SEQ ID NO: 265, 297, 103 | hsa-miR-129-5p, hsa-miR-663b, hsa-miR-146b-3p | 87.2% | 89.6% | 84.8% |
| 601 | SEQ ID NO: 62, 243, 68 | hsa-miR-1281, hsa-miR-151-5p, hsa-miR-23b* | 87.0% | 93.2% | 80.8% |
| 602 | SEQ ID NO: 16, 280, 52 | hsa-miR-455-3p, hsa-miR-497*, hsa-miR-302 | 87.0% | 94.0% | 80.0% |
| 603 | SEQ ID NO: 234, 16, 70 | hsa-miR-498, hsa-miR-455-3p, hsa-miR-1250 | 87.0% | 93.4% | 80.6% |
| 604 | SEQ ID NO: 52, 157, 162 | hsa-miR-302, hsa-miR-566, hsa-miR-142-5p | 87.0% | 93.0% | 81.0% |
| 605 | SEQ ID NO: 70, 268, 297 | hsa-miR-1250, hsa-miR-615-5p, hsa-miR-663b | 87.0% | 94.6% | 79.4% |
| 606 | SEQ ID NO: 265, 150, 123 | hsa-miR-129-5p, hsa-miR-1254, hsa-miR-146b-3p | 87.0% | 90.2% | 83.8% |
| 607 | SEQ ID NO: 22, 31, 16 | hsa-miR-20b*, hsa-miR-139-5p, hsa-miR-455-3p | 87.0% | 85.0% | 89.0% |
| 608 | SEQ ID NO: 150, 157, 253 | hsa-miR-1254, hsa-miR-566, hsa-miR-345 | 86.9% | 94.0% | 79.8% |
| 609 | SEQ ID NO: 157, 31, 123 | hsa-miR-566, hsa-miR-139-5p, hsa-miR-146b-3p | 86.9% | 95.0% | 78.8% |
| 610 | SEQ ID NO: 239, 150, 253 | hsa-miR-631, hsa-miR-1254, hsa-miR-345 | 86.9% | 83.4% | 90.4% |
| 611 | SEQ ID NO: 331, 22, 32 | hsa-miR-93, hsa-miR-20b*, hsa-miR-380* | 86.9% | 84.2% | 89.6% |
| 612 | SEQ ID NO: 135, 16, 32 | hsa-miR-7-1*, hsa-miR-455-3p, hsa-miR-380* | 86.9% | 79.2% | 93.6% |
| 613 | SEQ ID NO: 15, 123, 174 | hsa-miR-892b, hsa-miR-146b-3p, hsa-miR-636 | 86.8% | 98.2% | 75.4% |
| 614 | SEQ ID NO: 123, 244, 135 | hsa-miR-146b-3p, hsa-miR-874, hsa-miR-7-1* | 86.8% | 95.8% | 77.8% |
| 615 | SEQ ID NO: 123, 150, 265 | hsa-miR-146b-3p, hsa-miR-1254, hsa-miR-129-5p | 86.8% | 90.0% | 83.6% |
| 616 | SEQ ID NO: 268, 150, 15 | hsa-miR-615-5p, hsa-miR-1254, hsa-miR-892b | 86.8% | 89.6% | 84.0% |
| 617 | SEQ ID NO: 135, 254, 85 | hsa-miR-7-1*, hsa-miR-323-3p, hsa-miR-140- | 86.7% | 77.8% | 95.6% |

Figure 28 cont.

| Set No. | SEQ-ID NO: | miRNAs | Acc | Spec | Sens |
|---|---|---|---|---|---|
|  |  | 5p |  |  |  |
| 618 | SEQ ID NO: 15, 22, 244 | hsa-miR-892b, hsa-miR-20b*, hsa-miR-874 | 86.7% | 89.8% | 83.6% |
| 619 | SEQ ID NO: 70, 32, 95 | hsa-miR-1250, hsa-miR-380*, hsa-miR-135b* | 86.7% | 90.0% | 81.4% |
| 620 | SEQ ID NO: 95, 157, 15 | hsa-miR-135b*, hsa-miR-566, hsa-miR-892b | 86.7% | 94.8% | 76.6% |
| 621 | SEQ ID NO: 252, 137, 92 | hsa-miR-497*, hsa-miR-920, hsa-miR-802 | 86.7% | 95.4% | 75.0% |
| 622 | SEQ ID NO: 257, 123, 95 | hsa-miR-663b, hsa-miR-146b-3p, hsa-miR-135b* | 86.7% | 93.8% | 79.6% |
| 623 | SEQ ID NO: 157, 253, 31 | hsa-miR-566, hsa-miR-345, hsa-miR-139-5p | 86.6% | 93.0% | 83.2% |
| 624 | SEQ ID NO: 259, 157, 253 | hsa-miR-631, hsa-miR-566, hsa-miR-345 | 86.6% | 83.6% | 88.6% |
| 625 | SEQ ID NO: 24, 22, 32 | hsa-miR-330-3p, hsa-miR-20b*, hsa-miR-380* | 86.6% | 83.0% | 90.0% |
| 626 | SEQ ID NO: 266, 257, 15 | hsa-miR-615-5p, hsa-miR-663b, hsa-miR-892b | 86.6% | 93.4% | 79.2% |
| 627 | SEQ ID NO: 22, 244, 135 | hsa-miR-20b*, hsa-miR-874, hsa-miR-7-1* | 86.5% | 89.8% | 83.2% |
| 628 | SEQ ID NO: 217, 252, 62 | hsa-miR-146b, hsa-miR-497*, hsa-miR-1281 | 86.5% | 93.6% | 79.4% |
| 629 | SEQ ID NO: 196, 266, 24 | hsa-miR-217, hsa-miR-615-5p, hsa-miR-330-3p | 86.5% | 93.0% | 80.0% |
| 630 | SEQ ID NO: 22, 263, 32 | hsa-miR-20b*, hsa-miR-105, hsa-miR-380* | 86.5% | 84.4% | 88.6% |
| 631 | SEQ ID NO: 231, 32, 232 | hsa-miR-93, hsa-miR-380*, hsa-miR-624 | 86.5% | 84.6% | 88.4% |
| 632 | SEQ ID NO: 242, 244, 125 | hsa-let-7i, hsa-miR-874, hsa-miR-1280 | 86.4% | 83.6% | 89.2% |
| 633 | SEQ ID NO: 242, 243, 231 | hsa-let-7i, hsa-miR-151-5p, hsa-miR-93 | 86.4% | 83.4% | 89.4% |
| 634 | SEQ ID NO: 252, 92, 243 | hsa-miR-497*, hsa-miR-802, hsa-miR-151-5p | 86.3% | 87.6% | 85.0% |
| 635 | SEQ ID NO: 243, 259, 125 | hsa-miR-151-5p, hsa-miR-631, hsa-miR-1280 | 86.2% | 85.4% | 87.0% |
| 636 | SEQ ID NO: 184, 266, 265 | hsa-miR-492, hsa-miR-615-5p, hsa-miR-129-5p | 86.2% | 88.4% | 84.0% |
| 637 | SEQ ID NO: 68, 70, 32 | hsa-miR-23b*, hsa-miR-1250, hsa-miR-380* | 86.1% | 89.0% | 83.2% |
| 638 | SEQ ID NO: 243, 22, 19 | hsa-miR-151-5p, hsa-miR-20b*, hsa-miR-767-5p | 86.1% | 83.0% | 89.2% |
| 639 | SEQ ID NO: 160, 266, 150 | hsa-miR-142-5p, hsa-miR-615-5p, hsa-miR-1234 | 86.1% | 86.4% | 85.8% |
| 640 | SEQ ID NO: 68, 70, 259 | hsa-miR-23b*, hsa-miR-1250, hsa-miR-631 | 86.0% | 92.4% | 79.6% |
| 641 | SEQ ID NO: 259, 95, 253 | hsa-miR-631, hsa-miR-135b*, hsa-miR-345 | 86.0% | 82.0% | 90.0% |
| 642 | SEQ ID NO: 31, 123, 174 | hsa-miR-139-5p, hsa-miR-146b-3p, hsa-miR-636 | 86.0% | 94.8% | 77.2% |
| 643 | SEQ ID NO: 150, 266, 24 | hsa-miR-1254, hsa-miR-615-5p, hsa-miR-330-3p | 86.0% | 92.0% | 80.0% |
| 644 | SEQ ID NO: 31, 15, 123 | hsa-miR-139-5p, hsa-miR-892b, hsa-miR-146b-3p | 85.9% | 96.8% | 75.0% |
| 645 | SEQ ID NO: 92, 68, 70 | hsa-miR-802, hsa-miR-23b*, hsa-miR-1250 | 85.9% | 91.8% | 80.0% |
| 646 | SEQ ID NO: 32, 273, 24 | hsa-miR-380*, hsa-miR-194*, hsa-miR-330-3p | 85.8% | 85.8% | 86.0% |
| 647 | SEQ ID NO: 27, 217, 62 | hsa-miR-423-5p, hsa-miR-146b, hsa-miR-1281 | 85.8% | 86.0% | 85.6% |
| 648 | SEQ ID NO: 27, 252, 62 | hsa-miR-423-5p, hsa-miR-497*, hsa-miR-1281 | 85.8% | 92.4% | 79.2% |
| 649 | SEQ ID NO: 242, 259, 244 | hsa-let-7i, hsa-miR-631, hsa-miR-874 | 85.8% | 77.8% | 93.8% |
| 650 | SEQ ID NO: 70, 265, 257 | hsa-miR-1250, hsa-miR-129-5p, hsa-miR-663b | 85.8% | 86.0% | 85.6% |
| 651 | SEQ ID NO: 265, 15, 123 | hsa-miR-129-5p, hsa-miR-892b, hsa-miR-146b-3p | 85.8% | 89.2% | 82.4% |
| 652 | SEQ ID NO: 95, 253, 31 | hsa-miR-135b*, hsa-miR-345, hsa-miR-139-5p | 85.7% | 85.4% | 86.0% |
| 653 | SEQ ID NO: 244, 254, 85 | hsa-miR-874, hsa-miR-323-3p, hsa-miR-140-5p | 85.7% | 79.6% | 91.8% |
| 654 | SEQ ID NO: 162, 234, 184 | hsa-miR-142-3p, hsa-miR-498, hsa-miR-492 | 85.7% | 85.8% | 85.6% |
| 655 | SEQ ID NO: 252, 137, 15 | hsa-miR-497*, hsa-miR-920, hsa-miR-892b | 85.7% | 95.6% | 75.8% |
| 656 | SEQ ID NO: 70, 137, 92 | hsa-miR-1250, hsa-miR-920, hsa-miR-802 | 85.7% | 90.8% | 80.6% |
| 657 | SEQ ID NO: 243, 135, 31 | hsa-miR-151-5p, hsa-miR-7-1*, hsa-miR-139-5p | 85.7% | 86.0% | 85.4% |
| 658 | SEQ ID NO: 32, 95, 157 | hsa-miR-380*, hsa-miR-135b*, hsa-miR-566 | 85.6% | 96.2% | 75.0% |
| 659 | SEQ ID NO: 15, 123, 22 | hsa-miR-892b, hsa-miR-146b-3p, hsa-miR-20b* | 85.6% | 94.0% | 77.0% |
| 660 | SEQ ID NO: 22, 174, 135 | hsa-miR-20b*, hsa-miR-636, hsa-miR-7-1* | 85.5% | 91.0% | 80.0% |
| 661 | SEQ ID NO: 16, 174, 135 | hsa-miR-455-3p, hsa-miR-636, hsa-miR-7-1* | 85.5% | 80.0% | 91.0% |
| 662 | SEQ ID NO: 70, 252, 137 | hsa-miR-1250, hsa-miR-497*, hsa-miR-920 | 85.5% | 91.0% | 80.0% |
| 663 | SEQ ID NO: 24, 231, 22 | hsa-miR-330-3p, hsa-miR-93, hsa-miR-20b* | 85.5% | 87.6% | 83.4% |
| 664 | SEQ ID NO: 16, 32, 252 | hsa-miR-455-3p, hsa-miR-380*, hsa-miR-497* | 85.5% | 86.0% | 85.0% |

Figure 28 cont.

| Set No. | SEQ-ID NO: | miRNAs | Acc | Spec | Sens |
|---|---|---|---|---|---|
| 665 | SEQ ID NO: 174, 135, 254 | hsa-miR-636, hsa-miR-7-1*, hsa-miR-323-3p | 85.4% | 80.4% | 90.4% |
| 666 | SEQ ID NO: 123, 22, 135 | hsa-miR-146b-3p, hsa-miR-20b*, hsa-miR-7-1* | 85.4% | 83.0% | 87.8% |
| 667 | SEQ ID NO: 31, 32, 273 | hsa-miR-139-5p, hsa-miR-380*, hsa-miR-194* | 85.4% | 90.4% | 80.4% |
| 668 | SEQ ID NO: 184, 162, 265 | hsa-miR-492, hsa-miR-142-5p, hsa-miR-129-5p | 85.4% | 85.4% | 85.4% |
| 669 | SEQ ID NO: 31, 273, 292 | hsa-miR-139-5p, hsa-miR-194*, hsa-miR-497* | 85.4% | 100.0% | 70.8% |
| 670 | SEQ ID NO: 71, 255, 24 | hsa-miR-30e, hsa-miR-193a-3p, hsa-miR-330-3p | 85.3% | 85.2% | 85.4% |
| 671 | SEQ ID NO: 70, 150, 257 | hsa-miR-1260, hsa-miR-1254, hsa-miR-663b | 85.3% | 91.8% | 78.8% |
| 672 | SEQ ID NO: 184, 243, 68 | hsa-miR-492, hsa-miR-151-5p, hsa-miR-23b* | 85.2% | 85.8% | 84.6% |
| 673 | SEQ ID NO: 70, 150, 95 | hsa-miR-1260, hsa-miR-1254, hsa-miR-135b* | 85.2% | 91.8% | 78.6% |
| 674 | SEQ ID NO: 250, 27, 217 | hsa-miR-374a, hsa-miR-423-5p, hsa-miR-148b | 85.2% | 84.8% | 85.6% |
| 675 | SEQ ID NO: 252, 16, 150 | hsa-miR-497*, hsa-miR-455-3p, hsa-miR-1254 | 85.2% | 90.4% | 80.0% |
| 676 | SEQ ID NO: 255, 35, 242 | hsa-miR-193a-3p, hsa-miR-188-3p, hsa-let-7i | 85.2% | 85.8% | 84.5% |
| 677 | SEQ ID NO: 16, 252, 137 | hsa-miR-455-3p, hsa-miR-497*, hsa-miR-920 | 85.2% | 83.0% | 81.4% |
| 678 | SEQ ID NO: 70, 286, 265 | hsa-miR-1260, hsa-miR-615-5p, hsa-miR-129-5p | 85.2% | 89.2% | 81.2% |
| 679 | SEQ ID NO: 19, 32, 273 | hsa-miR-767-5p, hsa-miR-380*, hsa-miR-194* | 85.2% | 88.6% | 81.8% |
| 680 | SEQ ID NO: 31, 22, 174 | hsa-miR-139-5p, hsa-miR-20b*, hsa-miR-636 | 85.1% | 87.6% | 82.6% |
| 681 | SEQ ID NO: 217, 116, 16 | hsa-miR-148b, hsa-miR-339-3p, hsa-miR-455-3p | 85.1% | 81.6% | 88.6% |
| 682 | SEQ ID NO: 135, 255, 35 | hsa-miR-7-1*, hsa-miR-193a-3p, hsa-miR-188-3p | 85.1% | 85.2% | 85.0% |
| 683 | SEQ ID NO: 156, 24, 22 | hsa-miR-217, hsa-miR-330-3p, hsa-miR-20b* | 85.1% | 85.6% | 84.6% |
| 684 | SEQ ID NO: 135, 255, 24 | hsa-miR-7-1*, hsa-miR-193a-3p, hsa-miR-330-3p | 85.0% | 86.0% | 84.0% |
| 685 | SEQ ID NO: 253, 174, 255 | hsa-miR-345, hsa-miR-636, hsa-miR-193a-3p | 85.0% | 89.8% | 80.2% |
| 686 | SEQ ID NO: 123, 95, 156 | hsa-miR-146b-3p, hsa-miR-135b*, hsa-miR-217 | 85.0% | 95.4% | 74.6% |
| 687 | SEQ ID NO: 71, 85, 35 | hsa-miR-30e, hsa-miR-140-5p, hsa-miR-188-3p | 84.9% | 85.6% | 84.2% |
| 688 | SEQ ID NO: 116, 252, 61 | hsa-miR-339-3p, hsa-miR-497*, hsa-miR-1281 | 84.9% | 89.8% | 80.0% |
| 689 | SEQ ID NO: 255, 24, 167 | hsa-miR-193a-3p, hsa-miR-330-3p, hsa-miR-627 | 84.9% | 89.6% | 80.2% |
| 690 | SEQ ID NO: 24, 22, 269 | hsa-miR-330-3p, hsa-miR-20b*, hsa-miR-105 | 84.9% | 92.4% | 77.4% |
| 691 | SEQ ID NO: 269, 135, 71 | hsa-miR-105, hsa-miR-7-1*, hsa-miR-30e | 84.9% | 90.0% | 79.8% |
| 692 | SEQ ID NO: 150, 253, 135 | hsa-miR-1254, hsa-miR-345, hsa-miR-7-1* | 84.8% | 90.0% | 79.6% |
| 693 | SEQ ID NO: 16, 70, 137 | hsa-miR-455-3p, hsa-miR-1260, hsa-miR-920 | 84.8% | 82.2% | 87.4% |
| 694 | SEQ ID NO: 257, 15, 95 | hsa-miR-663b, hsa-miR-892b, hsa-miR-135b* | 84.8% | 94.4% | 75.2% |
| 695 | SEQ ID NO: 137, 184, 286 | hsa-miR-920, hsa-miR-492, hsa-miR-615-5p | 84.8% | 94.8% | 74.8% |
| 696 | SEQ ID NO: 157, 253, 15 | hsa-miR-566, hsa-miR-345, hsa-miR-892b | 84.7% | 85.2% | 84.2% |
| 697 | SEQ ID NO: 253, 31, 22 | hsa-miR-345, hsa-miR-139-5p, hsa-miR-20b* | 84.7% | 83.8% | 85.6% |
| 698 | SEQ ID NO: 265, 156, 24 | hsa-miR-129-5p, hsa-miR-217, hsa-miR-330-3p | 84.7% | 84.4% | 85.0% |
| 699 | SEQ ID NO: 285, 286, 231 | hsa-miR-129-5p, hsa-miR-615-5p, hsa-miR-93 | 84.7% | 84.4% | 85.0% |
| 700 | SEQ ID NO: 254, 85, 255 | hsa-miR-323-3p, hsa-miR-140-5p, hsa-miR-193a-3p | 84.6% | 84.6% | 84.6% |
| 701 | SEQ ID NO: 217, 116, 62 | hsa-miR-148b, hsa-miR-339-3p, hsa-miR-1281 | 84.6% | 86.2% | 83.0% |
| 702 | SEQ ID NO: 174, 135, 35 | hsa-miR-636, hsa-miR-7-1*, hsa-miR-188-3p | 84.6% | 79.8% | 89.4% |
| 703 | SEQ ID NO: 123, 95, 265 | hsa-miR-146b-3p, hsa-miR-135b*, hsa-miR-129-5p | 84.6% | 89.2% | 80.0% |
| 704 | SEQ ID NO: 15, 123, 95 | hsa-miR-892b, hsa-miR-146b-3p, hsa-miR-135b* | 84.6% | 99.0% | 70.2% |
| 705 | SEQ ID NO: 31, 32, 292 | hsa-miR-139-5p, hsa-miR-380*, hsa-miR-497* | 84.6% | 90.0% | 79.2% |
| 706 | SEQ ID NO: 32, 150, 157 | hsa-miR-380*, hsa-miR-1254, hsa-miR-566 | 84.5% | 84.6% | 84.4% |
| 707 | SEQ ID NO: 52, 243, 70 | hsa-miR-602, hsa-miR-151-5p, hsa-miR-1260 | 84.5% | 84.0% | 85.0% |
| 708 | SEQ ID NO: 242, 244, 231 | hsa-let-7i, hsa-miR-874, hsa-miR-93 | 84.5% | 79.4% | 89.6% |
| 709 | SEQ ID NO: 255, 35, 24 | hsa-miR-193a-3p, hsa-miR-188-3p, hsa-miR-330-3p | 84.5% | 92.0% | 77.0% |
| 710 | SEQ ID NO: 24, 231, 32 | hsa-miR-330-3p, hsa-miR-93, hsa-miR-380* | 84.5% | 77.8% | 91.2% |
| 711 | SEQ ID NO: 32, 259, 150 | hsa-miR-380*, hsa-miR-631, hsa-miR-1254 | 84.4% | 80.4% | 88.4% |
| 712 | SEQ ID NO: 31, 15, 22 | hsa-miR-139-5p, hsa-miR-892b, hsa-miR-20b* | 84.4% | 93.8% | 75.0% |

| Set No. | SEQ-ID NO: | miRNAs | Acc | Spec | Sens |
|---|---|---|---|---|---|
| 814 | SEQ ID NO: 243, 22, 31 | hsa-miR-151-5p, hsa-miR-20b*, hsa-miR-139-5p | 81.7% | 74.3% | 88.6% |
| 815 | SEQ ID NO: 18, 73, 150 | hsa-miR-489-3p, hsa-miR-1290, hsa-miR-1254 | 81.6% | 77.2% | 86.0% |
| 816 | SEQ ID NO: 135, 71, 243 | hsa-miR-7-1*, hsa-miR-30e, hsa-miR-151-5p | 81.6% | 80.4% | 82.8% |
| 817 | SEQ ID NO: 251, 27, 252 | hsa-miR-182, hsa-miR-423-5p, hsa-miR-497* | 81.6% | 96.9% | 66.4% |
| 818 | SEQ ID NO: 73, 252, 92 | hsa-miR-1290, hsa-miR-497*, hsa-miR-362 | 81.5% | 90.0% | 73.0% |
| 819 | SEQ ID NO: 174, 244, 135 | hsa-miR-636, hsa-miR-874, hsa-miR-7-1* | 81.4% | 71.2% | 91.6% |
| 820 | SEQ ID NO: 243, 22, 135 | hsa-miR-151-5p, hsa-miR-20b*, hsa-miR-7-1* | 81.4% | 70.0% | 92.8% |
| 821 | SEQ ID NO: 156, 243, 22 | hsa-miR-217, hsa-miR-151-5p, hsa-miR-20b* | 81.4% | 72.8% | 90.0% |
| 822 | SEQ ID NO: 246, 59, 181 | hsa-miR-20a, hsa-miR-1301, hsa-miR-145 | 81.3% | 84.6% | 78.0% |
| 823 | SEQ ID NO: 71, 24, 244 | hsa-miR-30e, hsa-miR-330-3p, hsa-miR-874 | 81.3% | 75.8% | 86.8% |
| 824 | SEQ ID NO: 244, 135, 85 | hsa-miR-874, hsa-miR-7-1*, hsa-miR-140-5p | 81.2% | 68.6% | 92.8% |
| 825 | SEQ ID NO: 27, 116, 62 | hsa-miR-423-5p, hsa-miR-339-3p, hsa-miR-1231 | 81.2% | 86.8% | 75.6% |
| 826 | SEQ ID NO: 251, 116, 252 | hsa-miR-182, hsa-miR-339-3p, hsa-miR-497* | 81.2% | 83.0% | 79.4% |
| 827 | SEQ ID NO: 22, 32, 232 | hsa-miR-20b*, hsa-miR-380*, hsa-miR-624 | 81.1% | 85.2% | 77.0% |
| 828 | SEQ ID NO: 16, 32, 273 | hsa-miR-455-3p, hsa-miR-380*, hsa-miR-194* | 81.1% | 81.2% | 81.0% |
| 829 | SEQ ID NO: 174, 135, 71 | hsa-miR-636, hsa-miR-7-1*, hsa-miR-30e | 81.0% | 75.8% | 86.2% |
| 830 | SEQ ID NO: 27, 116, 252 | hsa-miR-423-5p, hsa-miR-339-3p, hsa-miR-497* | 81.0% | 87.4% | 74.6% |
| 831 | SEQ ID NO: 70, 265, 150 | hsa-miR-1258, hsa-miR-129-5p, hsa-miR-1254 | 81.0% | 83.8% | 78.2% |
| 832 | SEQ ID NO: 156, 243, 135 | hsa-miR-217, hsa-miR-151-5p, hsa-miR-7-1* | 81.0% | 71.2% | 90.8% |
| 833 | SEQ ID NO: 18, 73, 259 | hsa-miR-489-3p, hsa-miR-1290, hsa-miR-631 | 80.9% | 75.0% | 86.8% |
| 834 | SEQ ID NO: 156, 22, 135 | hsa-miR-217, hsa-miR-20b*, hsa-miR-7-1* | 80.9% | 70.4% | 91.4% |
| 835 | SEQ ID NO: 24, 242, 259 | hsa-miR-330-3p, hsa-let-7i, hsa-miR-631 | 80.8% | 73.4% | 88.2% |
| 836 | SEQ ID NO: 71, 24, 167 | hsa-miR-30e, hsa-miR-330-3p, hsa-miR-607 | 80.7% | 75.4% | 86.0% |
| 837 | SEQ ID NO: 135, 31, 32 | hsa-miR-7-1*, hsa-miR-139-5p, hsa-miR-380* | 80.7% | 80.6% | 80.8% |
| 838 | SEQ ID NO: 71, 242, 244 | hsa-miR-30e, hsa-let-7i, hsa-miR-874 | 80.6% | 74.2% | 87.0% |
| 839 | SEQ ID NO: 35, 167, 243 | hsa-miR-188-3p, hsa-miR-627, hsa-miR-151-5p | 80.6% | 80.8% | 80.4% |
| 840 | SEQ ID NO: 156, 266, 231 | hsa-miR-217, hsa-miR-615-3p, hsa-miR-93 | 80.6% | 83.4% | 77.8% |
| 841 | SEQ ID NO: 231, 268, 32 | hsa-miR-93, hsa-miR-105, hsa-miR-380* | 80.6% | 77.0% | 84.2% |
| 842 | SEQ ID NO: 31, 123, 22 | hsa-miR-139-5p, hsa-miR-146b-3p, hsa-miR-20b* | 80.4% | 85.6% | 75.2% |
| 843 | SEQ ID NO: 246, 247, 181 | hsa-miR-20a, hsa-miR-148a, hsa-miR-143 | 80.4% | 86.8% | 74.2% |
| 844 | SEQ ID NO: 245, 199, 247 | hsa-miR-106a, hsa-miR-484, hsa-miR-148a | 80.4% | 89.4% | 71.4% |
| 845 | SEQ ID NO: 66, 199, 169 | hsa-miR-1285, hsa-miR-484, hsa-miR-324-3p | 80.4% | 79.8% | 81.0% |
| 846 | SEQ ID NO: 95, 150, 156 | hsa-miR-135b*, hsa-miR-1254, hsa-miR-217 | 80.4% | 85.0% | 75.8% |
| 847 | SEQ ID NO: 31, 16, 32 | hsa-miR-139-5p, hsa-miR-455-3p, hsa-miR-380* | 80.4% | 80.4% | 80.4% |
| 848 | SEQ ID NO: 22, 232, 135 | hsa-miR-20b*, hsa-miR-624, hsa-miR-7-1* | 80.3% | 77.2% | 83.4% |
| 849 | SEQ ID NO: 59, 181, 248 | hsa-miR-1301, hsa-miR-145, hsa-let-7b | 80.2% | 95.0% | 65.4% |
| 850 | SEQ ID NO: 16, 32, 23 | hsa-miR-455-3p, hsa-miR-380*, hsa-miR-491-3p | 80.2% | 75.8% | 84.6% |
| 851 | SEQ ID NO: 244, 135, 71 | hsa-miR-874, hsa-miR-7-1*, hsa-miR-30e | 80.1% | 75.0% | 85.2% |
| 852 | SEQ ID NO: 169, 246, 181 | hsa-miR-324-3p, hsa-miR-20a, hsa-miR-145 | 80.1% | 79.6% | 80.6% |
| 853 | SEQ ID NO: 150, 265, 266 | hsa-miR-1254, hsa-miR-129-5p, hsa-miR-615-5p | 80.1% | 85.2% | 75.0% |
| 854 | SEQ ID NO: 15, 123, 244 | hsa-miR-892b, hsa-miR-146b-3p, hsa-miR-874 | 80.0% | 90.0% | 70.0% |
| 855 | SEQ ID NO: 253, 109, 68 | hsa-miR-631, hsa-miR-1289, hsa-miR-1293 | 80.0% | 84.6% | 75.4% |
| 856 | SEQ ID NO: 24, 242, 244 | hsa-miR-330-3p, hsa-let-7i, hsa-miR-874 | 79.9% | 75.0% | 84.8% |
| 857 | SEQ ID NO: 123, 95, 150 | hsa-miR-146b-3p, hsa-miR-135b*, hsa-miR-1254 | 79.9% | 87.4% | 72.4% |
| 858 | SEQ ID NO: 32, 232, 135 | hsa-miR-380*, hsa-miR-624, hsa-miR-7-1* | 79.7% | 85.2% | 74.2% |
| 859 | SEQ ID NO: 156, 231, 22 | hsa-miR-217, hsa-miR-93, hsa-miR-20b* | 79.7% | 75.8% | 83.6% |
| 860 | SEQ ID NO: 199, 169, 247 | hsa-miR-484, hsa-miR-324-3p, hsa-miR-148a | 79.6% | 85.0% | 74.2% |
| 861 | SEQ ID NO: 244, 135, 155 | hsa-miR-874, hsa-miR-1285, hsa-miR-484 | 79.5% | 79.0% | 80.0% |
| 862 | SEQ ID NO: 156, 24, 231 | hsa-miR-217, hsa-miR-330-3p, hsa-miR-93 | 79.5% | 79.8% | 79.2% |
| 863 | SEQ ID NO: 150, 123, 95 | hsa-miR-1254, hsa-miR-146b-3p, hsa-miR- | 79.4% | 87.2% | 71.6% |

Figure 28 cont.

| Set No. | SEQ-ID NO: | miRNAs | Acc | Spec | Sens |
|---|---|---|---|---|---|
| | | 135b* | | | |
| 864 | SEQ ID NO: 32, 23, 24 | hsa-miR-380*, hsa-miR-491-3p, hsa-miR-330-3p | 79.3% | 73.8% | 84.8% |
| 865 | SEQ ID NO: 22, 174, 244 | hsa-miR-206*, hsa-miR-636, hsa-miR-874 | 79.2% | 75.0% | 83.2% |
| 866 | SEQ ID NO: 244, 231, 155 | hsa-miR-874, hsa-miR-93, hsa-miR-484 | 79.2% | 72.8% | 85.6% |
| 867 | SEQ ID NO: 24, 242, 125 | hsa-miR-330-3p, hsa-let-7i, hsa-miR-1285 | 79.2% | 72.6% | 85.8% |
| 868 | SEQ ID NO: 250, 217, 116 | hsa-miR-374a, hsa-miR-148b, hsa-miR-339-3p | 79.2% | 76.8% | 81.3% |
| 869 | SEQ ID NO: 244, 125, 245 | hsa-miR-874, hsa-miR-1285, hsa-miR-196a | 79.1% | 77.6% | 80.6% |
| 870 | SEQ ID NO: 99, 181, 249 | hsa-miR-1301, hsa-miR-145, hsa-miR-336* | 79.1% | 73.2% | 85.0% |
| 871 | SEQ ID NO: 266, 265, 150 | hsa-miR-615-5p, hsa-miR-129-5p, hsa-miR-1254 | 79.1% | 83.8% | 74.4% |
| 872 | SEQ ID NO: 22, 135, 31 | hsa-miR-206*, hsa-miR-7-1*, hsa-miR-139-5p | 79.1% | 71.8% | 86.4% |
| 873 | SEQ ID NO: 135, 234, 71 | hsa-miR-7-1*, hsa-miR-323-3p, hsa-miR-30e | 79.0% | 77.0% | 81.0% |
| 874 | SEQ ID NO: 24, 167, 242 | hsa-miR-330-3p, hsa-miR-627, hsa-let-7i | 79.0% | 71.2% | 86.8% |
| 875 | SEQ ID NO: 31, 16, 273 | hsa-miR-139-5p, hsa-miR-455-3p, hsa-miR-194* | 79.0% | 79.8% | 78.2% |
| 876 | SEQ ID NO: 155, 247, 59 | hsa-miR-484, hsa-miR-148a, hsa-miR-1301 | 78.9% | 88.0% | 69.8% |
| 877 | SEQ ID NO: 265, 150, 15 | hsa-miR-129-5p, hsa-miR-1254, hsa-miR-890b | 78.9% | 83.8% | 74.0% |
| 878 | SEQ ID NO: 150, 265, 156 | hsa-miR-1254, hsa-miR-129-5p, hsa-miR-217 | 78.8% | 86.8% | 70.8% |
| 879 | SEQ ID NO: 156, 266, 22 | hsa-miR-217, hsa-miR-615-5p, hsa-miR-206* | 78.8% | 76.0% | 81.4% |
| 880 | SEQ ID NO: 265, 24, 231 | hsa-miR-129-5p, hsa-miR-330-3p, hsa-miR-93 | 78.8% | 73.2% | 82.4% |
| 881 | SEQ ID NO: 16, 252, 23 | hsa-miR-455-3p, hsa-miR-497*, hsa-miR-491-3p | 78.6% | 84.6% | 72.6% |
| 882 | SEQ ID NO: 125, 231, 66 | hsa-miR-1285, hsa-miR-93, hsa-miR-1295 | 78.5% | 80.4% | 76.6% |
| 883 | SEQ ID NO: 95, 150, 266 | hsa-miR-135b*, hsa-miR-1254, hsa-miR-615-5p | 78.5% | 79.6% | 77.4% |
| 884 | SEQ ID NO: 125, 66, 245 | hsa-miR-1285, hsa-miR-1295, hsa-miR-196a | 78.2% | 83.6% | 72.8% |
| 885 | SEQ ID NO: 174, 259, 39 | hsa-miR-636, hsa-miR-193a-3p, hsa-miR-188-3p | 78.2% | 86.6% | 69.8% |
| 886 | SEQ ID NO: 273, 252, 23 | hsa-miR-194*, hsa-miR-497*, hsa-miR-491-3p | 78.2% | 85.6% | 70.8% |
| 887 | SEQ ID NO: 19, 31, 32 | hsa-miR-767-5p, hsa-miR-139-5p, hsa-miR-380* | 78.2% | 76.6% | 79.8% |
| 888 | SEQ ID NO: 248, 12, 250 | hsa-let-7b, hsa-miR-128, hsa-miR-374a | 78.1% | 73.6% | 83.6% |
| 889 | SEQ ID NO: 125, 66, 155 | hsa-miR-1285, hsa-miR-1295, hsa-miR-484 | 78.0% | 74.0% | 82.0% |
| 890 | SEQ ID NO: 247, 59, 181 | hsa-miR-148a, hsa-miR-1301, hsa-miR-145 | 77.8% | 77.8% | 78.2% |
| 891 | SEQ ID NO: 245, 246, 247 | hsa-miR-196a, hsa-miR-20a, hsa-miR-148a | 77.8% | 86.6% | 69.2% |
| 892 | SEQ ID NO: 250, 251, 217 | hsa-miR-374a, hsa-miR-182, hsa-miR-148b | 77.8% | 78.4% | 77.0% |
| 893 | SEQ ID NO: 32, 239, 95 | hsa-miR-380*, hsa-miR-621, hsa-miR-135b* | 77.7% | 78.4% | 77.0% |
| 894 | SEQ ID NO: 217, 116, 252 | hsa-miR-148b, hsa-miR-339-3p, hsa-miR-497* | 77.7% | 78.8% | 76.6% |
| 895 | SEQ ID NO: 231, 66, 155 | hsa-miR-93, hsa-miR-1295, hsa-miR-484 | 77.7% | 73.4% | 82.0% |
| 896 | SEQ ID NO: 181, 12, 249 | hsa-miR-145, hsa-miR-128, hsa-miR-33b* | 77.6% | 71.8% | 83.4% |
| 897 | SEQ ID NO: 244, 125, 66 | hsa-miR-874, hsa-miR-1285, hsa-miR-1295 | 77.6% | 75.4% | 79.6% |
| 898 | SEQ ID NO: 150, 135, 71 | hsa-miR-1254, hsa-miR-7-1*, hsa-miR-30e | 77.5% | 66.4% | 88.6% |
| 899 | SEQ ID NO: 252, 23, 24 | hsa-miR-497*, hsa-miR-491-3p, hsa-miR-330-3p | 77.5% | 80.4% | 74.6% |
| 900 | SEQ ID NO: 135, 242, 243 | hsa-miR-7-1*, hsa-let-7i, hsa-miR-151-5p | 77.4% | 84.8% | 70.0% |
| 901 | SEQ ID NO: 265, 156, 266 | hsa-miR-129-5p, hsa-miR-217, hsa-miR-615-5p | 77.4% | 88.4% | 66.4% |
| 902 | SEQ ID NO: 259, 231, 66 | hsa-miR-631, hsa-miR-93, hsa-miR-1295 | 77.1% | 78.4% | 75.8% |
| 903 | SEQ ID NO: 95, 265, 156 | hsa-miR-135b*, hsa-miR-129-5p, hsa-miR-217 | 77.1% | 84.0% | 70.2% |
| 904 | SEQ ID NO: 231, 155, 169 | hsa-miR-93, hsa-miR-484, hsa-miR-324-3p | 77.0% | 71.4% | 82.6% |
| 905 | SEQ ID NO: 269, 32, 71 | hsa-miR-105, hsa-miR-380*, hsa-miR-30e | 77.0% | 80.0% | 74.0% |
| 906 | SEQ ID NO: 24, 167, 259 | hsa-miR-330-3p, hsa-miR-627, hsa-miR-631 | 76.9% | 77.4% | 76.4% |
| 907 | SEQ ID NO: 66, 169, 246 | hsa-miR-1295, hsa-miR-324-3p, hsa-miR-20a | 76.8% | 80.6% | 73.0% |
| 908 | SEQ ID NO: 95, 156, 266 | hsa-miR-135b*, hsa-miR-217, hsa-miR-615-5p | 76.7% | 73.6% | 79.8% |
| 909 | SEQ ID NO: 125, 231, 155 | hsa-miR-1285, hsa-miR-93, hsa-miR-484 | 76.6% | 68.4% | 84.8% |
| 910 | SEQ ID NO: 244, 231, 245 | hsa-miR-874, hsa-miR-93, hsa-miR-196a | 76.6% | 73.6% | 79.6% |
| 911 | SEQ ID NO: 247, 181, 12 | hsa-miR-148a, hsa-miR-145, hsa-miR-128 | 76.6% | 83.4% | 69.8% |
| 912 | SEQ ID NO: 125, 231, 169 | hsa-miR-1285, hsa-miR-93, hsa-miR-324-3p | 76.6% | 69.2% | 83.8% |

Figure 28 cont.

| Set No. | SEQ-ID NO: | miRNAs | Acc | Spec | Sens |
|---|---|---|---|---|---|
| 913 | SEQ ID NO: 242, 125, 131 | hsa-let-7i, hsa-miR-1285, hsa-miR-93 | 76.6% | 75.0% | 83.2% |
| 914 | SEQ ID NO: 251, 27, 217 | hsa-miR-182, hsa-miR-423-5p, hsa-miR-148b | 76.5% | 71.0% | 82.0% |
| 915 | SEQ ID NO: 190, 156, 266 | hsa-miR-1254, hsa-miR-217, hsa-miR-615-5p | 76.5% | 78.8% | 74.2% |
| 916 | SEQ ID NO: 16, 273, 252 | hsa-miR-455-3p, hsa-miR-194*, hsa-miR-487* | 76.4% | 80.6% | 72.0% |
| 917 | SEQ ID NO: 169, 247, 181 | hsa-miR-324-3p, hsa-miR-148a, hsa-miR-145 | 76.3% | 72.8% | 79.8% |
| 918 | SEQ ID NO: 155, 246, 247 | hsa-miR-484, hsa-miR-20a, hsa-miR-148a | 76.1% | 84.6% | 67.6% |
| 919 | SEQ ID NO: 169, 59, 181 | hsa-miR-324-3p, hsa-miR-1301, hsa-miR-145 | 76.1% | 85.2% | 67.0% |
| 920 | SEQ ID NO: 19, 31, 273 | hsa-miR-767-5p, hsa-miR-139-5p, hsa-miR-194* | 76.1% | 81.8% | 70.4% |
| 921 | SEQ ID NO: 155, 169, 59 | hsa-miR-484, hsa-miR-324-3p, hsa-miR-1301 | 76.0% | 76.6% | 75.4% |
| 922 | SEQ ID NO: 244, 231, 66 | hsa-miR-874, hsa-miR-93, hsa-miR-1295 | 76.0% | 77.6% | 74.4% |
| 923 | SEQ ID NO: 59, 248, 249 | hsa-miR-1301, hsa-let-7b, hsa-miR-33b* | 75.9% | 83.0% | 68.8% |
| 924 | SEQ ID NO: 41, 251, 217 | hsa-miR-654-5p, hsa-miR-182, hsa-miR-148b | 75.7% | 75.4% | 76.0% |
| 925 | SEQ ID NO: 95, 190, 265 | hsa-miR-135b*, hsa-miR-1254, hsa-miR-129-5p | 75.7% | 81.0% | 70.4% |
| 926 | SEQ ID NO: 95, 156, 243 | hsa-miR-135b*, hsa-miR-217, hsa-miR-151-5p | 75.7% | 68.0% | 83.4% |
| 927 | SEQ ID NO: 255, 35, 167 | hsa-miR-193a-3p, hsa-miR-188-3p, hsa-miR-627 | 75.6% | 70.0% | 81.2% |
| 928 | SEQ ID NO: 231, 66, 245 | hsa-miR-93, hsa-miR-1295, hsa-miR-106a | 75.5% | 75.0% | 76.0% |
| 929 | SEQ ID NO: 167, 259, 244 | hsa-miR-627, hsa-miR-631, hsa-miR-874 | 75.5% | 79.8% | 71.2% |
| 930 | SEQ ID NO: 125, 155, 169 | hsa-miR-1285, hsa-miR-484, hsa-miR-324-3p | 75.4% | 69.6% | 81.2% |
| 931 | SEQ ID NO: 16, 273, 23 | hsa-miR-455-3p, hsa-miR-194*, hsa-miR-491-3p | 75.4% | 74.4% | 76.4% |
| 932 | SEQ ID NO: 59, 12, 249 | hsa-miR-1301, hsa-miR-128, hsa-miR-33b* | 75.3% | 83.8% | 66.8% |
| 933 | SEQ ID NO: 66, 245, 246 | hsa-miR-1295, hsa-miR-106a, hsa-miR-20a | 75.3% | 80.4% | 70.2% |
| 934 | SEQ ID NO: 41, 250, 27 | hsa-miR-654-5p, hsa-miR-374a, hsa-miR-423-5p | 75.1% | 68.4% | 81.8% |
| 935 | SEQ ID NO: 66, 155, 246 | hsa-miR-1295, hsa-miR-484, hsa-miR-20a | 74.9% | 79.6% | 70.2% |
| 936 | SEQ ID NO: 244, 66, 245 | hsa-miR-874, hsa-miR-1295, hsa-miR-106a | 74.9% | 76.0% | 73.8% |
| 937 | SEQ ID NO: 265, 156, 231 | hsa-miR-129-5p, hsa-miR-217, hsa-miR-93 | 74.8% | 77.6% | 72.0% |
| 938 | SEQ ID NO: 32, 135, 71 | hsa-miR-380*, hsa-miR-7-3*, hsa-miR-30e | 74.8% | 67.4% | 82.2% |
| 939 | SEQ ID NO: 231, 66, 169 | hsa-miR-93, hsa-miR-1295, hsa-miR-324-3p | 74.7% | 76.4% | 73.0% |
| 940 | SEQ ID NO: 259, 244, 66 | hsa-miR-631, hsa-miR-874, hsa-miR-1295 | 74.5% | 79.6% | 69.4% |
| 941 | SEQ ID NO: 251, 27, 116 | hsa-miR-182, hsa-miR-423-5p, hsa-miR-339-3p | 74.4% | 69.8% | 79.0% |
| 942 | SEQ ID NO: 181, 12, 41 | hsa-miR-145, hsa-miR-128, hsa-miR-654-5p | 74.4% | 67.2% | 81.6% |
| 943 | SEQ ID NO: 190, 95, 31 | hsa-miR-1254, hsa-miR-135b*, hsa-miR-139-5p | 74.0% | 77.8% | 70.2% |
| 944 | SEQ ID NO: 27, 217, 116 | hsa-miR-423-5p, hsa-miR-148b, hsa-miR-339-3p | 74.0% | 78.2% | 69.8% |
| 945 | SEQ ID NO: 247, 59, 248 | hsa-miR-148a, hsa-miR-1301, hsa-let-7b | 74.0% | 84.2% | 63.8% |
| 946 | SEQ ID NO: 244, 245, 155 | hsa-miR-874, hsa-miR-106a, hsa-miR-484 | 74.0% | 64.6% | 83.4% |
| 947 | SEQ ID NO: 35, 24, 167 | hsa-miR-188-3p, hsa-miR-330-3p, hsa-miR-627 | 73.9% | 70.4% | 77.4% |
| 948 | SEQ ID NO: 248, 249, 250 | hsa-let-7b, hsa-miR-33b*, hsa-miR-374a | 73.7% | 69.8% | 77.6% |
| 949 | SEQ ID NO: 125, 231, 245 | hsa-miR-1285, hsa-miR-93, hsa-miR-106a | 73.6% | 71.6% | 75.6% |
| 950 | SEQ ID NO: 248, 12, 41 | hsa-let-7b, hsa-miR-128, hsa-miR-654-5p | 73.6% | 62.0% | 85.2% |
| 951 | SEQ ID NO: 248, 249, 41 | hsa-let-7b, hsa-miR-33b*, hsa-miR-654-5p | 73.3% | 70.4% | 76.2% |
| 952 | SEQ ID NO: 95, 265, 266 | hsa-miR-135b*, hsa-miR-129-5p, hsa-miR-615-5p | 73.3% | 72.0% | 74.6% |
| 953 | SEQ ID NO: 156, 169, 243 | hsa-miR-217, hsa-miR-185, hsa-miR-151-5p | 73.2% | 74.6% | 71.8% |
| 954 | SEQ ID NO: 41, 250, 251 | hsa-miR-654-5p, hsa-miR-374a, hsa-miR-182 | 73.1% | 82.8% | 63.4% |
| 955 | SEQ ID NO: 41, 251, 27 | hsa-miR-654-5p, hsa-miR-182, hsa-miR-423-5p | 73.0% | 77.4% | 68.6% |
| 956 | SEQ ID NO: 248, 12, 249 | hsa-let-7b, hsa-miR-128, hsa-miR-33b* | 72.8% | 62.6% | 83.0% |
| 957 | SEQ ID NO: 19, 16, 273 | hsa-miR-767-5p, hsa-miR-455-3p, hsa-miR-194* | 72.7% | 77.8% | 67.6% |
| 958 | SEQ ID NO: 12, 249, 41 | hsa-miR-128, hsa-miR-33b*, hsa-miR-654-5p | 72.6% | 68.6% | 76.6% |
| 959 | SEQ ID NO: 247, 59, 12 | hsa-miR-148a, hsa-miR-1301, hsa-miR-128 | 72.4% | 86.8% | 58.0% |
| 960 | SEQ ID NO: 66, 245, 169 | hsa-miR-1295, hsa-miR-106a, hsa-miR-324-3p | 72.3% | 78.2% | 66.4% |

Figure 28 cont.

| Set No. | SEQ ID NO: | miRNAs | Acc | Spec | Sens |
|---|---|---|---|---|---|
| 961 | SEQ ID NO: 231, 169, 246 | hsa-miR-93, hsa-miR-324-3p, hsa-miR-20a | 72.1% | 65.0% | 79.2% |
| 962 | SEQ ID NO: 249, 41, 27 | hsa-miR-33b*, hsa-miR-654-5p, hsa-miR-423-5p | 71.9% | 64.0% | 79.8% |
| 963 | SEQ ID NO: 155, 169, 246 | hsa-miR-484, hsa-miR-324-3p, hsa-miR-20a | 71.6% | 64.4% | 78.8% |
| 964 | SEQ ID NO: 231, 155, 246 | hsa-miR-93, hsa-miR-484, hsa-miR-20a | 71.4% | 72.2% | 70.6% |
| 965 | SEQ ID NO: 248, 41, 250 | hsa-let-7b, hsa-miR-654-5p, hsa-miR-374a | 71.4% | 70.6% | 72.2% |
| 966 | SEQ ID NO: 231, 245, 155 | hsa-miR-93, hsa-miR-106a, hsa-miR-484 | 71.3% | 72.2% | 70.4% |
| 967 | SEQ ID NO: 135, 71, 242 | hsa-miR-7-1*, hsa-miR-30a, hsa-let-7i | 71.3% | 69.2% | 73.4% |
| 968 | SEQ ID NO: 273, 23, 34 | hsa-miR-194*, hsa-miR-491-3p, hsa-miR-339-3p | 71.2% | 70.6% | 71.8% |
| 969 | SEQ ID NO: 181, 248, 41 | hsa-miR-145, hsa-let-7b, hsa-miR-654-5p | 71.0% | 78.8% | 63.2% |
| 970 | SEQ ID NO: 245, 155, 169 | hsa-miR-106a, hsa-miR-484, hsa-miR-324-3p | 70.9% | 68.4% | 73.4% |
| 971 | SEQ ID NO: 251, 217, 116 | hsa-miR-182, hsa-miR-148b, hsa-miR-339-3p | 70.8% | 60.0% | 81.8% |
| 972 | SEQ ID NO: 12, 249, 251 | hsa-miR-128, hsa-miR-33b*, hsa-miR-182 | 70.8% | 61.6% | 80.2% |
| 973 | SEQ ID NO: 246, 247, 99 | hsa-miR-20a, hsa-miR-148a, hsa-miR-1301 | 70.8% | 86.6% | 55.0% |
| 974 | SEQ ID NO: 231, 245, 169 | hsa-miR-93, hsa-miR-106a, hsa-miR-324-3p | 70.6% | 67.2% | 74.0% |
| 975 | SEQ ID NO: 249, 41, 251 | hsa-miR-33b*, hsa-miR-654-5p, hsa-miR-182 | 70.6% | 77.0% | 64.2% |
| 976 | SEQ ID NO: 245, 169, 246 | hsa-miR-106a, hsa-miR-324-3p, hsa-miR-20a | 70.6% | 70.8% | 70.4% |
| 977 | SEQ ID NO: 247, 181, 248 | hsa-miR-148a, hsa-miR-145, hsa-let-7b | 70.4% | 64.6% | 76.2% |
| 978 | SEQ ID NO: 125, 245, 169 | hsa-miR-1285, hsa-miR-106a, hsa-miR-324-3p | 70.4% | 67.0% | 73.8% |
| 979 | SEQ ID NO: 247, 248, 12 | hsa-miR-148a, hsa-let-7b, hsa-miR-128 | 70.3% | 73.2% | 67.4% |
| 980 | SEQ ID NO: 12, 250, 251 | hsa-miR-128, hsa-miR-374a, hsa-miR-182 | 70.1% | 74.4% | 65.8% |
| 981 | SEQ ID NO: 12, 249, 250 | hsa-miR-128, hsa-miR-33b*, hsa-miR-374a | 70.0% | 71.4% | 68.6% |
| 982 | SEQ ID NO: 246, 247, 248 | hsa-miR-20a, hsa-miR-148a, hsa-let-7b | 69.6% | 73.0% | 66.2% |
| 983 | SEQ ID NO: 181, 248, 249 | hsa-miR-145, hsa-let-7b, hsa-miR-33b* | 69.3% | 78.6% | 60.0% |
| 984 | SEQ ID NO: 249, 250, 27 | hsa-miR-33b*, hsa-miR-374a, hsa-miR-423-5p | 69.3% | 71.8% | 66.8% |
| 985 | SEQ ID NO: 99, 248, 12 | hsa-miR-1301, hsa-let-7b, hsa-miR-128 | 69.1% | 80.4% | 57.8% |
| 986 | SEQ ID NO: 169, 246, 99 | hsa-miR-324-3p, hsa-miR-20a, hsa-miR-1301 | 68.9% | 73.4% | 64.4% |
| 987 | SEQ ID NO: 125, 245, 155 | hsa-miR-1285, hsa-miR-106a, hsa-miR-484 | 68.7% | 68.4% | 69.0% |
| 988 | SEQ ID NO: 231, 245, 246 | hsa-miR-93, hsa-miR-106a, hsa-miR-20a | 67.6% | 78.8% | 56.4% |
| 989 | SEQ ID NO: 169, 248, 247 | hsa-miR-324-3p, hsa-miR-20a, hsa-miR-148a | 67.6% | 70.8% | 64.4% |
| 990 | SEQ ID NO: 245, 169, 247 | hsa-miR-106a, hsa-miR-324-3p, hsa-miR-148a | 67.3% | 73.2% | 61.3% |
| 991 | SEQ ID NO: 181, 249, 41 | hsa-miR-145, hsa-miR-33b*, hsa-miR-654-5p | 66.8% | 77.6% | 56.0% |
| 992 | SEQ ID NO: 250, 27, 116 | hsa-miR-374a, hsa-miR-423-5p, hsa-miR-339-3p | 66.7% | 72.2% | 61.0% |
| 993 | SEQ ID NO: 155, 246, 99 | hsa-miR-484, hsa-miR-20a, hsa-miR-1301 | 66.5% | 64.0% | 69.0% |
| 994 | SEQ ID NO: 249, 251, 27 | hsa-miR-33b*, hsa-miR-182, hsa-miR-423-5p | 65.9% | 65.6% | 66.2% |
| 995 | SEQ ID NO: 12, 41, 251 | hsa-miR-128, hsa-miR-654-5p, hsa-miR-182 | 65.7% | 64.8% | 66.6% |
| 996 | SEQ ID NO: 12, 41, 250 | hsa-miR-128, hsa-miR-654-5p, hsa-miR-374a | 65.5% | 60.0% | 71.0% |
| 997 | SEQ ID NO: 246, 99, 248 | hsa-miR-20a, hsa-miR-1301, hsa-let-7b | 65.3% | 72.6% | 58.0% |
| 998 | SEQ ID NO: 169, 247, 99 | hsa-miR-324-3p, hsa-miR-148a, hsa-miR-1301 | 64.8% | 65.0% | 64.6% |
| 999 | SEQ ID NO: 181, 248, 12 | hsa-miR-145, hsa-let-7b, hsa-miR-128 | 62.9% | 63.4% | 62.4% |
| 1000 | SEQ ID NO: 249, 41, 250 | hsa-miR-33b*, hsa-miR-654-5p, hsa-miR-374a | 62.4% | 35.8% | 89.0% |
| 1001 | SEQ ID NO: 250, 251, 116 | hsa-miR-374a, hsa-miR-182, hsa-miR-339-3p | 62.4% | 63.4% | 61.4% |
| 1002 | SEQ ID NO: 245, 155, 246 | hsa-miR-106a, hsa-miR-484, hsa-miR-20a | 61.0% | 59.4% | 62.6% |
| 1003 | SEQ ID NO: 249, 250, 251 | hsa-miR-33b*, hsa-miR-374a, hsa-miR-182 | 60.5% | 70.6% | 50.4% |
| 1004 | SEQ ID NO: 250, 251, 27 | hsa-miR-374a, hsa-miR-182, hsa-miR-423-5p | 60.2% | 63.8% | 56.6% |
| 1005 | SEQ ID NO: 182, 157, 234, 184, 68, 16, 76, 252, 52, 15, 243, 62, 123, 95, 158, 22, 32, 089, 253, 31 | hsa-miR-142-5p, hsa-miR-566, hsa-miR-498, hsa-miR-492, hsa-miR-23b*, hsa-miR-455-3p, hsa-miR-1250, hsa-miR-497*, hsa-miR-802, hsa-miR-892b, hsa-miR-151-5p, hsa-miR-1231, hsa-miR-146b-3p, hsa-miR-135b*, hsa-miR-1254, hsa-miR-20b*, hsa-miR-380*, hsa-miR-631, hsa-miR-345, hsa-miR-139-5p | 93% | 96% | 90% |

Figure 28 cont.

| SEQ ID NO: | miRNA | median g1 | median g2 | q median | logq median | ttest_rawp | ttest_adjp | AUC | limma rawp | limma_adj p |
|---|---|---|---|---|---|---|---|---|---|---|
| 162 | hsa-miR-142-5p | 844 | 1413 | 0.46 | -0.79 | 4.00E-06 | 2.79E-05 | 0.063 | 2.35E-06 | 2.34E-04 |
| 257 | hsa-miR-663b | 119 | 46 | 2.65 | 0.98 | 1.86E-03 | 2.35E-02 | 0.935 | 3.34E-05 | 1.73E-03 |
| 234 | hsa-miR-498 | 1 | 41 | 0.02 | -3.70 | 1.15E-06 | 4.02E-04 | 0.065 | 7.78E-11 | 5.42E-08 |
| 157 | hsa-miR-566 | 92 | 13 | 6.11 | 1.81 | 5.26E-06 | 2.47E-03 | 0.903 | 1.07E-06 | 1.97E-04 |
| 184 | hsa-miR-492 | 79 | 12 | 6.59 | 1.93 | 3.22E-06 | 1.37E-03 | 0.888 | 1.82E-06 | 2.16E-04 |
| 68 | hsa-miR-23b* | 1 | 68 | 0.01 | -4.23 | 2.05E-05 | 1.78E-03 | 0.190 | 1.66E-07 | 5.77E-05 |
| 16 | hsa-miR-455-3p | 200 | 52 | 3.84 | 1.35 | 2.31E-05 | 1.79E-03 | 0.879 | 2.28E-04 | 5.96E-03 |
| 70 | hsa-miR-1250 | 5 | 97 | 0.05 | -2.93 | 3.00E-06 | 2.03E-03 | 0.115 | 4.26E-06 | 3.30E-04 |
| 252 | hsa-miR-487* | 141 | 56 | 2.49 | 0.91 | 9.83E-06 | 1.37E-03 | 0.876 | 2.88E-04 | 6.91E-03 |
| 197 | hsa-miR-920 | 1 | 71 | 0.02 | -3.88 | 2.44E-03 | 2.80E-02 | 0.123 | 1.86E-06 | 2.16E-04 |
| 52 | hsa-miR-802 | 92 | 1 | 92.20 | 4.41 | 1.78E-06 | 1.78E-03 | 0.875 | 7.22E-07 | 1.68E-04 |
| 15 | hsa-miR-892b | 9 | 89 | 0.10 | -2.34 | 7.98E-05 | 2.96E-03 | 0.129 | 5.12E-05 | 2.32E-03 |
| 62 | hsa-miR-1281 | 66 | 210 | 0.31 | -1.16 | 9.64E-06 | 1.37E-03 | 0.129 | 1.48E-02 | 6.88E-02 |
| 243 | hsa-miR-151-5p | 6353 | 5101 | 1.23 | 0.31 | 1.59E-05 | 1.78E-03 | 0.875 | 1.01E-04 | 3.72E-03 |
| 95 | hsa-miR-135b* | 23 | 82 | 0.28 | -1.27 | 5.01E-05 | 2.47E-03 | 0.130 | 7.09E-06 | 2.91E-03 |
| 123 | hsa-miR-148b-3p | 83 | 28 | 2.98 | 1.09 | 8.06E-05 | 2.96E-03 | 0.873 | 5.81E-05 | 2.38E-03 |
| 150 | hsa-miR-1254 | 162 | 78 | 2.07 | 0.73 | 5.67E-05 | 2.47E-03 | 0.868 | 2.81E-05 | 1.63E-03 |
| 265 | hsa-miR-129-5p | 1 | 42 | 0.02 | -3.74 | 1.00E-03 | 1.55E-02 | 0.161 | 1.81E-05 | 1.02E-03 |
| 266 | hsa-miR-615-5p | 1 | 66 | 0.02 | -4.03 | 1.13E-03 | 1.63E-02 | 0.163 | 1.19E-05 | 8.26E-04 |
| 155 | hsa-miR-217 | 127 | 27 | 4.63 | 1.53 | 1.58E-03 | 2.06E-02 | 0.868 | 6.71E-05 | 2.91E-03 |
| 24 | hsa-miR-330-3p | 432 | 156 | 2.76 | 1.02 | 4.35E-04 | 1.03E-02 | 0.864 | 3.80E-04 | 8.02E-03 |
| 231 | hsa-miR-93 | 4593 | 5727 | 0.80 | -0.22 | 1.15E-03 | 1.63E-02 | 0.163 | 2.27E-03 | 3.14E-02 |
| 22 | hsa-miR-202* | 67 | 17 | 3.95 | 1.37 | 1.17E-04 | 4.08E-03 | 0.860 | 1.32E-04 | 4.28E-03 |
| 269 | hsa-miR-185 | 12 | 47 | 0.25 | -1.37 | 1.39E-03 | 1.86E-02 | 0.170 | 8.34E-05 | 3.33E-03 |
| 32 | hsa-miR-382* | 65 | 30 | 2.19 | 0.78 | 3.42E-05 | 2.17E-03 | 0.854 | 2.30E-04 | 5.95E-03 |
| 232 | hsa-miR-624 | 21 | 72 | 0.29 | -1.23 | 5.18E-04 | 1.03E-02 | 0.170 | 7.98E-03 | 4.63E-02 |
| 135 | hsa-miR-7-1* | 462 | 223 | 2.07 | 0.73 | 1.58E-04 | 4.78E-03 | 0.845 | 1.35E-04 | 4.28E-03 |
| 71 | hsa-miR-30a | 239 | 486 | 0.49 | -0.71 | 2.97E-04 | 9.00E-03 | 0.183 | 3.64E-03 | 2.85E-02 |
| 259 | hsa-miR-631 | 157 | 95 | 1.64 | 0.49 | 5.63E-06 | 2.47E-03 | 0.845 | 3.03E-03 | 2.47E-02 |
| 85 | hsa-miR-140-5p | 1 | 76 | 0.01 | -4.36 | 3.41E-04 | 8.81E-03 | 0.184 | 4.51E-04 | 8.49E-03 |
| 253 | hsa-miR-345 | 196 | 91 | 2.17 | 0.78 | 5.25E-05 | 2.47E-03 | 0.843 | 5.61E-04 | 1.00E-02 |
| 261 | hsa-miR-200b* | 5 | 84 | 0.06 | -2.82 | 4.77E-04 | 1.03E-02 | 0.186 | 4.24E-04 | 8.49E-03 |
| 19 | hsa-miR-767-5p | 156 | 48 | 3.23 | 1.17 | 5.72E-04 | 1.05E-02 | 0.839 | 1.56E-04 | 4.42E-03 |
| 267 | hsa-miR-193b | 33 | 81 | 0.41 | -0.90 | 1.06E-03 | 1.63E-02 | 0.186 | 3.02E-03 | 2.65E-02 |
| 174 | hsa-miR-635 | 168 | 84 | 2.01 | 0.79 | 1.28E-04 | 4.23E-03 | 0.839 | 3.74E-04 | 8.02E-03 |
| 148 | hsa-miR-1304 | 32 | 67 | 0.48 | -0.73 | 6.09E-03 | 4.37E-02 | 0.195 | 2.59E-03 | 2.27E-02 |
| 255 | hsa-miR-193a-3p | 166 | 75 | 2.21 | 0.79 | 3.31E-04 | 8.81E-03 | 0.835 | 7.00E-02 | 1.89E-01 |

Figure 29

| SEQ ID NO: | miRNA | median g1 | median g2 | q median | logq median | ttest_rawp | ttest_adjp | AUC | limma rawp | limma_adj p |
|---|---|---|---|---|---|---|---|---|---|---|
| 256 | hsa-miR-134 | 10 | 102 | 0.10 | -2.31 | 8.80E-04 | 1.44E-02 | 0.198 | 1.43E-03 | 1.89E-02 |
| 31 | hsa-miR-139-5p | 122 | 38 | 3.25 | 1.18 | 7.17E-05 | 2.94E-03 | 0.833 | 1.63E-04 | 4.47E-03 |
| 263 | hsa-miR-409-3p | 3 | 63 | 0.05 | -3.00 | 5.55E-04 | 1.05E-02 | 0.198 | 2.00E-03 | 2.08E-02 |
| 244 | hsa-miR-874 | 230 | 145 | 1.58 | 0.46 | 1.52E-04 | 4.78E-03 | 0.833 | 1.74E-03 | 2.07E-02 |
| 260 | hsa-miR-544 | 9 | 49 | 0.18 | -1.71 | 4.36E-04 | 9.99E-03 | 0.198 | 2.92E-03 | 2.46E-02 |
| 29 | hsa-miR-33a | 103 | 35 | 2.91 | 1.07 | 4.44E-04 | 9.99E-03 | 0.830 | 1.88E-03 | 2.07E-02 |
| 273 | hsa-miR-194* | 1 | 70 | 0.01 | -4.24 | 3.46E-03 | 3.18E-02 | 0.200 | 2.46E-04 | 6.13E-03 |
| 35 | hsa-miR-188-3p | 137 | 51 | 2.71 | 1.00 | 3.83E-04 | 9.53E-03 | 0.824 | 6.63E-04 | 1.13E-02 |
| 268 | hsa-miR-877 | 18 | 81 | 0.23 | -1.49 | 1.30E-03 | 1.78E-02 | 0.201 | 3.68E-03 | 2.85E-02 |
| 84 | hsa-miR-1303 | 9 | 87 | 0.10 | -2.36 | 4.10E-04 | 9.95E-03 | 0.206 | 7.85E-04 | 1.22E-02 |
| 125 | hsa-miR-1285 | 303 | 191 | 1.59 | 0.46 | 6.91E-04 | 1.18E-02 | 0.815 | 1.07E-02 | 5.55E-02 |
| 262 | hsa-miR-326 | 96 | 36 | 2.69 | 0.99 | 5.01E-04 | 1.03E-02 | 0.808 | 7.37E-04 | 1.20E-02 |
| 195 | hsa-miR-142-3p | 1 | 85 | 0.01 | -4.44 | 1.11E-03 | 1.63E-02 | 0.210 | 7.05E-04 | 1.17E-02 |
| 264 | hsa-miR-513a-5p | 60 | 12 | 4.86 | 1.58 | 8.31E-04 | 1.13E-02 | 0.805 | 1.24E-03 | 1.76E-02 |
| 278 | hsa-miR-296-3p | 13 | 61 | 0.21 | -1.56 | 2.52E-03 | 2.93E-02 | 0.210 | 9.41E-04 | 1.37E-02 |
| 55 | hsa-miR-30e* | 21 | 129 | 0.16 | -1.83 | 5.81E-04 | 1.18E-02 | 0.213 | 1.58E-03 | 2.01E-02 |
| 169 | hsa-miR-324-3p | 927 | 598 | 1.55 | 0.44 | 2.56E-03 | 2.90E-02 | 0.805 | 4.03E-02 | 1.30E-01 |
| 254 | hsa-miR-323-3p | 103 | 12 | 8.22 | 2.11 | 2.81E-04 | 8.00E-03 | 0.803 | 3.34E-03 | 2.65E-02 |
| 216 | hsa-miR-659 | 21 | 75 | 0.28 | -1.28 | 1.74E-03 | 2.25E-02 | 0.214 | 7.77E-04 | 1.22E-02 |
| 276 | hsa-miR-337-5p | 48 | 19 | 2.59 | 0.95 | 5.02E-03 | 3.93E-02 | 0.799 | 5.32E-03 | 3.64E-02 |
| 279 | hsa-miR-323-5p | 42 | 95 | 0.44 | -0.82 | 6.70E-03 | 4.62E-02 | 0.218 | 4.88E-03 | 3.50E-02 |
| 242 | hsa-let-7i | 478 | 970 | 0.49 | -0.71 | 9.99E-04 | 1.55E-02 | 0.219 | 6.45E-03 | 4.06E-02 |
| 233 | hsa-miR-433 | 90 | 18 | 5.12 | 1.63 | 4.23E-03 | 3.58E-02 | 0.794 | 1.76E-03 | 2.07E-02 |
| 167 | hsa-miR-627 | 156 | 71 | 2.19 | 0.78 | 5.69E-04 | 1.05E-02 | 0.793 | 2.11E-03 | 2.10E-02 |
| 245 | hsa-miR-106a | 6564 | 8895 | 0.74 | -0.30 | 2.03E-03 | 2.43E-02 | 0.219 | 1.57E-02 | 7.06E-02 |
| 215 | hsa-miR-409-5p | 85 | 31 | 2.76 | 1.01 | 3.08E-03 | 3.00E-02 | 0.790 | 4.71E-04 | 8.63E-03 |
| 259 | hsa-miR-374a | 283 | 502 | 0.56 | -0.57 | 4.63E-03 | 3.67E-02 | 0.229 | 4.30E-02 | 1.37E-01 |
| 23 | hsa-miR-491-3p | 63 | 1 | 62.78 | 4.14 | 2.72E-03 | 2.93E-02 | 0.788 | 3.36E-04 | 7.55E-03 |
| 181 | hsa-miR-145 | 233 | 334 | 0.70 | -0.36 | 3.79E-03 | 3.32E-02 | 0.233 | 1.99E-02 | 8.48E-02 |
| 60 | hsa-miR-1302 | 28 | 1 | 28.19 | 3.34 | 2.64E-03 | 2.93E-02 | 0.788 | 4.38E-04 | 8.49E-03 |
| 205 | hsa-miR-521 | 38 | 113 | 0.34 | -1.09 | 4.45E-03 | 3.65E-02 | 0.235 | 2.96E-03 | 2.47E-02 |
| 129 | hsa-miR-1537 | 37 | 2 | 17.33 | 2.85 | 1.17E-03 | 1.63E-02 | 0.788 | 8.44E-04 | 1.28E-02 |
| 246 | hsa-miR-30a | 2944 | 4318 | 0.68 | -0.38 | 2.53E-03 | 2.93E-02 | 0.236 | 9.02E-03 | 4.89E-02 |
| 32 | hsa-miR-508-5p | 82 | 44 | 1.86 | 0.62 | 2.79E-03 | 2.96E-02 | 0.788 | 1.99E-03 | 2.08E-02 |
| 113 | hsa-miR-342* | 23 | 68 | 0.33 | -1.10 | 3.38E-03 | 3.14E-02 | 0.239 | 1.07E-03 | 1.53E-02 |
| 43 | hsa-miR-145* | 68 | 1 | 67.58 | 4.21 | 7.81E-04 | 1.30E-02 | 0.793 | 1.91E-03 | 2.08E-02 |
| 271 | hsa-miR-27a* | 2 | 53 | 0.04 | -3.21 | 3.11E-03 | 3.00E-02 | 0.243 | 5.23E-03 | 3.62E-02 |
| 76 | hsa-miR-942 | 6 | 77 | 0.08 | -2.49 | 2.91E-03 | 2.94E-02 | 0.245 | 6.77E-03 | 4.16E-02 |

Figure 29 cont.

| SEQ ID NO. | miRNA | median g1 | median g2 | q median | logq median | ttest_rawp | ttest_adjp | AUC | limma_rawp | limma_adjp |
|---|---|---|---|---|---|---|---|---|---|---|
| 58 | hsa-miR-1301 | 194 | 108 | 1.80 | 0.59 | 3.08E-03 | 3.30E-02 | 0.783 | 5.24E-03 | 3.62E-02 |
| 272 | hsa-miR-98* | 17 | 58 | 0.29 | -1.25 | 3.23E-03 | 3.04E-02 | 0.246 | 8.97E-03 | 4.99E-02 |
| 14 | hsa-miR-541 | 82 | 16 | 5.06 | 1.62 | 6.67E-03 | 4.37E-02 | 0.780 | 5.89E-04 | 1.03E-02 |
| 258 | hsa-miR-499-3p | 106 | 34 | 3.12 | 1.14 | 2.69E-03 | 2.83E-02 | 0.780 | 5.60E-03 | 3.72E-02 |
| 276 | hsa-miR-608 | 1 | 44 | 0.02 | -3.78 | 4.50E-03 | 3.65E-02 | 0.250 | 4.15E-03 | 3.14E-02 |
| 126 | hsa-miR-371-5p | 43 | 1 | 42.90 | 3.76 | 2.30E-03 | 2.72E-02 | 0.779 | 4.45E-04 | 8.49E-03 |
| 134 | hsa-miR-411* | 39 | 64 | 0.46 | -0.78 | 3.69E-03 | 3.34E-02 | 0.255 | 3.07E-02 | 1.11E-01 |
| 66 | hsa-miR-1295 | 108 | 57 | 1.91 | 0.85 | 1.98E-03 | 2.43E-02 | 0.773 | 1.05E-03 | 2.08E-02 |
| 248 | hsa-let-7b | 821 | 1180 | 0.53 | -0.84 | 3.88E-03 | 3.38E-02 | 0.256 | 5.50E-03 | 3.69E-02 |
| 85 | hsa-miR-218-1* | 63 | 28 | 2.24 | 0.81 | 1.93E-03 | 2.40E-02 | 0.771 | 1.86E-03 | 2.07E-02 |
| 278 | hsa-miR-579 | 1 | 19 | 0.06 | -2.94 | 6.56E-03 | 4.57E-02 | 0.273 | 7.41E-03 | 4.42E-02 |
| 141 | hsa-miR-875-5p | 16 | 67 | 0.24 | -1.43 | 4.43E-03 | 3.65E-02 | 0.274 | 5.50E-03 | 1.61E-01 |
| 92 | hsa-miR-30c-1* | 28 | 5 | 5.55 | 1.73 | 6.19E-03 | 4.37E-02 | 0.770 | 2.19E-03 | 2.13E-02 |
| 41 | hsa-miR-654-5p | 194 | 102 | 1.90 | 0.94 | 4.62E-03 | 3.67E-02 | 0.768 | 4.39E-03 | 3.29E-02 |
| 12 | hsa-miR-128 | 663 | 480 | 1.44 | 0.36 | 3.88E-03 | 3.38E-02 | 0.765 | 1.49E-02 | 6.88E-02 |
| 39 | hsa-miR-218a | 119 | 41 | 2.90 | 1.06 | 4.87E-03 | 3.77E-02 | 0.763 | 4.97E-03 | 3.53E-02 |
| 247 | hsa-miR-148a | 1524 | 1049 | 1.45 | 0.37 | 3.14E-03 | 3.08E-02 | 0.759 | 9.75E-03 | 4.96E-02 |
| 217 | hsa-miR-148b | 690 | 524 | 1.32 | 0.27 | 5.03E-03 | 3.80E-02 | 0.759 | 2.19E-02 | 8.86E-02 |
| 7 | hsa-miR-1278 | 39 | 3 | 13.08 | 2.40 | 5.81E-03 | 4.26E-02 | 0.759 | 1.61E-03 | 2.01E-02 |
| 274 | hsa-miR-653 | 77 | 11 | 7.14 | 1.97 | 4.03E-03 | 3.47E-02 | 0.758 | 4.80E-03 | 3.49E-02 |
| 155 | hsa-miR-484 | 8679 | 6342 | 1.37 | 0.31 | 3.57E-03 | 2.90E-02 | 0.753 | 1.86E-02 | 8.13E-02 |
| 116 | hsa-miR-339-3p | 338 | 223 | 1.51 | 0.41 | 5.35E-03 | 3.97E-02 | 0.751 | 6.65E-03 | 4.10E-02 |
| 277 | hsa-miR-1207-3p | 58 | 2 | 32.09 | 3.47 | 6.20E-03 | 4.37E-02 | 0.749 | 5.94E-03 | 3.86E-02 |
| 249 | hsa-miR-33b* | 172 | 115 | 1.50 | 0.40 | 4.27E-03 | 3.58E-02 | 0.743 | 5.67E-03 | 3.73E-02 |
| 27 | hsa-miR-423-5p | 3538 | 2224 | 1.59 | 0.46 | 5.06E-03 | 3.80E-02 | 0.743 | 1.04E-02 | 5.47E-02 |
| 251 | hsa-miR-182 | 7424 | 6034 | 1.23 | 0.21 | 4.84E-03 | 3.77E-02 | 0.743 | 2.33E-02 | 9.21E-02 |

Figure 29 cont.

| Set No. | Signature | SEQ ID NO: | miRNAs | Acc |
|---|---|---|---|---|
| 2000 | ACS-NRS-1 | SEQ ID NO: 257, SEQ ID NO: 261 | hsa-miR-663b, hsa-miR-200b* | 90,48% |
| 2001 | ACS-NRS-2 | SEQ ID NO: 257, SEQ ID NO: 283 | hsa-miR-663b, hsa-miR-191* | 91,45% |
| 2002 | ACS-NRS-3 | SEQ ID NO: 257, SEQ ID NO: 280, SEQ ID NO: 261 | hsa-miR-663b, hsa-miR-634, hsa-miR-200b* | 95,65% |
| 2003 | ACS-NRS-4 | SEQ ID NO: 257, SEQ ID NO: 281, SEQ ID NO: 280, SEQ ID NO: 261 | hsa-miR-663b, hsa-miR-144*, hsa-miR-634, hsa-miR-200b* | 96,10% |
| 2004 | ACS-NRS-5 | SEQ ID NO: 257, SEQ ID NO: 280, SEQ ID NO: 261 | hsa-miR-663b, hsa-miR-634, hsa-miR-200b* | 96,33% |
| 2005 | ACS-NRS-6 | SEQ ID NO: 257, SEQ ID NO: 281, SEQ ID NO: 280, SEQ ID NO: 261, SEQ ID NO: 159, SEQ ID NO: 282 | hsa-miR-663b, hsa-miR-144*, hsa-miR-634, hsa-miR-200b*, hsa-miR-126*, hsa-miR-519d | 97,00% |
| 2006 | ACS-NRS-7 | SEQ ID NO: 257, SEQ ID NO: 280, SEQ ID NO: 261, SEQ ID NO: 282 | hsa-miR-663b, hsa-miR-634, hsa-miR-200b*, hsa-miR-519d | 97,30% |
| 2007 | ACS-NRS-8 | SEQ ID NO: 257, SEQ ID NO: 280, SEQ ID NO: 261, SEQ ID NO: 159, SEQ ID NO: 282 | hsa-miR-663b, hsa-miR-634, hsa-miR-200b*, hsa-miR-126*, hsa-miR-519d | 97,35% |
| 2008 | ACS-NRS-9 | SEQ ID NO: 257, SEQ ID NO: 280, SEQ ID NO: 261, SEQ ID NO: 159, SEQ ID NO: 282 | hsa-miR-663b, hsa-miR-634, hsa-miR-200b*, hsa-miR-126*, hsa-miR-519d | 97,78% |
| 2009 | ACS-NRS-10 | SEQ ID NO: 257, SEQ ID NO: 19, SEQ ID NO: 280, SEQ ID NO: 261, SEQ ID NO: 159, SEQ ID NO: 282 | hsa-miR-663b, hsa-miR-767-5p, hsa-miR-634, hsa-miR-200b*, hsa-miR-126*, hsa-miR-519d | 98,48% |
| 2010 | ACS-NRS-11 | SEQ ID NO: 257, SEQ ID NO: 281, SEQ ID NO: 280, SEQ ID NO: 55, SEQ ID NO: 261, SEQ ID NO: 159, SEQ ID NO: 282 | hsa-miR-663b, hsa-miR-144*, hsa-miR-634, hsa-miR-30e*, hsa-miR-200b*, hsa-miR-126*, hsa-miR-519d | 99,33% |
| 2011 | ACS-NRS-12 | SEQ ID NO: 257, SEQ ID NO: 281, SEQ ID NO: 280, SEQ ID NO: 55, SEQ ID NO: 261, SEQ ID NO: 159, SEQ ID NO: 282 | hsa-miR-663b, hsa-miR-144*, hsa-miR-634, hsa-miR-30e*, hsa-miR-200b*, hsa-miR-126*, hsa-miR-519d | 99,53% |

Figure 30

SEQUENCE LISTING

<160> NUMBER OF SEQ ID NOS: 283

<210> SEQ ID NO 1
<211> LENGTH: 24
<212> TYPE: RNA
<213> ORGANISM: Homo sapiens

```
<400> SEQUENCE: 1
uggcccugac ugaagaccag cagu                                              24

<210> SEQ ID NO 2
<211> LENGTH: 22
<212> TYPE: RNA
<213> ORGANISM: Homo sapiens

<400> SEQUENCE: 2
ucuacaaagg aaagcgcuuu cu                                                22

<210> SEQ ID NO 3
<211> LENGTH: 24
<212> TYPE: RNA
<213> ORGANISM: Homo sapiens

<400> SEQUENCE: 3
agccugauua aacacaugcu cuga                                              24

<210> SEQ ID NO 4
<211> LENGTH: 21
<212> TYPE: RNA
<213> ORGANISM: Homo sapiens

<400> SEQUENCE: 4
aagugaucua aaggccuaca u                                                 21

<210> SEQ ID NO 5
<211> LENGTH: 22
<212> TYPE: RNA
<213> ORGANISM: Homo sapiens

<400> SEQUENCE: 5
auaagacgaa caaaagguuu gu                                                22

<210> SEQ ID NO 6
<211> LENGTH: 22
<212> TYPE: RNA
<213> ORGANISM: Homo sapiens

<400> SEQUENCE: 6
uacccagagc augcagugug aa                                                22

<210> SEQ ID NO 7
<211> LENGTH: 22
<212> TYPE: RNA
<213> ORGANISM: Homo sapiens

<400> SEQUENCE: 7
uaguacugug cauaucaucu au                                                22

<210> SEQ ID NO 8
<211> LENGTH: 22
<212> TYPE: RNA
<213> ORGANISM: Homo sapiens

<400> SEQUENCE: 8
uagcaaaaac ugcaguuacu uu                                                22

<210> SEQ ID NO 9
<211> LENGTH: 22
<212> TYPE: RNA
```

```
<400> SEQUENCE: 9
uuuucaacuc uaaugggaga ga                                              22

<210> SEQ ID NO 10
<211> LENGTH: 22
<212> TYPE: RNA
<213> ORGANISM: Homo sapiens

<400> SEQUENCE: 10
aggcauugac uucucacuag cu                                              22

<210> SEQ ID NO 11
<211> LENGTH: 26
<212> TYPE: RNA
<213> ORGANISM: Homo sapiens

<400> SEQUENCE: 11
gugagggcau gcaggccugg augggg                                          26

<210> SEQ ID NO 12
<211> LENGTH: 21
<212> TYPE: RNA
<213> ORGANISM: Homo sapiens

<400> SEQUENCE: 12
ucacagugaa ccggucucuu u                                               21

<210> SEQ ID NO 13
<211> LENGTH: 22
<212> TYPE: RNA
<213> ORGANISM: Homo sapiens

<400> SEQUENCE: 13
uauacaaggg cagacucucu cu                                              22

<210> SEQ ID NO 14
<211> LENGTH: 22
<212> TYPE: RNA
<213> ORGANISM: Homo sapiens

<400> SEQUENCE: 14 ugguggggcac agaaucugga cu                                             22

<210> SEQ ID NO 15
<211> LENGTH: 22
<212> TYPE: RNA
<213> ORGANISM: Homo sapiens

<400> SEQUENCE: 15
cacuggcucc uuucugggua ga                                              22

<210> SEQ ID NO 16
<211> LENGTH: 21
<212> TYPE: RNA
<213> ORGANISM: Homo sapiens

<400> SEQUENCE: 16
gcaguccaug ggcauauaca c                                               21

<210> SEQ ID NO 17
<211> LENGTH: 22
<212> TYPE: RNA
<213> ORGANISM: Homo sapiens
```

```
<400> SEQUENCE: 17
ugcuaugcca acauauugcc au                                              22

<210> SEQ ID NO 18
<211> LENGTH: 22
<212> TYPE: RNA
<213> ORGANISM: Homo sapiens

<400> SEQUENCE: 18
cugccaauuc cauaggucac ag                                              22

<210> SEQ ID NO 19
<211> LENGTH: 23
<212> TYPE: RNA
<213> ORGANISM: Homo sapiens

<400> SEQUENCE: 19
ugcaccaugg uugucugagc aug                                             23

<210> SEQ ID NO 20
<211> LENGTH: 22
<212> TYPE: RNA
<213> ORGANISM: Homo sapiens

<400> SEQUENCE: 20
acugcugagc uagcacuucc cg                                              22

<210> SEQ ID NO 21
<211> LENGTH: 22
<212> TYPE: RNA
<213> ORGANISM: Homo sapiens

<400> SEQUENCE: 21
cuccuacaua uuagcauuaa ca                                              22

<210> SEQ ID NO 22
<211> LENGTH: 22
<212> TYPE: RNA
<213> ORGANISM: Homo sapiens

<400> SEQUENCE: 22
acuguaguau gggcacuucc ag                                              22

<210> SEQ ID NO 23
<211> LENGTH: 22
<212> TYPE: RNA
<213> ORGANISM: Homo sapiens

<400> SEQUENCE: 23
cuuaugcaag auucccuucu ac                                              22

<210> SEQ ID NO 24
<211> LENGTH: 23
<212> TYPE: RNA
<213> ORGANISM: Homo sapiens

<400> SEQUENCE: 24
gcaaagcaca cggccugcag aga                                             23

<210> SEQ ID NO 25
<211> LENGTH: 22
<212> TYPE: RNA
<213> ORGANISM: Homo sapiens
```

-continued

```
<400> SEQUENCE: 25
ugagaacuga auuccauagg cu                                        22

<210> SEQ ID NO 26
<211> LENGTH: 22
<212> TYPE: RNA
<213> ORGANISM: Homo sapiens

<400> SEQUENCE: 26
gaugagcuca uuguaauaug ag                                        22

<210> SEQ ID NO 27
<211> LENGTH: 23
<212> TYPE: RNA
<213> ORGANISM: Homo sapiens

<400> SEQUENCE: 27 ugagggcag agagcgagac uuu                                        23

<210> SEQ ID NO 28
<211> LENGTH: 22
<212> TYPE: RNA
<213> ORGANISM: Homo sapiens

<400> SEQUENCE: 28
acagauucga uucuagggga au                                        22

<210> SEQ ID NO 29
<211> LENGTH: 21
<212> TYPE: RNA
<213> ORGANISM: Homo sapiens

<400> SEQUENCE: 29
gugcauugua guugcauugc a                                         21

<210> SEQ ID NO 30
<211> LENGTH: 23
<212> TYPE: RNA
<213> ORGANISM: Homo sapiens

<400> SEQUENCE: 30
uacuccagag ggcgucacuc aug                                       23

<210> SEQ ID NO 31
<211> LENGTH: 22
<212> TYPE: RNA
<213> ORGANISM: Homo sapiens

<400> SEQUENCE: 31
ucuacagugc acgugucucc ag                                        22

<210> SEQ ID NO 32
<211> LENGTH: 22
<212> TYPE: RNA
<213> ORGANISM: Homo sapiens

<400> SEQUENCE: 32
ugguugacca uagaacaugc gc                                        22

<210> SEQ ID NO 33
<211> LENGTH: 22
<212> TYPE: RNA
```

```
<213> ORGANISM: Homo sapiens

<400> SEQUENCE: 33
aaucaugugc agugccaaua ug                                              22

<210> SEQ ID NO 34
<211> LENGTH: 22
<212> TYPE: RNA
<213> ORGANISM: Homo sapiens

<400> SEQUENCE: 34
gaaagcgcuu cccuuugcug ga                                              22

<210> SEQ ID NO 35
<211> LENGTH: 21
<212> TYPE: RNA
<213> ORGANISM: Homo sapiens

<400> SEQUENCE: 35
cucccacaug caggguuugc a                                               21

<210> SEQ ID NO 36
<211> LENGTH: 22
<212> TYPE: RNA
<213> ORGANISM: Homo sapiens

<400> SEQUENCE: 36
acugcauuau gagcacuuaa ag                                              22

<210> SEQ ID NO 37
<211> LENGTH: 20
<212> TYPE: RNA
<213> ORGANISM: Homo sapiens

<400> SEQUENCE: 37
cuacaaaggg aagcccuuuc                                                 20

<210> SEQ ID NO 38
<211> LENGTH: 22
<212> TYPE: RNA
<213> ORGANISM: Homo sapiens

<400> SEQUENCE: 38
caucaucguc ucaaaugagu cu                                              22

<210> SEQ ID NO 39
<211> LENGTH: 22
<212> TYPE: RNA
<213> ORGANISM: Homo sapiens

<400> SEQUENCE: 39
uaaucucagc uggcaacugu ga                                              22

<210> SEQ ID NO 40
<211> LENGTH: 22
<212> TYPE: RNA
<213> ORGANISM: Homo sapiens

<400> SEQUENCE: 40
ccucccacac ccaaggcuug ca                                              22

<210> SEQ ID NO 41
<211> LENGTH: 22
```

```
<212> TYPE: RNA
<213> ORGANISM: Homo sapiens

<400> SEQUENCE: 41 ugguggccg cagaacaugu gc                                           22

<210> SEQ ID NO 42
<211> LENGTH: 22
<212> TYPE: RNA
<213> ORGANISM: Homo sapiens

<400> SEQUENCE: 42
cuauacaauc uauugccuuc cc                                          22

<210> SEQ ID NO 43
<211> LENGTH: 22
<212> TYPE: RNA
<213> ORGANISM: Homo sapiens

<400> SEQUENCE: 43
ggauuccugg aaauacuguu cu                                          22

<210> SEQ ID NO 44
<211> LENGTH: 23
<212> TYPE: RNA
<213> ORGANISM: Homo sapiens

<400> SEQUENCE: 44
ucucacacag aaaucgcacc cgu                                         23

<210> SEQ ID NO 45
<211> LENGTH: 21
<212> TYPE: RNA
<213> ORGANISM: Homo sapiens

<400> SEQUENCE: 45
cccagauaau ggcacucuca a                                           21

<210> SEQ ID NO 46
<211> LENGTH: 21
<212> TYPE: RNA
<213> ORGANISM: Homo sapiens

<400> SEQUENCE: 46
uacugcagac aguggcaauc a                                           21

<210> SEQ ID NO 47
<211> LENGTH: 22
<212> TYPE: RNA
<213> ORGANISM: Homo sapiens

<400> SEQUENCE: 47
cucuagaggg aagcgcuuuc ug                                          22

<210> SEQ ID NO 48
<211> LENGTH: 22
<212> TYPE: RNA
<213> ORGANISM: Homo sapiens

<400> SEQUENCE: 48
uucacaagga ggugucauuu au                                          22

<210> SEQ ID NO 49
```

```
<211> LENGTH: 22
<212> TYPE: RNA
<213> ORGANISM: Homo sapiens

<400> SEQUENCE: 49
ugucuuacuc ccucaggcac au                                         22

<210> SEQ ID NO 50
<211> LENGTH: 22
<212> TYPE: RNA
<213> ORGANISM: Homo sapiens

<400> SEQUENCE: 50
cggcaacaag aaacugccug ag                                         22

<210> SEQ ID NO 51
<211> LENGTH: 27
<212> TYPE: RNA
<213> ORGANISM: Homo sapiens

<400> SEQUENCE: 51
auugaucauc gacacuucga acgcaau                                    27

<210> SEQ ID NO 52
<211> LENGTH: 23
<212> TYPE: RNA
<213> ORGANISM: Homo sapiens

<400> SEQUENCE: 52
caguaacaaa gauucauccu ugu                                        23

<210> SEQ ID NO 53
<211> LENGTH: 26
<212> TYPE: RNA
<213> ORGANISM: Homo sapiens

<400> SEQUENCE: 53
gaugaugaug gcagcaaauu cugaaa                                     26

<210> SEQ ID NO 54
<211> LENGTH: 22
<212> TYPE: RNA
<213> ORGANISM: Homo sapiens

<400> SEQUENCE: 54
acacagggcu guugugaaga cu                                         22

<210> SEQ ID NO 55
<211> LENGTH: 22
<212> TYPE: RNA
<213> ORGANISM: Homo sapiens

<400> SEQUENCE: 55
cuuucagucg gauguuuaca gc                                         22

<210> SEQ ID NO 56
<211> LENGTH: 22
<212> TYPE: RNA
<213> ORGANISM: Homo sapiens

<400> SEQUENCE: 56
uaugugccuu uggacuacau cg                                         22
```

```
<210> SEQ ID NO 57
<211> LENGTH: 22
<212> TYPE: RNA
<213> ORGANISM: Homo sapiens

<400> SEQUENCE: 57
ugccuacuga gcugaaacac ag                                              22

<210> SEQ ID NO 58
<211> LENGTH: 22
<212> TYPE: RNA
<213> ORGANISM: Homo sapiens

<400> SEQUENCE: 58
aaccaucgac cguugagugg ac                                              22

<210> SEQ ID NO 59
<211> LENGTH: 24
<212> TYPE: RNA
<213> ORGANISM: Homo sapiens

<400> SEQUENCE: 59
uugcagcugc cugggaguga cuuc                                            24

<210> SEQ ID NO 60
<211> LENGTH: 21
<212> TYPE: RNA
<213> ORGANISM: Homo sapiens

<400> SEQUENCE: 60
uugggacaua cuuaugcuaa a                                               21

<210> SEQ ID NO 61
<211> LENGTH: 22
<212> TYPE: RNA
<213> ORGANISM: Homo sapiens

<400> SEQUENCE: 61
ugugcgcagg gagaccucuc cc                                              22

<210> SEQ ID NO 62
<211> LENGTH: 17
<212> TYPE: RNA
<213> ORGANISM: Homo sapiens

<400> SEQUENCE: 62
ucgccuccuc cucuccc                                                    17

<210> SEQ ID NO 63
<211> LENGTH: 22
<212> TYPE: RNA
<213> ORGANISM: Homo sapiens

<400> SEQUENCE: 63
acccgucccg uucgucccg ga                                               22

<210> SEQ ID NO 64
<211> LENGTH: 22
<212> TYPE: RNA
<213> ORGANISM: Homo sapiens

<400> SEQUENCE: 64
aaggagcuca cagucuauug ag                                              22
```

```
<210> SEQ ID NO 65
<211> LENGTH: 22
<212> TYPE: RNA
<213> ORGANISM: Homo sapiens

<400> SEQUENCE: 65
uggugguuua caaaguaauu ca                                              22

<210> SEQ ID NO 66
<211> LENGTH: 21
<212> TYPE: RNA
<213> ORGANISM: Homo sapiens

<400> SEQUENCE: 66
uuaggccgca gaucugggug a                                               21

<210> SEQ ID NO 67
<211> LENGTH: 22
<212> TYPE: RNA
<213> ORGANISM: Homo sapiens

<400> SEQUENCE: 67
caagcuugua ucuauaggua ug                                              22

<210> SEQ ID NO 68
<211> LENGTH: 22
<212> TYPE: RNA
<213> ORGANISM: Homo sapiens

<400> SEQUENCE: 68
uggguuccug gcaugcugau uu                                              22

<210> SEQ ID NO 69
<211> LENGTH: 22
<212> TYPE: RNA
<213> ORGANISM: Homo sapiens

<400> SEQUENCE: 69
ugccuacuga gcugauauca gu                                              22

<210> SEQ ID NO 70
<211> LENGTH: 21
<212> TYPE: RNA
<213> ORGANISM: Homo sapiens

<400> SEQUENCE: 70
acggugcugg auguggccuu u                                               21

<210> SEQ ID NO 71
<211> LENGTH: 22
<212> TYPE: RNA
<213> ORGANISM: Homo sapiens

<400> SEQUENCE: 71
uguaaacauc cuugacugga ag                                              22

<210> SEQ ID NO 72
<211> LENGTH: 22
<212> TYPE: RNA
<213> ORGANISM: Homo sapiens

<400> SEQUENCE: 72
aaaucucugc aggcaaaugu ga                                              22
```

```
<210> SEQ ID NO 73
<211> LENGTH: 21
<212> TYPE: RNA
<213> ORGANISM: Homo sapiens

<400> SEQUENCE: 73
cuccguuugc cguuucgcu g                                              21

<210> SEQ ID NO 74
<211> LENGTH: 22
<212> TYPE: RNA
<213> ORGANISM: Homo sapiens

<400> SEQUENCE: 74
ccaaaacugc aguuacuuuu gc                                            22

<210> SEQ ID NO 75
<211> LENGTH: 22
<212> TYPE: RNA
<213> ORGANISM: Homo sapiens

<400> SEQUENCE: 75
uuagggcccu ggcuccaucu cc                                            22

<210> SEQ ID NO 76
<211> LENGTH: 22
<212> TYPE: RNA
<213> ORGANISM: Homo sapiens

<400> SEQUENCE: 76
ucuucucugu uuuggccaug ug                                            22

<210> SEQ ID NO 77
<211> LENGTH: 22
<212> TYPE: RNA
<213> ORGANISM: Homo sapiens

<400> SEQUENCE: 77
caaucagcaa guauacugcc cu                                            22

<210> SEQ ID NO 78
<211> LENGTH: 22
<212> TYPE: RNA
<213> ORGANISM: Homo sapiens

<400> SEQUENCE: 78
cucuagaggg aagcgcuuuc ug                                            22

<210> SEQ ID NO 79
<211> LENGTH: 20
<212> TYPE: RNA
<213> ORGANISM: Homo sapiens

<400> SEQUENCE: 79
agagucuugu gaugucuugc                                               20

<210> SEQ ID NO 80
<211> LENGTH: 22
<212> TYPE: RNA
<213> ORGANISM: Homo sapiens

<400> SEQUENCE: 80
```
cucuagaggg aagcgcuuuc ug                                                22

<210> SEQ ID NO 81
<211> LENGTH: 19
<212> TYPE: RNA
<213> ORGANISM: Homo sapiens

<400> SEQUENCE: 81
uggauuuuug gaucaggga                                                    19

<210> SEQ ID NO 82
<211> LENGTH: 17
<212> TYPE: RNA
<213> ORGANISM: Homo sapiens

<400> SEQUENCE: 82
ucccuguucg ggcgcca                                                      17

<210> SEQ ID NO 83
<211> LENGTH: 23
<212> TYPE: RNA
<213> ORGANISM: Homo sapiens

<400> SEQUENCE: 83
uucucgagga aagaagcacu uuc                                               23

<210> SEQ ID NO 84
<211> LENGTH: 22
<212> TYPE: RNA
<213> ORGANISM: Homo sapiens

<400> SEQUENCE: 84
uuuagagacg gggucuugcu cu                                                22

<210> SEQ ID NO 85
<211> LENGTH: 22
<212> TYPE: RNA
<213> ORGANISM: Homo sapiens

<400> SEQUENCE: 85
cagugguuuu acccuauggu ag                                                22

<210> SEQ ID NO 86
<211> LENGTH: 22
<212> TYPE: RNA
<213> ORGANISM: Homo sapiens

<400> SEQUENCE: 86
augguuccgu caagcaccau gg                                                22

<210> SEQ ID NO 87
<211> LENGTH: 22
<212> TYPE: RNA
<213> ORGANISM: Homo sapiens

<400> SEQUENCE: 87
cuuggcaccu agcaagcacu ca                                                22

<210> SEQ ID NO 88
<211> LENGTH: 21
<212> TYPE: RNA
<213> ORGANISM: Homo sapiens

<400> SEQUENCE: 88
uacuuggaaa ggcaucaguu g                                              21

<210> SEQ ID NO 89
<211> LENGTH: 21
<212> TYPE: RNA
<213> ORGANISM: Homo sapiens

<400> SEQUENCE: 89
ugauauguuu gauauugggu u                                              21

<210> SEQ ID NO 90
<211> LENGTH: 22
<212> TYPE: RNA
<213> ORGANISM: Homo sapiens

<400> SEQUENCE: 90
ugcccuuaaa ggugaaccca gu                                             22

<210> SEQ ID NO 91
<211> LENGTH: 22
<212> TYPE: RNA
<213> ORGANISM: Homo sapiens

<400> SEQUENCE: 91
cugcaaugua agcacuucuu ac                                             22

<210> SEQ ID NO 92
<211> LENGTH: 22
<212> TYPE: RNA
<213> ORGANISM: Homo sapiens

<400> SEQUENCE: 92
cugggagagg guuguuuacu cc                                             22

<210> SEQ ID NO 93
<211> LENGTH: 22
<212> TYPE: RNA
<213> ORGANISM: Homo sapiens

<400> SEQUENCE: 93
ugcaacgaac cugagccacu ga                                             22

<210> SEQ ID NO 94
<211> LENGTH: 23
<212> TYPE: RNA
<213> ORGANISM: Homo sapiens

<400> SEQUENCE: 94
ccucagggcu guagaacagg gcu                                            23

<210> SEQ ID NO 95
<211> LENGTH: 22
<212> TYPE: RNA
<213> ORGANISM: Homo sapiens

<400> SEQUENCE: 95
auguagggcu aaaagccaug gg                                             22

<210> SEQ ID NO 96
<211> LENGTH: 22
<212> TYPE: RNA
<213> ORGANISM: Homo sapiens

```
<400> SEQUENCE: 96
cguguauuug acaagcugag uu                                              22

<210> SEQ ID NO 97
<211> LENGTH: 22
<212> TYPE: RNA
<213> ORGANISM: Homo sapiens

<400> SEQUENCE: 97
cugaagcuca gagggcucug au                                              22

<210> SEQ ID NO 98
<211> LENGTH: 21
<212> TYPE: RNA
<213> ORGANISM: Homo sapiens

<400> SEQUENCE: 98
aguuaggauu aggucgugga a                                               21

<210> SEQ ID NO 99
<211> LENGTH: 22
<212> TYPE: RNA
<213> ORGANISM: Homo sapiens

<400> SEQUENCE: 99
cugcgcaagc uacugccuug cu                                              22

<210> SEQ ID NO 100
<211> LENGTH: 20
<212> TYPE: RNA
<213> ORGANISM: Homo sapiens

<400> SEQUENCE: 100
uaaggcacgc ggugaaugcc                                                 20

<210> SEQ ID NO 101
<211> LENGTH: 23
<212> TYPE: RNA
<213> ORGANISM: Homo sapiens

<400> SEQUENCE: 101
gcagcagaga auaggacuac guc                                             23

<210> SEQ ID NO 102
<211> LENGTH: 23
<212> TYPE: RNA
<213> ORGANISM: Homo sapiens

<400> SEQUENCE: 102
uagugcaaua uugcuuauag ggu                                             23

<210> SEQ ID NO 103
<211> LENGTH: 22
<212> TYPE: RNA
<213> ORGANISM: Homo sapiens

<400> SEQUENCE: 103
ugucuacuac uggagacacu gg                                              22

<210> SEQ ID NO 104
<211> LENGTH: 23
<212> TYPE: RNA
<213> ORGANISM: Homo sapiens
```

```
<400> SEQUENCE: 104
ucccuguccu ccaggagcuc acg                                           23

<210> SEQ ID NO 105
<211> LENGTH: 22
<212> TYPE: RNA
<213> ORGANISM: Homo sapiens

<400> SEQUENCE: 105
uuuugcaaua uguuccugaa ua                                            22

<210> SEQ ID NO 106
<211> LENGTH: 22
<212> TYPE: RNA
<213> ORGANISM: Homo sapiens

<400> SEQUENCE: 106
acucaaaacc cuucagugac uu                                            22

<210> SEQ ID NO 107
<211> LENGTH: 25
<212> TYPE: RNA
<213> ORGANISM: Homo sapiens

<400> SEQUENCE: 107
aggcaccagc caggcauugc ucagc                                         25

<210> SEQ ID NO 108
<211> LENGTH: 22
<212> TYPE: RNA
<213> ORGANISM: Homo sapiens

<400> SEQUENCE: 108
aaaagcuggg uugagagggc ga                                            22

<210> SEQ ID NO 109
<211> LENGTH: 22
<212> TYPE: RNA
<213> ORGANISM: Homo sapiens

<400> SEQUENCE: 109
uauguaacau gguccacuaa cu                                            22

<210> SEQ ID NO 110
<211> LENGTH: 23
<212> TYPE: RNA
<213> ORGANISM: Homo sapiens

<400> SEQUENCE: 110
cuggagauau ggaagagcug ugu                                           23

<210> SEQ ID NO 111
<211> LENGTH: 22
<212> TYPE: RNA
<213> ORGANISM: Homo sapiens

<400> SEQUENCE: 111
auauuaccau uagcucaucu uu                                            22

<210> SEQ ID NO 112
<211> LENGTH: 22
<212> TYPE: RNA
```

```
<213> ORGANISM: Homo sapiens

<400> SEQUENCE: 112
acugcaguga aggcacuugu ag                                              22

<210> SEQ ID NO 113
<211> LENGTH: 23
<212> TYPE: RNA
<213> ORGANISM: Homo sapiens

<400> SEQUENCE: 113
uaggcagugu cauuagcuga uug                                             23

<210> SEQ ID NO 114
<211> LENGTH: 22
<212> TYPE: RNA
<213> ORGANISM: Homo sapiens

<400> SEQUENCE: 114
accuugccuu gcugcccggg cc                                              22

<210> SEQ ID NO 115
<211> LENGTH: 22
<212> TYPE: RNA
<213> ORGANISM: Homo sapiens

<400> SEQUENCE: 115
uacugcagac guggcaauca ug                                              22

<210> SEQ ID NO 116
<211> LENGTH: 23
<212> TYPE: RNA
<213> ORGANISM: Homo sapiens

<400> SEQUENCE: 116
ugagcgccuc gacgacagag ccg                                             23

<210> SEQ ID NO 117
<211> LENGTH: 19
<212> TYPE: RNA
<213> ORGANISM: Homo sapiens

<400> SEQUENCE: 117
aaaagcuggg uugagagga                                                  19

<210> SEQ ID NO 118
<211> LENGTH: 22
<212> TYPE: RNA
<213> ORGANISM: Homo sapiens

<400> SEQUENCE: 118
uccgucucag uuacuuuaua gc                                              22

<210> SEQ ID NO 119
<211> LENGTH: 21
<212> TYPE: RNA
<213> ORGANISM: Homo sapiens

<400> SEQUENCE: 119
caaaacguga ggcgcugcua u                                               21

<210> SEQ ID NO 120
<211> LENGTH: 21
```

```
<212> TYPE: RNA
<213> ORGANISM: Homo sapiens

<400> SEQUENCE: 120
ucguggccug gucuccauua u                                              21

<210> SEQ ID NO 121
<211> LENGTH: 18
<212> TYPE: RNA
<213> ORGANISM: Homo sapiens

<400> SEQUENCE: 121
ugcuuccuuu cagagggu                                                  18

<210> SEQ ID NO 122
<211> LENGTH: 22
<212> TYPE: RNA
<213> ORGANISM: Homo sapiens

<400> SEQUENCE: 122
augcaccugg gcaaggauuc ug                                             22

<210> SEQ ID NO 123
<211> LENGTH: 22
<212> TYPE: RNA
<213> ORGANISM: Homo sapiens

<400> SEQUENCE: 123
ugcccugugg acucaguucu gg                                             22

<210> SEQ ID NO 124
<211> LENGTH: 22
<212> TYPE: RNA
<213> ORGANISM: Homo sapiens

<400> SEQUENCE: 124
acaguagucu gcacauuggu ua                                             22

<210> SEQ ID NO 125
<211> LENGTH: 22
<212> TYPE: RNA
<213> ORGANISM: Homo sapiens

<400> SEQUENCE: 125
ucugggcaac aaagugagac cu                                             22

<210> SEQ ID NO 126
<211> LENGTH: 20
<212> TYPE: RNA
<213> ORGANISM: Homo sapiens

<400> SEQUENCE: 126
acucaaacug uggggggcacu                                               20

<210> SEQ ID NO 127
<211> LENGTH: 22
<212> TYPE: RNA
<213> ORGANISM: Homo sapiens

<400> SEQUENCE: 127
cacgcucaug cacacaccca ca                                             22

<210> SEQ ID NO 128
```

```
<211> LENGTH: 22
<212> TYPE: RNA
<213> ORGANISM: Homo sapiens

<400> SEQUENCE: 128
augggugaau uuguagaagg au                                            22

<210> SEQ ID NO 129
<211> LENGTH: 22
<212> TYPE: RNA
<213> ORGANISM: Homo sapiens

<400> SEQUENCE: 129
aaaaccgucu aguuacaguu gu                                            22

<210> SEQ ID NO 130
<211> LENGTH: 24
<212> TYPE: RNA
<213> ORGANISM: Homo sapiens

<400> SEQUENCE: 130
agcagaagca gggagguucu ccca                                          24

<210> SEQ ID NO 131
<211> LENGTH: 22
<212> TYPE: RNA
<213> ORGANISM: Homo sapiens

<400> SEQUENCE: 131
uaacugguug aacaacugaa cc                                            22

<210> SEQ ID NO 132
<211> LENGTH: 22
<212> TYPE: RNA
<213> ORGANISM: Homo sapiens

<400> SEQUENCE: 132
cugguuucac augguggcuu ag                                            22

<210> SEQ ID NO 133
<211> LENGTH: 22
<212> TYPE: RNA
<213> ORGANISM: Homo sapiens

<400> SEQUENCE: 133
caaaacuggc aauuacuuuu gc                                            22

<210> SEQ ID NO 134
<211> LENGTH: 22
<212> TYPE: RNA
<213> ORGANISM: Homo sapiens

<400> SEQUENCE: 134
uauguaacac gguccacuaa cc                                            22

<210> SEQ ID NO 135
<211> LENGTH: 22
<212> TYPE: RNA
<213> ORGANISM: Homo sapiens

<400> SEQUENCE: 135
caacaaauca cagucugcca ua                                            22
```

```
<210> SEQ ID NO 136
<211> LENGTH: 22
<212> TYPE: RNA
<213> ORGANISM: Homo sapiens

<400> SEQUENCE: 136
aaagugcuuc ccuuuggacu gu                                              22

<210> SEQ ID NO 137
<211> LENGTH: 20
<212> TYPE: RNA
<213> ORGANISM: Homo sapiens

<400> SEQUENCE: 137
ggggagcugu ggaagcagua                                                 20

<210> SEQ ID NO 138
<211> LENGTH: 22
<212> TYPE: RNA
<213> ORGANISM: Homo sapiens

<400> SEQUENCE: 138
aacgccauua ucacacuaaa ua                                              22

<210> SEQ ID NO 139
<211> LENGTH: 22
<212> TYPE: RNA
<213> ORGANISM: Homo sapiens

<400> SEQUENCE: 139
uccgagccug ggucucccuc uu                                              22

<210> SEQ ID NO 140
<211> LENGTH: 22
<212> TYPE: RNA
<213> ORGANISM: Homo sapiens

<400> SEQUENCE: 140
ugcggggcua gggcuaacag ca                                              22

<210> SEQ ID NO 141
<211> LENGTH: 22
<212> TYPE: RNA
<213> ORGANISM: Homo sapiens

<400> SEQUENCE: 141
uauaccucag uuuuaucagg ug                                              22

<210> SEQ ID NO 142
<211> LENGTH: 22
<212> TYPE: RNA
<213> ORGANISM: Homo sapiens

<400> SEQUENCE: 142
acccuaucaa uauugucucu gc                                              22

<210> SEQ ID NO 143
<211> LENGTH: 21
<212> TYPE: RNA
<213> ORGANISM: Homo sapiens

<400> SEQUENCE: 143
caucccuugc augguggagg g                                               21
```

```
<210> SEQ ID NO 144
<211> LENGTH: 22
<212> TYPE: RNA
<213> ORGANISM: Homo sapiens

<400> SEQUENCE: 144
aguucuucag uggcaagcuu ua                                            22

<210> SEQ ID NO 145
<211> LENGTH: 24
<212> TYPE: RNA
<213> ORGANISM: Homo sapiens

<400> SEQUENCE: 145
ucccugagac ccuuuaaccu guga                                          24

<210> SEQ ID NO 146
<211> LENGTH: 22
<212> TYPE: RNA
<213> ORGANISM: Homo sapiens

<400> SEQUENCE: 146
cuauacaguc uacugucuuu cc                                            22

<210> SEQ ID NO 147
<211> LENGTH: 21
<212> TYPE: RNA
<213> ORGANISM: Homo sapiens

<400> SEQUENCE: 147
ucacuccucu ccucccgucu u                                             21

<210> SEQ ID NO 148
<211> LENGTH: 22
<212> TYPE: RNA
<213> ORGANISM: Homo sapiens

<400> SEQUENCE: 148
uuugaggcua cagugagaug ug                                            22

<210> SEQ ID NO 149
<211> LENGTH: 22
<212> TYPE: RNA
<213> ORGANISM: Homo sapiens

<400> SEQUENCE: 149
ucaguaaaug uuuauuagau ga                                            22

<210> SEQ ID NO 150
<211> LENGTH: 24
<212> TYPE: RNA
<213> ORGANISM: Homo sapiens

<400> SEQUENCE: 150
agccuggaag cuggagccug cagu                                          24

<210> SEQ ID NO 151
<211> LENGTH: 23
<212> TYPE: RNA
<213> ORGANISM: Homo sapiens

<400> SEQUENCE: 151
agguugggau cgguugcaau gcu                                           23
```

```
<210> SEQ ID NO 152
<211> LENGTH: 22
<212> TYPE: RNA
<213> ORGANISM: Homo sapiens

<400> SEQUENCE: 152
cguuugccac uaaccucaac cu                                          22

<210> SEQ ID NO 153
<211> LENGTH: 22
<212> TYPE: RNA
<213> ORGANISM: Homo sapiens

<400> SEQUENCE: 153
cucuagaggg aagcacuuuc ug                                          22

<210> SEQ ID NO 154
<211> LENGTH: 22
<212> TYPE: RNA
<213> ORGANISM: Homo sapiens

<400> SEQUENCE: 154
uucaaguaau ccaggauagg cu                                          22

<210> SEQ ID NO 155
<211> LENGTH: 22
<212> TYPE: RNA
<213> ORGANISM: Homo sapiens

<400> SEQUENCE: 155
ucaggcucag uccccucccg au                                          22

<210> SEQ ID NO 156
<211> LENGTH: 23
<212> TYPE: RNA
<213> ORGANISM: Homo sapiens

<400> SEQUENCE: 156
uacugcauca ggaacugauu gga                                         23

<210> SEQ ID NO 157
<211> LENGTH: 19
<212> TYPE: RNA
<213> ORGANISM: Homo sapiens

<400> SEQUENCE: 157
gggcgccugu gaucccaac                                              19

<210> SEQ ID NO 158
<211> LENGTH: 24
<212> TYPE: RNA
<213> ORGANISM: Homo sapiens

<400> SEQUENCE: 158
uucuccaaaa gaaagcacuu ucg                                         24

<210> SEQ ID NO 159
<211> LENGTH: 21
<212> TYPE: RNA
<213> ORGANISM: Homo sapiens

<400> SEQUENCE: 159
```

-continued

```
cauuauuacu uuugguacgc g                                          21

<210> SEQ ID NO 160
<211> LENGTH: 22
<212> TYPE: RNA
<213> ORGANISM: Homo sapiens

<400> SEQUENCE: 160
uaacacuguc ugguaacgau gu                                         22

<210> SEQ ID NO 161
<211> LENGTH: 22
<212> TYPE: RNA
<213> ORGANISM: Homo sapiens

<400> SEQUENCE: 161
acuuuaacau ggaagugcuu uc                                         22

<210> SEQ ID NO 162
<211> LENGTH: 21
<212> TYPE: RNA
<213> ORGANISM: Homo sapiens

<400> SEQUENCE: 162
cauaaaguag aaagcacuac u                                          21

<210> SEQ ID NO 163
<211> LENGTH: 22
<212> TYPE: RNA
<213> ORGANISM: Homo sapiens

<400> SEQUENCE: 163
uucuccaaaa gggagcacuu uc                                         22

<210> SEQ ID NO 164
<211> LENGTH: 23
<212> TYPE: RNA
<213> ORGANISM: Homo sapiens

<400> SEQUENCE: 164
cacucagccu ugagggcacu uuc                                        23

<210> SEQ ID NO 165
<211> LENGTH: 21
<212> TYPE: RNA
<213> ORGANISM: Homo sapiens

<400> SEQUENCE: 165
uacaguacug ugauaacuga a                                          21

<210> SEQ ID NO 166
<211> LENGTH: 22
<212> TYPE: RNA
<213> ORGANISM: Homo sapiens

<400> SEQUENCE: 166
gugacaucac auauacggca gc                                         22

<210> SEQ ID NO 167
<211> LENGTH: 22
<212> TYPE: RNA
<213> ORGANISM: Homo sapiens

<400> SEQUENCE: 167
```

-continued gugagucucu aagaaaagag ga                                        22

<210> SEQ ID NO 168
<211> LENGTH: 22
<212> TYPE: RNA
<213> ORGANISM: Homo sapiens

<400> SEQUENCE: 168
ugagguagua guuuguacag uu                                        22

<210> SEQ ID NO 169
<211> LENGTH: 20
<212> TYPE: RNA
<213> ORGANISM: Homo sapiens

<400> SEQUENCE: 169
acugccccag gugcugcugg                                           20

<210> SEQ ID NO 170
<211> LENGTH: 20
<212> TYPE: RNA
<213> ORGANISM: Homo sapiens

<400> SEQUENCE: 170
auguauaaau guauacacac                                           20

<210> SEQ ID NO 171
<211> LENGTH: 19
<212> TYPE: RNA
<213> ORGANISM: Homo sapiens

<400> SEQUENCE: 171
aagcagcugc cucugaggc                                            19

<210> SEQ ID NO 172
<211> LENGTH: 21
<212> TYPE: RNA
<213> ORGANISM: Homo sapiens

<400> SEQUENCE: 172
uucacagugg cuaaguuccg c                                         21

<210> SEQ ID NO 173
<211> LENGTH: 20
<212> TYPE: RNA
<213> ORGANISM: Homo sapiens

<400> SEQUENCE: 173
agaccauggg uucucauugu                                           20

<210> SEQ ID NO 174
<211> LENGTH: 23
<212> TYPE: RNA
<213> ORGANISM: Homo sapiens

<400> SEQUENCE: 174
ugugcuugcu cgucccgccc gca                                       23

<210> SEQ ID NO 175
<211> LENGTH: 22
<212> TYPE: RNA
<213> ORGANISM: Homo sapiens

```
<400> SEQUENCE: 175
ucguaccgug aguaauaaug cg                                          22

<210> SEQ ID NO 176
<211> LENGTH: 21
<212> TYPE: RNA
<213> ORGANISM: Homo sapiens

<400> SEQUENCE: 176
uucaaguaau ucaggauagg u                                           21

<210> SEQ ID NO 177
<211> LENGTH: 21
<212> TYPE: RNA
<213> ORGANISM: Homo sapiens

<400> SEQUENCE: 177
ggcuagcaac agcgcuuacc u                                           21

<210> SEQ ID NO 178
<211> LENGTH: 22
<212> TYPE: RNA
<213> ORGANISM: Homo sapiens

<400> SEQUENCE: 178
uacgucaucg uugucaucgu ca                                          22

<210> SEQ ID NO 179
<211> LENGTH: 22
<212> TYPE: RNA
<213> ORGANISM: Homo sapiens

<400> SEQUENCE: 179
cacacacugc aauuacuuuu gc                                          22

<210> SEQ ID NO 180
<211> LENGTH: 22
<212> TYPE: RNA
<213> ORGANISM: Homo sapiens

<400> SEQUENCE: 180
acagcaggca cagacaggca gu                                          22

<210> SEQ ID NO 181
<211> LENGTH: 23
<212> TYPE: RNA
<213> ORGANISM: Homo sapiens

<400> SEQUENCE: 181
guccaguuuu cccaggaauc ccu                                         23

<210> SEQ ID NO 182
<211> LENGTH: 23
<212> TYPE: RNA
<213> ORGANISM: Homo sapiens

<400> SEQUENCE: 182
uuaaugcuaa ucgugauagg ggu                                         23

<210> SEQ ID NO 183
<211> LENGTH: 22
<212> TYPE: RNA
<213> ORGANISM: Homo sapiens
```

-continued

<400> SEQUENCE: 183
cucaucugca aagaaguaag ug                                          22

<210> SEQ ID NO 184
<211> LENGTH: 23
<212> TYPE: RNA
<213> ORGANISM: Homo sapiens

<400> SEQUENCE: 184
aggaccugcg ggacaagauu cuu                                         23

<210> SEQ ID NO 185
<211> LENGTH: 23
<212> TYPE: RNA
<213> ORGANISM: Homo sapiens

<400> SEQUENCE: 185
agcuacauug ucugcugggu uuc                                         23

<210> SEQ ID NO 186
<211> LENGTH: 22
<212> TYPE: RNA
<213> ORGANISM: Homo sapiens

<400> SEQUENCE: 186
uagcagcacg uaaauauugg cg                                          22

<210> SEQ ID NO 187
<211> LENGTH: 21
<212> TYPE: RNA
<213> ORGANISM: Homo sapiens

<400> SEQUENCE: 187
agcuacaucu ggcuacuggg u                                           21

<210> SEQ ID NO 188
<211> LENGTH: 23
<212> TYPE: RNA
<213> ORGANISM: Homo sapiens

<400> SEQUENCE: 188
uaagugcuuc cauguuuuag uag                                         23

<210> SEQ ID NO 189
<211> LENGTH: 19
<212> TYPE: RNA
<213> ORGANISM: Homo sapiens

<400> SEQUENCE: 189
aggcacggug ucagcaggc                                              19

<210> SEQ ID NO 190
<211> LENGTH: 22
<212> TYPE: RNA
<213> ORGANISM: Homo sapiens

<400> SEQUENCE: 190
agagguagua gguugcauag uu                                          22

<210> SEQ ID NO 191
<211> LENGTH: 21
<212> TYPE: RNA

```
<213> ORGANISM: Homo sapiens

<400> SEQUENCE: 191
aagccugccc ggcuccucgg g                                              21

<210> SEQ ID NO 192
<211> LENGTH: 20
<212> TYPE: RNA
<213> ORGANISM: Homo sapiens

<400> SEQUENCE: 192
gugcauugcu guugcauugc                                                20

<210> SEQ ID NO 193
<211> LENGTH: 22
<212> TYPE: RNA
<213> ORGANISM: Homo sapiens

<400> SEQUENCE: 193
acuggacuua gggucagaag gc                                             22

<210> SEQ ID NO 194
<211> LENGTH: 22
<212> TYPE: RNA
<213> ORGANISM: Homo sapiens

<400> SEQUENCE: 194
uacucaggag aguggcaauc ac                                             22

<210> SEQ ID NO 195
<211> LENGTH: 23
<212> TYPE: RNA
<213> ORGANISM: Homo sapiens

<400> SEQUENCE: 195
uguaguguuu ccuacuuuau gga                                            23

<210> SEQ ID NO 196
<211> LENGTH: 22
<212> TYPE: RNA
<213> ORGANISM: Homo sapiens

<400> SEQUENCE: 196
aaucguacag ggucauccac uu                                             22

<210> SEQ ID NO 197
<211> LENGTH: 22
<212> TYPE: RNA
<213> ORGANISM: Homo sapiens

<400> SEQUENCE: 197
uugcauaguc acaaaaguga uc                                             22

<210> SEQ ID NO 198
<211> LENGTH: 21
<212> TYPE: RNA
<213> ORGANISM: Homo sapiens

<400> SEQUENCE: 198
ugagaugaag cacguagcu c                                               21

<210> SEQ ID NO 199
<211> LENGTH: 21
```

```
<212> TYPE: RNA
<213> ORGANISM: Homo sapiens

<400> SEQUENCE: 199
cagcagcaca cugugguuug u                                              21

<210> SEQ ID NO 200
<211> LENGTH: 21
<212> TYPE: RNA
<213> ORGANISM: Homo sapiens

<400> SEQUENCE: 200
gcuaguccug acucagccag u                                              21

<210> SEQ ID NO 201
<211> LENGTH: 21
<212> TYPE: RNA
<213> ORGANISM: Homo sapiens

<400> SEQUENCE: 201
auugacacuu cugugaguag a                                              21

<210> SEQ ID NO 202
<211> LENGTH: 22
<212> TYPE: RNA
<213> ORGANISM: Homo sapiens

<400> SEQUENCE: 202
uuuguucguu cggcucgcgu ga                                             22

<210> SEQ ID NO 203
<211> LENGTH: 23
<212> TYPE: RNA
<213> ORGANISM: Homo sapiens

<400> SEQUENCE: 203
aaugacacga ucacucccgu uga                                            23

<210> SEQ ID NO 204
<211> LENGTH: 21
<212> TYPE: RNA
<213> ORGANISM: Homo sapiens

<400> SEQUENCE: 204
ugacaacuau ggaugagcuc u                                              21

<210> SEQ ID NO 205
<211> LENGTH: 22
<212> TYPE: RNA
<213> ORGANISM: Homo sapiens

<400> SEQUENCE: 205
aacgcacuuc ccuuuagagu gu                                             22

<210> SEQ ID NO 206
<211> LENGTH: 23
<212> TYPE: RNA
<213> ORGANISM: Homo sapiens

<400> SEQUENCE: 206
acuuacagac aagagccuug cuc                                            23

<210> SEQ ID NO 207
```

```
<211> LENGTH: 22
<212> TYPE: RNA
<213> ORGANISM: Homo sapiens

<400> SEQUENCE: 207
uauugcacau uacuaaguug ca                                              22

<210> SEQ ID NO 208
<211> LENGTH: 24
<212> TYPE: RNA
<213> ORGANISM: Homo sapiens

<400> SEQUENCE: 208
acaaagugcu ucccuuuaga gugu                                            24

<210> SEQ ID NO 209
<211> LENGTH: 22
<212> TYPE: RNA
<213> ORGANISM: Homo sapiens

<400> SEQUENCE: 209
uauggcacug guagaauuca cu                                              22

<210> SEQ ID NO 210
<211> LENGTH: 21
<212> TYPE: RNA
<213> ORGANISM: Homo sapiens

<400> SEQUENCE: 210
aucacauugc cagggauuac c                                               21

<210> SEQ ID NO 211
<211> LENGTH: 22
<212> TYPE: RNA
<213> ORGANISM: Homo sapiens

<400> SEQUENCE: 211
gugaaauguu uaggaccacu ag                                              22

<210> SEQ ID NO 212
<211> LENGTH: 23
<212> TYPE: RNA
<213> ORGANISM: Homo sapiens

<400> SEQUENCE: 212
uacccuguag auccgaauuu gug                                             23

<210> SEQ ID NO 213
<211> LENGTH: 23
<212> TYPE: RNA
<213> ORGANISM: Homo sapiens

<400> SEQUENCE: 213
ugucugcccg caugccugcc ucu                                             23

<210> SEQ ID NO 214
<211> LENGTH: 22
<212> TYPE: RNA
<213> ORGANISM: Homo sapiens

<400> SEQUENCE: 214
caucuuaccg gacagugcug ga                                              22
```

```
<210> SEQ ID NO 215
<211> LENGTH: 23
<212> TYPE: RNA
<213> ORGANISM: Homo sapiens

<400> SEQUENCE: 215
agguuacccg agcaacuuug cau                                          23

<210> SEQ ID NO 216
<211> LENGTH: 25
<212> TYPE: RNA
<213> ORGANISM: Homo sapiens

<400> SEQUENCE: 216
ggcggaggga aguagguccg uuggu                                        25

<210> SEQ ID NO 217
<211> LENGTH: 22
<212> TYPE: RNA
<213> ORGANISM: Homo sapiens

<400> SEQUENCE: 217
ucagugcauc acagaacuuu gu                                           22

<210> SEQ ID NO 218
<211> LENGTH: 22
<212> TYPE: RNA
<213> ORGANISM: Homo sapiens

<400> SEQUENCE: 218
cggguggauc acgaugcaau uu                                           22

<210> SEQ ID NO 219
<211> LENGTH: 22
<212> TYPE: RNA
<213> ORGANISM: Homo sapiens

<400> SEQUENCE: 219
uggcaguguc uuagcugguu gu                                           22

<210> SEQ ID NO 220
<211> LENGTH: 22
<212> TYPE: RNA
<213> ORGANISM: Homo sapiens

<400> SEQUENCE: 220
guagauucuc cuucuaugag ua                                           22

<210> SEQ ID NO 221
<211> LENGTH: 20
<212> TYPE: RNA
<213> ORGANISM: Homo sapiens

<400> SEQUENCE: 221
aggguguuuc ucucaucucu                                              20

<210> SEQ ID NO 222
<211> LENGTH: 22
<212> TYPE: RNA
<213> ORGANISM: Homo sapiens

<400> SEQUENCE: 222 uauguggau gguaaaccgc uu                                            22
```

```
<210> SEQ ID NO 223
<211> LENGTH: 23
<212> TYPE: RNA
<213> ORGANISM: Homo sapiens

<400> SEQUENCE: 223
ucggggauca ucaugucacg aga                                          23

<210> SEQ ID NO 224
<211> LENGTH: 23
<212> TYPE: RNA
<213> ORGANISM: Homo sapiens

<400> SEQUENCE: 224
agugccugag ggaguaagag ccc                                          23

<210> SEQ ID NO 225
<211> LENGTH: 19
<212> TYPE: RNA
<213> ORGANISM: Homo sapiens

<400> SEQUENCE: 225
gagccaguug gacaggagc                                               19

<210> SEQ ID NO 226
<211> LENGTH: 21
<212> TYPE: RNA
<213> ORGANISM: Homo sapiens

<400> SEQUENCE: 226
uggguuuacg uugggagaac u                                            21

<210> SEQ ID NO 227
<211> LENGTH: 22
<212> TYPE: RNA
<213> ORGANISM: Homo sapiens

<400> SEQUENCE: 227
aagcugccag uugaagaacu gu                                           22

<210> SEQ ID NO 228
<211> LENGTH: 23
<212> TYPE: RNA
<213> ORGANISM: Homo sapiens

<400> SEQUENCE: 228
ucuggcuccg ugucuucacu ccc                                          23

<210> SEQ ID NO 229
<211> LENGTH: 22
<212> TYPE: RNA
<213> ORGANISM: Homo sapiens

<400> SEQUENCE: 229
acaaagugcu ucccuuuaga gu                                           22

<210> SEQ ID NO 230
<211> LENGTH: 22
<212> TYPE: RNA
<213> ORGANISM: Homo sapiens

<400> SEQUENCE: 230
aaaccguuac cauuacugag uu                                           22
```

```
<210> SEQ ID NO 231
<211> LENGTH: 23
<212> TYPE: RNA
<213> ORGANISM: Homo sapiens

<400> SEQUENCE: 231
caaagugcug uucgugcagg uag                                        23

<210> SEQ ID NO 232
<211> LENGTH: 21
<212> TYPE: RNA
<213> ORGANISM: Homo sapiens

<400> SEQUENCE: 232
cacaagguau ugguauuacc u                                          21

<210> SEQ ID NO 233
<211> LENGTH: 22
<212> TYPE: RNA
<213> ORGANISM: Homo sapiens

<400> SEQUENCE: 233
aucaugaugg gcuccucggu gu                                         22

<210> SEQ ID NO 234
<211> LENGTH: 23
<212> TYPE: RNA
<213> ORGANISM: Homo sapiens

<400> SEQUENCE: 234
uuucaagcca gggggcguuu uuc                                        23

<210> SEQ ID NO 235
<211> LENGTH: 22
<212> TYPE: RNA
<213> ORGANISM: Homo sapiens

<400> SEQUENCE: 235
caaagcgcuc cccuuuagag gu                                         22

<210> SEQ ID NO 236
<211> LENGTH: 22
<212> TYPE: RNA
<213> ORGANISM: Homo sapiens

<400> SEQUENCE: 236
uugcauaugu aggauguccc au                                         22

<210> SEQ ID NO 237
<211> LENGTH: 23
<212> TYPE: RNA
<213> ORGANISM: Homo sapiens

<400> SEQUENCE: 237
aucgcugcgg uugcgagcgc ugu                                        23

<210> SEQ ID NO 238
<211> LENGTH: 22
<212> TYPE: RNA
<213> ORGANISM: Homo sapiens

<400> SEQUENCE: 238
```
uagcuuauca gacugauguu ga                                                    22

<210> SEQ ID NO 239
<211> LENGTH: 22
<212> TYPE: RNA
<213> ORGANISM: Homo sapiens

<400> SEQUENCE: 239
uggaauguaa agaaguaugu au                                                    22

<210> SEQ ID NO 240
<211> LENGTH: 22
<212> TYPE: RNA
<213> ORGANISM: Homo sapiens

<400> SEQUENCE: 240
ugucaguuug ucaaauaccc ca                                                    22

<210> SEQ ID NO 241
<211> LENGTH: 23
<212> TYPE: RNA
<213> ORGANISM: Homo sapiens

<400> SEQUENCE: 241
uguaaacauc cuacacucuc agc                                                   23

<210> SEQ ID NO 242
<211> LENGTH: 22
<212> TYPE: RNA
<213> ORGANISM: Homo sapiens

<400> SEQUENCE: 242
ugagguagua guuugugcug uu                                                    22

<210> SEQ ID NO 243
<211> LENGTH: 21
<212> TYPE: RNA
<213> ORGANISM: Homo sapiens

<400> SEQUENCE: 243
ucgaggagcu cacagucuag u                                                     21

<210> SEQ ID NO 244
<211> LENGTH: 22
<212> TYPE: RNA
<213> ORGANISM: Homo sapiens

<400> SEQUENCE: 244
cugcccuggc ccgagggacc ga                                                    22

<210> SEQ ID NO 245
<211> LENGTH: 23
<212> TYPE: RNA
<213> ORGANISM: Homo sapiens

<400> SEQUENCE: 245
aaaagugcuu acagugcagg uag                                                   23

<210> SEQ ID NO 246
<211> LENGTH: 23
<212> TYPE: RNA
<213> ORGANISM: Homo sapiens

<400> SEQUENCE: 246

-continued

| | |
|---|---|
| uaaagugcuu auagugcagg uag | 23 |

<210> SEQ ID NO 247
<211> LENGTH: 22
<212> TYPE: RNA
<213> ORGANISM: Homo sapiens

<400> SEQUENCE: 247

| | |
|---|---|
| ucagugcacu acagaacuuu gu | 22 |

<210> SEQ ID NO 248
<211> LENGTH: 22
<212> TYPE: RNA
<213> ORGANISM: Homo sapiens

<400> SEQUENCE: 248

| | |
|---|---|
| ugagguagua gguugugugg uu | 22 |

<210> SEQ ID NO 249
<211> LENGTH: 22
<212> TYPE: RNA
<213> ORGANISM: Homo sapiens

<400> SEQUENCE: 249

| | |
|---|---|
| cagugccucg gcagugcagc cc | 22 |

<210> SEQ ID NO 250
<211> LENGTH: 22
<212> TYPE: RNA
<213> ORGANISM: Homo sapiens

<400> SEQUENCE: 250

| | |
|---|---|
| uuauaauaca accugauaag ug | 22 |

<210> SEQ ID NO 251
<211> LENGTH: 24
<212> TYPE: RNA
<213> ORGANISM: Homo sapiens

<400> SEQUENCE: 251

| | |
|---|---|
| uuuggcaaug guagaacuca cacu | 24 |

<210> SEQ ID NO 252
<211> LENGTH: 22
<212> TYPE: RNA
<213> ORGANISM: Homo sapiens

<400> SEQUENCE: 252

| | |
|---|---|
| caaaccacac ugugguguua ga | 22 |

<210> SEQ ID NO 253
<211> LENGTH: 22
<212> TYPE: RNA
<213> ORGANISM: Homo sapiens

<400> SEQUENCE: 253

| | |
|---|---|
| gcugacuccu aguccagggc uc | 22 |

<210> SEQ ID NO 254
<211> LENGTH: 21
<212> TYPE: RNA
<213> ORGANISM: Homo sapiens

```
<400> SEQUENCE: 254
cacauuacac ggucgaccuc u                                          21

<210> SEQ ID NO 255
<211> LENGTH: 22
<212> TYPE: RNA
<213> ORGANISM: Homo sapiens

<400> SEQUENCE: 255
aacuggccua caaagcccca gu                                         22

<210> SEQ ID NO 256
<211> LENGTH: 22
<212> TYPE: RNA
<213> ORGANISM: Homo sapiens

<400> SEQUENCE: 256
ugugacuggu ugaccagagg gg                                         22

<210> SEQ ID NO 257
<211> LENGTH: 22
<212> TYPE: RNA
<213> ORGANISM: Homo sapiens

<400> SEQUENCE: 257
gguggcccgg ccgugccuga gg                                         22

<210> SEQ ID NO 258
<211> LENGTH: 22
<212> TYPE: RNA
<213> ORGANISM: Homo sapiens

<400> SEQUENCE: 258
aacaucacag caagucugug cu                                         22

<210> SEQ ID NO 259
<211> LENGTH: 21
<212> TYPE: RNA
<213> ORGANISM: Homo sapiens

<400> SEQUENCE: 259
agaccuggcc cagaccucag c                                          21

<210> SEQ ID NO 260
<211> LENGTH: 22
<212> TYPE: RNA
<213> ORGANISM: Homo sapiens

<400> SEQUENCE: 260
auucugcauu uuuagcaagu uc                                         22

<210> SEQ ID NO 261
<211> LENGTH: 22
<212> TYPE: RNA
<213> ORGANISM: Homo sapiens

<400> SEQUENCE: 261
caucuuacug ggcagcauug ga                                         22

<210> SEQ ID NO 262
<211> LENGTH: 20
<212> TYPE: RNA
<213> ORGANISM: Homo sapiens
```

-continued

```
<400> SEQUENCE: 262
ccucuggscc cuuccuccag                                              20

<210> SEQ ID NO 263
<211> LENGTH: 22
<212> TYPE: RNA
<213> ORGANISM: Homo sapiens

<400> SEQUENCE: 263
gaauguugcu cggugaaccc cu                                           22

<210> SEQ ID NO 264
<211> LENGTH: 18
<212> TYPE: RNA
<213> ORGANISM: Homo sapiens

<400> SEQUENCE: 264
uucacaggga ggugucau                                                18

<210> SEQ ID NO 265
<211> LENGTH: 21
<212> TYPE: RNA
<213> ORGANISM: Homo sapiens

<400> SEQUENCE: 265 cuuuugcgg ucugggcuug c                                             21

<210> SEQ ID NO 266
<211> LENGTH: 22
<212> TYPE: RNA
<213> ORGANISM: Homo sapiens

<400> SEQUENCE: 266
gggggucccc ggugucgga uc                                            22

<210> SEQ ID NO 267
<211> LENGTH: 22
<212> TYPE: RNA
<213> ORGANISM: Homo sapiens

<400> SEQUENCE: 267
aacuggcccu caaagucccg cu                                           22

<210> SEQ ID NO 268
<211> LENGTH: 21
<212> TYPE: RNA
<213> ORGANISM: Homo sapiens

<400> SEQUENCE: 268
uccucuucuc ccuccuccca g                                            21

<210> SEQ ID NO 269
<211> LENGTH: 23
<212> TYPE: RNA
<213> ORGANISM: Homo sapiens

<400> SEQUENCE: 269
ucaaaugcuc agacuccugu ggu                                          23

<210> SEQ ID NO 270
<211> LENGTH: 22
<212> TYPE: RNA
```

```
<213> ORGANISM: Homo sapiens

<400> SEQUENCE: 270
gaggguuggg uggaggcucu cc                                           22

<210> SEQ ID NO 271
<211> LENGTH: 22
<212> TYPE: RNA
<213> ORGANISM: Homo sapiens

<400> SEQUENCE: 271
agggcuuagc ugcuugugag ca                                           22

<210> SEQ ID NO 272
<211> LENGTH: 22
<212> TYPE: RNA
<213> ORGANISM: Homo sapiens

<400> SEQUENCE: 272
caagcucgug ucugugdgguc cg                                          22

<210> SEQ ID NO 273
<211> LENGTH: 22
<212> TYPE: RNA
<213> ORGANISM: Homo sapiens

<400> SEQUENCE: 273
ccaguggggc ugcuguuauc ug                                           22

<210> SEQ ID NO 274
<211> LENGTH: 21
<212> TYPE: RNA
<213> ORGANISM: Homo sapiens

<400> SEQUENCE: 274
guguugaaac aaucucuacu g                                            21

<210> SEQ ID NO 275
<211> LENGTH: 25
<212> TYPE: RNA
<213> ORGANISM: Homo sapiens

<400> SEQUENCE: 275 aggggguggug uugggacagc uccgu                                       25

<210> SEQ ID NO 276
<211> LENGTH: 21
<212> TYPE: RNA
<213> ORGANISM: Homo sapiens

<400> SEQUENCE: 276
gaacggcuuc auacaggagu u                                            21

<210> SEQ ID NO 277
<211> LENGTH: 18
<212> TYPE: RNA
<213> ORGANISM: Homo sapiens

<400> SEQUENCE: 277
ucagcuggcc cucauuuc                                                18

<210> SEQ ID NO 278
<211> LENGTH: 23
```

```
<210> SEQ ID NO 278
<211> LENGTH: 23
<212> TYPE: RNA
<213> ORGANISM: Homo sapiens

<400> SEQUENCE: 278
uucauuuggu auaaaccgcg auu                                              23

<210> SEQ ID NO 279
<211> LENGTH: 22
<212> TYPE: RNA
<213> ORGANISM: Homo sapiens

<400> SEQUENCE: 279
aggugguccg uggcgcguuc gc                                               22

<210> SEQ ID NO 280
<211> LENGTH: 22
<212> TYPE: RNA
<213> ORGANISM: Homo sapiens

<400> SEQUENCE: 280
aaccagcacc ccaacuuugg ac                                               22

<210> SEQ ID NO 281
<211> LENGTH: 22
<212> TYPE: RNA
<213> ORGANISM: Homo sapiens

<400> SEQUENCE: 281
ggauaucauc auauacugua ag                                               22

<210> SEQ ID NO 282
<211> LENGTH: 22
<212> TYPE: RNA
<213> ORGANISM: Homo sapiens

<400> SEQUENCE: 282
caaagugccu cccuuuagag ug                                               22

<210> SEQ ID NO 283
<211> LENGTH: 22
<212> TYPE: RNA
<213> ORGANISM: Homo sapiens

<400> SEQUENCE: 283
gcugcgcuug gauuucgucc cc                                               22
```

COMPLEX MIRNA SETS AS NOVEL BIOMARKERS FOR AN ACUTE CORONARY SYNDROME

This application is a U.S. national phase of International Application No. PCT/EP2011/001999 filed on Apr. 19, 2011, which claims priority to U.S. Provisional Application No. 61/326,043 filed on Apr. 20, 2010, European Patent Application No. 10004190.4 filed on Apr. 20, 2010 and European Patent Application No. 10185136.8 filed on Oct. 1, 2010, the disclosures of which are incorporated herein by reference in their entirety.

TECHNICAL FIELD OF INVENTION

The present invention relates to single polynucleotides or sets of polynucleotides for detecting single miRNAs or sets of miRNAs for diagnosing and/or prognosing of an acute coronary syndrome in a blood sample from a human. Further, the present invention relates to means for diagnosing and/or prognosing of an acute coronary syndrome comprising said polynucleotides or sets of polynucleotides. Furthermore, the present invention relates to a method for diagnosing and/or prognosing of an acute coronary syndrome based on the determination of expression profiles of single miRNAs or sets of miRNAs representative for an acute coronary syndrome compared to a reference. In addition, the present invention relates to a kit for diagnosing and/or prognosing of an acute coronary syndrome comprising means for determining expression profiles of single miRNAs or sets of miRNAs representative for an acute coronary syndrome and at least one reference.

BACKGROUND OF THE INVENTION

Today, biomarkers play a key role in early diagnosis, risk stratification, and therapeutic management of cardiac diseases such as acute myocardial infarction (AMI) and heart failure [10-13]. Established biomarkers such as the cardiac troponins and b-type natriuretic peptides were mainly discovered by candidate approach [13, 14]. By contrast, the recent development of high-throughput molecular technologies that allow with a reasonable effort the analysis of whole transcriptomes, proteomes, and metabolomes of individuals at risk, may lead to the discovery of novel biomarkers in an unbiased approach [15, 16].

MicroRNAs (miRNAs) are a new class of biomarkers. They represent a group of regulatory elements that enable cells to fine-tune complex gene expression cascades in a wide range of biological processes, such as proliferation, differentiation, apoptosis, stress-response, and oncogenesis [1-7]. In the cardiovascular system, miRNAs are not only important for heart and vascular development, but also play an essential role in cardiac pathophysiology, such as hypertrophy, arrhythmia, and ischemia [8, 9]. Particularly, miRNAs are important regulators of adaptive and maladaptive responses in cardiovascular diseases and hence are considered to be potential therapeutical targets.

Since recently it is known that miRNAs are not only present in tissues but also in human blood both as free circulating nucleic acids and in mononuclear cells. This may be due to the fact that miRNAs expressed in diverse tissues or cells may be able to be released into circulating blood. Although the mechanism why miRNAs are found in human blood is not fully understood yet, this finding makes miRNAs to biological markers for diagnostics for various types of diseases based on blood analysis including acute coronary syndrome or hypertrophic cardiomyopathy. For example, Ai et. al (Biochem. and Biophysical Research Communication, 2010, 391, 73-77) report that miRNAs are novel biomarkers for early diagnosis of acute myocardial infarction in plasma of humans. Expression levels of hsa-miR-1, hsa-miR-133a, hsa-miR-499 and hsa-miR-208a were found higher in subjects with acute myocardial infarction in comparison to healthy persons, patients with non-AMI coronary heart disease or patients with other cardiovascular diseases. Further, Wang et al. (European Heart Journal, 2010, 31, 659-666) found that the expression level of hsa-miR-1 was higher in plasma from human AMI patients compared with non-AMI subjects.

Thus, various miRNA markers have been proposed to indicate heart and cardiovascular system diseases. However, many of these markers have shortcomings such as reduced sensitivity, not sufficient specificity or do not allow timely diagnosis. Accordingly, there is still a need for novel and efficient miRNAs or sets of miRNAs as markers, effective methods and kits for the diagnosis of said diseases. Particularly, the potential role of miRNAs present in human blood as biomarkers for the diagnosis of heart and cardiovascular diseases has not been systematically evaluated yet.

The inventors of the present invention assessed for the first time the expression of miRNAs on a whole-genome level in patients with acute myocardial infarction (AMI). They identified novel miRNAs which are significantly dysregulated in blood of AMI patients in comparison to healthy controls. Said miRNAs predict AMI with high specificity and sensitivity. The inventors of the present invention also pursued a multiple biomarker strategy to circumvent the above-mentioned limitations by adding accuracy and predictive power. In detail, by using a machine learning algorithm, they identified unique miRNA signatures that predict diagnosis of AMI with even higher power, indicating that both, single miRNAs and especially complex miRNA signatures or sets derived from human blood can be used as novel biomarkers. The inventors of the present invention further found that some other single miRNAs directly correlate with heart infarct size estimated by Troponin T release.

SUMMARY OF THE INVENTION

In a first aspect, the invention provides a polynucleotide for detecting a miRNA or a set comprising at least two polynucleotides for detecting a set comprising at least two miRNAs for diagnosing and/or prognosing of an acute coronary syndrome in a blood sample from a human, particularly human patient, wherein the nucleotide sequence of said miRNA or the nucleotide sequences of said miRNAs is (are) selected from the group consisting of SEQ ID NO: 1 to SEQ ID NO: 283.

In a second aspect, the invention provides a method for diagnosing and/or prognosing of an acute coronary syndrome comprising the steps of:

(i) determining an expression profile of a miRNA or a set comprising at least two miRNAs representative for an acute coronary syndrome in a blood sample from a human, particularly human patient, wherein the nucleotide sequence of said miRNA or the nucleotide sequences of said miRNAs is (are) selected from the group consisting of SEQ ID NO: 1 to SEQ ID NO: 283, a fragment thereof, and a sequence having at least 80% sequence identity thereto, and (ii) comparing said expression profile to a reference, wherein the comparison of said expression profile to said reference allows for the diagnosis and/or prognosis of an acute coronary syndrome and/or applying an algorithm or a mathematical function to said expression profile, wherein the application of said algorithm or mathematical function to said expression profile allows for the diagnosis and/or prognosis of an acute coronary syndrome.

In a third aspect, the invention provides means for diagnosing and/or prognosing of an acute coronary syndrome comprising a polynucleotide or a set comprising at least two polynucleotides according to the first aspect.

In a fourth aspect, the invention provides a kit for diagnosing and/or prognosing of an acute coronary syndrome comprising (i) means for determining an expression profile of a miRNA or a set comprising at least two miRNAs representative for an acute coronary syndrome in a blood sample from a human, particularly human patient, wherein the nucleotide sequence of said miRNA or the nucleotide sequences of said miRNAs is (are) selected from the group consisting of SEQ ID NO: 1 to SEQ ID NO: 283, a fragment thereof, and a sequence having at least 80% sequence identity thereto; and (ii) at least one reference and/or algorithm or mathematical function, preferably comprised on at least one data carrier.

This summary of the invention does not necessarily describe all features of the invention.

BRIEF DESCRIPTION OF THE DRAWINGS

(FIG. 1A) Matrix plot showing high linear correlation of the mean expression ratios of miRNAs in AMI patients versus controls. (FIG. 1B) Histograms of the logarithm of fold changes, AUC, raw, and adjusted p-values for all screened miRNAs. The logqmedian diagram shows the logarithms of miRNA expression changes in AMI patients in comparison to controls. The expression changes are almost normally distributed between −4 and +4. The AUC for all expression values is given, the vertical blue line denotes the threshold of 0.1 and 0.9. The middle and bottom part of the figure represent histograms of adjusted p-values for the limma test and t-test. The vertical line denotes the significance threshold of 0.05.

(FIG. 4A to 4C) Matrix-plots showing correlation of miR-30c (FIG. 4A), miR-145 (FIG. 4B), and miR-223 (FIG. 4C) with peak Troponin T serum levels (left column) and Troponin T levels at day 3 (right column). hsTnT=highly sensitive Troponin T.

(FIG. 6A) ROC analysis of the complex miRNA expression signature used to predict AMI in the study population. (FIG. 6B) Representative example of a classification result using a trained SVM. The logarithm of the quotient of the probability to be an AMI sample and the probability to be a control sample for each study sample is given on the y-axis. Of all 48 samples, only 2 were misclassified, leading to an accuracy of 95%, a specificity of 100%, and a sensitivity of 90%.

FIG. 7: MiRNAs for diagnosis or prognosis of an acute coronary syndrome (AMI). Experimental details: median g1=median intensity value of the AMI patients; median g2=median intensity value of the healty controls; qmedian=ratio of median g1 and median g2; logqmedian=log of qmedian; ttest_rawp=p-value calculated according to ttest; ttest_adjp=adjusted p-value calculated according to ttest; limma_rawp=p-value calculated according to limma-test; limma_adjp=adjusted p-value calculated according to limma-test; AUC=area under the curve statistics.

FIG. 12: Listing of miRNAs for diagnosis or prognosis of an acute coronary syndrome (AMI). The miRNAs sequences are based on miRBase version 14.0.

(FIG. 22A) Matrix plot showing high linear correlation of the mean expression ratios of miRNAs in AMI patients (n=20) versus controls (n=20). (FIG. 22B) Histograms of the logarithm of fold changes, AUC, raw, and adjusted p-values for all screened miRNAs. The logqmedian diagram shows the logarithms of miRNA expression changes in AMI patients in comparison to controls. The expression changes are distributed between −4 and +4. The AUC for all expression values is given, the vertical blue line denotes the threshold of 0.1 and 0.9. The middle and bottom part of the figure represent histograms of adjusted p-values for the limma test and t-test. The vertical blue line denotes the significance threshold of 0.05.

(FIG. 24A) MiRNA-1291 is able to predict the presence of AMI with a specificity of 85% and a sensitivity of 85%, while (FIG. 24B) miRNA-663b shows a specificity of 95% and a sensitivity of 90%. TP=true positives, FP=false positives.

(FIG. 25C) Absolute expression values (±SEM) of miR-145 and miR-30c in AMI patients and controls. hsTnT=highly sensitive Troponin T.

FIGS. 27A-27C: Complex miRNA signatures predict AMI. (FIG. 27A) Classification plot demonstrating that a multi-marker signature increases test accuracy, specificity, and sensitivity depending upon the number of miRNAs that compose the diagnostic signature. (FIG. 27B) ROC analysis of the complex miRNA expression signature used to predict AMI in the study population. (FIG. 27C) Representative example of a classification result using a trained SVM. The logarithm of the quotient of the probability to be an AMI sample and the probability to be a control sample for each study sample is given on the y-axis. Of all 40 samples, only 3 were misclassified, leading to an accuracy of 93%, a specificity of 96%, and a sensitivity of 90% (AUC=0.99).

FIG. 28: Sets (Set No. 1-1005) of least two miRNAs for diagnosing and/or prognosing of an acute coronary syndrome in a blood sample from a human (with Acc=accuracy, Sens=sensitivity, Spec=specificity in percent). Subjects without acute coronary syndrome that underwent routine coronary angiography were selected as the healthy controls.

FIG. 29: miRNAs for diagnosis or prognosis of an acute coronary syndrome (AMI). Experimental details: median g1=median intensity value of the AMI patients; median g2=median intensity value of the healty controls; qmedian=ratio of median g1 and median g2;

Figure 1A:
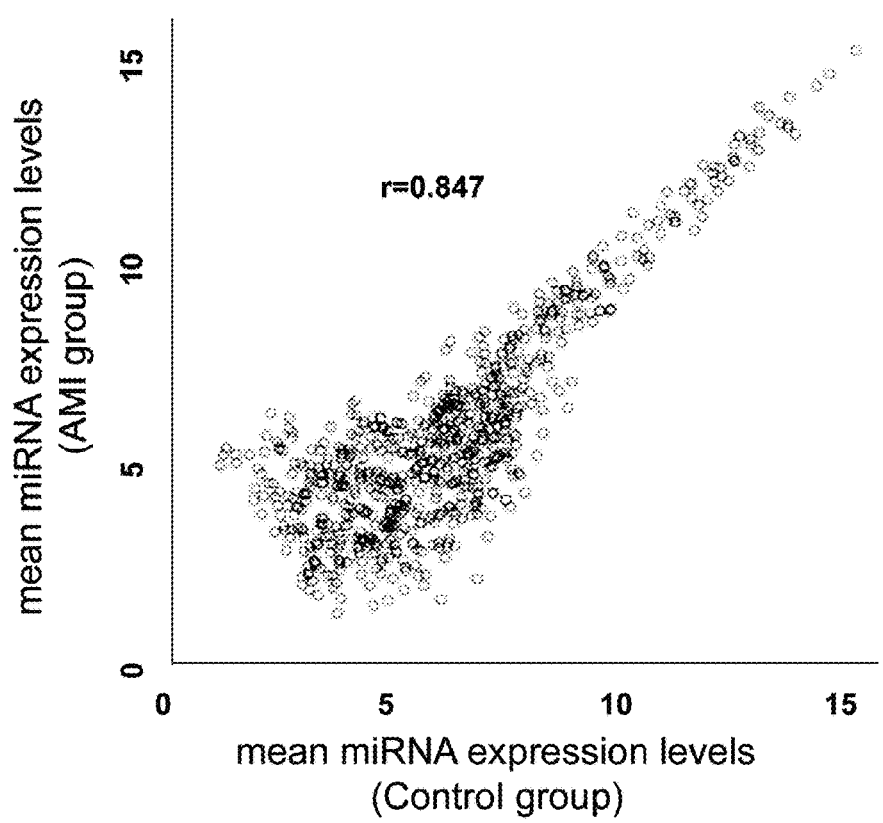
FIGS. 1A-1B: MiRNA expression profiling in peripheral blood cells of AMI patients and controls.

logqmedian=log of qmedian; ttest_rawp=p-value calculated according to ttest; ttest_adjp=adjusted p-value calculated according to ttest; limma_rawp=p-value calculated according to limma-test; limma_adjp=adjusted p-value calculated according to limma-test; AUC=area under the curve statistics. Subjects without acute coronary syndrome that underwent routine coronary angiography were selected as the healthy controls.

FIG. 30: Predetermined set of microRNAs for diagnosis or prognosis of acute myocardial infarction. High accuracy (Acc) of 90.48% to 99.53% for classification between patients suffering from acute myocardial infarction and healthy controls was obtained when defined sets of 2-7 miRNAs (Set No. 2000-2011) were employed.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and in the appended claims, the singular forms "a", "an", and "the" include plural referents, unless the content clearly dictates otherwise. For example, the term "a test compound" also includes "test compounds".

The terms "microRNA" or "miRNA" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 16 to 28 nucleotides or 17 to 27 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The miRNAs regulate gene expression and are encoded by genes from whose DNA they are transcribed but miRNAs are not translated into protein (i.e. miRNAs are non-coding RNAs). The genes encoding miRNAs are longer than the processed mature miRNA molecules. The miRNAs are first transcribed as primary transcripts or pri-miRNAs with a cap and poly-A tail and processed to short, 70 nucleotide stem-loop structures known as pre-miRNAs in the cell nucleus. This processing is performed in animals by a protein complex known as the Microprocessor complex consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the argonaute protein, the catalytically active RNase in the RISC, on the basis of the stability of the 5' end. The remaining strand, known as the miRNA*, anti-guide (antistrand), or passenger strand, is degraded as a RISC substrate. Therefore, the miRNA*s are derived from the same hairpin structure like the "normal" miRNAs. So if the "normal" miRNA is then later called the "mature miRNA" or "guide strand", the miRNA* is the "anti-guide strand" or "passenger strand".

The terms "microRNA*" or "miRNA*" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 16 to 28 nucleotides or 18 to 23 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The "miRNA*s", also known as the "anti-guide strands" or "passenger strands", are mostly complementary to the "mature miRNAs" or "guide strands", but have usually single-stranded overhangs on each end. There are usually one or more mispairs and there are sometimes extra or missing bases causing single-stranded "bubbles". The miRNA*s are likely to act in a regulatory fashion as the miRNAs (see also above). In the context of the present invention, the terms "miRNA" and "miRNA*" are interchangeable used.

The term "miRBase" refers to a well established repository of validated miRNAs. The miRBase is a searchable database of published miRNA sequences and annotation. Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download. The sequences of the miRNAs for diagnosis and/or prognosis of an acute coronary syndrome (AMI) listed in FIG. 12 are based on miRBase version 14.0.

As used herein, the term "nucleotides" refers to structural components, or building blocks, of DNA and RNA. Nucleotides consist of a base (one of four chemicals: adenine, thymine, guanine, and cytosine) plus a molecule of sugar and one of phosphoric acid. The term "nucleosides" refers to glycosylamine consisting of a nucleobase (often referred to simply base) bound to a ribose or deoxyribose sugar. Examples of nucleosides include cytidine, uridine, adenosine, guanosine, thymidine and inosine. Nucleosides can be phosphorylated by specific kinases in the cell on the sugar's primary alcohol group (—CH2-OH), producing nucleotides, which are the molecular building blocks of DNA and RNA.

The term "polynucleotide", as used herein, means a molecule of at least 10 nucleotides and of not more than 35 nucleotides covalently linked together. Preferably, the polynucleotides of the present invention are molecules of 10 to 33 nucleotides or 15 to 30 nucleotides in length, more preferably of 16 to 28 nucleotides or 17 to 27 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally spacer elements and/or elongation elements described below. The depiction of a single strand of a polynucleotide also defines the sequence of the complementary strand. Polynucleotides may be single stranded or double stranded, or may contain portions of both double stranded and single stranded sequences. The term "polynucleotide" means a polymer of deoxyribonucleotide or ribonucleotide bases and includes DNA and RNA molecules, both sense and anti-sense strands. In detail, the polynucleotide may be DNA, both cDNA and genomic DNA, RNA, cRNA or a hybrid, where the polynucleotide sequence may contain combinations of deoxyribonucleotide or ribonucleotide bases, and combinations of bases including uracil, adenine, thymine, cytosine, guanine, inosine, xanthine, hypoxanthine, isocytosine and isoguanine. Polynucleotides may be obtained by chemical synthesis methods or by recombinant methods.

In the context of the present invention, a polynucleotide as a single polynucleotide strand provides a probe (e.g. miRNA capture probe) that is capable of binding to, hybridizing with, or detecting a target of complementary sequence, such as a nucleotide sequence of a miRNA or miRNA*, through one or more types of chemical bonds, usually through complementary base pairing, usually through hydrogen bond formation. Polynucleotides in their function as probes may bind target sequences, such as nucleotide sequences of miRNAs or miRNAs*, lacking complete complementarity with the polynucleotide sequences depending upon the stringency of the hybridization condition. There may be any number of base pair mismatches which will interfere with hybridization between the target sequence, such as a nucleotide sequence of a miRNA or miRNA*, and the single stranded polynucleotide described herein. However, if the number of mutations is so great that no hybridization can occur under even the least stringent hybridization conditions, the sequences are no complementary sequences. The polynucleotide variants including polynucleotide fragments or polynucleotide mutants and the miRNA variants including miRNA fragments or miRNA mutants are further defined below. The present invention encompasses polynucleotides in form of single polynucleotide strands as probes for binding to, hybridizing with or detecting complementary sequences of miRNAs (target), which are selected from the group consisting of SEQ ID NO: 1 to SEQ ID NO: 283, particularly of SEQ ID NO: 1 to SEQ ID NO: 241.

Figure 9:
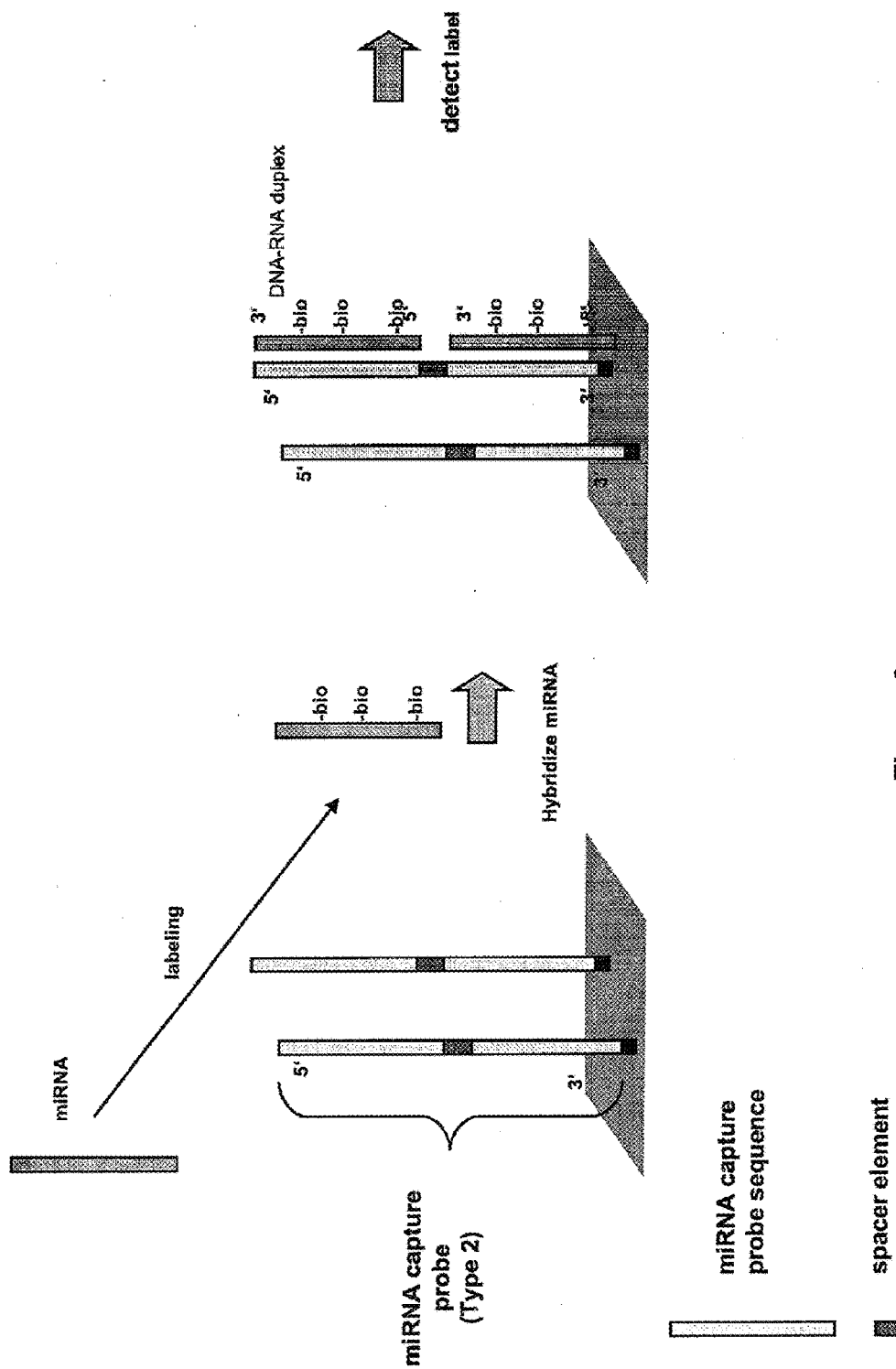
FIG. 9: Schema of a miRNA tandem hybridization assay for use in the invention. The polynucleotide tandem or hybrid (miRNA captured tandem or hybrid probe) may consist of two DNA-based sequence stretches that may be linked to each other by a spacer element and which may be identical. The polynucleotide tandem or hybrid (miRNA captured tandem or hybrid probe) is complementary to the respective miRNA sequence. Each polynucleotide tandem or hybrid may bind two miRNA target sequences. The spacer sequence may consist of between 0 and 12 nucleotides. The miRNA target sequence may be labeled prior to hybridization (e.g. by biotin labeling).
Figure 10:
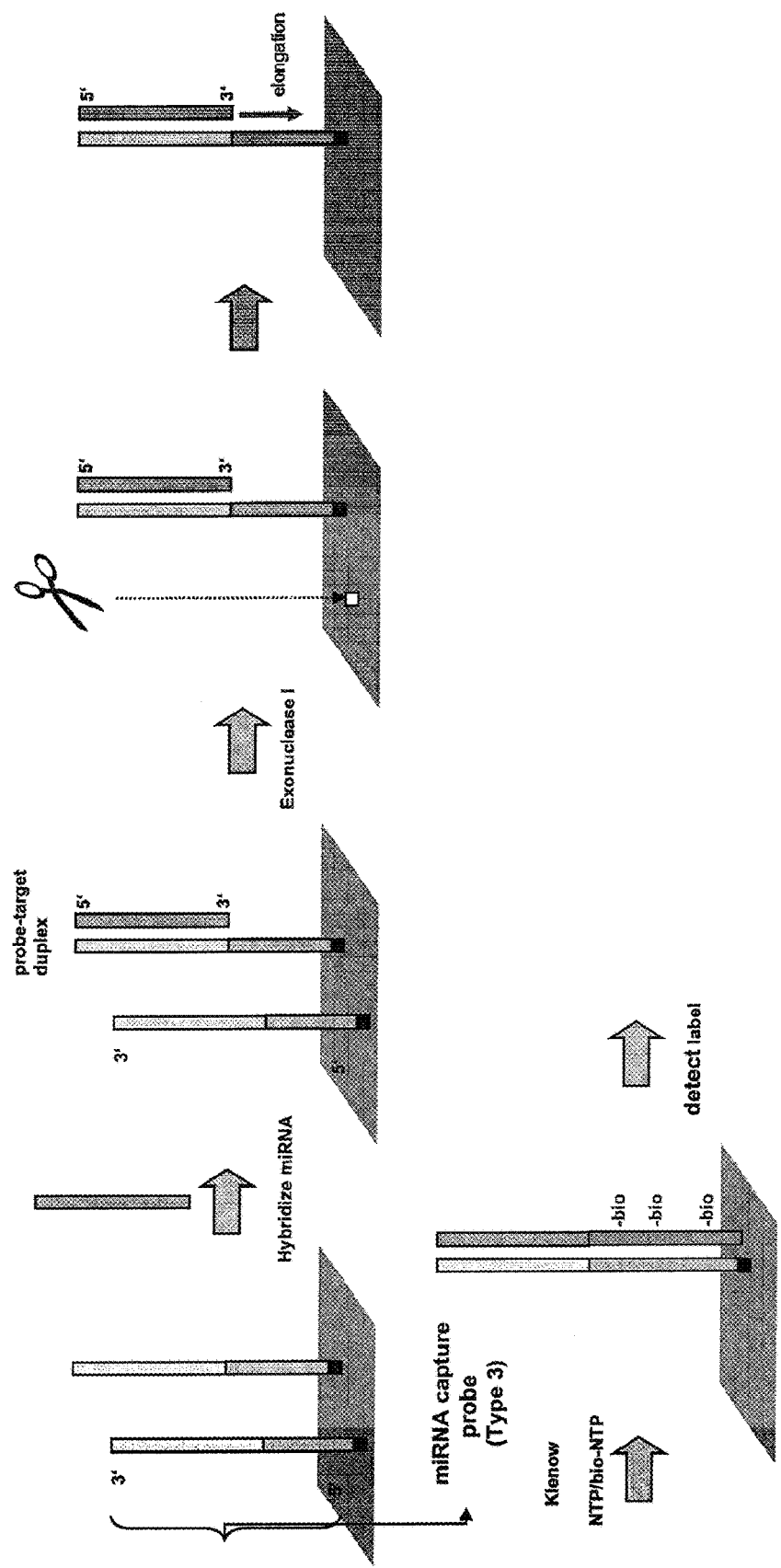
FIG. 10: miRNA RAKE-Assay for use in the invention (PT Nelson et al., Nature methods, 2004, 1 (2), 1). The polynucleotide (miRNA capture probe) for detecting a miRNA consists of a sequence stretch and an elongation element. The polynucleotide (miRNA capture probe) is oriented 5'→3', presenting a free terminal 3'-OH. The miRNA probe sequence stretch is complementary to the miRNA target sequence. The elongation sequence can be freely chosen and is typically between 1 to 12 nucleotides long, preferably is a homomeric sequence. Each miRNA probe can bind a respective miRNA target sequence. miRNA target sequences are not labeled prior to hybridization. The labeling occurs after hybridization during elongation by a polymerase extension reaction.
Figure 11:
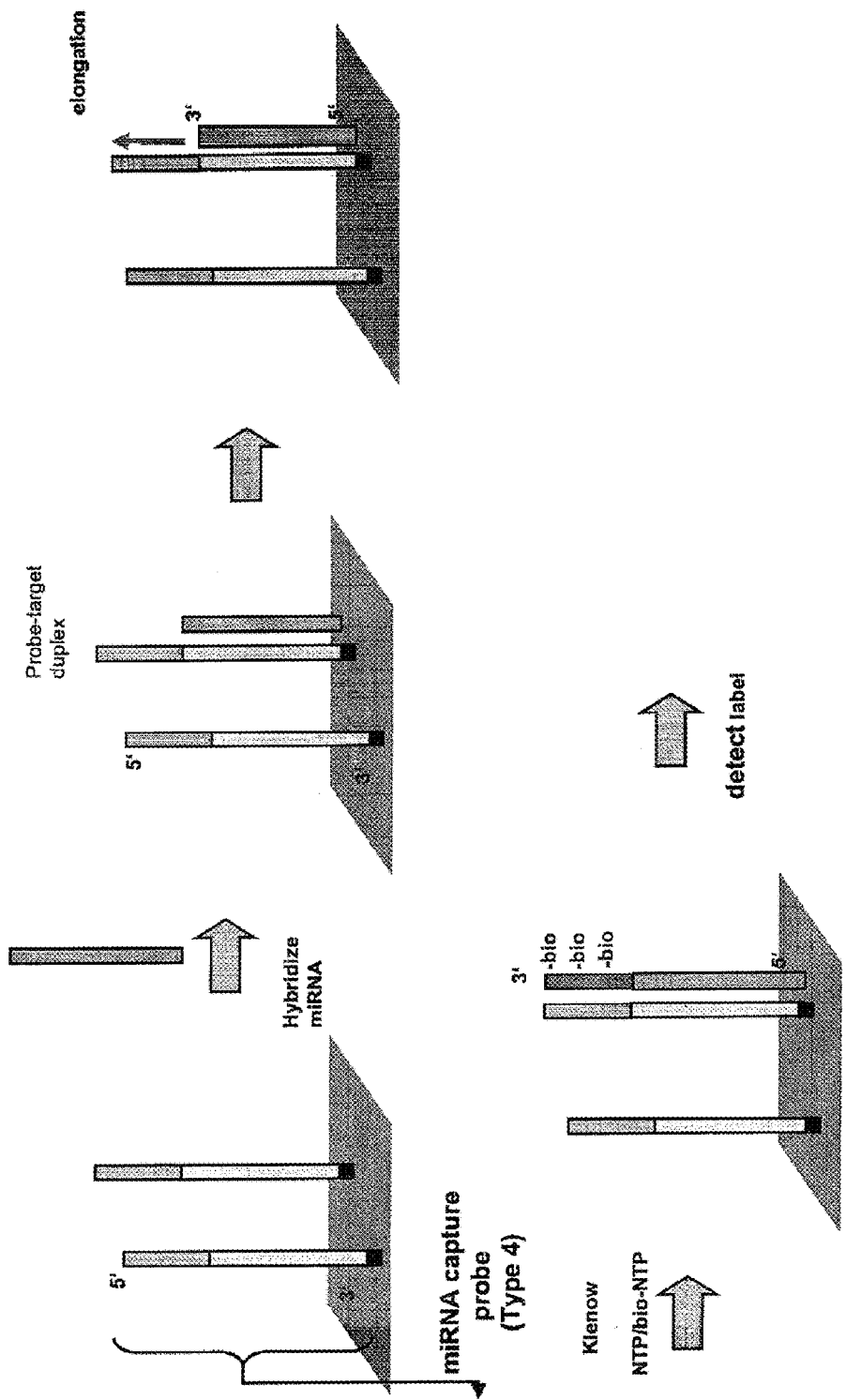
FIG. 11: miRNA MPEA-Assay for use in the invention (Vorwerk S. et al., Microfluidic based enzymatic on-chip labeling of miRNAs, N. Biotechnol. 2008; 25(2-3): 142-9. Epub, 2008, Aug. 20). The polynucleotide (miRNA capture probe) for detecting a miRNA consists of a sequence stretch and an elongation element. The polynucleotide (miRNA capture probe) is oriented 3'→5', presenting a free terminal 5'-OH. The miRNA probe sequence stretch is complementary to the miRNA target sequence. The elongation sequence can be freely chosen and is typically between 1 to 12 nucleotides long, preferably is a homomeric sequence. Each miRNA probe can bind a respective miRNA target sequence. miRNA target sequences are not labeled prior to hybridization. The labeling occurs after hybridization during elongation by a polymerase extension reaction. The biochip is reusable after target removal/elongated target.
Figure 13:
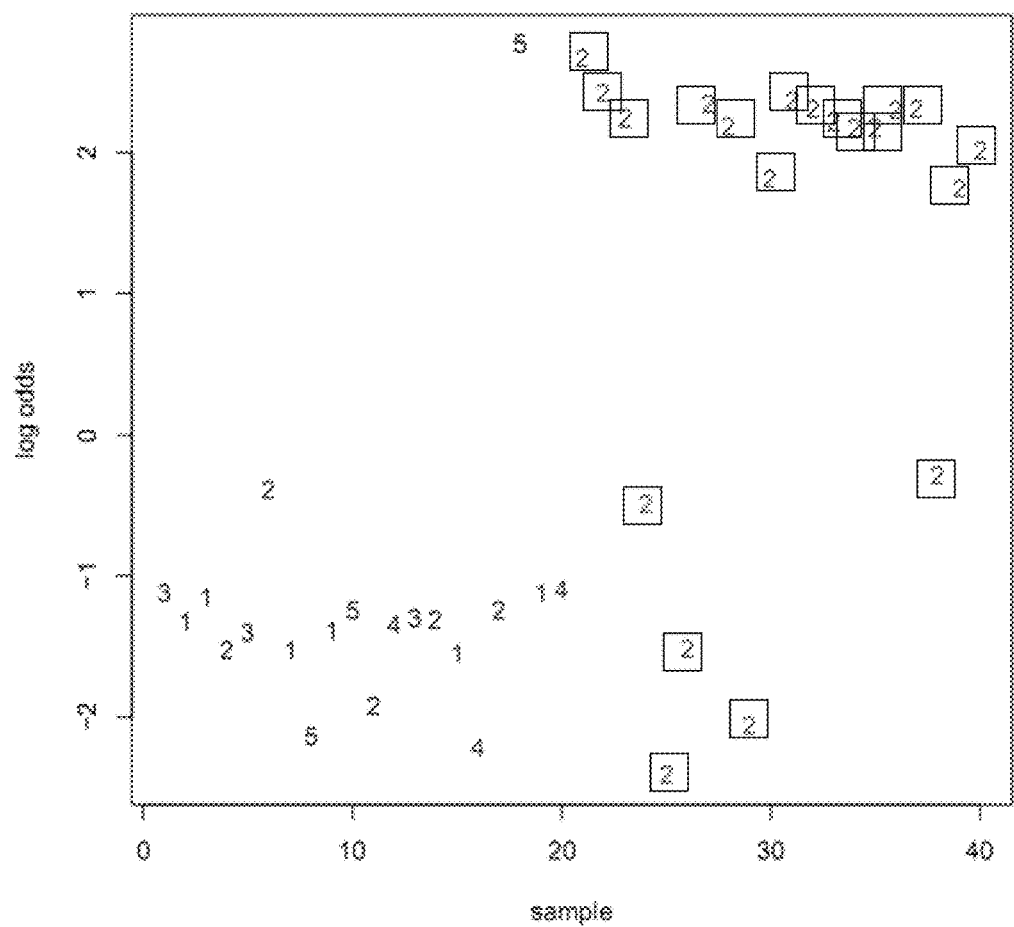
FIG. 13: Classification plot; classification of patients with AMI from healthy controls on the basis of the 2 miRNA-Biomarkers (SEQ ID NO 1-2) leading on average to accuracy of 70%, specificity of 72% and sensitivity of 68%. (numbers without border=healthy controls, numbers within squares=AMI patients and with 1, 2, 3, 4, 5 assigning control samples from 5 independent institutions).
Figure 14:
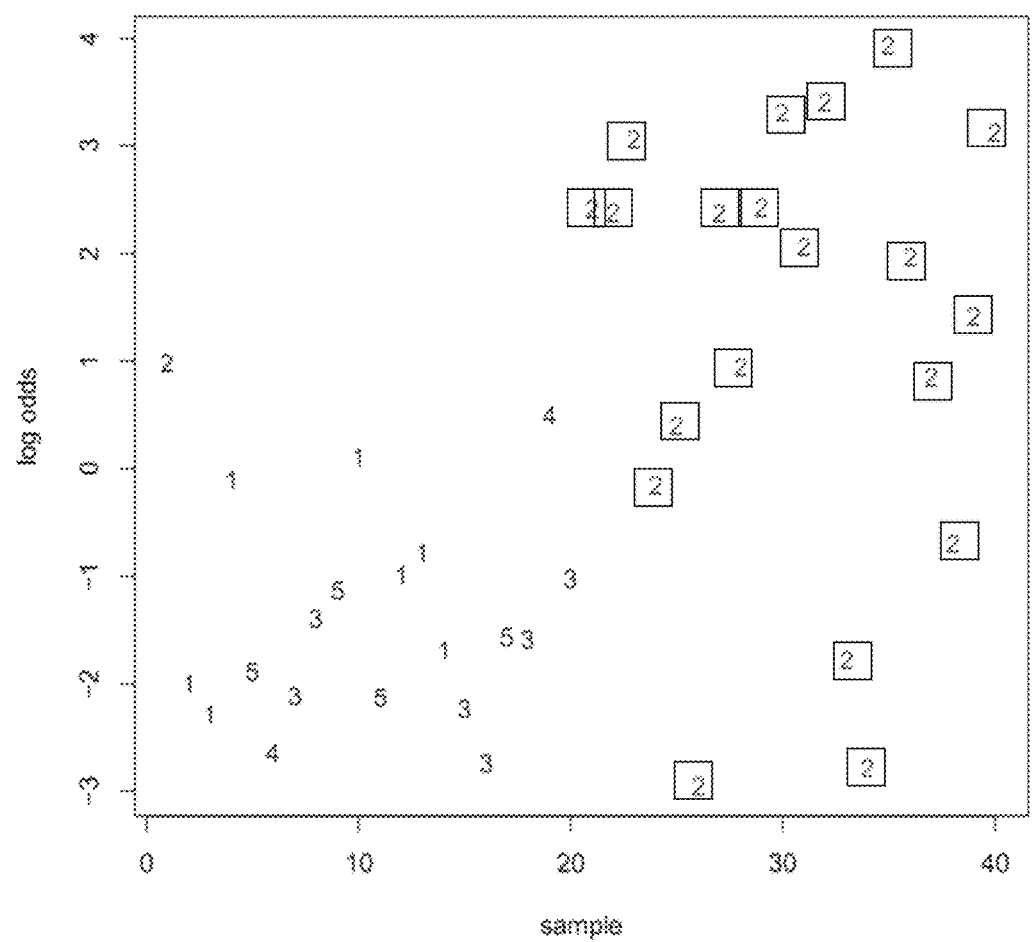
FIG. 14: Classification plot; classification of patients with AMI from healthy controls on the basis of the 4 miRNA-Biomarkers (SEQ ID NO 1-4) leading on average to accuracy of 85.5%, specificity of 89% and sensitivity of 82% (numbers without border=healthy controls, numbers within squares=AMI patients and with 1, 2, 3, 4, 5 assigning control samples from 5 independent institutions).
Figure 15:
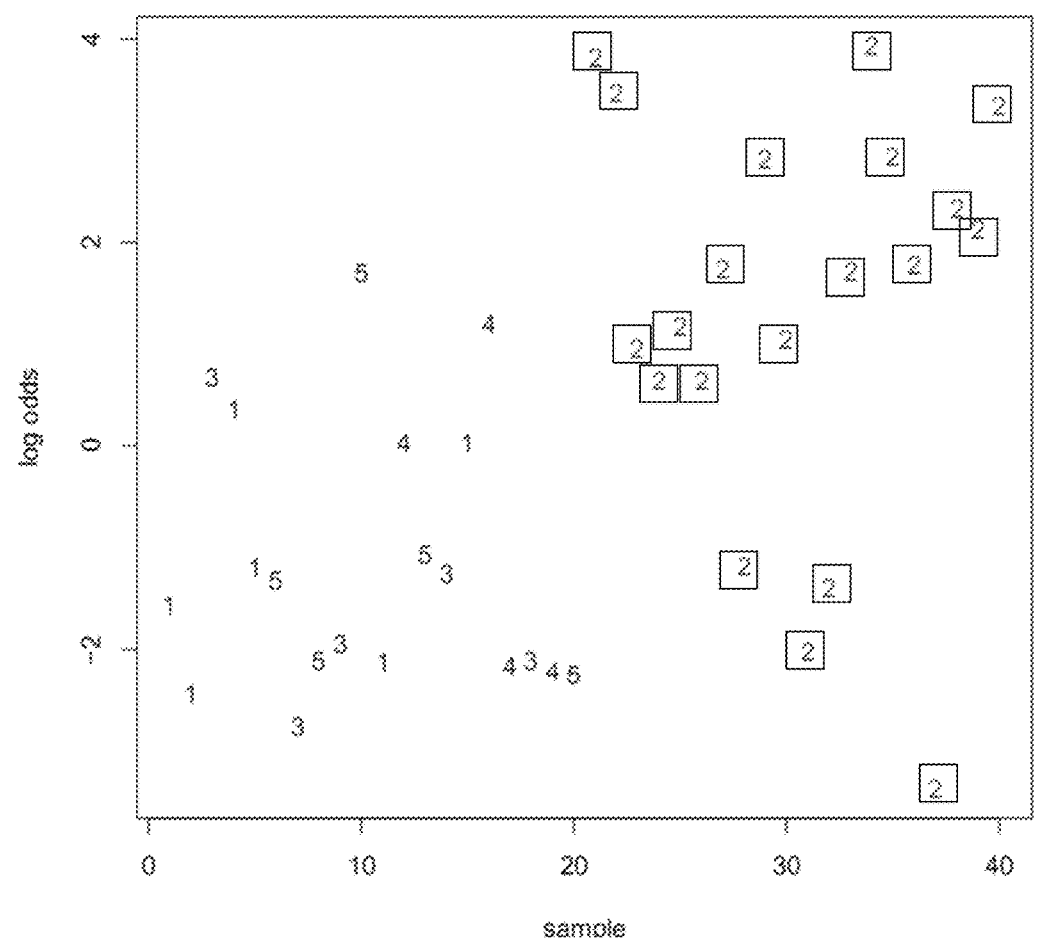
FIG. 15: Classification plot; classification of patients with AMI from healthy controls on the basis of the 6 miRNA-Biomarkers (SEQ ID NO 1-6) leading on average to accuracy of 79.5%, specificity of 83% and sensitivity of 76%. (numbers without border=healthy controls, numbers within squares=AMI patients and with 1, 2, 3, 4, 5 assigning control samples from 5 independent institutions).
Figure 16:
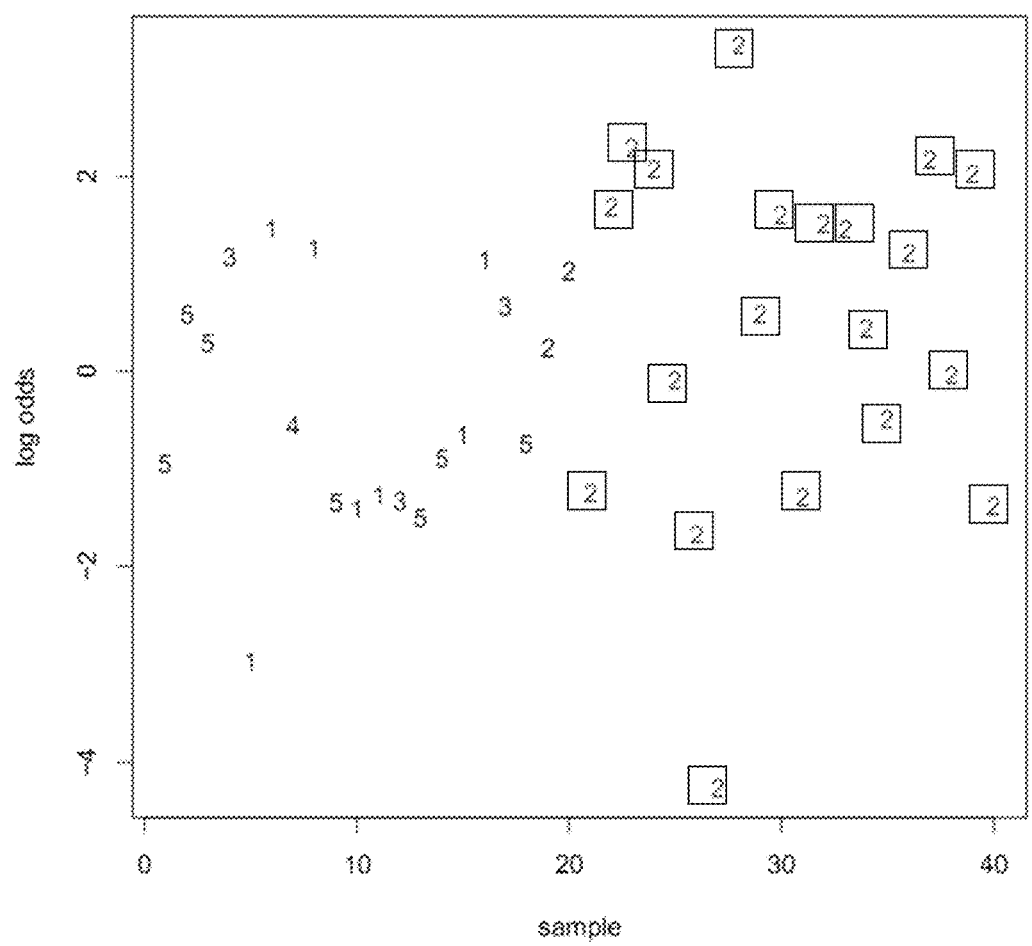
FIG. 16: Classification plot; classification of patients with AMI from healthy controls on the basis of the 8 miRNA-Biomarkers (SEQ ID NO 1-8) leading on average to accuracy of 81.5%, specificity of 83% and sensitivity of 80%. (numbers without border=healthy controls, numbers within squares=AMI patients and with 1, 2, 3, 4, 5 assigning control samples from 5 independent institutions).
Figure 17:
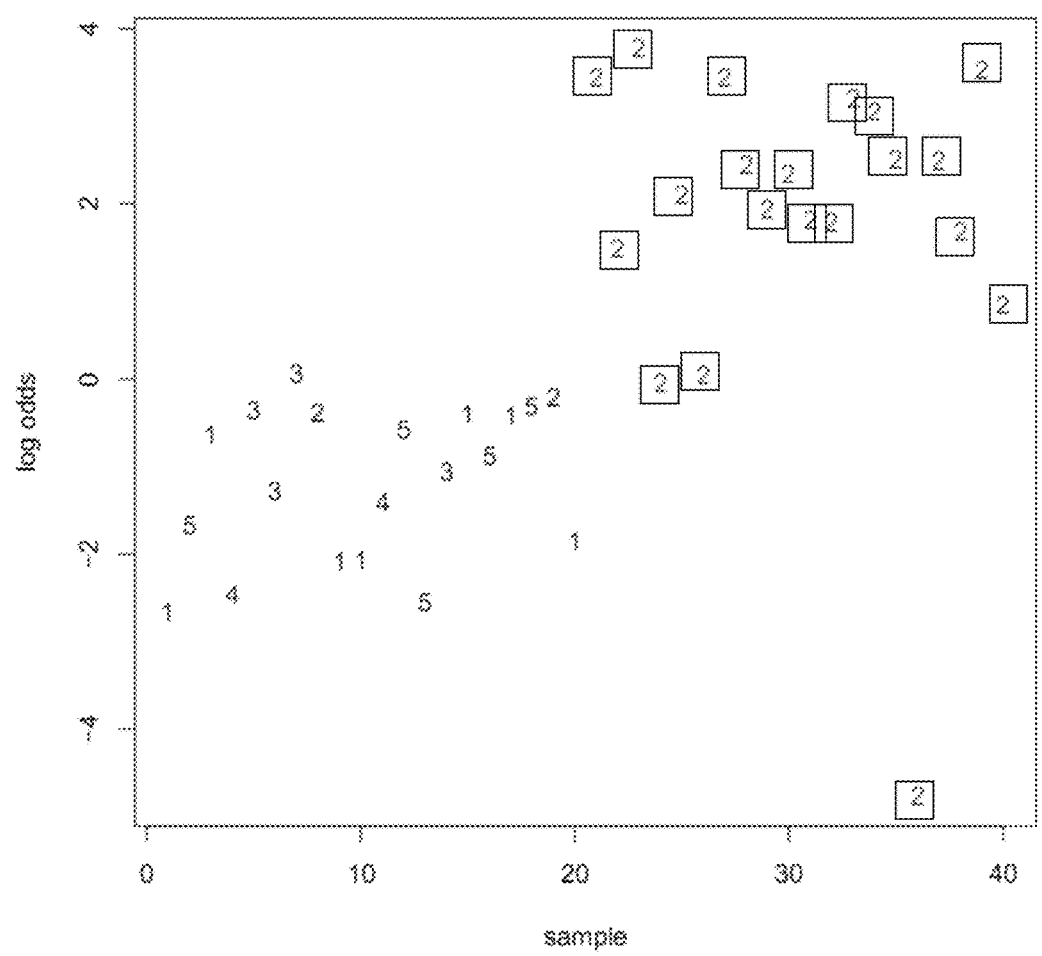
FIG. 17: Classification plot; classification of patients with AMI from healthy controls on the basis of the 10 miRNA-Biomarkers (SEQ ID NO 1-10) leading on average to accuracy of 82.5%, specificity of 88% and sensitivity of 77% (numbers without border=healthy controls, numbers within squares=AMI patients and with 1, 2, 3, 4, 5 assigning control samples from 5 independent institutions).
Figure 18:
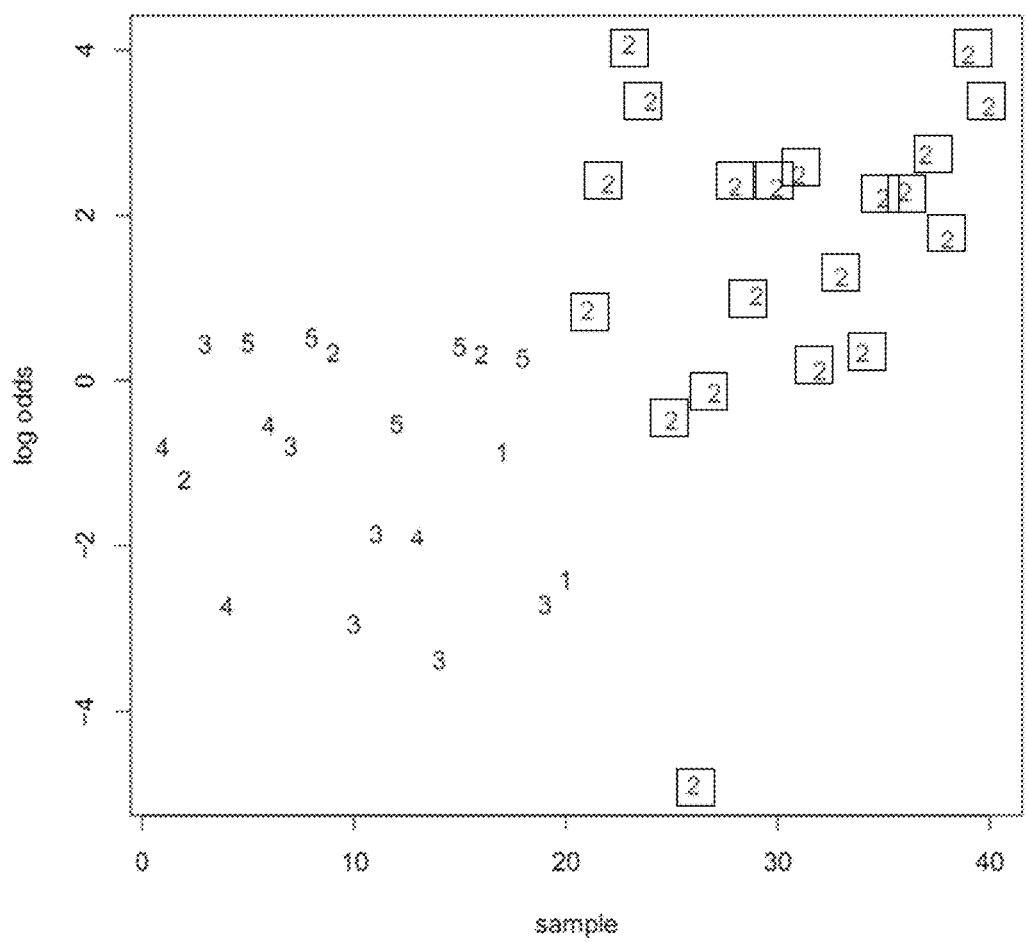
FIG. 18: Classification plot; classification of patients with AMI from healthy controls on the basis of the 50 miRNA-Biomarkers (SEQ ID NO 1-50) leading on average to accuracy of 83%, specificity of 86% and sensitivity of 80%. (numbers without border=healthy controls, numbers within squares=AMI patients and with 1, 2, 3, 4, 5 assigning control samples from 5 independent institutions).
Figure 19:
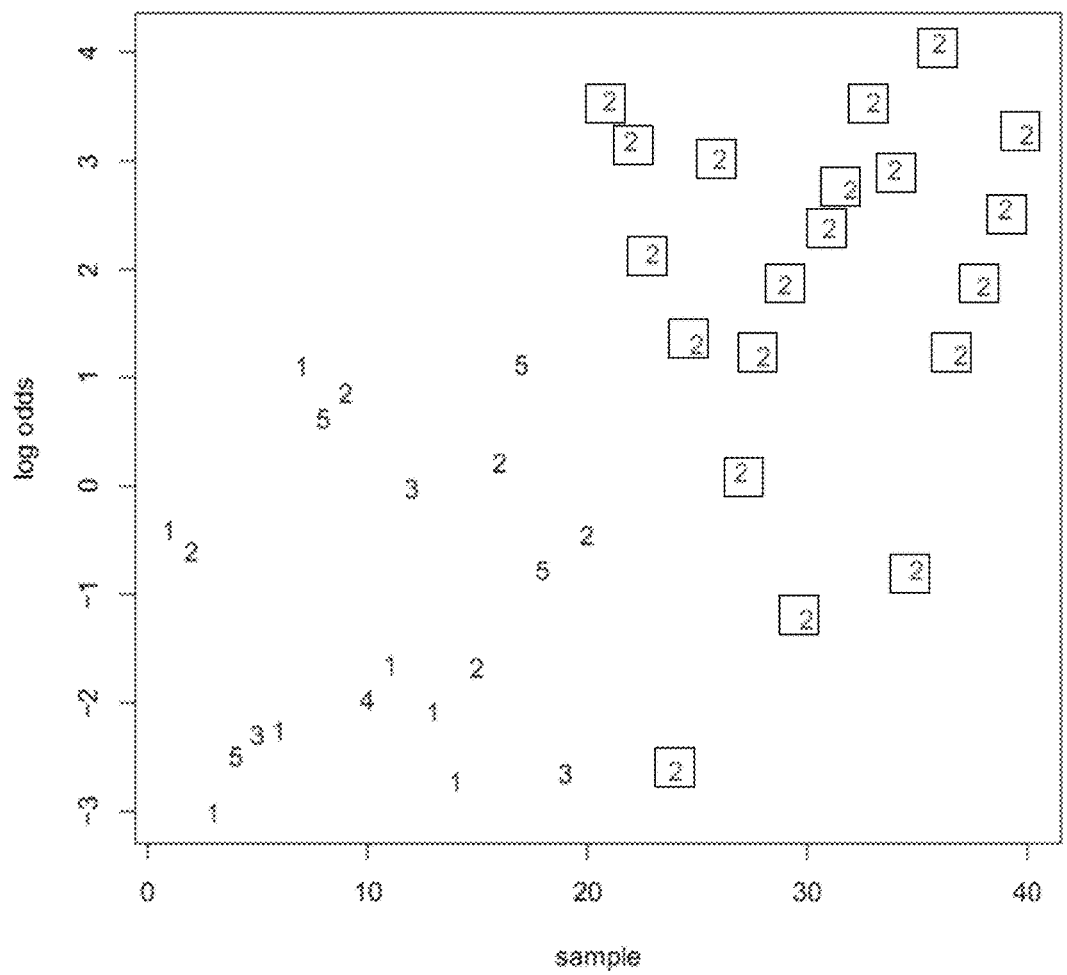
FIG. 19: Classification plot; classification of patients with AMI from healthy controls on the basis of the 80 miRNA-Biomarkers (SEQ ID NO 1-80) leading on average to accuracy of 85.5%, specificity of 93% and sensitivity of 78%. (numbers without border=healthy controls, numbers within squares=AMI patients and with 1, 2, 3, 4, 5 assigning control samples from 5 independent institutions)
Figure 20:
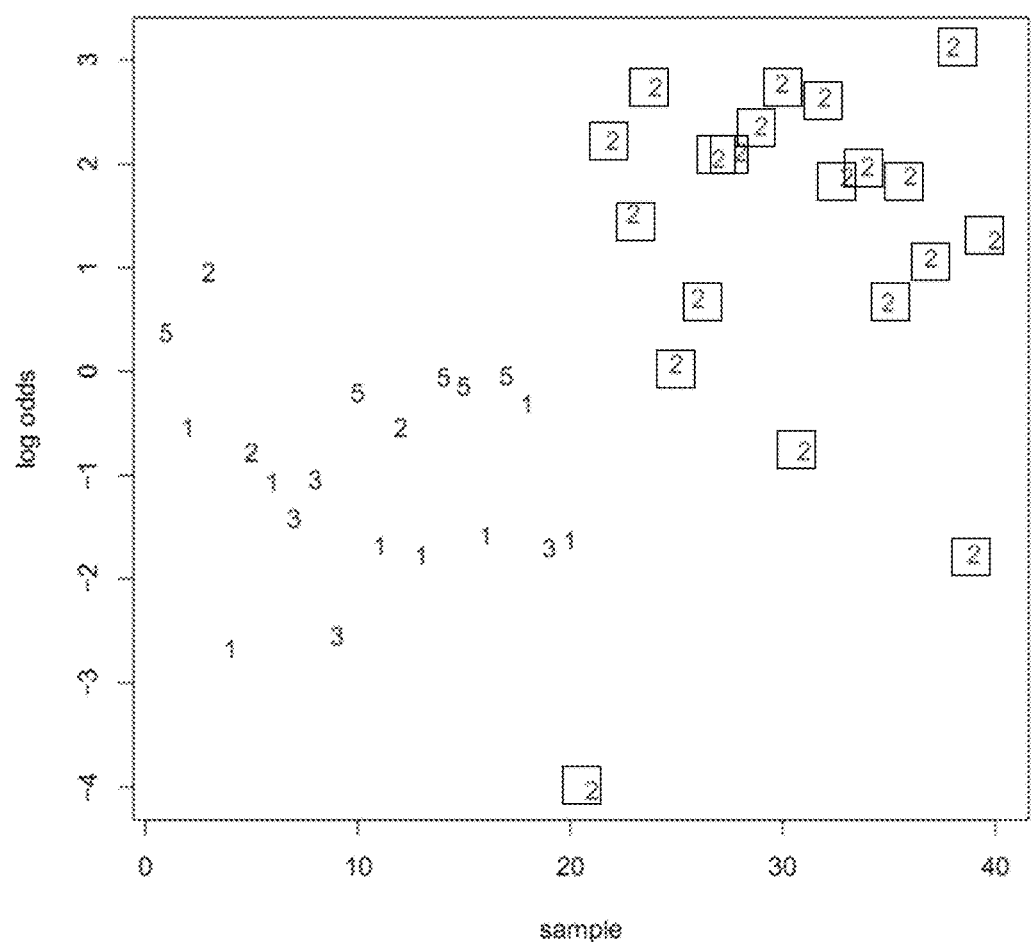
FIG. 20: Classification plot; classification of patient % with AMI from healthy controls on the basis of the 100 miRNA-Biomarkers (SEQ ID NO 1-100) leading on average to accuracy of 85%, specificity of 90% and sensitivity of 80%. (numbers without border=healthy controls, numbers within squares=AMI patients and with 1, 2, 3, 4, 5 assigning control samples from 5 independent institutions)

The polynucleotide, e.g. the polynucleotide used as a probe for detecting a miRNA or miRNA*, may be unlabeled, directly labeled, or indirectly labeled, such as with biotin to which a streptavidin complex may later bind. The polynucleotide, e.g. the polynucleotide used as a probe for detecting a miRNA or miRNA*, may also be modified, e.g. may comprise an elongation (EL) element. For use in a RAKE or MPEA assay as shown in FIGS. 10 and 11, a polynucleotide with an elongation element may be used as a probe. The elongation element comprises a nucleotide sequence with 1 to 30 nucleotides chosen on the basis of showing low complementarity to potential target sequences, such as nucleotide sequences of miRNAs or miRNAs*, therefore resulting in not to low degree of cross-hybridization to a target mixture. Preferred is a homomeric sequence stretch $N_n$ with n=1 to 30, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, and N=A or C, or T or G. Particularly preferred is a homomeric sequence stretch $N_n$ with n=1 to 12, i.e. 1, 2, 3, 4, 5, 6, 7, 8, 9, 10, 11, or 12, and N=A or C, or T or G. The polynucleotide, e.g. the polynucleotide used as a probe for detecting a miRNA or miRNA*, may be present in form of a tandem (FIG. 9), i.e. in form of a polynucleotide hybrid of two different or identical polynucleotides, both in the same orientation, i.e. 5' to 3' or 3' to 5', or in different orientation, i.e. 5' to 3' and 3' to 5'. Said polynucleotide hybrid/tandem may comprise a spacer element. For use in a tandem hybridization assay as shown in FIG. 9, the polynucleotide hybrid/tandem as a probe may comprise a spacer (SP) element. The spacer element represents a nucleotide sequence with n=0 to 12, i.e. 0, 1, 2, 3, 4, 5, 6, 7, 8, 9, 10, 11, or 12, nucleotides chosen on the basis of showing low complementarity to potential target sequences, such as nucleotide sequences of miRNAs or anti-miRNAs, therefore resulting in not to low degree of cross-hybridization to a target mixture. It is preferred that n is 0, i.e. that there is no spacer between the two miRNA sequence stretches.

Figure 8:
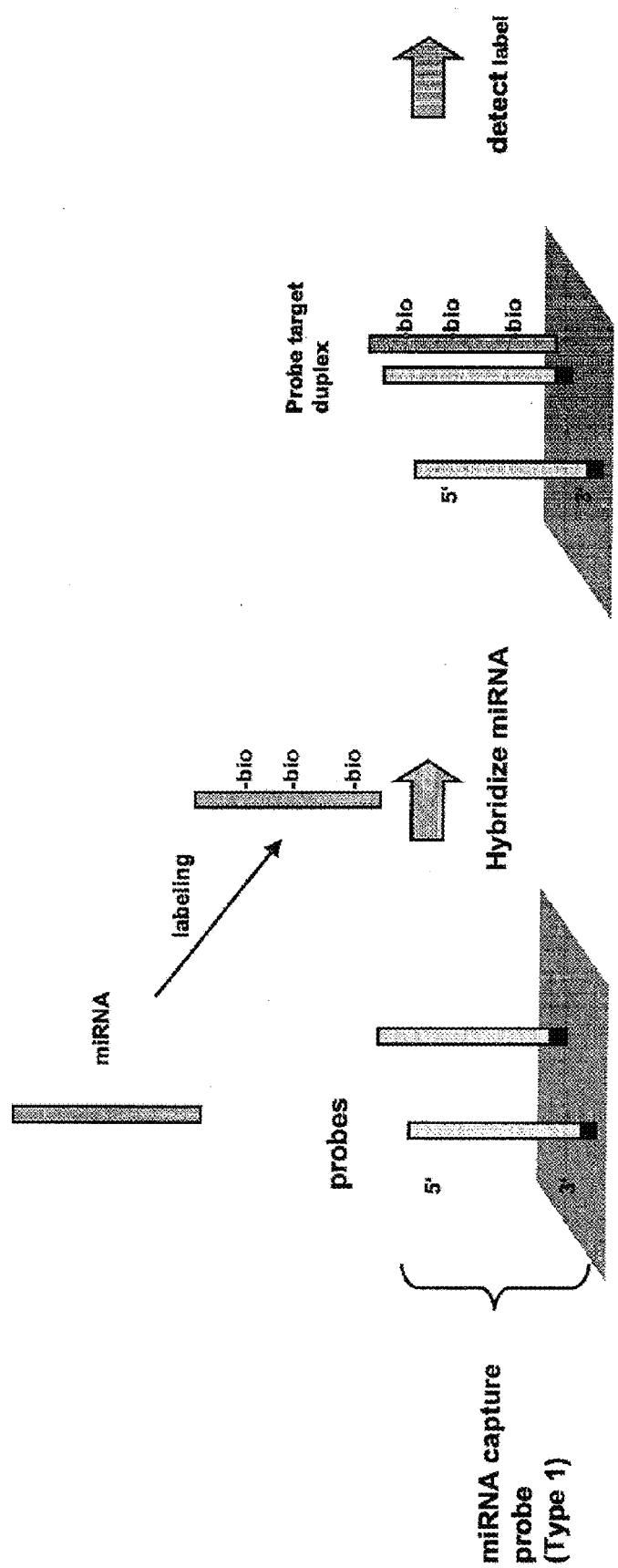
FIG. 8: Scheme of a miRNA hybridization assay for use in the invention. The polynucleotide (miRNA capture probe) for detecting a miRNA consists of a sequence stretch which is complementary to said miRNA. Said stretch is linked to the support via its 3' end or alternatively via its 5' end (not depicted here). Each polynucleotide (miRNA capture probe) can bind the respective miRNA target sequence. The miRNA target sequence may be labeled prior to hybridization (e.g. by biotin labeling).

For detection purposes, the miRNA(s) or miRNA*(s) may be employed unlabeled (FIGS. 10, 11), directly labeled, or indirectly labeled (FIGS. 8, 9), such as with biotin to which a streptavidin complex may later bind.

The term "label", as used herein, means a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and other entities which can be made detectable. A label may be incorporated into nucleic acids at any position, e.g. at the 3' or 5' end or internally. The polynucleotide for detecting a miRNA (polynucleotide probe) and/or the miRNA itself may be labeled.

The term "stringent hybridization conditions", as used herein, means conditions under which a first nucleic acid sequence (e.g. polynucleotide in its function as a probe for detecting a miRNA or miRNA*) will hybridize to a second nucleic acid sequence (e.g. target sequence such as nucleotide sequence of a miRNA or miRNA*), such as in a complex mixture of nucleic acids. Stringent conditions are sequence-dependent and will be different in different circumstances. Stringent conditions may be selected to be about 5 to 10° C. lower than the thermal melting point (Tm) for the specific sequence at a defined ionic strength pH. The Tm may be the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01 to 1.0 M sodium ion concentration (or other salts) at pH 7.0 to 8.3 and the temperature is at least about 20° C. for short probes (e.g., about 10-35 nucleotides) and up to 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 05×SSPE and 6×SSPE at 45° C.

The term "antisense", as used herein, refers to nucleotide sequences which are complementary to a specific DNA or RNA sequence. The term "antisense strand" is used in reference to a nucleic acid strand that is complementary to the "sense" strand.

Residues in two or more polynucleotide s are said to "correspond" to each other if the residues occupy an analogous position in the polynucleotide structures. It is well known in the art that analogous positions in two or more polynucleotides can be determined by aligning the polynucleotide sequences based on nucleic acid sequence or structural similarities. Such alignment tools are well known to the person skilled in the art and can be, for example, obtained on the World Wide Web, for example, ClustalW or Align using standard settings, preferably for Align EMBOSS::needle, Matrix: Blosum62, Gap Open 10.0, Gap Extend 0.5.

The term "sensitivity", as used herein, means a statistical measure of how well a binary classification test correctly identifies a condition, for example how frequently it correctly classifies a heart and cardiovascular system disease into the correct type out of two or more possible types (e.g. heart and cardiovascular system disease type and healthy type). The sensitivity for class A is the proportion of cases that are determined to belong to class "A" by the test out of the cases that are in class "A". A theoretical, optimal prediction can achieve 100% sensitivity (i.e. predict all patients from the sick group as sick).

The term "specificity", as used herein, means a statistical measure of how well a binary classification test correctly identifies a condition, for example how frequently it correctly classifies a heart and cardiovascular system disease into the correct type out of two or more possible types. The specificity for class A is the proportion of cases that are determined to belong to class "not A" by the test out of the cases that are in class "not A". A theoretical, optimal prediction can achieve 100% specificity (i.e. not predict anyone from the healthy group as sick).

The term "accuracy", as used herein, means a statistical measure for the correctness of classification or identification of sample types. The accuracy is the proportion of true results (both true positives and true negatives).

The term "acute coronary syndrome", as used herein, encompasses any group of clinical symptoms compatible with acute myocardial ischemia. Acute myocardial ischemia is chest pain due to insufficient blood supply to the heart muscle that results from coronary artery disease (also called coronary heart disease) (definition by American Heart Association). Subtypes of acute myocardial ischemia are Unstable angina (UA) and two forms of (acute) myocardial infarction (AMI or MI, heart attack), in which the heart muscle is damaged. Unstable angina (UA) (also "crescendo angina") is defined as angina pectoris that changes or worsens. The two (acute) myocardial infarction types are named according to the appearance of the electrocardiogram (ECG/EKG) as non-ST segment elevation myocardial infarction (NSTEMI) and ST segment elevation myocardial infarction (STEMI).

The inventors of the present invention analysed the expression level of miRNAs in blood samples of a cohort of controls (healthy persons) and patients suffering from an acute coronary syndrome. They succeeded in determining the miRNAs that are differentially regulated in blood samples from human patients having an acute coronary syndrome compared to healthy persons (controls) (see experimental section for experimental details). Additionally, the inventors of the present invention performed hypothesis tests (e.g. t-test, limma-test) or other measure (e.g. AUC, mutual information) on the expression level of the found miRNAs, in all controls (healthy persons) and patients suffering from an acute coronary syndrome. These tests resulted in a significance value (p-value) for each miRNA. This p-value is a measure for the diagnostic power of each of these single miRNAs to discriminate between the two clinical conditions, healthy, i.e. not suffering from an acute coronary syndrome, and diseased, i.e. suffering from an acute coronary syndrome. Since a manifold of tests are carried out, one for each miRNA, the p-values may be too optimistic and, thus, over-estimate the actual discriminatory power. Hence, the p-values are corrected for multiple testing by the Benjamini Hochberg approach.

An overview of the miRNAs that are found to be significantly differentially regulated in blood samples of acute coronary syndrome and that performed best according to t-test, limma-test or AUC is provided in FIG. 7 (see experimental explanations: median g1=median intensity value of the AMI patients; median g2=median intensity value of the healty controls; qmedian=ratio of median g1 and median g2; logqmedian=log of qmedian; ttest_rawp=p-value calculated according to ttest; ttest_adjp=adjusted p-value calculated according to ttest; limma_rawp=p-value calculated according to limma-test; limma_adjp=adjusted p-value calculated according to limma-test; AUC=area under the curve statistics.). Three miRNA groups are formed. The first group (group I) comprises miRNAs according to SEQ ID NO: 1 to SEQ ID NO: 153, the second group (group II) comprises miRNAs according to SEQ ID NO: 154 to 241 and the third group (group III) comprises miRNAs according to SEQ ID NO: 242 to SEQ ID NO: 283. The miRNAs comprised in the first group and second group are sorted in order of their t-test significance as described in more detail in the experimental section (see ttest_adjp=adjusted p-value calculated according to ttest). In addition, the most predictive miRNAs in group I are listed first. It should be noted that the lower the ttest_adjp value of a single miRNA, the higher is the diagnostic power of said miRNA.

Usually the diagnostic power of a single miRNA biomarker is not sufficient to reach high accuracy, specificity and sensitivity for discrimination between healthy persons (controls) and patients suffering from an acute coronary syndrome, hence no simple threshold method can be used for diagnostic.

Figure 3:
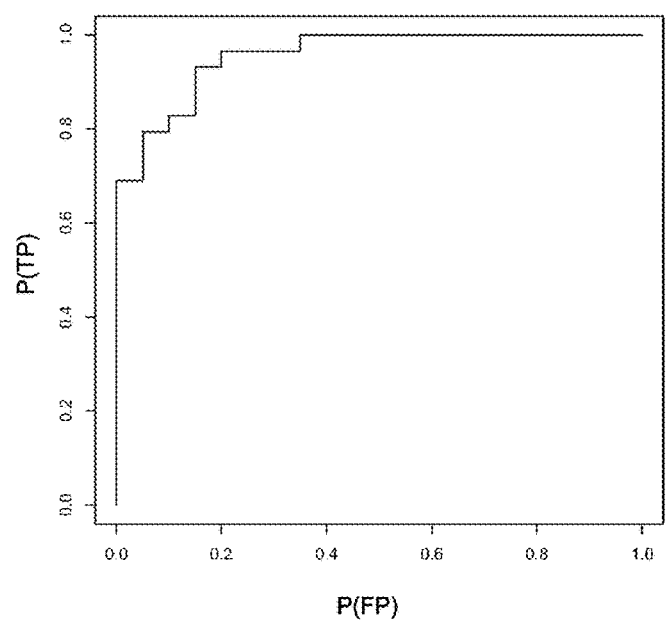
FIG. 3: miRNA-1291 predicts myocardial infarction. Receiver Operating Characteristic (ROC) analysis of miRNA-1291 to predict AMI in the study population. MiRNA-1291 is able to predict the presence of AMI with a specificity of 92.9% and a sensitivity of 85%. TP=true positives, FP=false positives.

However, the inventors of the present invention surprisingly found that also a single miRNA, wherein the nucleotide sequence of said miRNA is selected from the group consisting of SEQ ID NO: 1 to SEQ ID NO: 283, particularly of SEQ ID NO: 1 to SEQ ID NO: 153, provide high diagnostic accuracy, specificity and sensitivity in the determination of an acute coronary syndrome in human patients (see for example FIG. 3, FIG. 7, and FIG. 29).

The inventors of the present invention also employed more than one miRNA biomarker, i.e. sets (signatures) of miRNA biomarkers, to further increase and/or improve the performance for diagnosing and/or prognosing of individuals suffering from an acute coronary syndrome.

In order to be able to discriminate between two or more clinical conditions, e.g. healthy and suffering from an acute coronary syndrome, for a defined set of miRNA biomrkers, the inventors of the present invention applied a machine learning approach (e.g. t-test, AUC, support vector machine, hierarchical clustering, or k-means) which leads to an algorithm that is trained by reference data (i.e. data of reference miRNA expression profiles from the two clinical conditions, e.g. healthy and suffering from an acute coronary syndrome, for the defined set of miRNA markers) to discriminate between the two statistical classes (i.e. two clinical conditions, e.g. healthy or suffering from an acute coronary syndrome).

The inventors of the present invention surprisingly found that this approach yields in miRNA sets (signatures) that provide high diagnostic accuracy, specificity and sensitivity in the determination of an acute coronary syndrome in human patients (see FIGS. 13 to 20, FIG. 28, and FIG. 30). Said miRNA sets (signatures) comprise at least two miR-NAs, wherein the nucleotide sequences of said miRNAs are selected from the group consisting of SEQ ID NO: 1 to SEQ ID NO: 283, particularly of SEQ ID NO: 1 to SEQ ID NO: 153. The inventors of the present invention further found that the sets of at least two miRNAs, wherein the nucleotide sequences of said miRNAs are selected from the group consisting of SEQ ID NO: 1 to SEQ ID NO: 153, can be completed by at least one further miRNA, wherein the nucleotide sequence of said miRNA is selected from the group consisting of SEQ ID NO: 154 to SEQ ID NO: 241, preferably in order to improve the diagnostic accuracy, specificity and sensitivity in the determination of an acute coronary syndrome.

Figure 21:
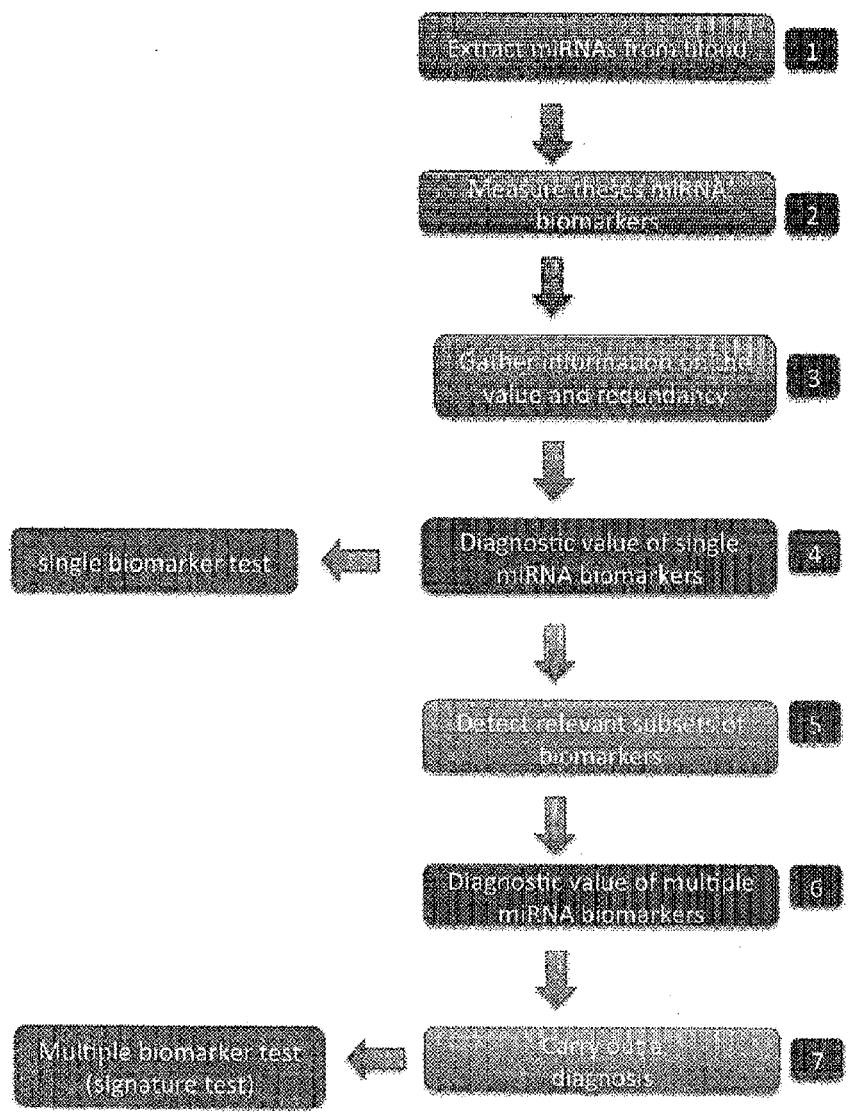
FIG. 21: Diagram describing the general approach for determining miRNA signatures for use as biomarkers in the diagnosis and/or prognosis of an acute coronary syndrome.

An exemplarily approach to arrive at miRNA sets/signatures that correlate with an acute coronary syndrome is summarized below. In addition, the general work flow is shown in FIG. 21.

Step 1: Total RNA (or subfractions thereof) is extracted from blood (including plasma, serum, PBMC or other blood fractions) using suitable kits and/or purification methods.

Step 2: From the respective samples, the quantity (expression level) of one miRNA or sets of at least two miRNAs selected from the group consisting of SEQ ID NO: 1 to SEQ ID NO: 283, particularly of SEQ ID NO: 1 to SEQ ID NO: 153, is measured using experimental techniques. These techniques include but are not restricted to: array based approaches, amplification methods (PCR, RT-PCR, qPCR), sequencing, next generation sequencing, and mass spectroscopy.

Step 3: In order to gather information on the diagnostic/prognostic value and the redundancy of each of the single miRNA biomarkers, mathematical methods are applied. These methods include, but are not restricted to basic mathematic approaches (e.g. Fold Quotients, Signal to Noise ratios, Correlation), statistical methods as hypothesis tests (e.g. t-test, Wilcoxon-Mann-Whitney test), the Area under the Receiver operator Characteristics Curve, information theory approaches, (e.g. the Mutual Information, Cross-entropy), probability theory (e.g. joint and conditional probabilities) or combinations and modifications of the previously mentioned methods.

Step 4: The information gathered in step 3) is used to estimate for each miRNA biomarker the diagnostic content or value. Usually, however, this diagnostic value is too small to get a highly accurate diagnosis with accuracy rates, specificities and sensitivities beyond the 80%, particularly 90% barrier.

The diagnostic content of the miRNAs suitable for diagnosing/prognosing an acute coronary syndrome is listed in FIG. 7. This table includes said miRNAs (SEQ ID NO: 1 to SEQ ID NO: 283, particularly SEQ ID NO: 1 to SEQ ID NO: 153) (Experimental explanations: median g1=median intensity value of the AMI patients; median g2=median intensity value of the healty controls; qmedian=ratio of median g1 and median g2; logqmedian=log of qmedian; and the statistical significance value a as computed by a t-test, limma-test or AUC-test: ttest_rawp=p-value calculated according to ttest; ttest_adjp=adjusted p-value calculated according to ttest; limma_rawp=p-value calculated according to limma-test; limma_adjp=adjusted p-value calculated according to limma-test; AUC=area under the curve).

Step 5: In order to use increase the performance for diagnosing/prognosing of individuals suffering from an acute coronary syndrome, more than one miRNA biomarker need to be employed. Thus statistical learning/machine learning/bioinformatics/computational approaches are applied for set selection in order to select/define sets of miRNA biomarkers (comprising miRNAs SEQ ID NO: 1 to SEQ ID NO: 283, particularly SEQ ID NO 1 to SEQ ID NO: 153) that are tailored for the detection of an acute coronary syndrome. These techniques include but are not restricted to: Wrapper subset selection techniques (e.g. forward step-wise, backward step-wise, combinatorial approaches, optimization approaches), filter subset selection methods (e.g. the methods mentioned in Step 3), principal component analysis, or combinations and modifications of such methods (e.g. hybrid approaches).

Step 6: The subsets, selected/defined in Step 5, which may range from only a small number (at least two for the set) to all measured biomarkers is then used to carry out a diagnosis/prognosis of an acute coronary syndrome. To this end, statistical learning/machine learning/bioinformatics/computational approaches are applied that include but are not restricted to any type of supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

By combination of subset selection (Step 5) and machine learning (Step 6) an algorithm or mathematical function for diagnosing/prognosing an acute coronary syndrome is obtained. This algorithm or mathematical function is applied to a miRNA expression profile of an individual to be diagnosed for an acute coronary syndrome.

Thus, in a first aspect, the present invention relates to (the use of) a (single) polynucleotide for detecting a (single) miRNA or a set (signature) comprising, essentially consisting of, or consisting of at least two polynucleotides for detecting a set (signature) comprising, essentially consisting of, or consisting of at least two miRNAs for diagnosing and/or prognosing of an acute coronary syndrome, preferably myocardial infarction or Unstable angina (UA), in a blood sample from a human, particularly human patient, wherein the nucleotide sequence of said miRNA or the nucleotide sequences of said miRNAs is (are) selected from the group consisting of SEQ ID NO: 1 to SEQ ID NO: 283.

In preferred embodiments, the blood sample from a human is whole blood or a blood fraction such as serum or plasma. It is also preferred to use blood cells also known as hemopoietic cells. The term "hemopoietic cells" refers to mature cell types and their immature precursors that are identifiable either by morphology or, mostly, by a distinct pattern of cell surface markers. The term is used to distinguish these cells from other cell types found in the body and also includes T-cells and distinctive subsets, which are the only hematopoietic cells that are not generated in the bone marrow. Preferably, the blood cells are erythrocytes, leukocytes and/or thrombocytes. It is also preferred to use peripheral blood mononuclear cells (PBMCs) such as lymphocytes, monocytes or macrophages.

Preferably, the blood sample from a human has a volume of between 0.1 and 20 ml, more preferably of between 0.5 and 10 ml, i.e. 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20 ml. It is preferred that the blood sample is from a human that has not been therapeutically treated or has been therapeutically treated. In one embodiment, the therapeutical treatment is monitored on the basis of the detection of the miRNA or set of miRNAs by the nucleotide or set of polynucleotides. It is also preferred that total RNA or subfractions thereof, isolated (e.g. extracted) from a blood sample of a human is used for detecting the miRNA or set of miRNAs by the polynucleotide or set of polynucleotides.

The polynucleotide or polynucleotides comprised in the set of the present invention may be single stranded or double stranded. The skilled person in the art will understand that the polynucleotide as a single polynucleotide strand provides a probe (e.g. miRNA capture probe) that is capable of binding to, hybridizing with, or detecting a target miRNA of complementary sequence through one or more types of chemical bonds, usually through complementary base pairing, usually through hydrogen bond formation.

It is preferred that the polynucleotides of the present invention are for detecting a set comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282 miRNAs, or comprising/consisting of 283 miRNAs, wherein the nucleotide sequences of said miRNAs are selected from the group consisting of SEQ ID NO: 1 to SEQ ID NO: 283.

It is particularly preferred that the number of polynucleotides is equivalent to the number of miRNAs comprised in the set.

It is more preferred that the present invention relates to (the use of) a (single) polynucleotide for detecting a (single) miRNA or a set (signature) comprising, essentially consisting of, or consisting of at least two polynucleotides for detecting a set (signature) comprising, essentially consisting of, or consisting of at least two miRNAs for diagnosing and/or prognosing of an acute coronary syndrome, preferably myocardial infarction or Unstable angina (UA), in a blood sample from a human, particularly human patient, wherein the nucleotide sequence of said miRNA or the nucleotide sequences of said miRNAs is (are) selected from the group consisting of SEQ ID NO: 1 to SEQ ID NO: 153.

It is particularly more preferred that the polynucleotides of the present invention are for detecting a set comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 miRNAs, or comprising/consisting of 153 miRNAs, wherein the nucleotide sequences of said miRNAs are selected from the group consisting of SEQ ID NO: 1 to SEQ ID NO: 153.

Preferably, the nucleotide sequences of the at least 2 miRNAs comprised in the set have SEQ ID NO: 1 and SEQ ID NO: 2, the nucleotide sequences of the at least 3 miRNAs comprised in the set have SEQ ID NO: 1 to SEQ ID NO: 3, the nucleotide sequences of the at least 4 miRNAs comprised in the set have SEQ ID NO: 1 to SEQ ID NO: 4, the nucleotide sequences of the at least 5 miRNAs comprised in the set have SEQ ID NO: 1 to SEQ ID NO: 5, the nucleotide sequences of the at least 6 miRNAs comprised in the set have SEQ ID NO: 1 to SEQ ID NO: 6, the nucleotide sequences of the at least 7 miRNAs comprised in the set have SEQ ID NO: 1 to SEQ ID NO: 7, the nucleotide sequences of the at least 8 miRNAs comprised in the set have SEQ ID NO: 1 to SEQ ID NO: 8, the nucleotide sequences of the at least 9 miRNAs comprised in the set have SEQ ID NO: 1 to SEQ ID NO: 9, the nucleotide sequences of the at least 10 miRNAs comprised in the set have SEQ ID NO: 1 to SEQ ID NO: 10, the nucleotide sequences of the at least 11 miRNAs comprised in the set have SEQ ID NO: 1 to SEQ ID NO: 11, the nucleotide sequences of the at least 12 miRNAs comprised in the set have SEQ ID NO: 1 to SEQ ID NO: 12, the nucleotide sequences of the at least 13 miRNAs comprised in the set have SEQ ID NO: 1 to SEQ ID NO: 13, the nucleotide sequences of the at least 14 miRNAs comprised in the set have SEQ ID NO: 1 to SEQ ID NO: 14, the nucleotide sequences of the at least 15 miRNAs comprised in the set have SEQ ID NO: 1 to SEQ ID NO: 15, the nucleotide sequences of the at least 16 miRNAs comprised in the set have SEQ ID NO: 1 to SEQ ID NO: 16, the nucleotide sequences of the at least 17 miRNAs comprised in the set have SEQ ID NO: 1 to SEQ ID NO: 17, the nucleotide sequences of the at least 18 miRNAs comprised in the set have SEQ ID NO: 1 to SEQ ID NO: 18, the nucleotide sequences of the at least 19 miRNAs comprised in the set have SEQ ID NO: 1 to SEQ ID NO: 19, the nucleotide sequences of the at least 20 miRNAs comprised in the set have SEQ ID NO: 1 to SEQ ID NO: 20, the nucleotide sequences of the at least 21 miRNAs comprised in the set have SEQ ID NO: 1 to SEQ ID NO: 21, the nucleotide sequences of the at least 22 miRNAs comprised in the set have SEQ ID NO: 1 to SEQ ID NO: 22, the nucleotide sequences of the at least 23 miRNAs comprised in the set have SEQ ID NO: 1 to SEQ ID NO: 23, the nucleotide sequences of the at least 24 miRNAs comprised in the set have SEQ ID NO: 1 to SEQ ID NO: 24, the nucleotide sequences of the at least 25 miRNAs comprised in the set have SEQ ID NO: 1 to SEQ ID NO: 25, the nucleotide sequences of the at least 26 miRNAs comprised in the set have SEQ ID NO: 1 to SEQ ID NO: 26, the nucleotide sequences of the at least 27 miRNAs comprised in the set have SEQ ID NO: 1 to SEQ ID NO: 27, the nucleotide sequences of the at least 28 miRNAs comprised in the set have SEQ ID NO: 1 to SEQ ID NO: 28, the nucleotide sequences of the at least 29 miRNAs comprised in the set have SEQ ID NO: 1 to SEQ ID NO: 29, the nucleotide sequences of the at least 30 miRNAs comprised in the set have SEQ ID NO: 1 to SEQ ID NO: 30, the nucleotide sequences of the at least 31 miRNAs comprised in the set have SEQ ID NO: 1 to SEQ ID NO: 31, the nucleotide sequences of the at least 32 miRNAs comprised in the set have SEQ ID NO: 1 to SEQ ID NO: 32, the nucleotide sequences of the at least 33 miRNAs comprised in the set have SEQ ID NO: 1 to SEQ ID NO: 33, the nucleotide sequences of the at least 34 miRNAs comprised in the set have SEQ ID NO: 1 to SEQ ID NO: 34, the nucleotide sequences of the at least 35 miRNAs comprised in the set have SEQ ID NO: 1 to SEQ ID NO: 35, the nucleotide sequences of the at least 36 miRNAs comprised in the set have SEQ ID NO: 1 to SEQ ID NO: 36, the nucleotide sequences of the at least 37 miRNAs comprised in the set have SEQ ID NO: 1 to SEQ ID NO: 37, the nucleotide sequences of the at least 38 miRNAs comprised in the set have SEQ ID NO: 1 to SEQ ID NO: 38, the nucleotide sequences of the at least 39 miRNAs comprised in the set have SEQ ID NO: 1 to SEQ ID NO: 39, the nucleotide sequences of the at least 40 miRNAs comprised in the set have SEQ ID NO: 1 to SEQ ID NO: 40, the nucleotide sequences of the at least 41 miRNAs comprised in the set have SEQ ID NO: 1 to SEQ ID NO: 41, the nucleotide sequences of the at least 42 miRNAs comprised in the set have SEQ ID NO: 1 to SEQ ID NO: 42, the nucleotide sequences of the at least 43 miRNAs comprised in the set have SEQ ID NO: 1 to SEQ ID NO: 43, the nucleotide sequences of the at least 44 miRNAs comprised in the set have SEQ ID NO: 1 to SEQ ID NO: 44, the nucleotide sequences of the at least 45 miRNAs comprised in the set have SEQ ID NO: 1 to SEQ ID NO: 45, the nucleotide sequences of the at least 46 miRNAs comprised in the set have SEQ ID NO: 1 to SEQ ID NO: 46, the nucleotide sequences of the at least 47 miRNAs comprised in the set have SEQ ID NO: 1 to SEQ ID NO: 47, the nucleotide sequences of the at least 48 miRNAs comprised in the set have SEQ ID NO: 1 to SEQ ID NO: 48, the nucleotide sequences of the at least 49 miRNAs comprised in the set have SEQ ID NO: 1 to SEQ ID NO: 49, the nucleotide sequences of the at least 50 miRNAs comprised in the set have SEQ ID NO: 1 to SEQ ID NO: 50, the nucleotide sequences of the at least 51 miRNAs comprised in the set have SEQ ID NO: 1 to SEQ ID NO: 51, the nucleotide sequences of the at least 52 miRNAs comprised in the set have SEQ ID NO: 1 to SEQ ID NO: 52, the nucleotide sequences of the at least 53 miRNAs comprised in the set have SEQ ID NO: 1 to SEQ ID NO: 53, the nucleotide sequences of the at least 54 miRNAs comprised in the set have SEQ ID NO: 1 to SEQ ID NO: 54, the nucleotide sequences of the at least 55 miRNAs comprised in the set have SEQ ID NO: 1 to SEQ ID NO: 55, the nucleotide sequences of the at least 56 miRNAs comprised in the set have SEQ ID NO: 1 to SEQ ID NO: 56, the nucleotide sequences of the at least 57 miRNAs comprised in the set have SEQ ID NO: 1 to SEQ ID NO: 57, the nucleotide sequences of the at least 58 miRNAs comprised in the set have SEQ ID NO: 1 to SEQ ID NO: 58, the nucleotide sequences of the at least 59 miRNAs comprised in the set have SEQ ID NO: 1 to SEQ ID NO: 59, the nucleotide sequences of the at least 60 miRNAs comprised in the set have SEQ ID NO: 1 to SEQ ID NO: 60, the nucleotide sequences of the at least 61 miRNAs comprised in the set have SEQ ID NO: 1 to SEQ ID NO: 61, the nucleotide sequences of the at least 62 miRNAs comprised in the set have SEQ ID NO: 1 to SEQ ID NO: 62, the nucleotide sequences of the at least 63 miRNAs comprised in the set have SEQ ID NO: 1 to SEQ ID NO: 63, the nucleotide sequences of the at least 64 miRNAs comprised in the set have SEQ ID NO: 1 to SEQ ID NO: 64, the nucleotide sequences of the at least 65 miRNAs comprised in the set have SEQ ID NO: 1 to SEQ ID NO: 65, the nucleotide sequences of the at least 66 miRNAs comprised in the set have SEQ ID NO: 1 to SEQ ID NO: 66, the nucleotide sequences of the at least 67 miRNAs comprised in the set have SEQ ID NO: 1 to SEQ ID NO: 67, the nucleotide sequences of the at least 68 miRNAs comprised in the set have SEQ ID NO: 1 to SEQ ID NO: 68, the nucleotide sequences of the at least 69 miRNAs comprised in the set have SEQ ID NO: 1 to SEQ ID NO: 69, the nucleotide sequences of the at least 70 miRNAs comprised in the set have SEQ ID NO: 1 to SEQ ID NO: 70, the nucleotide sequences of the at least 71 miRNAs comprised in the set have SEQ ID NO: 1 to SEQ ID NO: 71, the nucleotide sequences of the at least 72 miRNAs comprised in the set have SEQ ID NO: 1 to SEQ ID NO: 72, the nucleotide sequences of the at least 73 miRNAs comprised in the set have SEQ ID NO: 1 to SEQ ID NO: 73, the nucleotide sequences of the at least 74 miRNAs comprised in the set have SEQ ID NO: 1 to SEQ ID NO: 74, the nucleotide sequences of the at least 75 miRNAs comprised in the set have SEQ ID NO: 1 to SEQ ID NO: 75, the nucleotide sequences of the at least 76 miRNAs comprised in the set have SEQ ID NO: 1 to SEQ ID NO: 76, the nucleotide sequences of the at least 77 miRNAs comprised in the set have SEQ ID NO: 1 to SEQ ID NO: 77, the nucleotide sequences of the at least 78 miRNAs comprised in the set have SEQ ID NO: 1 to SEQ ID NO: 78, the nucleotide sequences of the at least 79 miRNAs comprised in the set have SEQ ID NO: 1 to SEQ ID NO: 79, the nucleotide sequences of the at least 80 miRNAs comprised in the set have SEQ ID NO: 1 to SEQ ID NO: 80, the nucleotide sequences of the at least 81 miRNAs comprised in the set have SEQ ID NO: 1 to SEQ ID NO: 81, the nucleotide sequences of the at least 82 miRNAs comprised in the set have SEQ ID NO: 1 to SEQ ID NO: 82, the nucleotide sequences of the at least 83 miRNAs comprised in the set have SEQ ID NO: 1 to SEQ ID NO: 83, the nucleotide sequences of the at least 84 miRNAs comprised in the set have SEQ ID NO: 1 to SEQ ID NO: 84, the nucleotide sequences of the at least 85 miRNAs comprised in the set have SEQ ID NO: 1 to SEQ ID NO: 85, the nucleotide sequences of the at least 86 miRNAs comprised in the set have SEQ ID NO: 1 to SEQ ID NO: 86, the nucleotide sequences of the at least 87 miRNAs comprised in the set have SEQ ID NO: 1 to SEQ ID NO: 87, the nucleotide sequences of the at least 88 miRNAs comprised in the set have SEQ ID NO: 1 to SEQ ID NO: 88, the nucleotide sequences of the at least 89 miRNAs comprised in the set have SEQ ID NO: 1 to SEQ ID NO: 89, the nucleotide sequences of the at least 90 miRNAs comprised in the set have SEQ ID NO: 1 to SEQ ID NO: 90, the nucleotide sequences of the at least 91 miRNAs comprised in the set have SEQ ID NO: 1 to SEQ ID NO: 91, the nucleotide sequences of the at least 92 miRNAs comprised in the set have SEQ ID NO: 1 to SEQ ID NO: 92, the nucleotide sequences of the at least 93 miRNAs comprised in the set have SEQ ID NO: 1 to SEQ ID NO: 93, the nucleotide sequences of the at least 94 miRNAs comprised in the set have SEQ ID NO: 1 to SEQ ID NO: 94, the nucleotide sequences of the at least 95 miRNAs comprised in the set have SEQ ID NO: 1 to SEQ ID NO: 95, the nucleotide sequences of the at least 96 miRNAs comprised in the set have SEQ ID NO: 1 to SEQ ID NO: 96, the nucleotide sequences of the at least 97 miRNAs comprised in the set have SEQ ID NO: 1 to SEQ ID NO: 97, the nucleotide sequences of the at least 98 miRNAs comprised in the set have SEQ ID NO: 1 to SEQ ID NO: 98, the nucleotide sequences of the at least 99 miRNAs comprised in the set have SEQ ID NO: 1 to SEQ ID NO: 99, the nucleotide sequences of the at least 100 miRNAs comprised in the set have SEQ ID NO: 1 to SEQ ID NO: 100, the nucleotide sequences of the at least 101 miRNAs comprised in the set have SEQ ID NO: 1 to SEQ ID NO: 101, the nucleotide sequences of the at least 102 miRNAs comprised in the set have SEQ ID NO: 1 to SEQ ID NO: 102, the nucleotide sequences of the at least 103 miRNAs comprised in the set have SEQ ID NO: 1 to SEQ ID NO: 103, the nucleotide sequences of the at least 104 miRNAs comprised in the set have SEQ ID NO: 1 to SEQ ID NO: 104, the nucleotide sequences of the at least 105 miRNAs comprised in the set have SEQ ID NO: 1 to SEQ ID NO: 105, the nucleotide sequences of the at least 106 miRNAs comprised in the set have SEQ ID NO: 1 to SEQ ID NO: 106, the nucleotide sequences of the at least 107 miRNAs comprised in the set have SEQ ID NO: 1 to SEQ ID NO: 107, the nucleotide sequences of the at least 108 miRNAs comprised in the set have SEQ ID NO: 1 to SEQ ID NO: 108, the nucleotide sequences of the at least 109 miRNAs comprised in the set have SEQ ID NO: 1 to SEQ ID NO: 109, the nucleotide sequences of the at least 110 miRNAs comprised in the set have SEQ ID NO: 1 to SEQ ID NO: 110, the nucleotide sequences of the at least 111 miRNAs comprised in the set have SEQ ID NO: 1 to SEQ ID NO: 111, the nucleotide sequences of the at least 112 miRNAs comprised in the set have SEQ ID NO: 1 to SEQ ID NO: 112, the nucleotide sequences of the at least 113 miRNAs comprised in the set have SEQ ID NO: 1 to SEQ ID NO: 113, the nucleotide sequences of the at least 114 miRNAs comprised in the set have SEQ ID NO: 1 to SEQ ID NO: 114, the nucleotide sequences of the at least 115 miRNAs comprised in the set have SEQ ID NO: 1 to SEQ ID NO: 115, the nucleotide sequences of the at least 116 miRNAs comprised in the set have SEQ ID NO: 1 to SEQ ID NO: 116, the nucleotide sequences of the at least 117 miRNAs comprised in the set have SEQ ID NO: 1 to SEQ ID NO: 117, the nucleotide sequences of the at least 118 miRNAs comprised in the set have SEQ ID NO: 1 to SEQ ID NO: 118, the nucleotide sequences of the at least 119 miRNAs comprised in the set have SEQ ID NO: 1 to SEQ ID NO: 119, the nucleotide sequences of the at least 120 miRNAs comprised in the set have SEQ ID NO: 1 to SEQ ID NO: 120, the nucleotide sequences of the at least 121 miRNAs comprised in the set have SEQ ID NO: 1 to SEQ ID NO: 121, the nucleotide sequences of the at least 122 miRNAs comprised in the set have SEQ ID NO: 1 to SEQ ID NO: 122, the nucleotide sequences of the at least 123 miRNAs comprised in the set have SEQ ID NO: 1 to SEQ ID NO: 123, the nucleotide sequences of the at least 124 miRNAs comprised in the set have SEQ ID NO: 1 to SEQ ID NO: 124, the nucleotide sequences of the at least 125 miRNAs comprised in the set have SEQ ID NO: 1 to SEQ ID NO: 125, the nucleotide sequences of the at least 126 miRNAs comprised in the set have SEQ ID NO: 1 to SEQ ID NO: 126, the nucleotide sequences of the at least 127 miRNAs comprised in the set have SEQ ID NO: 1 to SEQ ID NO: 127, the nucleotide sequences of the at least 128 miRNAs comprised in the set have SEQ ID NO: 1 to SEQ ID NO: 128, the nucleotide sequences of the at least 129 miRNAs comprised in the set have SEQ ID NO: 1 to SEQ ID NO: 129, the nucleotide sequences of the at least 130 miRNAs comprised in the set have SEQ ID NO: 1 to SEQ ID NO: 130, the nucleotide sequences of the at least 131 miRNAs comprised in the set have SEQ ID NO: 1 to SEQ ID NO: 131, the nucleotide sequences of the at least 132 miRNAs comprised in the set have SEQ ID NO: 1 to SEQ ID NO: 132, the nucleotide sequences of the at least 133 miRNAs comprised in the set have SEQ ID NO: 1 to SEQ ID NO: 133, the nucleotide sequences of the at least 134 miRNAs comprised in the set have SEQ ID NO: 1 to SEQ ID NO: 134, the nucleotide sequences of the at least 135 miRNAs comprised in the set have SEQ ID NO: 1 to SEQ ID NO: 135, the nucleotide sequences of the at least 136 miRNAs comprised in the set have SEQ ID NO: 1 to SEQ ID NO: 136, the nucleotide sequences of the at least 137 miRNAs comprised in the set have SEQ ID NO: 1 to SEQ ID NO: 137, the nucleotide sequences of the at least 138 miRNAs comprised in the set have SEQ ID NO: 1 to SEQ ID NO: 138, the nucleotide sequences of the at least 139 miRNAs comprised in the set have SEQ ID NO: 1 to SEQ ID NO: 139, the nucleotide sequences of the at least 140 miRNAs comprised in the set have SEQ ID NO: 1 to SEQ ID NO: 140, the nucleotide sequences of the at least 141 miRNAs comprised in the set have SEQ ID NO: 1 to SEQ ID NO: 141, the nucleotide sequences of the at least 142 miRNAs comprised in the set have SEQ ID NO: 1 to SEQ ID NO: 142, the nucleotide sequences of the at least 143 miRNAs comprised in the set have SEQ ID NO: 1 to SEQ ID NO: 143, the nucleotide sequences of the at least 144 miRNAs comprised in the set have SEQ ID NO: 1 to SEQ ID NO: 144, the nucleotide sequences of the at least 145 miRNAs comprised in the set have SEQ ID NO: 1 to SEQ ID NO: 145, the nucleotide sequences of the at least 146 miRNAs comprised in the set have SEQ ID NO: 1 to SEQ ID NO: 146, the nucleotide sequences of the at least 147 miRNAs comprised in the set have SEQ ID NO: 1 to SEQ ID NO: 147, the nucleotide sequences of the at least 148 miRNAs comprised in the set have SEQ ID NO: 1 to SEQ ID NO: 148, the nucleotide sequences of the at least 149 miRNAs comprised in the set have SEQ ID NO: 1 to SEQ ID NO: 149, the nucleotide sequences of the at least 150 miRNAs comprised in the set have SEQ ID NO: 1 to SEQ ID NO: 150, the nucleotide sequences of the at least 151 miRNAs comprised in the set have SEQ ID NO: 1 to SEQ ID NO: 151, or the nucleotide sequences of the at least 152 miRNAs comprised in the set have SEQ ID NO: 1 to SEQ ID NO: 152, and more preferably, the nucleotide sequences of the 153 miRNAs comprised in the set have SEQ ID NO: 1 to SEQ ID NO: 153.

It is also preferred that the nucleotide sequences of the at least 2 miRNAs comprised in the set have SEQ ID NO: 1 and SEQ ID NO: 2, the nucleotide sequences of the at least 2 miRNAs comprised in the set have SEQ ID NO: 3 and SEQ ID NO: 4, the nucleotide sequences of the at least 3 miRNAs comprised in the set have SEQ ID NO: 5, SEQ ID NO: 6, and SEQ ID NO: 7, the nucleotide sequences of the at least 3 miRNAs comprised in the set have SEQ ID NO: 8, SEQ ID NO: 9, and SEQ ID NO: 10, the nucleotide sequences of the at least 3 miRNAs comprised in the set have SEQ ID NO: 11, SEQ ID NO: 12, and SEQ ID NO: 13, the nucleotide sequences of the at least 3 miRNAs comprised in the set have SEQ ID NO: 14, SEQ ID NO: 15, and SEQ ID NO: 16, the nucleotide sequences of the at least 4 miRNAs comprised in the set have SEQ ID NO: 17, SEQ ID NO: 18, SEQ ID NO: 19, and SEQ ID NO: 20, the nucleotide sequences of the at least 4 miRNAs comprised in the set have SEQ ID NO: 21, SEQ ID NO: 22, SEQ ID NO: 23, and SEQ ID NO: 24, the nucleotide sequences of the at least 6 miRNAs comprised in the set have SEQ ID NO: 25, SEQ ID NO: 26, SEQ ID NO: 27, SEQ ID NO: 28, SEQ ID NO: 29, and SEQ ID NO: 30, the nucleotide sequences of the at least 6 miRNAs comprised in the set have SEQ ID NO: 31, SEQ ID NO: 32, SEQ ID NO: 33, SEQ ID NO: 34, SEQ ID NO: 35, and SEQ ID NO: 36, the nucleotide sequences of the at least 6 miRNAs comprised in the set have SEQ ID NO: 37, SEQ ID NO: 38, SEQ ID NO: 39, SEQ ID NO: 40, SEQ ID NO: 41, and SEQ ID NO: 42, the nucleotide sequences of the at least 6 miRNAs comprised in the set have SEQ ID NO: 43, SEQ ID NO: 44, SEQ ID NO: 45, SEQ ID NO: 46, SEQ ID NO: 47, and SEQ ID NO: 48, the nucleotide sequences of the at least 6 miRNAs comprised in the set have SEQ ID NO: 49, SEQ ID NO: 50, SEQ ID NO: 51, SEQ ID NO: 52, SEQ ID NO: 53, and SEQ ID NO: 54, the nucleotide sequences of the at least 6 miRNAs comprised in the set have SEQ ID NO: 55, SEQ ID NO: 56, SEQ ID NO: 57, SEQ ID NO: 58, SEQ ID NO: 59, and SEQ ID NO: 60, the nucleotide sequences of the at least 6 miRNAs comprised in the set have SEQ ID NO: 61, SEQ ID NO: 62, SEQ ID NO: 63, SEQ ID NO: 64, SEQ ID NO: 65, and SEQ ID NO: 66, the nucleotide sequences of the at least 6 miRNAs comprised in the set have SEQ ID NO: 67, SEQ ID NO: 68, SEQ ID NO: 69, SEQ ID NO: 70, SEQ ID NO: 71, and SEQ ID NO: 72, the nucleotide sequences of the at least 6 miRNAs comprised in the set have SEQ ID NO: 73, SEQ ID NO: 74, SEQ ID NO: 75, SEQ ID NO: 76, SEQ ID NO: 77, and SEQ ID NO: 78, the nucleotide sequences of the at least 6 miRNAs comprised in the set have SEQ ID NO: 79, SEQ ID NO: 80, SEQ ID NO: 81, SEQ ID NO: 82, SEQ ID NO: 83, and SEQ ID NO: 84, the nucleotide sequences of the at least 6 miRNAs comprised in the set have SEQ ID NO: 85, SEQ ID NO: 86, SEQ ID NO: 87, SEQ ID NO: 88, SEQ ID NO: 89, and SEQ ID NO: 90, the nucleotide sequences of the at least 6 miRNAs comprised in the set have SEQ ID NO: 91, SEQ ID NO: 92, SEQ ID NO: 93, SEQ ID NO: 94, SEQ ID NO: 95, and SEQ ID NO: 96, the nucleotide sequences of the at least 6 miRNAs comprised in the set have SEQ ID NO: 97, SEQ ID NO: 98, SEQ ID NO: 99, SEQ ID NO: 100, SEQ ID NO: 101, and SEQ ID NO: 102, the nucleotide sequences of the at least 6 miRNAs comprised in the set have SEQ ID NO: 103, SEQ ID NO: 104, SEQ ID NO: 105, SEQ ID NO: 106, SEQ ID NO: 107, and SEQ ID NO: 108, the nucleotide sequences of the at least 6 miRNAs comprised in the set have SEQ ID NO: 109, SEQ ID NO: 110, SEQ ID NO: 111, SEQ ID NO: 112, SEQ ID NO: 113, and SEQ ID NO: 114, the nucleotide sequences of the at least 6 miRNAs comprised in the set have SEQ ID NO: 115, SEQ ID NO: 116, SEQ ID NO: 117, SEQ ID NO: 118, SEQ ID NO: 119, and SEQ ID NO: 120, the nucleotide sequences of the at least 6 miRNAs comprised in the set have SEQ ID NO: 121, SEQ ID NO: 122, SEQ ID NO: 123, SEQ ID NO: 124, SEQ ID NO: 125, and SEQ ID NO: 126, the nucleotide sequences of the at least 6 miRNAs comprised in the set have SEQ ID NO: 127, SEQ ID NO: 128, SEQ ID NO: 129, SEQ ID NO: 130, SEQ ID NO: 131, and SEQ ID NO: 132, the nucleotide sequences of the at least 6 miRNAs comprised in the set have SEQ ID NO: 133, SEQ ID NO: 134, SEQ ID NO: 135, SEQ ID NO: 136, SEQ ID NO: 137, and SEQ ID NO: 138, the nucleotide sequences of the at least 6 miRNAs comprised in the set have SEQ ID NO: 139, SEQ ID NO: 140, SEQ ID NO: 141, SEQ ID NO: 142, SEQ ID NO: 143, and SEQ ID NO: 144, the nucleotide sequences of the at least 5 miRNAs comprised in the set have SEQ ID NO: 145, SEQ ID NO: 146, SEQ ID NO: 147, SEQ ID NO: 148, and SEQ ID NO: 149, or the nucleotide sequences of the at least 4 miRNAs comprised in the set have SEQ ID NO: 150, SEQ ID NO: 151, SEQ ID NO: 152, and SEQ ID NO: 153.

It is particularly preferred that the nucleotide sequences of the at least 10 miRNAs comprised in the set have SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or have SEQ ID NO: 1 to SEQ ID NO: 10.

It is also particularly preferred that (i) the nucleotide sequences of the at least 5 miRNAs comprised in the set have SEQ ID NO: 16, SEQ ID NO: 17, SEQ ID NO: 18, SEQ ID NO: 3 and SEQ ID NO: 2, (ii) the nucleotide sequences of the at least 5 miRNAs comprised in the set have SEQ ID NO: 1, SEQ ID NO: 5, SEQ ID NO: 20, SEQ ID NO: 21 and SEQ ID NO: 22, (iii) the nucleotide sequences of the at least 5 miRNAs comprised in the set have SEQ ID NO: 2, SEQ ID NO: 16, SEQ ID NO: 17, SEQ ID NO: 18 and SEQ ID NO: 24, (iv) the nucleotide sequences of the at least 5 miRNAs comprised in the set have SEQ ID NO: 1, SEQ ID NO: 34, SEQ ID NO: 30, SEQ ID NO: 22 and SEQ ID NO: 28, (v) that the nucleotide sequences of the at least 5 miRNAs comprised in the set have SEQ ID NO: 2, SEQ ID NO: 17, SEQ ID NO: 81, SEQ ID NO: 1 and SEQ ID NO: 34, (vi) that the nucleotide sequences of the at least 5 miRNAs comprised in the set have SEQ ID NO: 45, SEQ ID NO: 7, SEQ ID NO: 6, SEQ ID NO: 37 and SEQ ID NO: 90, or (vii) the nucleotide sequences of the at least 5 miRNAs comprised in the set have SEQ ID NO: 1, SEQ ID NO: 5, SEQ ID NO: 19, SEQ ID NO: 20 and SEQ ID NO: 21.

The above-mentioned sets may also be combined with each other, e.g. (i) with (ii), (ii) with (iii), (iii) with (iv), (iv) with (v), (v) with (vi), (vi) with (vii), etc.

Preferably, the polynucleotides of the present invention are for detecting a set (signature) as defined above comprising at least one further miRNA, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 further miRNA(s), wherein the nucleotide sequence of said miRNA is selected from the group consisting of SEQ ID NO: 154 to SEQ ID NO: 241.

Accordingly, it is preferred that the polynucleotides of the present invention are for detecting a set (signature) comprising, essentially consisting of, or consisting of at least two miRNAs for diagnosing and/or prognosing of an acute coronary syndrome, preferably myocardial infarction or Unstable angina (UA), in a blood sample from a human, particularly human patient, wherein the nucleotide sequences of said miRNAs are selected from the group consisting of SEQ ID NO: 1 to SEQ ID NO: 153, and wherein the polynucleotides of the present invention are for detecting a set (signature) comprising at least one further miRNA, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 further miRNA(s), wherein the nucleotide sequence of said miRNA is selected from the group consisting of SEQ ID NO: 154 to SEQ ID NO: 241.

Thus, in a preferred embodiment of the present invention, the polynucleotides of the present invention are for detecting a set comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153 miRNAs, wherein the nucleotide sequences of said miRNAs are selected from the group consisting of SEQ ID NO: 1 to SEQ ID NO: 153, and the polynucleotides of the present invention are for detecting (i) at least one further miRNA having the nucleotide sequence according to SEQ ID NO: 154, (ii) at least 2 further miRNAs having the nucleotide sequence according to SEQ ID NO: 154 and SEQ ID NO: 155, (iii) at least 3 further miRNAs having the nucleotide sequence according to SEQ ID NO: 154 to SEQ ID NO: 156, (iv) at least 4 further miRNAs having the nucleotide sequences according to SEQ ID NO: 154 to SEQ ID NO: 157, (v) at least 5 further miRNAs having the nucleotide sequences according to SEQ ID NO: 154 to SEQ ID NO: 158, (vi) at least 6 further miRNAs having the nucleotide sequences according to SEQ ID NO: 154 to SEQ ID NO: 159, or (vii) at least 7 further miRNAs having the nucleotide sequences according to SEQ ID NO: 154 to SEQ ID NO: 160, which is (are) also comprised in said set of miRNAs.

In another preferred embodiment of the present invention, the polynucleotides of the present invention are for detecting a set comprising at least 10 miRNAs, wherein the nucleotide sequences of the at least 10 miRNAs comprised in the set have SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or have SEQ ID NO: 1 to SEQ ID NO: 10, and the polynucleotides of the present invention are for detecting (i) at least one further miRNA having the nucleotide sequence according to SEQ ID NO: 154, (ii) at least 2 further miRNAs having the nucleotide sequence according to SEQ ID NO: 154 and SEQ ID NO: 155, (iii) at least 3 further miRNAs having the nucleotide sequence according to SEQ ID NO: 154 to SEQ ID NO: 156, (iv) at least 4 further miRNAs having the nucleotide sequences according to SEQ ID NO: 154 to SEQ ID NO: 157, (v) at least 5 further miRNAs having the nucleotide sequences according to SEQ ID NO: 154 to SEQ ID NO: 158, (vi) at least 6 further miRNAs having the nucleotide sequences according to SEQ ID NO: 154 to SEQ ID NO: 159, or (vii) at least 7 further miRNAs having the nucleotide sequences according to SEQ ID NO: 154 to SEQ ID NO: 160, which is (are) also comprised in said set of miRNAs.

It is also preferred that the polynucleotide(s) of the present invention is (are) for detecting a miRNA or a set comprising, essentially consisting of, or consisting of at least two miRNAs for diagnosing and/or prognosing of an acute coronary syndrome, preferably myocardial infarction or Unstable angina (UA), in a blood sample from a human, particularly human patient, wherein the nucleotide sequence of said miRNA or the nucleotide sequences of said miRNAs is (are) selected from SEQ ID NO: 242 to SEQ ID NO: 283.

Figure 28:
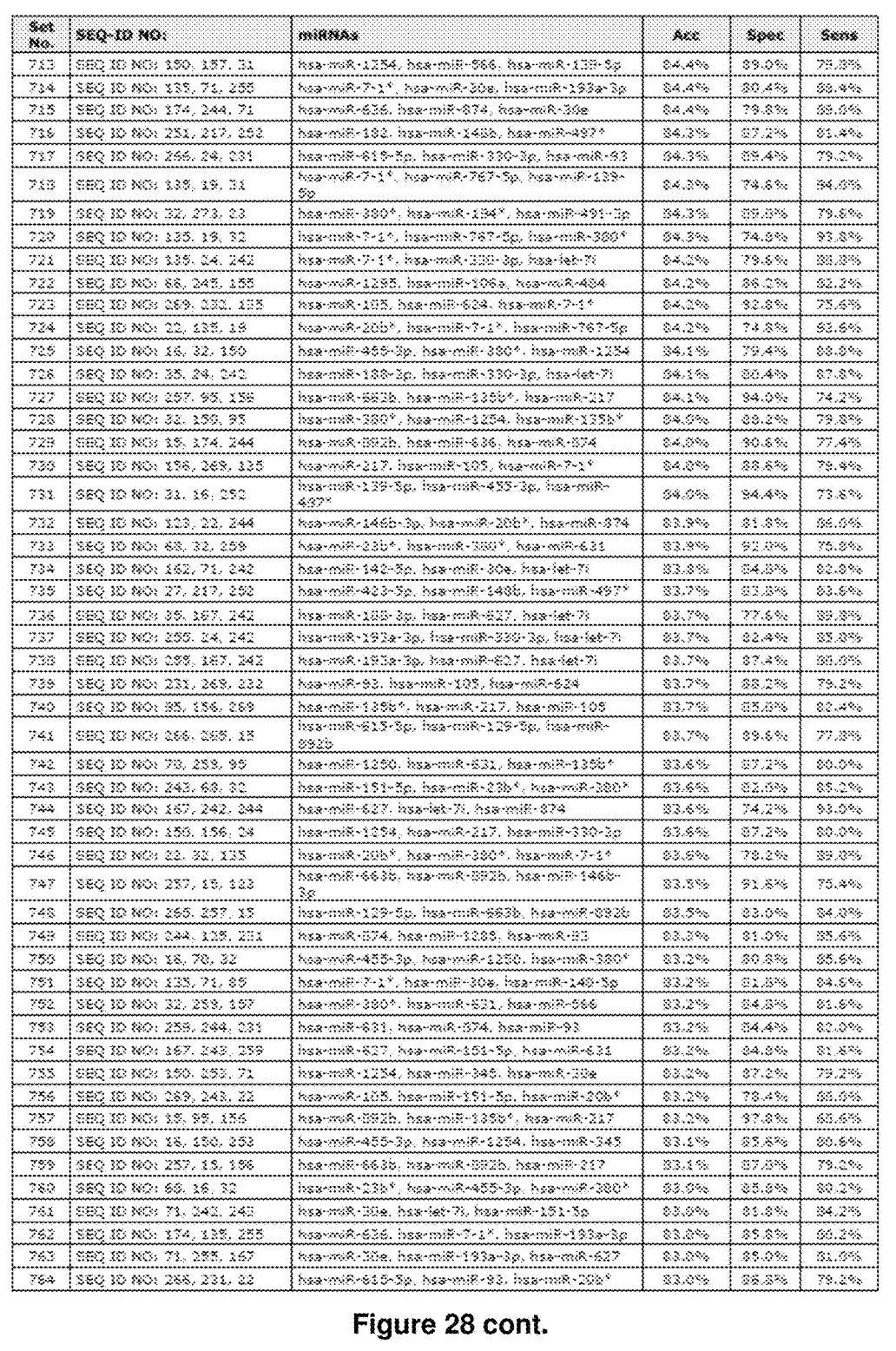
Figure 28:
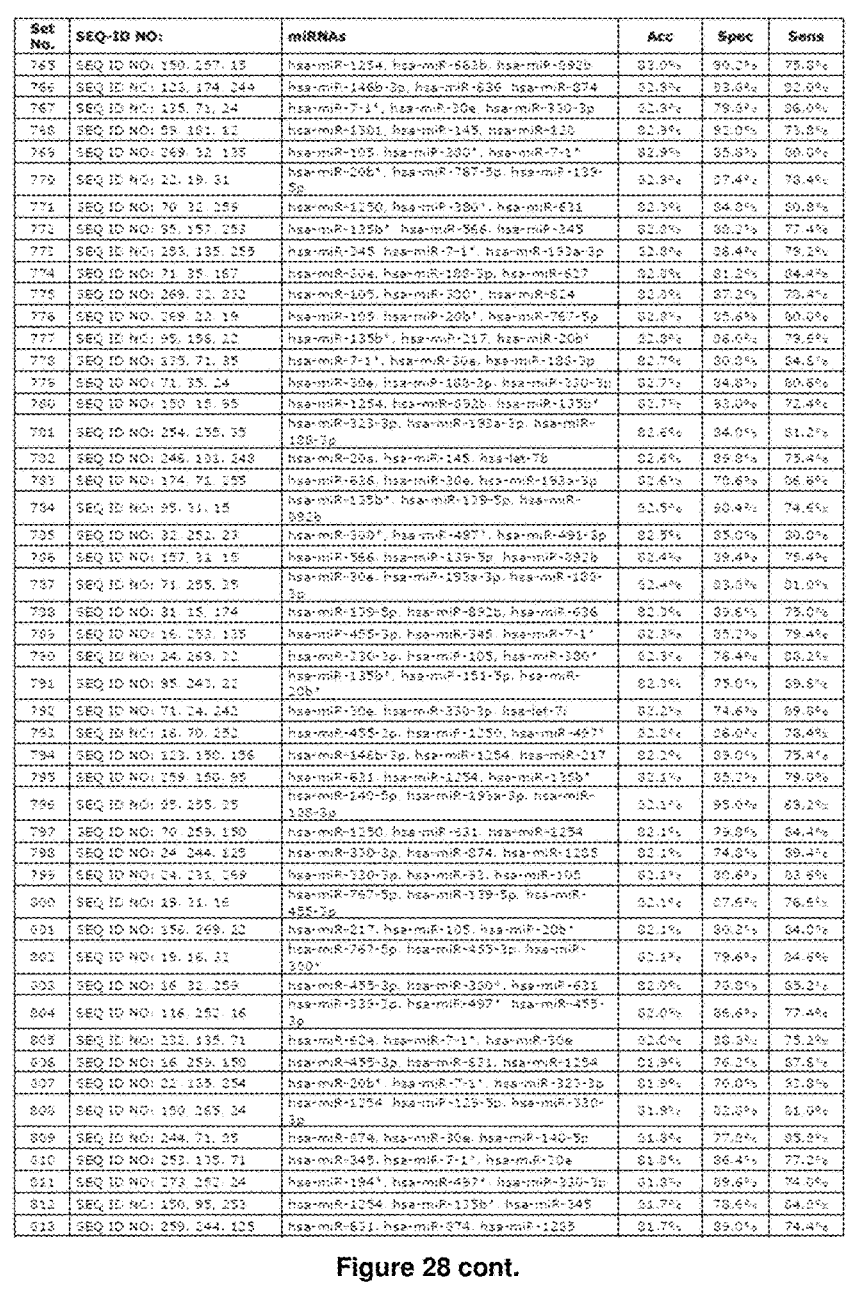

It is further preferred that the polynucleotides of the present invention are for detecting a set (signature) comprising, essentially consisting of, or consisting of at least two miRNAs for diagnosing and/or prognosing of an acute coronary syndrome, preferably myocardial infarction or Unstable angina (UA), in a blood sample from a human, particularly human patient, wherein the nucleotide sequences of said miRNAs are selected from one or more sets listed in FIG. 28 and/or FIG. 30. For example, the nucleotide sequences of said miRNAs may be selected from 1, 2, 3, 4, 5, 6, 7, 8, 9, 10 or more sets listed in FIG. 28 and/or FIG. 30. Thus, polynucleotides or individual sets of polynucleotides for detecting sets comprising at least two miRNAs may also be combined with each other, e.g. polynucleotides for detecting Set No. 1 with polynucleotides for detecting Set No. 2, polynucleotides for detecting Set No. 2 with polynucleotides for detecting Set No. 3, polynucleotides for detecting Set No. 1 with polynucleotides for detecting Set No. 2 and Set No. 3, polynucleotides for detecting Set No. 3 with polynucleotides for detecting Set No. 5 and Set No. 8, etc.

Furthermore, it is preferred that (i) the polynucleotide of the present invention is complementary to the miRNA, wherein the nucleotide sequence of said miRNA is selected from the group consisting of SEQ ID NO: 1 to SEQ ID NO: 283, or the polynucleotides comprised in the set of the present invention are complementary to the miRNAs comprised in the set, wherein the nucleotide sequences of said miRNAs are selected from the group consisting of SEQ ID NO: 1 to SEQ ID NO: 283, (ii) the polynucleotide is a fragment of the polynucleotide according to (i), preferably the polynucleotide is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the polynucleotide according to (i), or the polynucleotides comprised in the set are fragments of the polynucleotides comprised in the set according to (i), preferably the polynucleotides comprised in the set are fragments which are between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the polynucleotides comprised in the set according to (i), or (iii) the polynucleotide has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the polynucleotide sequence of the polynucleotide according to (i) or polynucleotide fragment according to (ii), or the polynucleotides comprised in the set have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the polynucleotide sequences of the polynucleotides comprised in the set according to (i) or polynucleotide fragments comprised in the set according to (ii), and It is more preferred that (i) the polynucleotide of the present invention is complementary to the miRNA, wherein the nucleotide sequence of said miRNA is selected from the group consisting of SEQ ID NO: 1 to SEQ ID NO: 153, or the polynucleotides comprised in the set of the present invention are complementary to the miRNAs comprised in the set, wherein the nucleotide sequences of said miRNAs are selected from the group consisting of SEQ ID NO: 1 to SEQ ID NO: 153, and preferably, wherein the nucleotide sequence of the at least one further miRNA is selected from the group consisting of SEQ ID NO: 154 to SEQ ID NO: 241, (ii) the polynucleotide is a fragment of the polynucleotide according to (i), preferably the polynucleotide is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the polynucleotide according to (i), or the polynucleotides comprised in the set are fragments of the polynucleotides comprised in the set according to (i), preferably the polynucleotides comprised in the set are fragments which are between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the polynucleotides comprised in the set according to (i), or (iii) the polynucleotide has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the polynucleotide sequence of the polynucleotide according to (i) or polynucleotide fragment according to (ii), or the polynucleotides comprised in the set have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the polynucleotide sequences of the polynucleotides comprised in the set according to (i) or polynucleotide fragments comprised in the set according to (ii).

It is particularly preferred that the polynucleotide as defined in (iii) has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the polynucleotide sequence of the polynucleotide according to (i) or polynucleotide fragment according to (ii), or that the polynucleotides comprised in the set as defined in (iii) have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the polynucleotide sequences of the polynucleotides comprised in the set according to (i) or polynucleotide fragments comprised in the set according to (ii).

In addition, the polynucleotide or polynucleotides as defined in (ii) (i.e. polynucleotide fragment(s)) or (iii) (i.e. polynucleotide variant(s) or polynucleotide fragment variant(s)) is (are) only regarded as a polynucleotide or polynucleotides as defined in (ii) (i.e. polynucleotide fragment(s)) or (iii) (i.e. polynucleotide variant(s) or polynucleotide fragment variant(s)) within the context of the present invention, if it is or they are still capable of binding to, hybridizing with, or detecting a target miRNA of complementary sequence or target miRNAs of complementary sequences, e.g. the respective target miRNA(s) according to SEQ ID NO: 1 to SEQ ID NO: 283, or particularly according to SEQ ID NO: 1 to SEQ ID NO: 241, through one or more types of chemical bonds, usually through complementary base pairing, usually through hydrogen bond formation under stringent hybridization conditions. The skilled person can readily assess whether a polynucleotide or polynucleotides as defined in (ii) (i.e. polynucleotide fragment(s)) or (iii) (i.e. polynucleotide variant(s) or polynucleotide fragment variant(s)) is (are) still capable of binding to, hybridizing with, recognizing or detecting a target miRNA of complementary sequence or target miRNAs of complementary sequences, e.g. the respective target miRNA(s) according to SEQ ID NO: 1 to SEQ ID NO: 283, or particularly according to SEQ ID NO: 1 to SEQ ID NO: 241. Suitable assays to determine whether hybridization under stringent conditions still occurs are well known in the art. However, as an example, a suitable assay to determine whether hybridization still occurs comprises the steps of: (a) incubating the polynucleotide or polynucleotides as defined in (ii) or (iii) attached onto a biochip with the miRNA(s) of complementary sequence(s), e.g. the respective target miRNA(s) according to SEQ ID NO: 1 to SEQ ID NO: 283, or particularly according to SEQ ID NO: 1 to SEQ ID NO: 241, labeled with biotin under stringent hybridization conditions, (b) washing the biochip to remove unspecific bindings, (c) subjecting the biochip to a detection system, and (c) analyzing whether the polynucleotide(s) can still hybridize with the target miRNA(s) of complementary sequence(s), e.g. the respective target miRNA(s) according to SEQ ID NO: 1 to SEQ ID NO: 283, or particularly according to SEQ ID NO: 1 to SEQ ID NO: 241. As a positive control, the respective non-mutated and not fragmented polynucleotide as defined in (i) may be used. Preferably stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 05×SSPE and 6×SSPE at 45° C.

In a preferred embodiment, the polynucleotide of the present invention is for detecting a nucleotide sequence of a miRNA selected from the group consisting of SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or selected from the group consisting of SEQ ID NO: 1 to SEQ ID NO: 10. It is particularly preferred that the polynucleotide is for detecting the nucleotide sequence of the miRNA of SEQ ID NO: 1 (hsa-miR-1291).

It another preferred embodiment, the polynucleotide of the present invention is for detecting a nucleotide sequence of a miRNA listed in FIG. 29.

In a second aspect, the present invention provides a method for diagnosing and/or prognosing of an acute coronary syndrome comprising the steps of:

(i) determining an expression profile of a miRNA or a set (signature) comprising, essentially consisting of, or consisting of at least two miRNAs representative for an acute coronary syndrome, preferably myocardial infarction or Unstable angina (UA), in a blood sample from a human, particularly human patient, wherein the nucleotide sequence of said miRNA or the nucleotide sequences of said miRNAs is (are) selected from the group consisting of SEQ ID NO: 1 to SEQ ID NO: 283, a fragment thereof, and a sequence having at least 80% sequence identity thereto, and (ii) comparing said expression profile to a reference, wherein the comparison of said expression profile to said reference allows for the diagnosis and/or prognosis of an acute coronary syndrome and/or applying an algorithm or a mathematical function to said expression profile, wherein the application of said algorithm or mathematical function to said expression profile allows for the diagnosis and/or prognosis of an acute coronary syndrome.

Preferably, the method for diagnosing and/or prognosing of an acute coronary syndrome comprises the steps of:

(i) determining an expression profile of a miRNA or a set (signature) comprising, essentially consisting of, or consisting of at least two miRNAs representative for an acute coronary syndrome, preferably myocardial infarction or Unstable angina (UA), in a blood sample from a human, particularly human patient, wherein the nucleotide sequence of said miRNA or the nucleotide sequences of said miRNAs is (are) selected from the group consisting of SEQ ID NO: 1 to SEQ ID NO: 153, a fragment thereof, and a sequence having at least 80% sequence identity thereto, and (ii) comparing said expression profile to a reference, wherein the comparison of said expression profile to said reference allows for the diagnosis and/or prognosis of an acute coronary syndrome and/or applying an algorithm or a mathematical function to said expression profile, wherein the application of said algorithm or mathematical function to said expression profile allows for the diagnosis and/or prognosis of an acute coronary syndrome.

The term "miRNA expression profile", as used herein, represents the expression level of a single miRNA or a collection of expression levels of at least two miRNAs comprised in a set (signature), preferably of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, or 283 miRNAs, wherein the nucleotide sequence of said miRNA or the nucleotide sequences of said miRNAs is (are) selected from the group consisting of SEQ ID NO: 1 to SEQ ID NO: 283.

(i) In a preferred embodiment, the term "miRNA expression profile", as used herein, represents the expression level of a single miRNA or a collection of expression levels of at least two miRNAs comprised in a set (signature), preferably of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, or 153 miRNAs, wherein the nucleotide sequence of said miRNA or the nucleotide sequences of said miRNAs is (are) selected from the group consisting of SEQ ID NO: 1 to SEQ ID NO: 153, and more preferably of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 223, 224, 225, 226, 227, 228, 229, 230, 231, 232, 233, 234, 235, 236, 237, 238, 239, 240, or 241 miRNAs, wherein the nucleotide sequences of said miRNAs are selected from the group consisting of SEQ ID NO: 1 to SEQ ID NO: 241.

According to the method of the present invention, the expression profile of a single miRNA or the expression profile of miRNAs comprised in a set is determined in a blood sample from a human. This is possible, as the miRNAs disclosed herein are expressed within and/or among cells or tissues and are subsequently released/transferred into circulating blood and/or as the miRNAs described herein are directly expressed in hemopoietic cells, also known as blood cells, e.g. erythrocytes, leukocytes and/or thrombocytes. Thus, the terms generating "an expression profile of miRNAs in a blood sample" by determining "miRNA expression levels in a blood sample" do not solely mean that said miRNAs are actually expressed in blood. Said terms refer to both miRNAs which are expressed in surrounding cells or tissues and are subsequently released into circulating blood and miRNAs which are directly expressed in blood, namely in blood cells, e.g. peripheral blood mononuclear cells (PBMCs). Accordingly, the expression levels of miRNAs determined in a blood sample indirectly represent the expression levels of that miRNAs in the cells or tissues from which they originate and/or directly represent the expression levels of miRNAs in blood cells.

Said miRNA expression profiles may be generated by any convenient means for determining a miRNA level, e.g. hybridization of miRNA, labeled miRNA, or amplified miRNA (e.g. to a microarray), quantitative PCR (qPCR) such as real time quantitative PCR (RT qPCR), ELISA for quantitation, next generation sequencing and the like and allow the analysis of differential miRNA expression levels between two blood samples, e.g. whole blood, serum, or plasma samples. Thus, for example, the differential miRNA level may be determined between a whole blood sample of a person having an acute coronary syndrome and a whole blood sample of a healthy person. The blood sample, e.g. whole blood, serum, or plasma sample, may be collected by any convenient method, as known in the art. Thereby, each miRNA is represented by a numerical value. The higher the value of an individual miRNA, the higher is the expression level of said miRNA. The miRNA expression profile may include expression data for 1, 2, 3, 4, 5, 7, 10, 15, 20, 25, 30, 35, 40, 50, 60, 70, 75, 100, or 153 miRNAs, preferably for 241 miRNAs, including miRNAs selected from the group consisting of SEQ ID NO: 1 to SEQ ID NO: 153 disclosed herein, preferably further including miRNAs selected from the group consisting of SEQ ID NO: 154 to SEQ ID NO: 241 disclosed herein.

The term "differential expression" of miRNA as used herein, means qualitative and/or quantitative differences in the temporal and/or cellular miRNA expression patterns within and/or among cells, tissues, or within blood. Thus, a differentially expressed miRNA may qualitatively have its expression altered, including an activation or inactivation in, for example, normal tissue versus disease tissue. The difference in miRNA expression may also be quantitative, e.g. in that expression is modulated, i.e. either up-regulated, resulting in an increased amount of miRNA, or down-regulated, resulting in a decreased amount of miRNA. The degree to which miRNA expression differs need only be large enough to be quantified via standard characterization techniques, e.g. quantitative hybridization of miRNA, labeled miRNA, or amplified miRNA, quantitative PCR (qPCR) such as real time quantitative PCR (RT qPCR), ELISA for quantitation, next generation sequencing and the like. As mentioned above, the expression profile of a single miRNA or the expression profile of miRNAs comprised in a set described herein is obtained from a blood sample, e.g. whole blood, blood serum, or blood plasma. This does not necessarily require that the miRNA is differentially expressed in blood. It can be differentially expressed in blood cells but it can also be expressed in surrounding cells or tissues and can be subsequently released/transferred into circulating blood or can be end up in blood by other mechanisms. Therefore, the differentially expression level of a miRNA determined in a blood sample represents a measure for diagnosing a clinical condition, e.g. an acute coronary syndrome.

The term "a single miRNA or a set comprising at least two miRNAs representative for an acute coronary syndrome", as used herein, refers to a fixed defined single miRNA which is known to be differential between human patients having an acute coronary syndrome (diseased state) and healthy humans (normal/control state) and, thus, representative for an acute coronary syndrome, or to at least two miRNAs comprised in a set which are known to be differential between human patients having an acute coronary syndrome (diseased state) and healthy humans (normal/control state) and, thus, representative for an acute coronary syndrome. The nucleotide sequence of said fixed defined single miRNA or the nucleotide sequences of said at least two fixed defined miRNAs comprised in the set is (are) selected from the group consisting of SEQ ID NO: 1 to SEQ ID NO: 283. In a preferred embodiment, the nucleotide sequence of said fixed defined single miRNA or the nucleotide sequences of said at least two fixed defined miRNAs comprised in the set is (are) selected from the group consisting of SEQ ID NO: 1 to SEQ ID NO: 153. The above-mentioned set may be supplemented by at least one further miRNA, wherein the nucleotide sequence of said miRNA is selected from group consisting of SEQ ID NO: 154 to SEQ ID NO: 241.

As already mentioned above, the inventors of the present invention analysed the expression level of miRNAs in blood samples of a cohort of controls (healthy persons) and patients suffering from an acute coronary syndrome. They succeeded in determining the miRNAs that are differentially regulated in blood samples from human patients having an acute coronary syndrome compared to healthy persons (controls) (see experimental section for details).

An overview of the 283 miRNAs (SEQ ID NO: 1 to SEQ ID NO: 283, particularly SEQ ID NO: 1 to SEQ ID NO: 241) that are found to be significantly differentially regulated in blood samples of acute coronary syndrome is provided in FIG. 7. Three groups are formed. The first group (group I) comprises miRNAs according to SEQ ID NO: 1 to SEQ ID NO: 153, the second group (group II) comprises miRNAs according to SEQ ID NO: 154 to SEQ ID NO: 241, and the third group (group II) comprises miRNAs according to SEQ ID NO: 242 to SEQ ID NO: 283. The miRNAs comprised in the first group and second group are sorted in order of their t-test significance as described in more detail in the experimental section (see ttest_adjp=adjusted p-value calculated according to ttest). The most predictive miRNAs in group I are listed first. It should be noted that the lower the ttest_adjp value of a single miRNA, the higher is the diagnostic power of said miRNA.

Thus, for analysis of a human blood sample in step (i) of the method of the present invention, an expression profile of a fixed defined single miRNA which is known to be differential between human patients having an acute coronary syndrome (diseased state) and healthy humans (normal/ control state) and, thus, representative for an acute coronary syndrome, or a set comprising at least two miRNAs which are known to be differential between human patients having an acute coronary syndrome (diseased state) and healthy humans (normal/control state) and, thus, representative for an acute coronary syndrome, is determined, wherein the nucleotide sequence of said miRNA or the nucleotide sequences of said miRNAs is (are) selected from the group consisting of SEQ ID NO: 1 to SEQ ID NO: 283. In preferred embodiments, the nucleotide sequence of said miRNA or the nucleotide sequences of said miRNAs is (are) selected from the group consisting of SEQ ID NO: 1 to SEQ ID NO: 153. In addition, for further analysis of said human blood sample in step (i) of the method of the present invention, at least one further miRNA which is known to be differential between human patients having an acute coronary syndrome (diseased state) and healthy humans (normal/control state) and, thus, also representative for an acute coronary syndrome, wherein the nucleotide sequence is selected from the group consisting of SEQ ID NO: 154 to SEQ ID NO: 241, may be added to the fixed defined set of at least two miRNAs, wherein the nucleotide sequences are selected from the group consisting of SEQ ID NO: 1 to SEQ ID NO: 153, and an expression profile may be determined from this supplemented set, for example, to improve the diagnostic accuracy, specificity and sensitivity in the determination of an acute coronary syndrome.

The inventors of the present invention have found that single miRNAs or sets of at least two miRNAs, wherein the nucleotide sequence of said miRNA or the nucleotide sequences of said miRNAs is (are) selected from the group consisting of SEQ ID NO: 1 to SEQ ID NO: 283, particularly of SEQ ID NO: 1 to SEQ ID NO: 153, provide high diagnostic accuracy, specificity and sensitivity in the determination of an acute coronary syndrome in human patients (see for example FIG. 3, FIG. 7, and FIG. 29 (t-test, limma-test, and AUC values) for single miRNAs and FIGS. 13 to 20, FIG. 28, and FIG. 30 for miRNA sets/signatures). The inventors of the present invention further found that the sets of at least two miRNAs, wherein the nucleotide sequence of said miRNA or nucleotide sequences of said miRNAs is (are) selected from the group consisting of SEQ ID NO: 1 to SEQ ID NO: 153, can be completed by at least one further miRNA, wherein the nucleotide sequence of said miRNA is selected from the group consisting of SEQ ID NO: 154 to SEQ ID NO: 241, preferably in order to improve the diagnostic accuracy, specificity and sensitivity in the determination of an acute coronary syndrome.

For human blood analysis, it may be required that a polynucleotide (probe) capable of detecting this fixed defined miRNA or polynucleotides (probes) capable of detecting these fixed defined miRNA set is (are) attached to a solid support, substrate, surface, platform, or matrix, e.g. biochip, which may be used for blood sample analysis. For example, if the fixed defined set of miRNAs for diagnosing an acute coronary syndrome may comprises or consists of 30 miRNAs, polynucleotides capable of detecting these 30 miRNAs may be attached to a solid support, substrate, surface, platform or matrix, e.g. biochip, in order to perform the diagnostic sample analysis.

As mentioned above, an expression profile of a miRNA or a set comprising, essentially consisting of, or consisting of at least two miRNAs representative for an acute coronary syndrome in a blood sample is determined in step (i) of the method of the present invention, wherein the nucleotide sequence of said miRNA or the nucleotide sequences of said miRNAs is (are) selected from the group consisting of SEQ ID NO: 1 to SEQ ID NO: 283. In preferred embodiments of the method of the present invention, the set comprises, essentially consists of, or consists of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282 miRNAs, or comprises/consists of 283 miRNAs, wherein the nucleotide sequences of said miRNAs are selected from the group consisting of SEQ ID NO: 1 to SEQ ID NO: 283.

In more preferred embodiments of the method of the present invention, an expression profile of a miRNA or a set comprising, essentially consisting of, or consisting of at least two miRNAs representative for an acute coronary syndrome in a blood sample is determined in step (i) of the method of the present invention, wherein the nucleotide sequence of said miRNA or the nucleotide sequences of said miRNAs is (are) selected from the group consisting of SEQ ID NO: 1 to SEQ ID NO: 153. In particularly more preferred embodiments of the method of the present invention, the set comprises, essentially consists of, or consists of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, or 152 miRNAs, or comprises/consists of 153 miRNAs, wherein the nucleotide sequences of said miRNAs are selected from the group consisting of SEQ ID NO: 1 to SEQ ID NO: 153.

Preferably, the nucleotide sequences of the at least 2 miRNAs comprised in the set have SEQ ID NO: 1 and SEQ ID NO: 2, the nucleotide sequences of the at least 3 miRNAs comprised in the set have SEQ ID NO: 1 to SEQ ID NO: 3, the nucleotide sequences of the at least 4 miRNAs comprised in the set have SEQ ID NO: 1 to SEQ ID NO: 4, the nucleotide sequences of the at least 5 miRNAs comprised in the set have SEQ ID NO: 1 to SEQ ID NO: 5, the nucleotide sequences of the at least 6 miRNAs comprised in the set have SEQ ID NO: 1 to SEQ ID NO: 6, the nucleotide sequences of the at least 7 miRNAs comprised in the set have SEQ ID NO: 1 to SEQ ID NO: 7, the nucleotide sequences of the at least 8 miRNAs comprised in the set have SEQ ID NO: 1 to SEQ ID NO: 8, the nucleotide sequences of the at least 9 miRNAs comprised in the set have SEQ ID NO: 1 to SEQ ID NO: 9, the nucleotide sequences of the at least 10 miRNAs comprised in the set have SEQ ID NO: 1 to SEQ ID NO: 10, the nucleotide sequences of the at least 11 miRNAs comprised in the set have SEQ ID NO: 1 to SEQ ID NO: 11, the nucleotide sequences of the at least 12 miRNAs comprised in the set have SEQ ID NO: 1 to SEQ ID NO: 12, the nucleotide sequences of the at least 13 miRNAs comprised in the set have SEQ ID NO: 1 to SEQ ID NO: 13, the nucleotide sequences of the at least 14 miRNAs comprised in the set have SEQ ID NO: 1 to SEQ ID NO: 14, the nucleotide sequences of the at least 15 miRNAs comprised in the set have SEQ ID NO: 1 to SEQ ID NO: 15, the nucleotide sequences of the at least 16 miRNAs comprised in the set have SEQ ID NO: 1 to SEQ ID NO: 16, the nucleotide sequences of the at least 17 miRNAs comprised in the set have SEQ ID NO: 1 to SEQ ID NO: 17, the nucleotide sequences of the at least 18 miRNAs comprised in the set have SEQ ID NO: 1 to SEQ ID NO: 18, the nucleotide sequences of the at least 19 miRNAs comprised in the set have SEQ ID NO: 1 to SEQ ID NO: 19, the nucleotide sequences of the at least 20 miRNAs comprised in the set have SEQ ID NO: 1 to SEQ ID NO: 20, the nucleotide sequences of the at least 21 miRNAs comprised in the set have SEQ ID NO: 1 to SEQ ID NO: 21, the nucleotide sequences of the at least 22 miRNAs comprised in the set have SEQ ID NO: 1 to SEQ ID NO: 22, the nucleotide sequences of the at least 23 miRNAs comprised in the set have SEQ ID NO: 1 to SEQ ID NO: 23, the nucleotide sequences of the at least 24 miRNAs comprised in the set have SEQ ID NO: 1 to SEQ ID NO: 24, the nucleotide sequences of the at least 25 miRNAs comprised in the set have SEQ ID NO: 1 to SEQ ID NO: 25, the nucleotide sequences of the at least 26 miRNAs comprised in the set have SEQ ID NO: 1 to SEQ ID NO: 26, the nucleotide sequences of the at least 27 miRNAs comprised in the set have SEQ ID NO: 1 to SEQ ID NO: 27, the nucleotide sequences of the at least 28 miRNAs comprised in the set have SEQ ID NO: 1 to SEQ ID NO: 28, the nucleotide sequences of the at least 29 miRNAs comprised in the set have SEQ ID NO: 1 to SEQ ID NO: 29, the nucleotide sequences of the at least 30 miRNAs comprised in the set have SEQ ID NO: 1 to SEQ ID NO: 30, the nucleotide sequences of the at least 31 miRNAs comprised in the set have SEQ ID NO: 1 to SEQ ID NO: 31, the nucleotide sequences of the at least 32 miRNAs comprised in the set have SEQ ID NO: 1 to SEQ ID NO: 32, the nucleotide sequences of the at least 33 miRNAs comprised in the set have SEQ ID NO: 1 to SEQ ID NO: 33, the nucleotide sequences of the at least 34 miRNAs comprised in the set have SEQ ID NO: 1 to SEQ ID NO: 34, the nucleotide sequences of the at least 35 miRNAs comprised in the set have SEQ ID NO: 1 to SEQ ID NO: 35, the nucleotide sequences of the at least 36 miRNAs comprised in the set have SEQ ID NO: 1 to SEQ ID NO: 36, the nucleotide sequences of the at least 37 miRNAs comprised in the set have SEQ ID NO: 1 to SEQ ID NO: 37, the nucleotide sequences of the at least 38 miRNAs comprised in the set have SEQ ID NO: 1 to SEQ ID NO: 38, the nucleotide sequences of the at least 39 miRNAs comprised in the set have SEQ ID NO: 1 to SEQ ID NO: 39, the nucleotide sequences of the at least 40 miRNAs comprised in the set have SEQ ID NO: 1 to SEQ ID NO: 40, the nucleotide sequences of the at least 41 miRNAs comprised in the set have SEQ ID NO: 1 to SEQ ID NO: 41, the nucleotide sequences of the at least 42 miRNAs comprised in the set have SEQ ID NO: 1 to SEQ ID NO: 42, the nucleotide sequences of the at least 43 miRNAs comprised in the set have SEQ ID NO: 1 to SEQ ID NO: 43, the nucleotide sequences of the at least 44 miRNAs comprised in the set have SEQ ID NO: 1 to SEQ ID NO: 44, the nucleotide sequences of the at least 45 miRNAs comprised in the set have SEQ ID NO: 1 to SEQ ID NO: 45, the nucleotide sequences of the at least 46 miRNAs comprised in the set have SEQ ID NO: 1 to SEQ ID NO: 46, the nucleotide sequences of the at least 47 miRNAs comprised in the set have SEQ ID NO: 1 to SEQ ID NO: 47, the nucleotide sequences of the at least 48 miRNAs comprised in the set have SEQ ID NO: 1 to SEQ ID NO: 48, the nucleotide sequences of the at least 49 miRNAs comprised in the set have SEQ ID NO: 1 to SEQ ID NO: 49, the nucleotide sequences of the at least 50 miRNAs comprised in the set have SEQ ID NO: 1 to SEQ ID NO: 50, the nucleotide sequences of the at least 51 miRNAs comprised in the set have SEQ ID NO: 1 to SEQ ID NO: 51, the nucleotide sequences of the at least 52 miRNAs comprised in the set have SEQ ID NO: 1 to SEQ ID NO: 52, the nucleotide sequences of the at least 53 miRNAs comprised in the set have SEQ ID NO: 1 to SEQ ID NO: 53, the nucleotide sequences of the at least 54 miRNAs comprised in the set have SEQ ID NO: 1 to SEQ ID NO: 54, the nucleotide sequences of the at least 55 miRNAs comprised in the set have SEQ ID NO: 1 to SEQ ID NO: 55, the nucleotide sequences of the at least 56 miRNAs comprised in the set have SEQ ID NO: 1 to SEQ ID NO: 56, the nucleotide sequences of the at least 57 miRNAs comprised in the set have SEQ ID NO: 1 to SEQ ID NO: 57, the nucleotide sequences of the at least 58 miRNAs comprised in the set have SEQ ID NO: 1 to SEQ ID NO: 58, the nucleotide sequences of the at least 59 miRNAs comprised in the set have SEQ ID NO: 1 to SEQ ID NO: 59, the nucleotide sequences of the at least 60 miRNAs comprised in the set have SEQ ID NO: 1 to SEQ ID NO: 60, the nucleotide sequences of the at least 61 miRNAs comprised in the set have SEQ ID NO: 1 to SEQ ID NO: 61, the nucleotide sequences of the at least 62 miRNAs comprised in the set have SEQ ID NO: 1 to SEQ ID NO: 62, the nucleotide sequences of the at least 63 miRNAs comprised in the set have SEQ ID NO: 1 to SEQ ID NO: 63, the nucleotide sequences of the at least 64 miRNAs comprised in the set have SEQ ID NO: 1 to SEQ ID NO: 64, the nucleotide sequences of the at least 65 miRNAs comprised in the set have SEQ ID NO: 1 to SEQ ID NO: 65, the nucleotide sequences of the at least 66 miRNAs comprised in the set have SEQ ID NO: 1 to SEQ ID NO: 66, the nucleotide sequences of the at least 67 miRNAs comprised in the set have SEQ ID NO: 1 to SEQ ID NO: 67, the nucleotide sequences of the at least 68 miRNAs comprised in the set have SEQ ID NO: 1 to SEQ ID NO: 68, the nucleotide sequences of the at least 69 miRNAs comprised in the set have SEQ ID NO: 1 to SEQ ID NO: 69, the nucleotide sequences of the at least 70 miRNAs comprised in the set have SEQ ID NO: 1 to SEQ ID NO: 70, the nucleotide sequences of the at least 71 miRNAs comprised in the set have SEQ ID NO: 1 to SEQ ID NO: 71, the nucleotide sequences of the at least 72 miRNAs comprised in the set have SEQ ID NO: 1 to SEQ ID NO: 72, the nucleotide sequences of the at least 73 miRNAs comprised in the set have SEQ ID NO: 1 to SEQ ID NO: 73, the nucleotide sequences of the at least 74 miRNAs comprised in the set have SEQ ID NO: 1 to SEQ ID NO: 74, the nucleotide sequences of the at least 75 miRNAs comprised in the set have SEQ ID NO: 1 to SEQ ID NO: 75, the nucleotide sequences of the at least 76 miRNAs comprised in the set have SEQ ID NO: 1 to SEQ ID NO: 76, the nucleotide sequences of the at least 77 miRNAs comprised in the set have SEQ ID NO: 1 to SEQ ID NO: 77, the nucleotide sequences of the at least 78 miRNAs comprised in the set have SEQ ID NO: 1 to SEQ ID NO: 78, the nucleotide sequences of the at least 79 miRNAs comprised in the set have SEQ ID NO: 1 to SEQ ID NO: 79, the nucleotide sequences of the at least 80 miRNAs comprised in the set have SEQ ID NO: 1 to SEQ ID NO: 80, the nucleotide sequences of the at least 81 miRNAs comprised in the set have SEQ ID NO: 1 to SEQ ID NO: 81, the nucleotide sequences of the at least 82 miRNAs comprised in the set have SEQ ID NO: 1 to SEQ ID NO: 82, the nucleotide sequences of the at least 83 miRNAs comprised in the set have SEQ ID NO: 1 to SEQ ID NO: 83, the nucleotide sequences of the at least 84 miRNAs comprised in the set have SEQ ID NO: 1 to SEQ ID NO: 84, the nucleotide sequences of the at least 85 miRNAs comprised in the set have SEQ ID NO: 1 to SEQ ID NO: 85, the nucleotide sequences of the at least 86 miRNAs comprised in the set have SEQ ID NO: 1 to SEQ ID NO: 86, the nucleotide sequences of the at least 87 miRNAs comprised in the set have SEQ ID NO: 1 to SEQ ID NO: 87, the nucleotide sequences of the at least 88 miRNAs comprised in the set have SEQ ID NO: 1 to SEQ ID NO: 88, the nucleotide sequences of the at least 89 miRNAs comprised in the set have SEQ ID NO: 1 to SEQ ID NO: 89, the nucleotide sequences of the at least 90 miRNAs comprised in the set have SEQ ID NO: 1 to SEQ ID NO: 90, the nucleotide sequences of the at least 91 miRNAs comprised in the set have SEQ ID NO: 1 to SEQ ID NO: 91, the nucleotide sequences of the at least 92 miRNAs comprised in the set have SEQ ID NO: 1 to SEQ ID NO: 92, the nucleotide sequences of the at least 93 miRNAs comprised in the set have SEQ ID NO: 1 to SEQ ID NO: 93, the nucleotide sequences of the at least 94 miRNAs comprised in the set have SEQ ID NO: 1 to SEQ ID NO: 94, the nucleotide sequences of the at least 95 miRNAs comprised in the set have SEQ ID NO: 1 to SEQ ID NO: 95, the nucleotide sequences of the at least 96 miRNAs comprised in the set have SEQ ID NO: 1 to SEQ ID NO: 96, the nucleotide sequences of the at least 97 miRNAs comprised in the set have SEQ ID NO: 1 to SEQ ID NO: 97, the nucleotide sequences of the at least 98 miRNAs comprised in the set have SEQ ID NO: 1 to SEQ ID NO: 98, the nucleotide sequences of the at least 99 miRNAs comprised in the set have SEQ ID NO: 1 to SEQ ID NO: 99, the nucleotide sequences of the at least 100 miRNAs comprised in the set have SEQ ID NO: 1 to SEQ ID NO: 100, the nucleotide sequences of the at least 101 miRNAs comprised in the set have SEQ ID NO: 1 to SEQ ID NO: 101, the nucleotide sequences of the at least 102 miRNAs comprised in the set have SEQ ID NO: 1 to SEQ ID NO: 102, the nucleotide sequences of the at least 103 miRNAs comprised in the set have SEQ ID NO: 1 to SEQ ID NO: 103, the nucleotide sequences of the at least 104 miRNAs comprised in the set have SEQ ID NO: 1 to SEQ ID NO: 104, the nucleotide sequences of the at least 105 miRNAs comprised in the set have SEQ ID NO: 1 to SEQ ID NO: 105, the nucleotide sequences of the at least 106 miRNAs comprised in the set have SEQ ID NO: 1 to SEQ ID NO: 106, the nucleotide sequences of the at least 107 miRNAs comprised in the set have SEQ ID NO: 1 to SEQ ID NO: 107, the nucleotide sequences of the at least 108 miRNAs comprised in the set have SEQ ID NO: 1 to SEQ ID NO: 108, the nucleotide sequences of the at least 109 miRNAs comprised in the set have SEQ ID NO: 1 to SEQ ID NO: 109, the nucleotide sequences of the at least 110 miRNAs comprised in the set have SEQ ID NO: 1 to SEQ ID NO: 110, the nucleotide sequences of the at least 111 miRNAs comprised in the set have SEQ ID NO: 1 to SEQ ID NO: 111, the nucleotide sequences of the at least 112 miRNAs comprised in the set have SEQ ID NO: 1 to SEQ ID NO: 112, the nucleotide sequences of the at least 113 miRNAs comprised in the set have SEQ ID NO: 1 to SEQ ID NO: 113, the nucleotide sequences of the at least 114 miRNAs comprised in the set have SEQ ID NO: 1 to SEQ ID NO: 114, the nucleotide sequences of the at least 115 miRNAs comprised in the set have SEQ ID NO: 1 to SEQ ID NO: 115, the nucleotide sequences of the at least 116 miRNAs comprised in the set have SEQ ID NO: 1 to SEQ ID NO: 116, the nucleotide sequences of the at least 117 miRNAs comprised in the set have SEQ ID NO: 1 to SEQ ID NO: 117, the nucleotide sequences of the at least 118 miRNAs comprised in the set have SEQ ID NO: 1 to SEQ ID NO: 118, the nucleotide sequences of the at least 119 miRNAs comprised in the set have SEQ ID NO: 1 to SEQ ID NO: 119, the nucleotide sequences of the at least 120 miRNAs comprised in the set have SEQ ID NO: 1 to SEQ ID NO: 120, the nucleotide sequences of the at least 121 miRNAs comprised in the set have SEQ ID NO: 1 to SEQ ID NO: 121, the nucleotide sequences of the at least 122 miRNAs comprised in the set have SEQ ID NO: 1 to SEQ ID NO: 122, the nucleotide sequences of the at least 123 miRNAs comprised in the set have SEQ ID NO: 1 to SEQ ID NO: 123, the nucleotide sequences of the at least 124 miRNAs comprised in the set have SEQ ID NO: 1 to SEQ ID NO: 124, the nucleotide sequences of the at least 125 miRNAs comprised in the set have SEQ ID NO: 1 to SEQ ID NO: 125, the nucleotide sequences of the at least 126 miRNAs comprised in the set have SEQ ID NO: 1 to SEQ ID NO: 126, the nucleotide sequences of the at least 127 miRNAs comprised in the set have SEQ ID NO: 1 to SEQ ID NO: 127, the nucleotide sequences of the at least 128 miRNAs comprised in the set have SEQ ID NO: 1 to SEQ ID NO: 128, the nucleotide sequences of the at least 129 miRNAs comprised in the set have SEQ ID NO: 1 to SEQ ID NO: 129, the nucleotide sequences of the at least 130 miRNAs comprised in the set have SEQ ID NO: 1 to SEQ ID NO: 130, the nucleotide sequences of the at least 131 miRNAs comprised in the set have SEQ ID NO: 1 to SEQ ID NO: 131, the nucleotide sequences of the at least 132 miRNAs comprised in the set have SEQ ID NO: 1 to SEQ ID NO: 132, the nucleotide sequences of the at least 133 miRNAs comprised in the set have SEQ ID NO: 1 to SEQ ID NO: 133, the nucleotide sequences of the at least 134 miRNAs comprised in the set have SEQ ID NO: 1 to SEQ ID NO: 134, the nucleotide sequences of the at least 135 miRNAs comprised in the set have SEQ ID NO: 1 to SEQ ID NO: 135, the nucleotide sequences of the at least 136 miRNAs comprised in the set have SEQ ID NO: 1 to SEQ ID NO: 136, the nucleotide sequences of the at least 137 miRNAs comprised in the set have SEQ ID NO: 1 to SEQ ID NO: 137, the nucleotide sequences of the at least 138 miRNAs comprised in the set have SEQ ID NO: 1 to SEQ ID NO: 138, the nucleotide sequences of the at least 139 miRNAs comprised in the set have SEQ ID NO: 1 to SEQ ID NO: 139, the nucleotide sequences of the at least 140 miRNAs comprised in the set have SEQ ID NO: 1 to SEQ ID NO: 140, the nucleotide sequences of the at least 141 miRNAs comprised in the set have SEQ ID NO: 1 to SEQ ID NO: 141, the nucleotide sequences of the at least 142 miRNAs comprised in the set have SEQ ID NO: 1 to SEQ ID NO: 142, the nucleotide sequences of the at least 143 miRNAs comprised in the set have SEQ ID NO: 1 to SEQ ID NO: 143, the nucleotide sequences of the at least 144 miRNAs comprised in the set have SEQ ID NO: 1 to SEQ ID NO: 144, the nucleotide sequences of the at least 145 miRNAs comprised in the set have SEQ ID NO: 1 to SEQ ID NO: 145, the nucleotide sequences of the at least 146 miRNAs comprised in the set have SEQ ID NO: 1 to SEQ ID NO: 146, the nucleotide sequences of the at least 147 miRNAs comprised in the set have SEQ ID NO: 1 to SEQ ID NO: 147, the nucleotide sequences of the at least 148 miRNAs comprised in the set have SEQ ID NO: 1 to SEQ ID NO: 148, the nucleotide sequences of the at least 149 miRNAs comprised in the set have SEQ ID NO: 1 to SEQ ID NO: 149, the nucleotide sequences of the at least 150 miRNAs comprised in the set have SEQ ID NO: 1 to SEQ ID NO: 150, the nucleotide sequences of the at least 151 miRNAs comprised in the set have SEQ ID NO: 1 to SEQ ID NO: 151, or the nucleotide sequences of the at least 152 miRNAs comprised in the set have SEQ ID NO: 1 to SEQ ID NO: 152, and more preferably, the nucleotide sequences of the 153 miRNAs comprised in the set have SEQ ID NO: 1 to SEQ ID NO: 153.

It is also preferred that the nucleotide sequences of the at least 2 miRNAs comprised in the set have SEQ ID NO: 1 and SEQ ID NO: 2, the nucleotide sequences of the at least 2 miRNAs comprised in the set have SEQ ID NO: 3 and SEQ ID NO: 4, the nucleotide sequences of the at least 3 miRNAs comprised in the set have SEQ ID NO: 5, SEQ ID NO: 6, and SEQ ID NO: 7, the nucleotide sequences of the at least 3 miRNAs comprised in the set have SEQ ID NO: 8, SEQ ID NO: 9, and SEQ ID NO: 10, the nucleotide sequences of the at least 3 miRNAs comprised in the set have SEQ ID NO: 11, SEQ ID NO: 12, and SEQ ID NO: 13, the nucleotide sequences of the at least 3 miRNAs comprised in the set have SEQ ID NO: 14, SEQ ID NO: 15, and SEQ ID NO: 16, the nucleotide sequences of the at least 4 miRNAs comprised in the set have SEQ ID NO: 17, SEQ ID NO: 18, SEQ ID NO: 19, and SEQ ID NO: 20, the nucleotide sequences of the at least 4 miRNAs comprised in the set have SEQ ID NO: 21, SEQ ID NO: 22, SEQ ID NO: 23, and SEQ ID NO: 24, the nucleotide sequences of the at least 6 miRNAs comprised in the set have SEQ ID NO: 25, SEQ ID NO: 26, SEQ ID NO: 27, SEQ ID NO: 28, SEQ ID NO: 29, and SEQ ID NO: 30, the nucleotide sequences of the at least 6 miRNAs comprised in the set have SEQ ID NO: 31, SEQ ID NO: 32, SEQ ID NO: 33, SEQ ID NO: 34, SEQ ID NO: 35, and SEQ ID NO: 36, the nucleotide sequences of the at least 6 miRNAs comprised in the set have SEQ ID NO: 37, SEQ ID NO: 38, SEQ ID NO: 39, SEQ ID NO: 40, SEQ ID NO: 41, and SEQ ID NO: 42, the nucleotide sequences of the at least 6 miRNAs comprised in the set have SEQ ID NO: 43, SEQ ID NO: 44, SEQ ID NO: 45, SEQ ID NO: 46, SEQ ID NO: 47, and SEQ ID NO: 48, the nucleotide sequences of the at least 6 miRNAs comprised in the set have SEQ ID NO: 49, SEQ ID NO: 50, SEQ ID NO. 51, SEQ ID NO: 52, SEQ ID NO: 53, and SEQ ID NO: 54, the nucleotide sequences of the at least 6 miRNAs comprised in the set have SEQ ID NO: 55, SEQ ID NO: 56, SEQ ID NO: 57, SEQ ID NO: 58, SEQ ID NO: 59, and SEQ ID NO: 60, the nucleotide sequences of the at least 6 miRNAs comprised in the set have SEQ ID NO: 61, SEQ ID NO: 62, SEQ ID NO: 63, SEQ ID NO: 64, SEQ ID NO. 65, and SEQ ID NO: 66, the nucleotide sequences of the at least 6 miRNAs comprised in the set have SEQ ID NO: 67, SEQ ID NO: 68, SEQ ID NO: 69, SEQ ID NO: 70, SEQ ID NO: 71, and SEQ ID NO: 72, the nucleotide sequences of the at least 6 miRNAs comprised in the set have SEQ ID NO: 73, SEQ ID NO: 74, SEQ ID NO: 75, SEQ ID NO: 76, SEQ ID NO: 77, and SEQ ID NO: 78, the nucleotide sequences of the at least 6 miRNAs comprised in the set have SEQ ID NO: 79, SEQ ID NO: 80, SEQ ID NO: 81, SEQ ID NO: 82, SEQ ID NO: 83, and SEQ ID NO: 84, the nucleotide sequences of the at least 6 miRNAs comprised in the set have SEQ ID NO: 85, SEQ ID NO: 86, SEQ ID NO: 87, SEQ ID NO: 88, SEQ ID NO: 89, and SEQ ID NO: 90, the nucleotide sequences of the at least 6 miRNAs comprised in the set have SEQ ID NO: 91, SEQ ID NO: 92, SEQ ID NO: 93, SEQ ID NO: 94, SEQ ID NO: 95, and SEQ ID NO: 96, the nucleotide sequences of the at least 6 miRNAs comprised in the set have SEQ ID NO: 97, SEQ ID NO: 98, SEQ ID NO: 99, SEQ ID NO: 100, SEQ ID NO: 101, and SEQ ID NO: 102, the nucleotide sequences of the at least 6 miRNAs comprised in the set have SEQ ID NO: 103, SEQ ID NO: 104, SEQ ID NO: 105, SEQ ID NO: 106, SEQ ID NO: 107, and SEQ ID NO: 108, the nucleotide sequences of the at least 6 miRNAs comprised in the set have SEQ ID NO: 109, SEQ ID NO: 110, SEQ ID NO: 111, SEQ ID NO: 112, SEQ ID NO: 113, and SEQ ID NO: 114, the nucleotide sequences of the at least 6 miRNAs comprised in the set have SEQ ID NO: 115, SEQ ID NO: 116, SEQ ID NO: 117, SEQ ID NO: 118, SEQ ID NO: 119, and SEQ ID NO: 120, the nucleotide sequences of the at least 6 miRNAs comprised in the set have SEQ ID NO: 121, SEQ ID NO: 122, SEQ ID NO: 123, SEQ ID NO: 124, SEQ ID NO: 125, and SEQ ID NO: 126, the nucleotide sequences of the at least 6 miRNAs comprised in the set have SEQ ID NO: 127, SEQ ID NO: 128, SEQ ID NO: 129, SEQ ID NO: 130, SEQ ID NO: 131, and SEQ ID NO: 132, the nucleotide sequences of the at least 6 miRNAs comprised in the set have SEQ ID NO: 133, SEQ ID NO: 134, SEQ ID NO: 135, SEQ ID NO: 136, SEQ ID NO: 137, and SEQ ID NO: 138, the nucleotide sequences of the at least 6 miRNAs comprised in the set have SEQ ID NO: 139, SEQ ID NO: 140, SEQ ID NO: 141, SEQ ID NO: 142, SEQ ID NO: 143, and SEQ ID NO: 144, the nucleotide sequences of the at least 5 miRNAs comprised in the set have SEQ ID NO: 145, SEQ ID NO: 146, SEQ ID NO: 147, SEQ ID NO: 148, and SEQ ID NO: 149, or the nucleotide sequences of the at least 4 miRNAs comprised in the set have SEQ ID NO: 150, SEQ ID NO: 151, SEQ ID NO: 152, and SEQ ID NO: 153.

In a preferred embodiment of the method of the present invention, an expression profile of a set comprising at least 10 miRNAs is determined in step (i), wherein the nucleotide sequences of the at least 10 miRNAs comprised in the set have SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or have SEQ ID NO: 1 to SEQ ID NO: 10.

It is also particularly preferred that (i) the nucleotide sequences of the at least 5 miRNAs comprised in the set have SEQ ID NO: 16, SEQ ID NO: 17, SEQ ID NO: 18, SEQ ID NO: 3 and SEQ ID NO: 2, (ii) the nucleotide sequences of the at least 5 miRNAs comprised in the set have SEQ ID NO: 1, SEQ ID NO: 5, SEQ ID NO: 20, SEQ ID NO: 21 and SEQ ID NO: 22, (iii) the nucleotide sequences of the at least 5 miRNAs comprised in the set have SEQ ID NO: 2, SEQ ID NO: 16, SEQ ID NO: 17, SEQ ID NO: 18 and SEQ ID NO: 24, (iv) the nucleotide sequences of the at least 5 miRNAs comprised in the set have SEQ ID NO: 1, SEQ ID NO: 34, SEQ ID NO: 30, SEQ ID NO: 22 and SEQ ID NO: 28, (v) that the nucleotide sequences of the at least 5 miRNAs comprised in the set have SEQ ID NO: 2, SEQ ID NO: 17, SEQ ID NO: 81, SEQ ID NO: 1 and SEQ ID NO: 34, (vi) that the nucleotide sequences of the at least 5 miRNAs comprised in the set have SEQ ID NO: 45, SEQ ID NO: 7, SEQ ID NO: 6, SEQ ID NO: 37 and SEQ ID NO: 90, or (vii) the nucleotide sequences of the at least 5 miRNAs comprised in the set have SEQ ID NO: 1, SEQ ID NO: 5, SEQ ID NO: 19, SEQ ID NO: 20 and SEQ ID NO: 21.

The above-mentioned sets may also be combined with each other, e.g. (i) with (ii), (ii) with (iii), (iii) with (iv), (iv) with (v), (v) with (vi), (vi) with (vii), etc.

Preferably, the set (signature) as defined above comprises at least one further miRNA, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 further miRNA(s), wherein the nucleotide sequence of said miRNA is selected from the group consisting of SEQ ID NO: 154 to SEQ ID NO: 241, a fragment thereof, and a sequence having at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity thereto. Accordingly, it is preferred that the set (signature) comprising, essentially consisting of, or consisting of at least two miRNAs representative for an acute coronary syndrome in a blood sample from a human, particularly human patient, wherein the nucleotide sequences of said miRNAs are selected from the group consisting of SEQ ID NO: 1 to SEQ ID NO: 153, comprises at least one further miRNA, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 further miRNA(s), wherein the nucleotide sequence of said miRNA is selected from the group consisting of SEQ ID NO: 154 to SEQ ID NO: 241, a fragment thereof, and a sequence having at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity thereto.

Thus, in a preferred embodiment of the method of the present invention, the set comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153 miRNAs, wherein the nucleotide sequences of said miRNAs are selected from the group consisting of SEQ ID NO: 1 to SEQ ID NO: 153, and comprises (i) at least one further miRNA having the nucleotide sequence according to SEQ ID NO: 154, (ii) at least 2 further miRNAs having the nucleotide sequence according to SEQ ID NO: 154 and SEQ ID NO: 155, (iii) at least 3 further miRNAs having the nucleotide sequence according to SEQ ID NO: 154 to SEQ ID NO: 156, (iv) at least 4 further miRNAs having the nucleotide sequences according to SEQ ID NO: 154 to SEQ ID NO: 157, (v) at least 5 further miRNAs having the nucleotide sequences according to SEQ ID NO: 154 to SEQ ID NO: 158, (vi) at least 6 further miRNAs having the nucleotide sequences according to SEQ ID NO: 154 to SEQ ID NO: 159, or (vii) at least 7 further miRNAs having the nucleotide sequences according to SEQ ID NO: 154 to SEQ ID NO: 160.

In another preferred embodiment of the method of the present invention, the set in step (i) comprises at least 10 miRNAs, wherein the nucleotide sequences of the at least 10 miRNAs comprised in the set have SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or have SEQ ID NO: 1 to SEQ ID NO: 10, and comprises (i) at least one further miRNA having the nucleotide sequence according to SEQ ID NO: 154, (ii) at least 2 further miRNAs having the nucleotide sequence according to SEQ ID NO: 154 and SEQ ID NO: 155, (iii) at least 3 further miRNAs having the nucleotide sequence according to SEQ ID NO: 154 to SEQ ID NO: 156, (iv) at least 4 further miRNAs having the nucleotide sequences according to SEQ ID NO: 154 to SEQ ID NO: 157, (v) at least 5 further miRNAs having the nucleotide sequences according to SEQ ID NO: 154 to SEQ ID NO: 158, (vi) at least 6 further miRNAs having the nucleotide sequences according to SEQ ID NO: 154 to SEQ ID NO: 159, or (vii) at least 7 further miRNAs having the nucleotide sequences according to SEQ ID NO: 154 to SEQ ID NO: 160.

It is also preferred that an expression profile of a miRNA or a set (signature) comprising, essentially consisting of, or consisting of at least two miRNAs representative for an acute coronary syndrome in a blood sample from a human, particularly human patient, is determined in the first step of the method of the present invention, wherein the nucleotide sequence of said miRNA or the nucleotide sequences of said miRNAs is (are) selected from SEQ ID NO: 242 to SEQ ID NO: 283.

It is further preferred that an expression profile of a set (signature) comprising, essentially consisting of, or consisting of at least two miRNAs representative for an acute coronary syndrome in a blood sample from a human, particularly human patient, is determined in the first step of the method of the present invention, wherein the nucleotide sequences of said miRNAs are selected from one or more sets listed in FIG. 28 and/or FIG. 30. For example, the nucleotide sequences of said miRNAs may be selected from 1, 2, 3, 4, 5, 6, 7, 8, 9, 10 or more sets listed in FIG. 28 and/or FIG. 30. Thus, the individual miRNA sets may also be combined with each other, e.g. miRNAs of Set No. 1 with miRNAs of Set No. 2, miRNAs of Set No. 2 with miRNAs of Set No. 3, miRNAs of Set No. 1 with miRNAs of Set No. 2 and Set No. 3, miRNAs of Set No. 3 with miRNAs of Set No. 5 and Set No. 8, etc.

As mentioned above, an expression profile of a miRNA or of a set (signature) comprising, essentially consisting of, or consisting of at least 2 miRNAs representative for an acute coronary syndrome in a blood sample from a human, particularly human patient, is determined in the first step of the method of the present invention, wherein the nucleotide sequence of said miRNA or the nucleotide sequences of said miRNAs is (are) selected from the group consisting of (i) a nucleotide sequence according to SEQ ID NO: 1 to SEQ ID NO: 283, a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

Further, as mentioned above, it is preferred that an expression profile of a miRNA or of a set (signature) comprising, essentially consisting of, or consisting of at least 2, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, or 152 miRNAs, or comprising/consisting of 153 miRNAs representative for an acute coronary syndrome in a blood sample, and more preferably comprising at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 further miRNA(s)) representative for an acute coronary syndrome in a blood sample, is determined in the first step of the method of the present invention, wherein the nucleotide sequence of said miRNA or the nucleotide sequences of said miRNAs is (are) selected from the group consisting of (i) a nucleotide sequence according to SEQ ID NO: 1 to SEQ ID NO: 153, (ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and (iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii), and wherein the nucleotide sequence of the at least one further miRNA comprised in the set is selected from the group consisting of (i) a nucleotide sequence according to SEQ ID NO: 154 to SEQ ID NO: 241, (ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and (iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

It is particularly preferred that the nucleotide sequence as defined in (iii) has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequence of the nucleotide according to (i) or nucleotide fragment according to (ii).

In addition, the nucleotide sequence as defined in (ii) (i.e. nucleotide sequence fragment) or (iii) (i.e. nucleotide sequence variant or nucleotide sequence fragment variant) is only regarded as a nucleotide sequence as defined in (ii) (i.e. nucleotide sequence fragment) or (iii) (i.e. nucleotide sequence variant or nucleotide sequence fragment variant) within the context of the present invention, if it can still be bound, hybridized, recognized, or detected by a polynucleotide (probe) of complementary sequence, e.g. a polynucleotide (probe) which is complementary to the respective nucleotide sequence as defined in (i), through one or more types of chemical bonds, usually through complementary base pairing, usually through hydrogen bond formation under stringent hybridization conditions. The skilled person can readily assess whether a nucleotide sequence as defined in (ii) (i.e. nucleotide sequence fragment) or (iii) (i.e. nucleotide sequence variant or nucleotide sequence fragment variant) can still be bound, hybridized, recognized, or detected by a polynucleotide (probe) of complementary sequence, e.g. a polynucleotide (probe) which is complementary to the respective nucleotide sequence as defined in (i). Suitable assays to determine whether hybridization under stringent conditions still occurs are well known in the art. However, as an example, a suitable assay to determine whether hybridization still occurs comprises the steps of: (a) incubating a nucleotide sequence as defined in (ii) or (iii) labelled with biotin with a polynucleotide (probe) of complementary sequence, e.g. a polynucleotide (probe) which is complementary to the respective nucleotide sequence as defined in (i), wherein the polynucleotide (probe) is attached onto a biochip, under stringent hybridization conditions, (b) washing the biochip to remove unspecific bindings, (c) subjecting the biochip to a detection system, and (c) analyzing whether the nucleotide sequence can still be hybridized or detected by a polynucleotide (probe) of complementary sequence, e.g. a polynucleotide (probe) which is complementary to the respective nucleotide sequence as defined in (i). As a positive control, the respective miRNA as defined in (i) may be used. Preferably stringent hybridization conditions include the following:

50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 05×SSPE and 6×SSPE at 45° C.

In preferred embodiments of the method of the present invention, an expression profile of a miRNA selected from the group consisting of SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or selected from the group consisting of SEQ ID NO: 1 to SEQ ID NO: 10 is determined in step (i). It a particularly preferred embodiment of the method of the present invention, the miRNAs of which the expression profile is determined has the SEQ ID NO: 1 (hsa-miR-1291).

In other preferred embodiments of the method of the present invention, an expression profile of a miRNA listed in FIG. 29 is determined in step (i).

It is preferred that in step (i) of the method of the present invention, a polynucleotide according to the present invention is used for determining an expression profile of a miRNA representative for an acute coronary syndrome in a blood sample from a human, particularly human patient, wherein the nucleotide sequence of said miRNA is selected from the group consisting of SEQ ID NO: 1 to SEQ ID NO: 283, particularly of SEQ ID NO: 1 to SEQ ID NO: 153. It is particularly preferred that the nucleotide sequence of said miRNA is selected from the list of FIG. 29.

Preferably, the polynucleotide according to the present invention is used for determining an expression profile of a miRNA representative for an acute coronary syndrome in a blood sample from a human, wherein the nucleotide sequence of said miRNA is selected from the group consisting of SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or selected from the group consisting of SEQ ID NO: 1 to SEQ ID NO: 10. It is particularly preferred that said polynucleotide used for determining an expression profile of a miRNA representative for an acute coronary syndrome in a blood sample from a human is complementary to the sequence of the miRNAs which are selected from the group consisting of SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or selected from the group consisting of SEQ ID NO: 1 to SEQ ID NO: 10. It is mostly preferred that the polynucleotide is in single stranded form and attached to a solid support, substrate, surface, platform or matrix, e.g. biochip, and is incubated with a miRNA of complementary sequence, wherein said miRNA is selected from the group consisting of SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or selected from the group consisting of SEQ ID NO: 1 to SEQ ID NO: 10, for determining an expression profile of said miRNA.

It is also preferred that in step (i) of the method of the present invention, a set comprising at least two polynucleotides according to the present invention is used for determining an expression profile of a set (signature) comprising at least two miRNAs representative for an acute coronary syndrome in a blood sample from a human, particularly human patient, wherein the nucleotide sequences of said miRNAs are selected from the group consisting of SEQ ID NO: 1 to SEQ ID NO: 283, particularly of SEQ ID NO: 1 to SEQ ID NO: 153. Preferably, the nucleotide sequences of said miRNAs are selected from one or more sets listed in FIG. 28 and/or FIG. 30.

It is particularly preferred that in step (i) of the method of the present invention, a set comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153 polynucleotides according to the present invention is used for determining an expression profile of a set (signature) comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153 miRNAs representative for an acute coronary syndrome in a blood sample from a human, particularly human patient, wherein the nucleotide sequences of said miRNAs are selected from the group consisting of SEQ ID NO: 1 to SEQ ID NO: 153; and wherein said preferred set of polynucleotides used in step (i) of the method of the present invention preferably comprises at least one further polynucleotide (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 polynucleotide(s)) according to the present invention for determining an expression profile of at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)) comprised in the above-mentioned set (signature) of miRNAs, wherein the nucleotide sequence of the at least one further miRNA is selected from the group consisting of SEQ ID NO: 154 to SEQ ID NO: 241.

It is further particularly preferred that in step (i) of the method of the present invention, a set comprising at least 10 polynucleotides according to the invention is used for determining an expression profile of a set comprising at least 10 miRNAs representative for an acute coronary syndrome in a blood sample from a human, wherein the nucleotide sequences of the at least 10 miRNAs comprised in the set have SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or have SEQ ID NO: 1 to SEQ ID NO: 10. It is also particularly preferred that the at least 10 polynucleotides according to the invention which are comprised in the set used for determining an expression profile of a set comprising at least 10 miRNAs representative for an acute coronary syndrome in a blood sample from a human are complementary to the sequences of said miRNAs, wherein the nucleotide sequences of the at least 10 miRNAs comprised in the set have SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or have SEQ ID NO: 1 to SEQ ID NO: 10. It is mostly preferred that the at least 10 polynucleotides according to the invention which are comprised in the set used for determining an expression profile of a set comprising at least 10 miRNAs representative for an acute coronary syndrome in a blood sample from a human are in single stranded form and attached to a solid surface, support, or matrix, e.g. biochip, and are incubated with said miRNAs of complementary sequence, wherein the nucleotide sequences of the at least 10 miRNAs comprised in the set have SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or have SEQ ID NO: 1 to SEQ ID NO: 10, for determining an expression profile of said miRNA.

In a preferred embodiment, the blood sample from a human is whole blood or a blood fraction such as serum or plasma. Blood cells also known as hemopoietic cells may also be used, e.g. erythrocytes, leukocytes and/or thrombocytes. Human blood samples may be collected by any convenient method, as known in the art. It is preferred that 0.1 to 20 ml blood, preferably 0.5 to 10 ml blood, i.e. 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20 ml blood, is collected. In another preferred embodiment, the blood sample is obtained from a human prior to initiation of therapeutic treatment, during therapeutic treatment and/or after therapeutic treatment. It is particularly preferred that total RNA or subfractions thereof including the miRNA is isolated, e.g. extracted, from the human blood sample in order to determine the expression profile of a miRNA or miRNAs comprised in the blood sample of a human.

The inventors of the present invention surprisingly found that miRNAs are not only present in a blood sample but also that miRNAs remain stable and that, thus, blood miRNAs can be used as biomarkers for detecting and/or prognosis of an acute coronary syndrome in humans. Furthermore, the inventors found that the miRNAs present in blood are different from the ones found in heart tissue of an individual suffering from an acute coronary syndrome. Therefore, the use of blood samples in the method of the present invention for detection and/or prognosis of an acute coronary syndrome has a number of advantage, for example, blood miRNAs have a high sensitivity, blood is relatively easy to obtain and even can be collected via routine physical examination, the costs for detection are low, and the samples can easily be preserved (e.g. at −20° C.). Further, blood circulates to all tissues in the body and, therefore, blood is able to reflect the physiological pathology of the whole organism and the detection of blood miRNAs results in an indicator of human health, and according to the present invention, as an indication whether a person suffers from an acute coronary syndrome. Furthermore, this method can widely be used in general survey of an acute coronary syndrome. Moreover, the inventors of the present invention surprisingly found that blood is an efficient mean for early diagnosis of an acute coronary syndrome. As novel disease markers, blood miRNAs improve the low-specificity and low-sensitivity caused by individual differences which other markers are difficult to overcome, and notable increase the clinical detection rate of an acute coronary syndrome so as to realize early diagnosis of an acute coronary syndrome.

Furthermore, according to the present invention, a first diagnosis of an acute coronary syndrome can be performed employing, as disclosed, miRNA-detection in blood, followed by a second diagnosis that is based on other methods (e.g. other biomarkers, miRNA-markers in heart tissue, and/or imaging methods).

As mentioned above, in step (i) of the method of the present invention, an expression profile of a miRNA or set comprising at least two miRNAs representative for an acute coronary syndrome in a blood sample from a human, particularly human patient, is determined. This determination may be carried out by any convenient means for determining the expression level of a nucleotide sequence such as miRNA. For expression profiling, qualitative, semi-quantitative and preferably quantitative detection methods can be used. A variety of techniques are well known to the person skilled in the art. It is preferred that an expression profile of the miRNA(s) representative for an acute coronary syndrome is determined by nucleic acid hybridization, nucleic acid amplification, polymerase extension, sequencing, mass spectroscopy, or any combination thereof.

Nucleic acid amplification may be performed using real time polymerase chain reaction (RT-PCR) such as real time quantitative PCR (RT qPCR). This technique is suitable for detecting the expression profile of single miRNAs. It is particularly suitable for detecting low abandoned miRNAs. The real time quantitative PCR (RT qPCR) allows the analysis of a single miRNA as well as a complex set of miRNAs comprised in a blood sample of a human, e.g. a single miRNA or a set comprising at least two miRNAs, wherein the nucleotide sequence of said miRNA or said miRNAs is (are) selected from the group consisting of SEQ ID NO: 1 to SEQ ID NO: 153 (e.g. a set of 153 miRNAs having SEQ ID NO: 1 to SEQ ID NO: 153), and wherein optionally the nucleotide sequence of at least one further miRNA is selected from the group consisting of SEQ ID NO: 154 to SEQ ID NO: 241 (e.g. set of 241 miRNAs having SEQ ID NO: 1 to SEQ ID NO: 241). The real time polymerase chain reaction (RT-PCR) such as real time quantitative PCR (RT qPCR) technique, however, is preferred for the analysis of single miRNAs or set comprising a low number of miRNAs (e.g. 2 to 50 miRNAs). It is particularly suitable for detecting low abandoned miRNAs.

The aforesaid real time polymerase chain reaction (RT-PCR) may include the following steps: (i) extracting the total RNA from the blood sample, e.g. whole blood, serum, or plasma, of a human with unknown clinical condition, e.g. healthy person or patient suffering from an acute coronary syndrome, and obtaining cDNA samples by RNA reverse transcription (RT) reaction using miRNA-specific primers; or collecting blood sample, e.g. whole blood, serum, or plasma, from a human and conducting reverse transcriptase reaction using miRNA-specific primers with blood, e.g. whole blood, serum, or plasma, being a puffer so as to prepare cDNA samples, (ii) designing miRNA-specific cDNA forward primers and providing universal reverse primers to amplify the cDNA via polymerase chain reaction (PCR), (iii) adding a fluorescent probe to conduct PCR, and (iv) detecting and comparing the variation in levels of miRNAs in the blood sample, e.g. whole blood, serum, or plasma, relative to those of miRNAs in normal (control) blood, e.g. whole blood, serum, or plasma, sample.

A variety of kits and protocols to determine an expression profile by real time polymerase chain reaction (RT-PCR) such as real time quantitative PCR (RT qPCR) are available. For example, reverse transcription of miRNAs may be performed using the TaqMan MicroRNA Reverse Transcription Kit (Applied Biosystems) according to manufacturer's recommendations. Briefly, miRNA may be combined with dNTPs, MultiScribe reverse transcriptase and the primer specific for the target miRNA. The resulting cDNA may be diluted and may be used for PCR reaction. The PCR may be performed according to the manufacturer's recommendation (Applied Biosystems). Briefly, cDNA may be combined with the TaqMan assay specific for the target miRNA and PCR reaction may be performed using ABI7300.

Furthermore, according to the present invention, the miRNA or the set comprising at least two miRNAs for diagnosing and/or prognosing of an acute coronary syndrome in a blood sample from a human, particularly human patient, may be established on one experimental platform (e.g. microarray), while for routine diagnosis/prognosis another experimental platform (e.g. qPCR) may be chosen.

Nucleic acid hybridization may be performed using a microarray/biochip, or in situ hybridization. The microarray/biochip allows the analysis of a single miRNA as well as a complex set of miRNAs comprised in a blood sample of a human, particularly human patient, e.g. a single miRNA or a set comprising at least two miRNAs, wherein the nucleotide sequence of said miRNA or said miRNAs is (are) selected from the group consisting of SEQ ID NO: 1 to SEQ ID NO: 153 (e.g. a set of 153 miRNAs having SEQ ID NO: 1 to SEQ ID NO: 153), and wherein optionally the nucleotide sequence of at least one further miRNA is selected from the group consisting of SEQ ID NO: 154 to SEQ ID NO: 241 (e.g. set of 241 miRNAs having SEQ ID NO: 1 to SEQ ID NO: 241). The microarray/biochip, however, is preferred for the analysis of complex sets of miRNAs (e.g. sets of 50, 100, 150, 200, or more miRNAs). For nucleic acid hybridization, for example, the polynucleotides (probes) according to the present invention with complementarity to the corresponding miRNA(s) to be detected are attached to a solid phase to generate a microarray/biochip (e.g. 153 polynucleotides (probes) which are complementary to the 153 miRNAs having SEQ ID NO: 1 to SEQ ID NO: 153 comprised in a set). Said microarray/biochip is then incubated with miRNAs, isolated (e.g. extracted) from the human blood sample, which may be labelled (FIGS. 8, 9), e.g. fluorescently labelled, pr unlabelled (FIGS. 10, 11). Upon hybridization of the labelled miRNAs to the complementary polynucleotide sequences on the microarray/biochip, the success of hybridisation may be controlled and the intensity of hybridization may be determined via the hybridisation signal of the label in order to determine the expression level of each tested miRNA in said blood probe. Examples of preferred hybridization assays are shown in FIGS. 8 to 11.

Thus, it is preferred that in step (i) of the method of the present invention, an expression profile of a set comprising at least two miRNAs representative for an acute coronary syndrome is determined by nucleic acid hybridization using a microarray/biochip which comprises a set comprising at least two polynucleotides (probes) that are complementary to the miRNAs, wherein the nucleotide sequences of said miRNAs are selected from the group consisting of SEQ ID NO: 1 to SEQ ID NO: 283.

(i) It is particularly preferred that in step (i) of the method of the present invention, an expression profile of a set comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153 miRNAs representative for an acute coronary syndrome is determined by nucleic acid hybridization using a microarray/biochip which comprises a set comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153 polynucleotides (probes) that are complementary to the miRNAs, wherein the nucleotide sequences of said miRNAs are selected from the group consisting of SEQ ID NO: 1 to SEQ ID NO: 153. Preferably, said biochip comprises the set of polynucleotides as mentioned above and comprises at least one further polynucleotide (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 polynucleotide(s)) according to the invention for determining an expression profile of at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)) comprised in the set of miRNAs, wherein the nucleotide sequence of the at least one further miRNA is selected from the group consisting of SEQ ID NO: 154 to SEQ ID NO: 241.

It is also particularly preferred that in step (i) of the method of the present invention, an expression profile of a set comprising at least 10 miRNAs representative for an acute coronary syndrome is determined by nucleic acid hybridization using a microarray/biochip which comprises a set comprising at least 10 polynucleotides (probes) that are complementary to the miRNAs, wherein the nucleotide sequences of the at least 10 miRNAs comprised in the set have SEQ ID NO: 16 (hsa-miR-455-3p), SEQ ID NO: 18 (hsa-miR-192*), SEQ ID NO: 2 (hsa-miR-1283), SEQ ID NO: 1 (hsa-miR-1291), SEQ ID NO: 19 (hsa-miR-767-5p), SEQ ID NO: 22 (hsa-miR-20b*), SEQ ID NO: 23 (hsa-miR-491-3p), SEQ ID NO: 29 (hsa-miR-33a), SEQ ID NO: 32 (hsa-miR-380*), and SEQ ID NO: 39 (hsa-miR-216a), or have SEQ ID NO: 1 to SEQ ID NO: 10. It is further particularly preferred that in step (i) of the method of the present invention, an expression profile of a set comprising at least 50 miRNAs representative for an acute coronary syndrome is determined by nucleic acid hybridization using a microarray/biochip which comprises a set comprising at least 50 polynucleotides (probes) that are complementary to the miRNAs, wherein the nucleotide sequences of the at least 50 miRNAs comprised in the set have SEQ ID NO: 1 to SEQ ID NO: 50. It is mostly preferred that in step (i) of the method of the present invention, an expression profile of a set comprising at least 80 miRNAs representative for an acute coronary syndrome is determined by nucleic acid hybridization using a microarray/biochip which comprises a set comprising at least 80 polynucleotides (probes) that are complementary to the miRNAs, wherein the nucleotide sequences of the at least 80 miRNAs comprised in the set have SEQ ID NO: 1 to SEQ ID NO: 80. It is also mostly preferred that in step (i) of the method of the present invention, an expression profile of a set comprising at least 100 miRNAs representative for an acute coronary syndrome is determined by nucleic acid hybridization using a microarray/biochip which comprises a set comprising at least 100 polynucleotides (probes) that are complementary to the miRNAs, wherein the nucleotide sequences of the at least 100 miRNAs comprised in the set have SEQ ID NO: 1 to SEQ ID NO: 100.

As already mentioned above, the method of the present invention may comprise, as a first alternative, the following second step:

(ii) comparing said expression profile to a reference, wherein the comparison of said expression profile to said reference allows for the diagnosis and/or prognosis of an acute coronary syndrome.

Thus, subsequent to the determination of an expression profile of a miRNA as defined above or a set comprising at least two miRNAs as defined above in a blood sample from a human, particularly human patient, (step (i)), the method of the present invention further comprises the step of comparing said expression profile to a reference, wherein the comparison of said expression profile to said reference allows for the diagnosis and/or prognosis of an acute coronary syndrome (step (ii)).

The human, particularly human patient, to be diagnosed with the method of the present invention for an acute coronary syndrome (e.g. myocardial infarction such as non-ST segment elevation myocardial infraction or ST segment elevation myocardial infarction, or Unstable angina (UA)) may be a healthy or may be diseased, e.g. suffer from an acute coronary syndrome (e.g. myocardial infarction or Unstable angina (UA)) or suffer from another disease not tested/known. The human to be diagnosed with the method of the present invention may suffer from a specific type of myocardial infarction, namely from non-ST segment elevation myocardial infraction (NSTEMI), or from ST segment elevation myocardial infarction (STEMI). It is also possible to determine, whether the human to be diagnosed will develop the above-mentioned syndrome as the inventors of the present invention surprisingly found that miRNAs representative for an acute coronary syndrome are already present in the blood before an acute coronary syndrome occurs or during the early stage of myocardial injury.

The reference may be any reference which allows for the diagnosis and/or prognosis of an acute coronary syndrome, e.g. indicated reference data or value(s).

The reference may be the reference expression profile of the same single miRNA or set of miRNAs selected in step (i) in a blood sample, preferably originated from the same source (e.g. serum, plasma, or blood cells) as the blood sample from the human, particularly human patient, to be tested, but obtained from a person known to be healthy. The reference may also be the reference expression profile of the same single miRNA or set of miRNAs selected in step (i) in a blood sample, preferably originated from the same source as the blood sample from the human, particularly human patient, to be tested, but obtained from a patient known to suffer from an acute coronary syndrome (e.g. myocardial infarction such as non-ST segment elevation myocardial infraction or ST segment elevation myocardial infarction, or Unstable angina (UA), or the like). Further, the reference may be the reference profiles of the same single miRNA or set of miRNAs selected in step (i) in a blood sample, preferably originated from the same source as the blood sample from the human, particularly human patient, to be tested, but obtained from a person known to be healthy and from a patient known to suffer from an acute coronary syndrome (e.g. myocardial infarction such as non-ST segment elevation myocardial infarction or ST segment elevation myocardial infarction, or Unstable angina (UA), or the like).

As to the single miRNA or set of miRNAs, that means in other words that the reference expression profile is the profile of a single miRNA that has a nucleotide sequence that corresponds (is identical) to the nucleotide sequence selected in step (i) or is the profile of a set comprising at least two miRNAs that have nucleotide sequences that correspond (are identical) to the nucleotide sequences in step (i) but obtained from a healthy person or patient known to suffer from an acute coronary syndrome (e.g. myocardial infarction such as non-ST segment elevation myocardial infraction or ST segment elevation myocardial infarction, or Unstable angina (UA)).

Preferably, both the reference expression profile of the reference and the expression profile of the above step (i) are determined in a blood serum sample, blood plasma sample or in a sample of blood cells (e.g. erythrocytes, leukocytes and/or thrombocytes). It is understood that the reference expression profile of the reference is not necessarily obtained from a single person (e.g. healthy or diseased person) but may be an average expression profile of a plurality of persons (e.g. healthy or diseased persons), preferably 2 to 40 persons, more preferably 10 to 25 persons, and most preferably 15 to 20 persons, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 persons. Preferably, the reference expression profile of the reference is obtained from a person of the same gender (e.g. female or male) and/or of a similar age/phase of life (e.g. infant, young children, juvenile, or adult) as the person to be tested or diagnosed.

The comparison of the expression profile of the human to be diagnosed to said reference, e.g. reference expression profile of at least one human, preferably 10 to 40 humans, more preferably 15 to 25 humans, known to be healthy, then allows for the diagnosis and/or prognosis of an acute coronary syndrome (step (ii)). For example, if two selected miRNAs in the expression profile of a human to be diagnosed for an acute coronary syndrome are down-regulated and if the two selected miRNAs in the reference expression profile of a person known to suffer from an acute coronary syndrome are up-regulated, the person tested is healthy, i.e. the person does not suffer from an acute coronary syndrome. In the converse case, if two selected miRNAs in the expression profile of a human to be diagnosed for an acute coronary syndrome are up-regulated and if the two selected miRNAs in the reference expression profile of a person known to suffer from an acute coronary syndrome are also up-regulated, particularly with the same level, the person tested is diseased, i.e. the person suffers from an acute coronary syndrome. It should be noted that a person that is diagnosed as being healthy, i.e. not suffering from an acute coronary syndrome, may possibly suffer from another disease not tested/known.

In preferred embodiments of the method of the present invention, the reference is obtained from a reference expression profile of at least one person, particularly human, preferably 2 to 40 persons, particularly humans, more preferably 10 to 25 persons, particularly humans, and most preferably 15 to 20 persons, particularly humans, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 persons, particularly humans, known to be healthy or diseased (i.e. suffering from an acute coronary syndrome (e.g. myocardial infarction such as non-ST segment elevation myocardial infraction or ST segment elevation myocardial infarction, or Unstable angina (UA)), wherein the reference expression profile is the profile of a single miRNA that has a nucleotide sequence that corresponds (is identical) to the nucleotide sequence selected in step (i) (e.g. miRNA according to SEQ ID NO: 1) or is the profile of a set comprising at least two miRNAs that have nucleotide sequences that correspond (are identical) to the nucleotide sequence selected in step (i) (e.g. miRNAs according to SEQ ID NO: 1 to SEQ ID NO: 10) of the method of the present invention.

More preferably, the reference is obtained from reference expression profiles of at least two humans, preferably 3 to 40 humans, more preferably 10 to 25 humans, and most preferably 15 to 20 humans, e.g. 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 humans, with at least two known clinical conditions, preferably 2 to 5, more preferably 2 or 3, from which at least one, e.g. 1, 2, 3, or 4, is an acute coronary syndrome (e.g. myocardial infarction such as non-ST segment elevation myocardial infraction or ST segment elevation myocardial infarction, or Unstable angina (UA)), wherein the reference expression profiles are the profiles of a single miRNA that has a nucleotide sequence that corresponds to the nucleotide sequence selected in step (i) or are the profiles of a set comprising at least two miRNAs that have nucleotide sequences that correspond to the nucleotide sequences selected in step (i).

The term "(clinical) condition" (biological state or health state) means a status of a subject that can be described by physical, mental or social criteria. It includes as well so-called "healthy" and "diseased" conditions. For the definition of called "healthy" and "diseased" conditions it is referred to the international classification of diseases (ICD) of the WHO. When two or more conditions are compared according to a preferred embodiment of the method of the present invention, it is understood that this is possible for all conditions that can be defined and is not limited to a comparison of a diseased versus healthy comparison and extends to multiway comparison, under the condition that at least one condition is an acute coronary syndrome, e.g. myocardial infarction such as non-ST segment elevation myocardial infraction or ST segment elevation myocardial infarction, or Unstable angina. (UA).

Examples of comparison are, but are not limited to:

Diagnosis/Prognosis within acute coronary syndromes encompass for example
  Unstable angina pectoris versus healthy control,
  acute myocardial infarction versus healthy control,
  Unstable angina pectoris versus acute myocardial infarction, or
  non-ST segment elevation myocardial infraction (NSTEMI) versus ST segment elevation myocardial infarction (STEMI).

Diagnosis/Prognosis of acute coronary syndrome versus other heart diseases, for example
  Acute myocardial infarction versus heart failure,
  Acute myocardial infarction versus cardiomyopathy,
  Acute myocardial infarction versus coronary heart disease, or
  unstable angina pectoris versus stable angina pectoris.

Diagnosis/Prognosis of acute coronary syndrome versus other diseases, for example,
Acute myocardial infarction versus cardiovascular disease,
acute coronary syndrome versus lung cancer,
acute coronary syndromes versus arteriosclerosis, or
acute coronary syndromes versus multiple sclerosis.

Thus, for example, the reference may be obtained from reference expression profiles of at least two humans, one human suffering from an acute coronary syndrome and one being healthy, i.e. not suffering from an acute coronary syndrome, wherein the reference expression profiles are the profiles of a single miRNA that has a nucleotide sequence that corresponds to the nucleotide sequence selected in step (i) or are the profiles of a set comprising at least two miRNAs that have nucleotide sequences that correspond to the nucleotide sequences selected in step (i). The comparison of the expression profile of the human to be diagnosed to said reference, may then allow for the diagnosis and/or prognosis of an acute coronary syndrome (step (ii)), either the human to be diagnosed is healthy, i.e. not suffering from an acute coronary syndrome, or diseased, i.e. suffering from an acute coronary syndrome.

The reference may also be obtained from reference expression profiles of at least two humans, one human suffering from myocardial infarction, e.g. non-ST segment elevation myocardial infraction or ST segment elevation myocardial infarction, and one suffering from Unstable angina (UA), wherein the reference expression profiles are the profiles of a single miRNA that has a nucleotide sequence that corresponds to the nucleotide sequence selected in step (i) or are the profiles of a set comprising at least two miRNAs that have nucleotide sequences that correspond to the nucleotide sequences selected in step (i). The comparison of the expression profile of the human to be diagnosed to said reference, may then allow whether the human to be diagnosed suffers from myocardial infarction or Unstable angina (UA).

The reference may also be obtained from reference expression profiles of at least three humans, one human suffering from an acute coronary syndrome, one suffering from cardiomyopathy, and one being healthy, wherein the reference expression profiles are the profiles of a single miRNA that has a nucleotide sequence that corresponds to the nucleotide sequence selected in step (i) or are the profiles of a set comprising at least two miRNAs that have nucleotide sequences that correspond to the nucleotide sequences selected in step (i). The comparison of the expression profile of the human to be diagnosed to said reference, may also allow to decide whether the human suffers from an acute coronary syndrome.

It is understood that the reference expression profiles of the reference are not necessarily obtained from a single human (e.g. healthy or diseased human) but may be average expression profiles of a plurality of humans (e.g. healthy or diseased humans), preferably 2 to 40 persons, more preferably 10 to 25 persons, and most preferably 15 to 20 persons, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 persons. Preferably, the reference expression profiles of the reference are obtained from a person of the same gender (e.g. female or male) and/or of a similar age/phase of life (e.g. infant, young children, juvenile, or adult) as the person to be tested or diagnosed.

Preferably, the reference is obtained from reference profiles of the same number of humans. For example, the reference may be obtained from reference profiles of 10 humans being healthy and 10 humans suffering from an acute coronary syndrome. The reference may be also obtained from reference profiles of 20 humans being healthy, 20 humans suffering from an acute coronary syndrome and 20 humans suffering from cardiomyopathy.

The inventors of the present invention surprisingly found that the application of a machine learning approach (e.g. t-test, AUC, support vector machine, hierarchical clustering, or k-means) allows a better discrimination between two (or more) clinical conditions, e.g. healthy and suffering from an acute coronary syndrome, for a defined set of miRNA biomarkers. The application of this approach namely leads to an algorithm that is trained by reference data (i.e. data of reference miRNA expression profiles from the two clinical conditions, e.g. healthy and suffering from an acute coronary syndrome, for the defined set of miRNA markers) to discriminate between the two (or more) statistical classes (i.e. two clinical conditions, e.g. healthy or suffering from an acute coronary syndrome). In this way, the performance for diagnosing/prognosing of individuals suffering from an acute coronary syndrome can be increased (see also experimental section for details).

Thus, most preferably, the comparison to the reference comprises the application of an algorithm or mathematical function. It is preferred that the algorithm or mathematical function is obtained using a machine learning approach. Machine learning approaches, may include but are not restricted to supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

For example, the machine learning approach may be applied to the reference expression profile data of a set comprising at least 2 miRNAs (e.g. 10 miRNAs such as miRNAs according to SEQ ID NO: 1 to 10) of a human known to suffer from an acute coronary syndrome and of a human known to be healthy and may led to the obtainment of a algorithm or mathematical function. This algorithm or mathematical function may then be applied to a miRNA expression profile of the same at least 2 miRNAs as mentioned above (e.g. 10 miRNAs such as miRNAs according to SEQ ID NO: 1 to 10) of a human to be diagnosed for an acute coronary syndrome and, thus, may then allow to discriminate whether the human to be tested is healthy, i.e. not suffering from an acute coronary syndrome, or diseased, i.e. suffering from an acute coronary syndrome.

In another preferred embodiment of the method of the present invention, the reference is a reference expression profile (data) of at least one subject, preferably the reference is an average expression profile (data) of at least 2 to 40 subjects, more preferably of at least 10 to 25 subjects, and most preferably of at least 15 to 20 subjects, e.g. of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with one known clinical condition which is an acute coronary syndrome, or which is no acute coronary syndrome (i.e. healthy/healthiness), wherein the reference expression profile is the profile of a (single) miRNA that has a nucleotide sequence that essentially corresponds (is essentially identical), preferably that corresponds (is identical), to the nucleotide sequence of the miRNA of step (i) or is the profile of a set comprising at least two miRNAs that have nucleotide sequences that essentially correspond (are essentially identical), preferably that correspond (are identical), to the nucleotide sequences of the miRNAs of step (i). It should be noted that said subject(s) is (are) human(s). Said subject(s) may also be designated as control subject(s).

For example, said reference may be a reference expression profile of at least one subject known to be not affected by an acute coronary syndrome (i.e. healthy) or known to be affected by an acute coronary syndrome (i.e. diseased), wherein the reference expression profile is the profile of a single miRNA that has a nucleotide sequence that essentially corresponds (is essentially identical), preferably that corresponds (is identical), to the nucleotide sequence of the miRNA of step (i) or is the profile of a set comprising at least two miRNAs that have nucleotide sequences that essentially correspond (are essentially identical), preferably that correspond (are identical), to the nucleotide sequences of the miRNAs of step (i).

The terms "essentially correspond(s)" or "essentially identical", as used in this aspect of the present invention, mean that the miRNA(s) of step (i) and the miRNA(s) of the reference expression profile may slightly differ in their nucleotide sequence, whereas said difference is so marginal that it may still allow for the diagnosis and/or prognosis of an acute coronary syndrome. Preferably, the nucleotide sequence(s) of the miRNA(s) of step (i) and the nucleotide sequence(s) of the miRNA(s) of the reference expression profile differ in 1 to 5, more preferably in 1 to 3, and most preferably in 1 to 2 nucleotides, i.e. in 1, 2, 3, 4, or 5 nucleotides. It is preferred that said difference resides in 1 to 5, more preferably 1 to 3, and most preferably 1 to 2 nucleotide mutations, i.e. 1, 2, 3, 4, or 5 nucleotide mutations (e.g. substitutions, additions, insertions, and/or deletions). This is caused by the fact that the miRNAs within the human species may differ. It is preferred that the miRNA(s) of step (i) and the miRNA(s) of the reference expression profile do not differ in their nucleotide sequence, i.e. are identical. It is particularly preferred that the miRNA(s) of step (i) and the miRNA(s) of the reference expression profile are derived from subject/patients of the same gender (e.g.

female or male) and/or similar age/phase of life (e.g. infant, young children, juvenile, or adult).

The comparison of the expression profile of the human, particularly human patient, to be diagnosed and/or prognosed to the (average) reference expression profile (data), may then allow for diagnosing and/or prognosing of an acute coronary syndrome (step (ii)).

Considering the above, diagnosing preferably means comparing the expression profile (data) of a human, particularly human patient, determined in step (i) to the (average) reference expression profile (data) as mentioned above to decide, if the at least one known clinical condition, which is an acute coronary syndrome, or which is no acute coronary syndrome (i.e. healthy), is present in said human, particularly human patient. Prognosing preferably means comparing the expression profile (data) of a human, particularly human patient, determined in step (i) to the (average) reference expression profile (data) as mentioned above to decide, if the at least one known clinical condition, which is an acute coronary syndrome, or which is no acute coronary syndrome (i.e. healthy), will likely be present in said human, particularly human patient.

For example, the human, particularly human patient, may be diagnosed as not suffering from an acute coronary syndrome (i.e. being healthy), or as suffering from an acute coronary syndrome (i.e. being diseased). Further, for example, the human, particularly human patient, may be prognosed as not developing an acute coronary syndrome (i.e. staying healthy), or as developing an acute coronary syndrome (i.e. getting diseased).

Diagnosing/prognosing of an acute coronary syndrome based on (a) reference expression profile (data) as reference may take place as follows: For instance, (i) if the miRNA(s) of step (i) (e.g. a single miRNA or a set of at least 2 miRNAs) in the expression profile of a human, particularly human patient, to be diagnosed for an acute coronary syndrome is (are), for example, at least 2 fold higher (up-regulated) compared to said miRNA(s) (e.g. a single miRNA or a set of at least 2 miRNAs) in the reference expression profile of a human subject known not to suffer from an acute coronary syndrome (i.e. being healthy), the human, particularly human patient, tested is diagnosed as suffering from an acute coronary syndrome (i.e. being diseased) or prognosed as likely developing an acute coronary syndrome (i.e. getting diseased), or (ii) if the miRNA(s) of step (i) (e.g. a single miRNA or a set of 2 miRNAs) in the expression profile of a human, particularly human patient, to be diagnosed for an acute coronary syndrome is (are), for example, at least 2 fold lower (down-regulated) compared to said miRNA(s) (e.g. a single miRNA or a set of at least 2 miRNAs) in the reference expression profile of a human subject known not to suffer from an acute coronary syndrome (i.e. being healthy), the human, particularly human patient, tested is diagnosed as suffering from an acute coronary syndrome (i.e. being diseased) or prognosed as likely developing an acute coronary syndrome (i.e. getting diseased).

In the converse case, (i) if the miRNA(s) of step (i) (e.g. a single miRNA or a set of at least 2 miRNAs) in the expression profile of a human, particularly human patient, to be diagnosed for an acute coronary syndrome is (are), for example, not at least 2 fold higher (up-regulated) compared to said miRNA(s) (e.g. a single miRNA or a set of at least 2 miRNAs) in the reference expression profile of a human subject known not to suffer from an acute coronary syndrome (i.e. being healthy), the human, particularly human patient, tested is diagnosed as not suffering from an acute coronary syndrome (i.e. being healthy) or prognosed as likely not developing an acute coronary syndrome (i.e. staying healthy), or (ii) if the miRNA(s) of step (i) (e.g. a single miRNA or a set of 2 miRNAs) in the expression profile of a human, particularly human patient, to be diagnosed for an acute coronary syndrome is (are), for example, not at least 2 fold lower (down-regulated) compared to said miRNA(s) (e.g. a single miRNA or a set of at least 2 miRNAs) in the reference expression profile of a human subject known not to suffer from an acute coronary syndrome (i.e. being healthy), the human, particularly human patient, tested is diagnosed as not suffering from an acute coronary syndrome (i.e. being healthy) or prognosed as likely not developing an acute coronary syndrome (i.e. staying healthy).

It should be noted that a human, particularly human patient, that is diagnosed as being healthy, i.e. not suffering from an acute coronary syndrome, may possibly suffer from another disease not tested/known, or a human, particularly human patient, that is prognosed as staying healthy, i.e. as likely not developing an acute coronary syndrome, may possibly developing another disease not tested/known.

As already mentioned above, the method of the present invention may comprise, as a second alternative, the following second step:
(ii) applying an algorithm or a mathematical function to said expression profile, wherein the application of said algorithm or mathematical function to said expression profile allows for the diagnosis and/or prognosis of an acute coronary syndrome.

Thus, subsequent to the determination of an expression profile (data) of a (single) miRNA representative for an acute coronary syndrome as defined above, or of a set comprising at least two miRNAs representative for an acute coronary syndrome as defined above in a blood sample from a human, particularly human patient, in step (i) of the method according to the present invention, an algorithm or a mathematical function is applied to said expression profile (data) in step (ii) of the method of the present invention, wherein the application of said algorithm or mathematical function to said expression profile allows for the diagnosis and/or prognosis of an acute coronary syndrome.

The algorithm or mathematical function may be any algorithm or mathematical function which allows for the diagnosis and/or prognosis of an acute coronary syndrome.

As already mentioned above, the term "(clinical) condition" (biological state or health state) means a status of a subject that can be described by physical, mental or social criteria. It includes so-called "healthy" and "diseased" conditions. For the definition of "healthy" and "diseased" conditions it is referred to the international classification of diseases (ICD) of the WHO. When an algorithm or a mathematical function obtained from a reference of one known (clinical) condition is applied to the expression profile (data) determined in a human, particularly human patient, according to preferred embodiments of the method of the present invention, it is understood that said condition is an acute coronary syndrome (i.e. diseased condition), or that said condition is no acute coronary syndrome (i.e. healthy/healthiness). When an algorithm or a mathematical function obtained from a reference of at least two known (clinical) conditions is applied to the expression profile (data) determined in a human, particularly human patient, according to other preferred embodiments of the method of the present invention, it is understood that this is possible for all (clinical) conditions that can be defined under the proviso that one known (clinical) condition is an acute coronary syndrome (i.e. diseased condition). For example, an algorithm or a mathematical function obtained from a reference of two known (clinical) conditions, which are an acute coronary syndrome and no acute coronary syndrome, may be applied to the expression profile (data) determined in a human, particularly human patient.

Preferably, the algorithm or mathematical function is obtained from a reference expression profile (data) of at least one subject, preferably of at least 2 to 40 subjects, more preferably of at least 10 to 25 subjects, and most preferably of at least 15 to 20 subjects, e.g. of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with one known clinical condition which is an acute coronary syndrome, or which is no acute coronary syndrome (i.e. healthy/healthiness), wherein the reference expression profile is the profile of a (single) miRNA that has a nucleotide sequence that essentially corresponds (is essentially identical), preferably that corresponds (is identical), to the nucleotide sequence of the miRNA of step (i), or is the profile of a set comprising at least two miRNAs that have nucleotide sequences that essentially correspond (are essentially identical), preferably that correspond (are identical), to the nucleotide sequences of the miRNAs of step (i). It should be noted that said subject(s) is (are) human(s). Said subject(s) may also be designated as control subject(s).

For example, said algorithm or mathematical function may be obtained from a reference expression profile of at least one subject known to be not affected by an acute coronary syndrome (i.e. healthy), or known to be affected by an acute coronary syndrome (i.e. diseased), wherein the reference expression profile is the profile of a single miRNA that has a nucleotide sequence that essentially corresponds (is essentially identical), preferably that corresponds (is identical), to the nucleotide sequence of the miRNA of step (i) or is the profile of a set comprising at least two miRNAs that have nucleotide sequences that essentially correspond (are essentially identical), preferably that correspond (are identical), to the nucleotide sequences of the miRNAs of step (i).

The terms "essentially correspond(s)" or "essentially identical", as used in this aspect of the present invention, mean that the miRNA(s) of step (i) and the miRNA(s) of the reference expression profile may slightly differ in their nucleotide sequence, whereas said difference is so marginal that it may still allow for the diagnosis and/or prognosis of an acute coronary syndrome. Preferably, the nucleotide sequence(s) of the miRNA(s) of step (i) and the nucleotide sequence(s) of the miRNA(s) of the reference expression profile differ in 1 to 5, more preferably in 1 to 3, and most preferably in 1 to 2 nucleotides, i.e. in 1, 2, 3, 4, or 5 nucleotides. It is preferred that said difference resides in 1 to 5, more preferably 1 to 3, and most preferably 1 to 2 nucleotide mutations, i.e. 1, 2, 3, 4, or 5 nucleotide mutations (e.g. substitutions, additions, insertions, and/or deletions). This is caused by the fact that the miRNAs within the human species may differ. It is preferred that the miRNA(s) of step (i) and the miRNA(s) of the reference expression profile do not differ in their nucleotide sequence, i.e. are identical. It is particularly preferred that the miRNA(s) of step (i) and the miRNA(s) of the reference expression profile are derived from subject/patients of the same gender (e.g. female or male) and/or similar age/phase of life (e.g. infant, young children, juvenile, or adult).

It is particularly preferred that the algorithm or mathematical function is obtained from reference expression profiles (data) of at least two subjects, preferably of at least 3 to 40 subjects, more preferably of at least 10 to 25 subjects, and most preferably of at least 15 to 20 subjects, e.g. of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with at least two known clinical conditions (only one known clinical condition per subject), preferably at least 2 to 5, more preferably at least 2 to 4 (e.g. at least 2, 3, 4, or 5) known clinical conditions, which are an acute coronary syndrome and any other known clinical condition(s), wherein the reference expression profiles are the profiles of a (single) miRNA that has a nucleotide sequence that essentially corresponds (is essentially identical), preferably that corresponds (is identical), to the nucleotide sequence of the miRNA of step (i) or are the profiles of a set comprising at least two miRNAs that have nucleotide sequences that essentially correspond (are essentially identical), preferably that correspond (are identical), to the nucleotide sequences of the miRNAs of step (i). It should be noted that said subject(s) is (are) human(s). Said subject(s) may also be designated as control subject(s).

Preferably, the two known clinical conditions are an acute coronary syndrome and no acute coronary syndrome.

For example, said algorithm or mathematical function may be obtained from reference expression profiles of at least two subjects, at least one subject known to suffer from an acute coronary syndrome (i.e. diseased) and at least one subject known not to suffer from an acute coronary syndrome (i.e. healthy), wherein the reference expression profile is the profile of a single miRNA that has a nucleotide sequence that essentially corresponds (is essentially identical), preferably that corresponds (is identical), to the nucleotide sequence of the miRNA of step (i) or is the profile of a set comprising at least two miRNAs that have nucleotide sequences that essentially correspond (are essentially identical), preferably that corresponds (are identical), to the nucleotide sequences of the miRNAs of step (i).

Preferably, the above-mentioned algorithm or mathematical function is obtained from reference expression profiles of the same number of (control) subjects (e.g. subjects known to be healthy or diseased). For example, the algorithm or mathematical function may be obtained from reference expression profiles of 10 subjects known to suffer from an acute coronary syndrome (positive control) and 10 subjects known not to suffer from an acute coronary syndrome (negative control). The algorithm or mathematical function may also be obtained from reference expression profiles of 20 subjects known to suffer from an acute coronary syndrome (positive control) and 20 subjects known not to suffer from an acute coronary syndrome (negative control).

It is preferred that the algorithm or mathematical function is obtained using a machine learning approach. Machine learning approaches may include but are not limited to supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal probit regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

The inventors of the present invention surprisingly found that the application of a machine learning approach (e.g. t-test, AUC, support vector machine, hierarchical clustering, or k-means) leads to the obtainment of an algorithm or a mathematical function that is trained by the reference expression profile(s) (data) mentioned above and that this allows (i) a better discrimination between the at least two (e.g. 2 or 3) known clinical conditions (the at least two statistical classes) or (ii) a better decision, whether the at least one known clinical condition (the at least one statistical class) is present. In this way, the performance for diagnosing/prognosing of individuals suffering from an acute coronary syndrome can be increased (see also experimental section for details).

Preferably, the machine learning approach involves the following steps:

(i) inputting the reference expression profile(s) of (a) subject(s) with the known clinical condition of an acute coronary syndrome and/or with any other known clinical condition(s), preferably with the known clinical condition of no acute coronary syndrome, and (ii) computing an algorithm or a mathematical function based on said reference expression profile(s) that is suitable to distinguish between the (likely) clinical condition of an acute coronary syndrome and any other (likely) clinical condition(s), preferably the clinical condition of no acute coronary syndrome, or to decide if the clinical condition of an acute coronary syndrome or no acute coronary syndrome is present or will likely be present in said human, particularly human patient.

It should be noted that item (ii) encompasses both that the computed algorithm or mathematical function is suitable to distinguish between the clinical condition of an acute coronary syndrome and any other clinical condition(s), preferably the clinical condition of no acute coronary syndrome, and that the computed algorithm or mathematical function is suitable to distinguish between the likely clinical condition of an acute coronary syndrome and any other likely clinical condition(s), preferably the clinical condition of no acute coronary syndrome. In this respect "likely" means that it is to be expected that the human, particularly human patient, will develop said clinical condition(s).

Thus, in a preferred embodiment, the machine learning approach involves the following steps:

(i) inputting the reference expression profile of at least one subject, preferably the reference expression profiles of at least 2 to 40 subjects, more preferably of at least 10 to 25 subjects, and most preferably of at least 15 to 20 subjects, e.g. of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with one known clinical condition which is an acute coronary syndrome, or no acute coronary syndrome, and (ii) computing an algorithm or a mathematical function based on said reference expression profile, preferably based on said reference expression profiles, that is suitable to decide if the clinical condition of an acute coronary syndrome, or no acute coronary syndrome is present or will likely be present in said human, particularly human patient.

Thus, in another preferred embodiment, the machine learning approach involves the following steps:

(i) inputting the reference expression profiles of at least two subjects, preferably of at least 3 to 40 subjects, more preferably of at least 10 to 25 subjects, and most preferably of at least 15 to 20 subjects, e.g. of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with at least two known clinical conditions (only one known clinical condition per subject) which are an acute coronary syndrome and any other known clinical condition(s), preferably the known clinical condition of no acute coronary syndrome, and (ii) computing an algorithm or a mathematical function based on said reference expression profiles that is suitable to distinguish between the (likely) clinical condition of an acute coronary syndrome, and any other (likely) clinical condition(s), preferably the clinical condition of no acute coronary syndrome.

The application of the algorithm or mathematical function as mentioned above to the expression profile of the human, particularly human patient, to be diagnosed and/or prognosed may then allow for diagnosing and/or prognosing of an acute coronary syndrome.

Considering the above, diagnosing preferably means applying the algorithm or mathematical function as mentioned above to the expression profile of a human, particularly human patient, to decide, if the at least one known clinical condition, which is an acute coronary syndrome (i.e. diseased condition), or which is no acute coronary syndrome (i.e. healthy condition), is present in said human, particularly human patient. Prognosing preferably means applying the algorithm or mathematical function as mentioned above to the expression profile of a human, particularly human patient, to decide, if the at least one known clinical condition, which is an acute coronary syndrome (i.e. diseased condition), or which is no acute coronary syndrome (i.e. healthy condition), will likely be present in said human, particularly human patient.

For example, the human, particularly human patient, may be diagnosed as not suffering from an acute coronary syndrome (i.e. being healthy), or as suffering from an acute coronary syndrome (i.e. being diseased). Further, for example, the human, particularly human patient, may be prognosed as not developing an acute coronary syndrome (i.e. staying healthy), or as developing an acute coronary syndrome (i.e. getting diseased).

Furthermore, considering the above, diagnosing preferably means applying the algorithm or mathematical function as mentioned above to the expression profile of a human, particularly human patient, to decide which of the at least two known clinical conditions, which are an acute coronary syndrome and any other known clinical condition(s), preferably the clinical condition of no acute coronary syndrome, is (are) present in said human, particularly human patient, or to distinguish between the at least two known clinical conditions, which are an acute coronary syndrome and any other known clinical condition(s), preferably the clinical condition of no acute coronary syndrome. Prognosing preferably means applying the algorithm or mathematical function as mentioned above to the expression profile of a human, particularly human patient, to decide which of the at least two known clinical conditions, which are an acute coronary syndrome and any other known clinical condition(s), preferably the clinical condition of no acute coronary syndrome, will likely be present in said human, particularly human patient, or to distinguish between the at least two likely clinical conditions, which are an acute coronary syndrome and any other known clinical condition(s), preferably the clinical condition of no acute coronary syndrome.

For example, if the at least two known clinical conditions are an acute coronary syndrome (i.e. diseased condition) and no acute coronary syndrome (i.e. healthy condition), the human, particularly human patient, may be diagnosed as suffering from an acute coronary syndrome (i.e. being diseased), or as not suffering from an acute coronary syndrome (i.e. being healthy). If the at least two known clinical conditions are an acute coronary syndrome (i.e. diseased condition) and no acute coronary syndrome (i.e. healthy condition), the human, particularly human patient, may be prognosed as developing an acute coronary syndrome (i.e. getting diseased), or as not developing an acute coronary syndrome (i.e. staying healthy).

Diagnosing/prognosing of an acute coronary syndrome based on an algorithm or a mathematical function may take place as follows: For instance, if the algorithm or mathematical function, which is obtained from a reference expression profile of at least one subject with the known clinical condition of an acute coronary syndrome, is applied to the expression profile (data) of a human (particularly human patient), the human (particularly human patient) is classified as suffering from an acute coronary syndrome (i.e. being diseased), if the resulting score is below a specified threshold, or if the algorithm or mathematical function, which is obtained from a reference expression profile of at least one subject with the known clinical condition of no acute coronary syndrome, is applied to the expression profile (data) of a human (particularly human patient), the human (particularly human patient) is classified as not suffering from an acute coronary syndrome (i.e. being healthy), if the resulting score is above a specified threshold.

Further, if the algorithm or mathematical function, which is obtained from a reference expression profile of at least one subject with the known clinical condition of an acute coronary syndrome and from a reference expression profile of at least one subject with the known clinical condition of no acute coronary syndrome, is applied to the expression profile (data) of a human (particularly human patient), the human (particularly human patient) is classified as suffering from an acute coronary syndrome (i.e. being diseased), if the resulting score is below a specified threshold, and the human (particularly human patient) is classified as not suffering from an acute coronary syndrome (i.e. being healthy), if the resulting score is above a specified threshold.

Preferably, machine learning approaches are employed to develop/obtain algorithms or mathematical functions for diagnosing and/or prognosing of clinical conditions such as an acute coronary syndrome. Support vector machines (SVMs) are a set of related supervised learning methods which are preferably used for classification and regression. For example, given a set of training examples, each marked as belonging to one of two categories (e.g. condition of an acute coronary syndrome and no acute coronary syndrome), an SVM algorithm builds a model that predicts whether a new example (e.g. sample from a human, particularly human patient, to be tested) falls into one category or the other (e.g. condition of an acute coronary syndrome or no acute coronary syndrome). A SVM model is a representation of the training examples as points in space, mapped so that the training examples of the separate categories (e.g. condition of an acute coronary syndrome or no acute coronary syndrome) are divided by a clear gap that is as wide as possible. New examples (e.g. sample from a human, particularly human patient, to be tested) are then mapped into that same space and predicted to belong to a category based on which side of the gap they fall on (e.g. an acute coronary syndrome or no acute coronary syndrome). More formally, a support vector machine constructs a hyperplane or set of hyperplanes in a high or infinite dimensional space, which can be used for classification, regression or other tasks. A good separation is achieved by the hyperplane that has the largest distance to the nearest training data points of any class (so-called functional margin), since in general the larger the margin the lower the generalization error of the classifier.

Classifying data is a preferred task in machine learning. For example, considering some given data points each belong to one (e.g. an acute coronary syndrome or no acute coronary syndrome) of two classes (e.g. an acute coronary syndrome and no acute coronary syndrome), the goal is to decide which class a new data point (e.g. achieved from a human, particularly human patient) will be in. In the preferred case of support vector machines, a data point is viewed as a p-dimensional vector (a list of p numbers), and the question is, whether it is possible to separate such points with a p-1-dimensional hyperplane. This is called a linear classifier. There are many hyperplanes that might classify the data. One reasonable choice as the best hyperplane is the one that represents the largest separation, or margin, between the two classes (e.g. condition of an acute coronary syndrome or no acute coronary syndrome). Thus, the hyperplane should be chosen so that the distance from it to the nearest data point on each side is maximized. If such a hyperplane exists, it is known as the maximum-margin hyperplane and the linear classifier it defines is known as a maximum margin classifier.

The formalization of the support vector machine is exemplary summarised below:

For example, given are training data $\mathcal{D}$ (e.g. reference expression profile(s) of (a) subject(s) with the known clinical condition of an acute coronary syndrome and/or with any other known clinical condition(s), preferably with the known clinical condition of no acute coronary syndrome), a set of n subject samples (e.g. subjects known to suffer from an acute coronary syndrome and/or any other known clinical condition, for example, no acute coronary syndrome) of the form $$\mathcal{D}=\{(x_i,c_i)|x_i\in\mathbb{R}^p, c_i\in\{-1,1\}\}_{i=1}^n$$

where the $c_i$ is either 1 or −1, indicating the class labels (e.g. an acute coronary syndrome and/or any other known clinical condition(s), for example, no acute coronary syndrome) to which the miRNA biomarker intensities $x_i$ belongs. Each $x_i$ is a p-dimensional real vector (with p being the number of miRNA biomarkers). The task is know to find the maximum-margin hyperplane that divides the points having $c_i=1$ from those having $c_i=-1$. Any hyperplane can be written as the set of points x satisfying $$w \cdot x - b = 0,$$

where "·" denotes the dot. The vector w is a normal vector: it is perpendicular to the hyperplane. The parameter $$\frac{b}{\|w\|}$$

determines the offset of the hyperplane from the origin along the normal vector w.

w and b should be chosen to maximize the margin, or distance between the parallel hyperplanes that are as far apart as possible while still separating the data. These hyperplanes can be described by the equations $$w \cdot x - b = 1$$

and $$w \cdot x - b = -1.$$

Note that if the training data are linearly separable, the two hyperplanes of the margin can be selected in a way that there are no points between them and then by trying to maximize their distance. For example, by using geometry, the distance between these two hyperplanes is $$\frac{2}{\|w\|},$$

$\|w\|$ should be minimized. To also prevent data points falling into the margin, the following constraint should be added: for each i either $w \cdot x_i - b \geq 1$ for $x_i$ of the first class (e.g. an acute coronary syndrome)

or $w \cdot x_i - b \leq -1$ for $x_i$ of the second class (no acute coronary syndrome).

This can be rewritten as:

$c_i(w \cdot x_i - b) \geq 1$, for all $1 \leq i \leq n$. (1)

This can be put together to get the optimization problem: Minimize (in w, b)

$\|w\|$ subject to (for any i=1, ..., n)

$c_i(w \cdot x_i - b) \geq 1$.

The optimization problem presented in the preceding section is difficult to solve because it depends on $\|w\|$, the norm of w, which involves a square root. It is, however, possible to alter the equation by substituting $\|w\|$ with $\frac{1}{2}\|W\|^2$ (the factor of $\frac{1}{2}$ being used for mathematical convenience) without changing the solution (the minimum of the original and the modified equation have the same w and b). This is a quadratic programming (QP) optimization problem. More clearly:

Minimize (in w, b)

$\frac{1}{2}\|w\|^2$ subject to (for any i=1, ..., n)

$c_i(w \cdot x_i - b) \geq 1$.

The previous problem may be expressed by means of non-negative Lagrange multipliers a as $$\min_{w,b,\alpha}\left\{\frac{1}{2}\|w\|^2 - \sum_{i=1}^{n}\alpha_i[c_i(w \cdot x_i - b) - 1]\right\}$$

but this would led to an incorrect result. The reason is the following: suppose that a family of hyperplanes which divide the points can be found; then all $c_i(w \cdot x_i - b) - 1 \geq 0$. Hence the minimum by sending all $\alpha_i$ to $|\infty$ could be found, and this minimum would be reached for all the members of the family, not only for the best one which can be chosen solving the original problem.

Nevertheless the previous constrained problem can be expressed as $$\min_{w,b}\max_{\alpha}\left\{\frac{1}{2}\|w\|^2 - \sum_{i=1}^{n}\alpha_i[c_i(w \cdot x_i - b) - 1]\right\}$$

looking for a saddle point. In doing so all the points which can be separated as $c_i(w \cdot x_i - b) - 1 > 0$ do not matter since the corresponding $\alpha_i$ must be set to zero.

This problem can be solved by standard quadratic programming techniques and programs. The solution can be expressed by terms of linear combination of the training vectors as $$w = \sum_{i=1}^{n} \alpha_i c_i x_i$$

Only a few $\alpha_i$ will be greater than zero. The corresponding $x_i$ are exactly the support vectors, which lie on the margin and satisfy $c_i(w \cdot x_i - b) = 1$. From this it can be derived that the support vectors also satisfy $w \cdot x_i - b = 1/c_i = c_i \Longleftrightarrow b = w \cdot x_i - c_i$ which allows one to define the offset b. In practice, it is more robust to average over all $N_{SV}$ support vectors:

$$b = \frac{1}{N_{SV}}\sum_{i=1}^{N_{SV}}(w \cdot x_i - c_i)$$

Writing the classification rule in its unconstrained dual form reveals that the maximum margin hyperplane and therefore the classification task is only a function of the support vectors, the training data that lie on the margin.

Using the fact, that $\|w\|^2 = w \cdot w$ and substituting $$w = \sum_{i=0}^{n} \alpha_i c_i x_i,$$

it can show shown that the dual of the SVM reduces to the following optimization problem:

Maximize (in $\alpha_i$)

$$\tilde{L}(\alpha) = \sum_{i=1}^{n}\alpha_i - \frac{1}{2}\sum_{i,j}\alpha_i\alpha_j c_i c_j x_i^T x_j$$

$$= \sum_{i=1}^{n}\alpha_i - \frac{1}{2}\sum_{i,j}\alpha_i\alpha_j c_i c_j k(x_i, x_j)$$

subject to (for any i=1, ..., n)

$\alpha_i \geq 0$, and to the constraint from the minimization in b $$\sum_{i=1}^{n}\alpha_i c_i = 0.$$

Here the kernel is defined by $k(x_i, x_j) = x_i \cdot x_j$.

The $\alpha$ terms constitute a dual representation for the weight vector in terms of the training set:

$$w = \sum_{i}\alpha_i c_i x_i.$$

For simplicity reasons, sometimes it is required that the hyperplane passes through the origin of the coordinate system. Such hyperplanes are called unbiased, whereas general hyperplanes not necessarily passing through the origin are called biased. An unbiased hyperplane can be enforced by setting b=0 in the primal optimization problem.

The corresponding dual is identical to the dual given above without the equality constraint $$\sum_{i=1}^{n} \alpha_i c_i = 0.$$

Transductive support vector machines extend SVMs in that they could also treat partially labeled data in semi-supervised learning. Here, in addition to the training set $\mathcal{D}$, the learner is also given a set $$\mathcal{D}^* = \{x_i^* | x_i^* \in \mathbb{R}^p\}_{i=1}^{k}$$

of test examples to be classified. Formally, a transductive support vector machine is defined by the following primal optimization problem:

Minimize (in w, b, c*)

$$\tfrac{1}{2}\|w\|^2$$

subject to (for any i=1, ..., n and any j=1, ..., k)

$$c_i(w \cdot x_i - b) \geq 1,$$

$$c_j^*(w \cdot x_j^* - b) \geq 1,$$

and $$c_j^* \in \{-1, 1\}.$$

Transductive support vector machines were introduced by Vladimir Vapnik in 1998.

SVMs belong to a family of generalized linear classifiers. They can also be considered a special case of Tikhonov regularization. A special property is that they simultaneously minimize the empirical classification error and maximize the geometric margin; hence they are also known as maximum margin classifiers.

In 1995, Corinna Cortes and Vladimir Vapnik suggested a modified maximum margin idea that allows for mislabeled examples. If there exists no hyperplane that can split the "yes" and "no" examples, the Soft Margin method will choose a hyperplane that splits the examples as cleanly as possible, while still maximizing the distance to the nearest cleanly split examples. The method introduces slack variables, $\xi_i$, which measure the degree of misclassification of the datum $x_i$ $$c_i(w \cdot x_i - b) \geq \lambda 1 - \xi_i, \quad 1 \leq i \leq n. \quad (2)$$

The objective function is then increased by a function which penalizes non-zero $\xi_i$, and the optimization becomes a trade off between a large margin, and a small error penalty. If the penalty function is linear, the optimization problem becomes:

$$\min_{w, \xi} \left\{ \frac{1}{2}\|w\|^2 + C \sum_{i=1}^{n} \xi_i \right\}$$

subject to (for any i=1, ... n)

$$c_i(w \cdot x_i - b) \geq 1 - \xi_i, \quad \xi_i \geq 0.$$

This constraint in (2) along with the objective of minimizing $\|w\|$ can be solved using Lagrange multipliers as done above. One has then to solve the following problem $$\min_{w, \xi, b} \max_{\alpha, \beta} \left\{ \frac{1}{2}\|w\|^2 + C \sum_{i=1}^{n} \xi_i - \sum_{i=1}^{n} \alpha_i [c_i(w \cdot x_i - b) - 1 + \xi_i] - \sum_{i=1}^{n} \beta_i \xi_i \right\}$$

with $\alpha_i, \beta_i \geq 0$.

The key advantage of a linear penalty function is that the slack variables vanish from the dual problem, with the constant C appearing only as an additional constraint on the Lagrange multipliers. For the above formulation and its huge impact in practice, Cortes and Vapnik received the 2008 ACM Paris Kanellakis Award. Non-linear penalty functions have been used, particularly to reduce the effect of outliers on the classifier, but unless care is taken, the problem becomes non-convex, and thus it is considerably more difficult to find a global solution.

The original optimal hyperplane algorithm proposed by Vladimir Vapnik in 1963 was a linear classifier. However, in 1992, Bernhard Boser, Isabelle Guyon and Vapnik suggested a way to create non-linear classifiers by applying the kernel trick (originally proposed by Aizerman et al.[4]) to maximum-margin hyperplanes. The resulting algorithm is formally similar, except that every dot product is replaced by a non-linear kernel function. This allows the algorithm to fit the maximum-margin hyperplane in a transformed feature space. The transformation may be non-linear and the transformed space high dimensional; thus though the classifier is a hyperplane in the high-dimensional feature space, it may be non-linear in the original input space.

If the kernel used is a Gaussian radial basis function, the corresponding feature space is a Hilbert space of infinite dimension. Maximum margin classifiers are well regularized, so the infinite dimension does not spoil the results. Some common kernels include, Polynomial(homogeneous): $k(x_i, x_j) = (x_i \cdot x_j)^d$ Polynomial (inhomogeneous): $k(x_i, x_j) = (x_i \cdot x_j + 1)^d$ Radial Basis Function: $k(x_i, x_j) = \exp(-\gamma \|x_i - x_j\|^2)$, for $\gamma > 0$ Gaussian Radial basis function:

$$k(x_i, x_j) = \exp\left(-\frac{\|x_i - x_j\|^2}{2\sigma^2}\right)$$

Hyperbolic tangent: $k(x_i, x_j) = \tan h(\kappa x_i \cdot x_j + c)$, for some (not every) $\kappa > 0$ and $c < 0$ The kernel is related to the transform $\phi(x_i)$ by the equation $k(x_i, x_j) = \phi(x_i) \cdot \phi(x_j)$. The value w is also in the transformed space, with $w = \Sigma_i \alpha_i c_i \phi(x_i)$. Dot products with w for classification can again be computed by the kernel trick, i.e. $w \cdot \phi(x) = \Sigma_i \alpha_i c_i k(x_i, x)$. However, there does not in general exist a value w' such that $w \cdot \phi(x) = k(w', x)$.

After the w and b are determined employing the above-mentioned methods these can be used for classifying new datasets (e.g. a expression profile of a patient with p miRNA biomarkers and corresponding $x_i$ intensity values).

As described above, the method of the present invention may also comprise the following second step with both afore-mentioned alternatives:

(ii) comparing said expression profile to a reference, wherein the comparison of said expression profile to said reference allows for the diagnosis and/or prognosis of an acute coronary syndrome and applying an algorithm or a mathematical function to said expression profile, wherein the application of said algorithm or mathematical function to said expression profile allows for the diagnosis and/or prognosis of an acute coronary syndrome.

Thus, subsequent to the determination of an expression profile (data) of a (single) miRNA representative for an acute coronary syndrome as defined above, or of a set comprising at least two miRNAs representative for an acute coronary syndrome as defined above in a blood sample from a human, particularly human patient, in step (i) of the method according to the present invention, said expression profile (data) is compared to a reference, as defined/described above, in step (ii) of the method according to the present invention, wherein the comparison of said expression profile (data) to said reference allows for the diagnosis and/or prognosis of an acute coronary syndrome, and an algorithm or a mathematical function is applied to said expression profile (data), as defined/described above, in step (ii) of the method of the present invention, wherein the application of said algorithm or mathematical function to said expression profile allows for the diagnosis and/or prognosis of an acute coronary syndrome.

As mentioned above, the measured miRNA expression profiles may be classified using machine learning approaches in order to compute accuracy, specificity, and sensitivity for the diagnosis and/or prognosis of an acute coronary syndrome (see experimental section for more details). Examples of miRNA sets (signatures) that performed best for the diagnosis of an acute coronary syndrome according to their accuracy, specificity, and sensitivity are miRNAs having SEQ ID NO: 1 and 2 (see FIG. 13), miRNAs having SEQ ID NO: 1 to 4 (see FIG. 14), SEQ ID NO: 1 to 6 (see FIG. 15), SEQ ID NO: 1 to 8 (see FIG. 16), SEQ ID NO: 1 to 10 (see FIG. 17), SEQ ID NO: 1 to 50 (see FIG. 18), SEQ ID NO: 1 to 80 (see FIG. 19), or SEQ ID NO: 1 to 100 (see FIG. 20). Further miRNA sets (signatures) that performed best for the diagnosis of an acute coronary syndrome according to their accuracy, specificity, and sensitivity are summarized in FIGS. 28 and 30.

Preferably, the reference and optionally the expression profile of the miRNA(s) representative for an acute coronary syndrome is (are) stored in a database.

The above-mentioned method is for diagnosing an acute coronary syndrome in a human, particularly human patient. Preferably, the diagnosis comprises (i) determining the occurrence/presence of an acute coronary syndrome, (ii) monitoring the course of an acute coronary syndrome, (iii) staging of an acute coronary syndrome, (iv) measuring the response of an individual, particularly human patient, with an acute coronary syndrome to therapeutic intervention, and/or (v) segmentation of individuals, particularly human patients, suffering from an acute coronary syndrome.

The above-mentioned method is also for prognosis of an acute coronary syndrome in a human, particularly human patient. Preferably, the prognosis comprises (i) identifying an individual, particularly human patient, who has a risk to develop an acute coronary syndrome, (ii) predicting/estimating the occurrence, preferably the severity of occurrence, of an acute coronary syndrome, and/or (iii) predicting the response of an individual, particularly human patient with an acute coronary syndrome to therapeutic intervention.

In a third aspect, the present invention provides means for diagnosing and/or prognosing of an acute coronary syndrome comprising a polynucleotide (probe) or a set comprising, essentially consisting of, or consisting of at least two polynucleotides (probes) according to the first aspect of the present invention, e.g. (i) a polynucleotide for detecting a miRNA or a set comprising, essentially consisting of, or consisting of at least two polynucleotides for detecting a set comprising, essentially consisting of, or consisting of at least two miRNAs, wherein the nucleotide sequence of said miRNA or nucleotide sequences of said miRNAs is (are) selected from the group consisting of SEQ ID NO: 1 to SEQ ID NO: 283, or particularly (ii) a polynucleotide for detecting a miRNA or a set comprising, essentially consisting of, or consisting of at least 2, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153, polynucleotides for detecting a set comprising, essentially consisting of, or consisting of at least 2, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153, miRNAs, wherein the nucleotide sequence of said miRNA or nucleotide sequences of said miRNAs is (are) selected from the group consisting of SEQ ID NO: 1 to SEQ ID NO: 153. It is preferred that said polynucleotide set, in (ii) above, comprises at least one further polynucleotide (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 polynucleotide(s)) for detecting the above-mentioned miRNA set comprising at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)), wherein the nucleotide sequence of said miRNA is selected from the group consisting of SEQ ID NO: 154 to SEQ ID NO: 241.

Preferably, the means for diagnosing and/or prognosing of an acute coronary syndrome comprises, essentially consists of, or consists of a solid support, substrate, surface, platform or matrix comprising a polynucleotide (probe) or a set comprising, essentially consisting of, or consisting of at least two polynucleotides (probes) according to the first aspect of the present invention, e.g. (i) a solid support, substrate, surface, platform or matrix comprising a polynucleotide for detecting a miRNA or a set comprising, essentially consisting of, or consisting of at least two polynucleotides for detecting a set comprising, essentially consisting of, or consisting of at least two miRNAs, wherein the nucleotide sequence of said miRNA or nucleotide sequences of said miRNAs is (are) selected from the group consisting of SEQ ID NO: 1 to SEQ ID NO: 283, or particularly (ii) a solid support, substrate, surface, platform or matrix comprising a polynucleotide for detecting a miRNA or a set comprising, essentially consisting of, or consisting of at least 2, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153, polynucleotides for detecting a set comprising, essentially consisting of, or consisting of at least 2, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153, miRNAs, wherein the nucleotide sequence of said miRNA or nucleotide sequences of said miRNAs is (are) selected from the group consisting of SEQ ID NO: 1 to SEQ ID NO: 153. It is preferred that said polynucleotide set, in (ii) above, comprises at least one further polynucleotide (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 polynucleotide(s)) for detecting the above-mentioned miRNA set comprising at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)), wherein the nucleotide sequence of said miRNA is selected from the group consisting of SEQ ID NO: 154 to SEQ ID NO: 241. Preferably, the above-mentioned polynucleotide(s) is (are) attached to or immobilized on a solid support, substrate, surface, platform or matrix. It is possible to include appropriate controls for non-specific hybridization on the solid support, substrate, surface, platform or matrix.

It is particularly preferred that said means for diagnosing and/or prognosing of an acute coronary syndrome comprises, essentially consists of, or consists of a microarray/biochip comprising a polynucleotide (probe) or a set comprising, essentially consisting of, or consisting of at least two polynucleotides (probes) according to the first aspect of the present invention, e.g. (i) a microarray/biochip comprising a polynucleotide for detecting a miRNA or a set comprising, essentially consisting of, or consisting of at least two polynucleotides for detecting a set comprising, essentially consisting of, or consisting of at least two miRNAs, wherein the nucleotide sequence of said miRNA or nucleotide sequences of said miRNAs is (are) selected from the group consisting of SEQ ID NO: 1 to SEQ ID NO: 283, or particularly (ii) a microarray/biochip comprising a polynucleotide for detecting a miRNA or a set comprising, essentially consisting of, or consisting of at least 2, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153, polynucleotides for detecting a set comprising, essentially consisting of, or consisting of at least 2, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153, miRNAs, wherein the nucleotide sequence of said miRNA or nucleotide sequences of said miRNAs is (are) selected from the group consisting of SEQ ID NO: 1 to SEQ ID NO: 153. It is preferred that said polynucleotide set, in (ii) above, comprises at least one further polynucleotide (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 polynucleotide(s)) for detecting the above-mentioned miRNA set comprising at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)), wherein the nucleotide sequence of said miRNA is selected from the group consisting of SEQ ID NO: 154 to SEQ ID NO: 241. Preferably, the above-mentioned polynucleotide(s) is (are) attached to or immobilized on the microarray/biochip. It is possible to include appropriate controls for non-specific hybridization on the microarray/biochip.

It is further particularly preferred that said means for diagnosing and/or prognosing of an acute coronary syndrome comprise, essentially consists of, or consists of a set comprising at least two polynucleotides for detecting a set comprising at least two miRNAs, wherein the nucleotide sequences of said miRNAs are selected from one or more sets listed in FIG. 28 and/or FIG. 30. Preferably, said polynucleotides are attached to or immobilized on a solid support, substrate, surface, platform or matrix, more preferably microarray/biochip.

The polynucleotide(s) (probe(s)) may also be comprised as polynucleotide fragments, polynucleotide variants, or polynucleotide fragment variants in the means for diagnosing and/or prognosing of an acute coronary syndrome. For example, polynucleotide fragments, polynucleotide variants, or polynucleotide fragment variants may be comprised in the solid support, substrate, surface, platform or matrix, preferably microarray/biochip. Said polynucleotide fragments, polynucleotide variants, or polynucleotide fragment variants may be attached or linked to the solid support, substrate, surface, platform or matrix, preferably microarray/biochip. As to the definition of said polynucleotide fragments, polynucleotide variants, or polynucleotide fragment variants and as to the preferred polynucleotide (probe) or sets of polynucleotides (probes), it is referred to the first aspect of the present invention.

The terms "biochip" or "microarray", as used herein, refer to a solid phase comprising an attached or immobilized polynucleotide described herein as probe or a set (plurality) of polynucleotides described herein attached or immobilized as probes. The polynucleotide probes may be capable of hybridizing to a target sequence, such as a complementary miRNA or miRNA* sequence, under stringent hybridization conditions. The polynucleotide probes may be attached or immobilized at spatially defined locations on the solid phase. One or more than one nucleotide (probe) per target sequence may be used. The polynucleotide probes may either be synthesized first, with subsequent attachment to the biochip, or may be directly synthesized on the biochip. The solid phase may be a material that may be modified to contain discrete individual sites appropriate for the attachment or association of the polynucleotide probes and is amenable to at least one detection method. Representative examples of solid phase materials include glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses and plastics. The solid phase may allow optical detection without appreciably fluorescing. The solid phase may be planar, although other configurations of solid phase may be used as well. For example, polynucleotide probes may be placed on the inside surface of a tube, for flow-through sample analysis to minimize sample volume. Similarly, the solid phase may be flexible, such as flexible foam, including closed cell foams made of particular plastics. The solid phase of the biochip and the probe may be modified with chemical functional groups for subsequent attachment of the two. For example, the biochip may be modified with a chemical functional group including, but not limited to, amino groups, carboxyl groups, oxo groups or thiol groups. Using these functional groups, the probes may be attached using functional groups on the probes either directly or indirectly using a linker. The polynucleotide probes may be attached to the solid support by either the 5' terminus, 3' terminus, or via an internal nucleotide. The polynucleotide probe may also be attached to the solid support non-covalently. For example, biotinylated polynucleotides can be made, which may bind to surfaces covalently coated with streptavidin, resulting in attachment. Alternatively, polynucleotide probes may be synthesized on the surface using techniques such as photopolymerization and photolithography. In the context of the present invention, the terms "biochip" and "microarray" are interchangeable used.

The terms "attached" or "immobilized", as used herein, refer to the binding between the polynucleotide and the solid support/phase and may mean that the binding between the polynucleotide probe and the solid support is sufficient to be stable under conditions of binding, washing, analysis and removal. The binding may be covalent or non-covalent. Covalent bonds may be formed directly between the polynucleotide and the solid support or may be formed by a cross linker or by inclusion of specific reactive groups on either the solid support or the polynucleotide, or both. Non-covalent binding may be electrostatic, hydrophilic and hydrophobic interactions or combinations thereof. Immobilization or attachment may also involve a combination of covalent and non-covalent interactions.

In a fourth aspect, the present invention provides a kit for diagnosing and/or prognosing of an acute coronary syndrome comprising (i) means for determining an expression profile of a miRNA or a set comprising, essentially consisting of, or consisting of at least 2 miRNAs, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 6, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, or 283 miRNAs, representative for an acute coronary syndrome in a blood sample from a human, particularly human patient, wherein the nucleotide sequence of said miRNA or the nucleotide sequences of said miRNAs is (are) selected from the group consisting of SEQ ID NO: 1 to SEQ ID NO: 283, a fragment thereof, and a sequence having at least 80% sequence identity thereto; and (ii) at least one reference and/or algorithm or mathematical function, preferably comprised on at least one data carrier.

In a preferred embodiment, the present invention provides a kit for diagnosing and/or prognosing of an acute coronary syndrome comprising (i) means for determining an expression profile of a miRNA or a set comprising, essentially consisting of, or consisting of at least 2 miRNAs, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, or 153 miRNAs, representative for an acute coronary syndrome in a blood sample from a human, particularly human patient, wherein the nucleotide sequence of said miRNA or the nucleotide sequences of said miRNAs is (are) selected from the group consisting of SEQ ID NO: 1 to SEQ ID NO: 153, a fragment thereof, and a sequence having at least 80% sequence identity thereto; and (ii) at least one reference and/or algorithm or mathematical function, preferably comprised on at least one data carrier.

Preferably, the above-mentioned set of miRNAs comprises at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)), wherein the nucleotide sequence of said miRNA is selected from the group consisting of SEQ ID NO: 154 to SEQ ID NO: 241, a fragment thereof, and a sequence having at least 80% sequence identity thereto.

The nucleotide sequence of said miRNA or the nucleotide sequences of said miRNAs may also be selected from the group consisting of SEQ ID NO: 242 to SEQ ID NO: 283, a fragment thereof, and a sequence having at least 80% sequence identity thereto.

In another preferred embodiment, the present invention provides a kit for diagnosing and/or prognosing of an acute coronary syndrome comprising (i) means for determining an expression profile of a miRNA or a set comprising, essentially consisting of, or consisting of at least two miRNAs representative for an acute coronary syndrome in a blood sample from a human, particularly human patient, wherein the nucleotide sequence of said miRNA is selected from the list of FIG. 29, or the nucleotide sequences of said miRNAs are selected from one or more sets listed in FIG. 28 and/or FIG. 30; and (ii) at least one reference and/or algorithm or mathematical function, preferably comprised on at least one data carrier.

For example, the nucleotide sequences of said miRNAs may be selected from 1, 2, 3, 4, 5, 6, 7, 8, 9, 10 or more sets listed in FIG. 28 and/or FIG. 30.

Said means may comprise (i) polynucleotides according to the first aspect of the present invention, (ii) means according to the third aspect of the present invention, (iii) primers suitable to perform reverse transcriptase reaction and/or real time polymerase chain reaction such as quantitative polymerase chain reaction.

It is preferred that said kit comprises (ia) a polynucleotide for detecting a miRNA or a set comprising, essentially consisting of, or consisting of at least two polynucleotides according to the first aspect of the present invention, and (ib) a solid support, substrate, surface, platform or matrix onto which the polynucleotide or the set comprising at least two polynucleotides according to the first aspect of the present invention may be attached or immobilized, and (ic) optionally at least one of the means selected from the group consisting of: at least one human blood sample, e.g. serum, plasma, or blood cells, or at least one sample of total RNA extracted from a human blood sample, means to extract RNA from a blood sample, means for input/injection of a blood sample, positive controls for hybridization, means for holding the solid support, substrate, platform or matrix, e.g. after immobilization of the polynucleotide probe(s), means for labelling the isolated miRNA (e.g. NTP/biotin-NTP), means for hybridization, means to carry out enzymatic reactions (e.g. exonuclease I and/or Klenow enzyme) means for washing steps, means for detecting the hybridization signal, and mean for analysing the detected hybridization signal, e.g. for determining an expression profile of a miRNA or a set comprising, essentially consisting of, or consisting of at least 2 miRNAs, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, or 153 miRNAs, representative for an acute coronary syndrome in a blood sample from a human, particularly human patient, wherein the nucleotide sequence of said miRNA or the nucleotide sequences of said miRNAs is (are) selected from the group consisting of SEQ ID NO: 1 to SEQ ID NO: 153, a fragment thereof, and a sequence having at least 80% sequence identity thereto, and more preferably for determining an expression profile of at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)) comprised in said miRNA set, wherein the nucleotide sequence of the at least one further miRNA is selected from the group consisting of SEQ ID NO: 154 to SEQ ID NO: 241, a fragment thereof, and a sequence having at least 80% sequence identity thereto.

It is further preferred that said kit comprises means according to the third aspect of the present invention, e.g. means for diagnosing and/or prognosis of an acute coronary syndrome comprising a polynucleotide or a set comprising at least two polynucleotides according to the first aspect of the present invention. It is also preferred that said kit comprises means for diagnosing and/or prognosis of an acute coronary syndrome comprising a biochip which comprises a polynucleotide or a set comprising at least two polynucleotides according to the first aspect of the present invention.

It is particularly preferred that said kit comprises (ia) a solid support, substrate, surface, platform or matrix according to the third aspect of the present invention comprising a polynucleotide or a set comprising, essentially consisting of, or consisting of at least two polynucleotides according of the first aspect of the present invention, and (ib) optionally at least one of the means selected from the group consisting of: at least one human blood sample, e.g. serum, plasma, or blood cells, or at least one sample of total RNA extracted from a human blood sample, means to extract RNA from a blood sample, means for input/injection of a blood sample, positive controls for the hybridization experiment, means for holding the solid support, substrate, platform or matrix comprising the polynucleotide probe(s), means for labelling the isolated miRNA (e.g. NTP/biotin-NTP), means for hybridization, means to carry out enzymatic reactions (e.g. exonuclease I and/or Klenow enzyme) means for washing steps, means for detecting the hybridization signal, and mean for analysing the detected hybridization signal, e.g. for determining an expression profile of a miRNA or a set comprising, essentially consisting of, or consisting of at least 2 miRNAs, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, or 153 miRNAs, representative for an acute coronary syndrome in a blood sample from a human, particularly human patient, wherein the nucleotide sequence of said miRNA or the nucleotide sequences of said miRNAs is (are) selected from the group consisting of SEQ ID NO: 1 to SEQ ID NO: 153, a fragment thereof, and a sequence having at least 80% sequence identity thereto, and more preferably for determining an expression profile of at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)) comprised in said miRNA set, wherein the nucleotide sequence of the at least one further miRNA is selected from the group consisting of SEQ ID NO: 154 to SEQ ID NO: 241, a fragment thereof, and a sequence having at least 80% sequence identity thereto.

It is mostly preferred that said kit comprises (ia) a microarray/biochip according to the third aspect of the present invention comprising a polynucleotide or a set comprising, essentially consisting of, or consisting of at least two polynucleotides according of the first aspect of the present invention, and (ib) optionally at least one of the means selected from the group consisting of: at least one human blood sample, e.g. serum, plasma, or blood cells, or at least one sample of total RNA extracted from a human blood sample, means to extract RNA from a blood sample, means for input/injection of a blood sample, positive controls for the hybridization experiment, means for holding the microarray/biochip comprising the polynucleotide probe(s), means for labelling the isolated miRNA (e.g. NTP/biotin-NTP), means for hybridization, means to carry out enzymatic reactions (e.g. exonuclease I and/or Klenow enzyme) means for washing steps, means for detecting the hybridization signal, and mean for analysing the detected hybridization signal, e.g. for determining an expression profile of a miRNA or a set comprising, essentially consisting of, or consisting of at least 2 miRNAs, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, or 153 miRNAs, representative for an acute coronary syndrome in a blood sample from a human, particularly human patient, wherein the nucleotide sequence of said miRNA or the nucleotide sequences of said miRNAs is (are) selected from the group consisting of SEQ ID NO: 1 to SEQ ID NO: 153, a fragment thereof, and a sequence having at least 80% sequence identity thereto, and more preferably for determining an expression profile of at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)) comprised in said miRNA set, wherein the nucleotide sequence of the at least one further miRNA is selected from the group consisting of SEQ ID NO: 154 to SEQ ID NO: 241, a fragment thereof, and a sequence having at least 80% sequence identity thereto.

Preferably, the above-mentioned polynucleotide(s) is (are) attached to or immobilized on a solid support, substrate, surface, platform or matrix, more preferably microarray/biochip.

It is particularly preferred that said kit comprises (ia) a miRNA-specific primer for reverse transcription of miRNA in miRNA-specific cDNA for a single miRNA or at least two miRNA-specific primers for reverse transcription of miRNAs in miRNA-specific cDNAs for at least 2, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153 miRNAs comprised in a set of miRNAs, wherein the nucleotide sequence of said miRNA or the nucleotide sequences of said miRNAs is (are) selected from the group consisting of SEQ ID NO: 1 to SEQ ID NO: 153, and more preferably at least one further miRNA-specific primer for reverse transcription of miRNA in miRNA-specific cDNA for at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)) comprised in the above-mentioned miRNA set, wherein the nucleotide sequence of said miRNA is selected from the group consisting of SEQ ID NO: 154 to SEQ ID NO: 241, and (ib) preferably, a primer set comprising a forward primer which is specific for the cDNA obtained from the miRNA and an universal reverse primer for amplifying the cDNA obtained from the miRNA via real time polymerase chain reaction (RT-PCR) such as real time quantitative polymerase chain reaction (RT qPCR) for the single cDNA obtained from the miRNA or at least two primer sets comprising a forward primer which is specific for the single cDNA obtained from the miRNA and an universal reverse primer for amplifying the cDNA obtained from the miRNA via real time polymerase chain reaction (RT-PCR) such as real time quantitative polymerase chain reaction (RT qPCR) for at least 2, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153 cDNAs obtained from miRNAs comprised in the set of miRNAs, wherein said cDNA is complementary to the nucleotide sequence of the miRNA or said cDNAs are complementary to the nucleotide sequences of miRNAs selected from the group consisting of SEQ ID NO: 1 to SEQ ID NO: 153, and more preferably at least one further primer set comprising a forward primer which is specific for the cDNA obtained from the miRNA and an universal reverse primer for amplifying the cDNA obtained from the miRNA via real time polymerase chain reaction (RT-PCR) such as real time quantitative polymerase chain reaction (RT qPCR) for at least one further cDNA obtained from the miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 cDNA(s) obtained from the miRNA(s)) comprised in the above-mentioned set, wherein said cDNA is complementary to the nucleotide sequence of the miRNA selected from the group consisting of SEQ ID NO: 154 to SEQ ID NO: 241, and (ic) optionally at least one of the means selected from the group consisting of: at least one human blood sample, e.g. serum, plasma, or blood cells, or at least one sample of total RNA extracted from a human blood sample, means to extract RNA from a blood sample, additional means to carry out the reverse transcriptase reaction (miRNA in cDNA) (e.g. reverse transcriptase (RT) enzyme, puffers, dNTPs, RNAse inhibitor), additional means to carry out real time polymerase chain reaction (RT-PCR) such as real time quantitative PCR (RT qPCR) (e.g. enzymes, puffers, water), means for labelling (e.g. fluorescent label and/or quencher), positive controls for reverse transcriptase reaction and real time PCR, and means for analysing the real time polymerase chain reaction (RT-PCR) result, e.g. for determining an expression profile of a miRNA or a set comprising, essentially consisting of, or consisting of at least 2 miRNAs, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153 miRNAs, representative for an acute coronary syndrome in a blood sample from a human, particularly human patient, wherein the nucleotide sequence of said miRNA or the nucleotide sequences of said miRNAs is (are) selected from the group consisting of SEQ ID NO: 1 to SEQ ID NO: 153, a fragment thereof, and a sequence having at least 80% sequence identity thereto, and more preferably for determining an expression profile of at least one further miRNA comprised in said miRNA set (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)), wherein the nucleotide sequence of the at least one further miRNA is selected from the group consisting of SEQ ID NO: 154 to SEQ ID NO: 241, a fragment thereof, and a sequence having at least 80% sequence identity thereto.

The primer as defined in (i) above may also be an oligo-dT primer, e.g. if the miRNA comprises a polyA tail (e.g. as result of a miRNA elongation, for example, subsequent to RNA extraction) or a miRNA specific looped RT primer.

It is further preferred that said kit comprises means for conducting next generation sequencing in order to determine an expression profile of a miRNA or a set comprising, essentially consisting of, or consisting of at least two miRNAs representative for an acute coronary syndrome in a blood sample from a human, particularly human patient, wherein the nucleotide sequence of said miRNA or the nucleotide sequences of said miRNAs is (are) selected from the group consisting of SEQ ID NO: 1 to SEQ ID NO: 283, particularly of SEQ ID NO: 1 to SEQ ID NO: 153, a fragment thereof, and a sequence having at least 80% sequence identity thereto. Preferably, said kit further comprises at least one human blood sample, e.g. blood serum, blood plasma, or blood cells. It is also preferred that said kit comprises at least one sample of total RNA extracted from a blood sample of a human, particularly human patient.

As to the definition of the miRNA fragment, miRNA variant, or miRNA fragment variant mentioned above and as to the preferred miRNA or sets of miRNAs detected, it is referred to the second aspect of the present invention.

As already mentioned above, the kit may comprise, as a first alternative, (ii) at least one reference.

It is preferred that said reference is comprised on at least one data carrier.

The at least one reference may allow for the diagnosis and/or prognosis of an acute coronary syndrome. The at least one reference may be any reference which allows for the diagnosis and/or prognosis of an acute coronary syndrome, e.g. indicated reference data or value(s). As mentioned above (second aspect of the present invention, first alternative of step (ii)), said reference may be, in the simplest case/form, a reference control, for example, the indication of reference expression level(s) of the same miRNA(s) tested in the human, particularly human patient, to be diagnosed, but determined in the blood of a human known to be healthy, i.e. not suffering from an acute coronary syndrome, and/or the indication of reference expression level(s) of the same miRNA(s) tested in the human, particularly human patient, to be diagnosed, but determined in a human known to suffer from an acute coronary syndrome (e.g. myocardial infarction such as non-ST segment elevation myocardial infraction or ST segment elevation myocardial infarction, or Unstable angina (UA), or the like).

It is particularly preferred that said reference is a reference expression profile (data) of at least one subject, preferably the reference is an average expression profile (data) of at least 2 to 40 subjects, more preferably at least 10 to 25 subjects, and most preferably at least 15 to 20 subjects, with one known clinical condition which is an acute coronary syndrome, or which is no acute coronary syndrome (i.e. healthy/healthiness), wherein the reference expression profile is the profile of a (single) miRNA that has a nucleotide sequence that essentially corresponds (is essentially identical), preferably that corresponds (is identical), to the nucleotide sequence of the miRNA which expression profile is determinable by the means of (i) or is the profile of a set comprising at least two miRNAs that have nucleotide sequences that essentially correspond (are essentially identical), preferably that correspond (are identical), to the nucleotide sequences of the miRNAs which expression profile is determinable by the means of (i). It should be noted that said subject(s) is (are) human(s). Said subject(s) may also be designated as control subject(s).

The term "essentially corresponds (essentially identical)", as used in this aspect of the present invention, means that the miRNA(s) which expression profile is determinable by the means of (i) and the miRNA(s) of the reference expression profile may slightly differ in their nucleotide sequence, whereas said difference is so marginal that it may still allow for the diagnosis and/or prognosis of an acute coronary syndrome. Preferably, the nucleotide sequence(s) of the miRNA(s) which expression profile is determinable by the means of (i) and the nucleotide sequence(s) of the miRNA(s) of the reference expression profile differ in 1 to 5, more preferably in 1 to 3, and most preferably in 1 to 2 nucleotides, i.e. in 1, 2, 3, 4, or 5 nucleotides. It is preferred that said difference resides in 1 to 5, more preferably 1 to 3, and most preferably 1 to 2 nucleotide mutations, i.e. 1, 2, 3, 4, or 5 nucleotide mutations (e.g. substitutions, additions, insertions, and/or deletions).

The at least one reference, particularly the above-mentioned reference control (reference information) or the above-mentioned reference expression profile (data) may be comprised in the kit in form of or on an information leaflet/information sheet (e.g. for comparing tested single reference miRNA biomarkers/data with the expression profile data of a human, particularly human patient, to be diagnosed and/or prognosed), or may be comprised, e.g. saved, on a or at least one data carrier (e.g. for comparing tested sets of miRNA biomarkers/data with the expression profile data of a human, particularly human patient, to be diagnosed and/or prognosed). Said data carrier may be an electronically data carrier such as a floppy disk, a compact disk (CD), or a digital versatile disk (DVD).

Preferably, it is indicated, e.g. on the information leaflet/information sheet or data carrier, in which type of blood sample (e.g. whole blood or blood fraction such as serum or plasma) and/or from which (control) subject(s) (e.g. gender and/or age or stage of life), the (average) reference expression profile (data), which is (are) provided with the kit, has (have) been determined. It is preferred that the expression profile (data) of the human, particularly human patient, will be determined in the same type of blood sample and/or will be obtained from a human, particularly human patient, of the same gender and/or similar age or stage of life.

Said reference may also be an algorithm or mathematical function, e.g. obtained using a machine learning approach. With said algorithm or mathematical function, the algorithm or mathematical function mentioned in a preferred embodiment of the first alternative of step (ii) of the method of the second aspect is particularly meant (see above). Said reference may further be a computer program, wherein the algorithm or mathematical function is comprised. Preferably, said algorithm or mathematical function is trained by reference data (e.g. miRNA reference expression data/profiles from humans known to be healthy and/or miRNA reference expression data/profiles of humans known to suffer from an acute coronary syndrome) to discriminate between the two or more statistical classes (the two or more clinical conditions, e.g. the two conditions healthy or suffering from an acute coronary syndrome). Preferably, the algorithm or mathematical function is comprised, e.g. saved, on a data carrier comprised in the kit or the computer program, wherein the algorithm or mathematical function is comprised, is comprised, e.g. saved, on a data carrier comprised in the kit. The data carrier can be a data carrier as described above.

The kit may alternatively comprise an access code, preferably comprised on a data carrier, which allows the access to a database, e.g. an internet database, a centralized, or a decentralized database, where (i) the reference, preferably the (average) reference expression profile (data), is comprised, or (ii) where a computer program comprising the reference, preferably the (average) reference expression profile (data), can be downloaded.

More than one reference may be comprised in the kit, e.g. 2, 3, 4, 5, or more references. Thus, for example, reference (expression profile) data/reference information may be comprised as or on an information leaflet/information sheet (e.g. for comparing tested single reference miRNA biomarkers/data with the expression profile data of a human, particularly human patient, to be diagnosed) and/or may be comprised in a computer program as mentioned above (e.g. for comparing tested sets of miRNA biomarkers/data with the expression profile data of a human, particularly human patient, to be diagnosed). Further, for example, reference (expression profile) data/reference information may be comprised as or on an information leaflet/information sheet and/or may be comprised on a data carrier as described above. Furthermore, the kit may comprise more than one algorithm or mathematical function, e.g. two algorithms or mathematical functions, e.g. one trained to discriminate between a healthy condition and an acute coronary syndrome and one trained to discriminate between a myocardial infarction and an Unstable angina (UA), e.g. as part of a computer program.

As already mentioned above, the kit may comprise, as a second alternative, (ii) at least one algorithm or mathematical function.

It is preferred that said algorithm or mathematical function is comprised on at least one data carrier.

With said algorithm or mathematical function, the algorithm or mathematical function mentioned in the second alternative of step (ii) of the method of the second aspect is particularly meant. The at least one algorithm or mathematical function may allow for the diagnosis and/or prognosis of an acute coronary syndrome. Particularly, the application of the at least one algorithm or mathematical function to the expression profile (data) of the human, particularly human patient, may allow for the diagnosis and/or prognosis of an acute coronary syndrome. The at least one algorithm or mathematical function may be any algorithm or mathematical function which allows for the diagnosis and/or prognosis of an acute coronary syndrome.

Preferably, the algorithm or mathematical function is obtained from a reference expression profile (data) of at least one subject, preferably of at least 2 to 40 subjects, more preferably of at least 10 to 25 subjects, and most preferably of at least 15 to 20 subjects, e.g. of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with one known clinical condition which is an acute coronary syndrome, or which is no acute coronary syndrome (i.e. healthy/healthiness), wherein the reference expression profile is the profile of a (single) miRNA that has a nucleotide sequence that essentially corresponds (is essentially identical), preferably that corresponds (is identical), to the nucleotide sequence of the miRNA which expression profile is determinable by the means of (i), or is the profile of a set comprising at least two miRNAs that have nucleotide sequences that essentially correspond (are essentially identical), preferably that correspond (are identical), to the nucleotide sequences of the miRNAs which expression profile is determinable by the means of (i).

It is also preferred that the algorithm or mathematical function is obtained from reference expression profiles (data) of at least two subjects, preferably of at least 3 to 40 subjects, more preferably of at least 10 to 25 subjects, and most preferably of at least 15 to 20 subjects, e.g. of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with at least two known clinical conditions (only one known clinical condition per subject), preferably at least 2 to 5, more preferably at least 2 to 4 (e.g. at least 2, 3, 4, or 5) known clinical conditions, which are acute coronary syndrome and any other known clinical condition(s), wherein the reference expression profiles are the profiles of a (single) miRNA that has a nucleotide sequence that essentially corresponds (is essentially identical), preferably that corresponds (is identical), to the nucleotide sequence of the miRNA which expression profile is determinable by the means of (i) or are the profiles of a set comprising at least two miRNAs that have nucleotide sequences that essentially correspond (are essentially identical), preferably that correspond (are identical), to the nucleotide sequences of the miRNAs which expression profile is determinable by the means of (i). It is preferred that the two known clinical conditions are an acute coronary syndrome and no acute coronary syndrome. It should be noted that said subject(s) is (are) human(s). Said subject(s) may also be designated as control subject(s).

The term "essentially corresponds (essentially identical)", as used in this aspect of the present invention, means that the miRNA(s) which expression profile is determinable by the means of (i) and the miRNA(s) of the reference expression profile may slightly differ in their nucleotide sequence, whereas said difference is so marginal that it may still allow for the diagnosis and/or prognosis of an acute coronary syndrome. Preferably, the nucleotide sequence(s) of the miRNA(s) which expression profile is determinable by the means of (i) and the nucleotide sequence(s) of the miRNA(s) of the reference expression profile differ in 1 to 5, more preferably in 1 to 3, and most preferably in 1 to 2 nucleotides, i.e. in 1, 2, 3, 4, or 5 nucleotides. It is preferred that said difference resides in 1 to 5, more preferably 1 to 3, and most preferably 1 to 2 nucleotide mutations, i.e. 1, 2, 3, 4, or 5 nucleotide mutations (e.g. substitutions, additions, insertions, and/or deletions).

Preferably, it is indicated in which type of blood sample (e.g. whole blood or blood fraction such as serum or plasma) and/or from which (control) subject(s) (e.g. gender and/or age or stage of life), the (average) reference expression profile (data), which is (are) provided with the kit, has (have) been determined. It is preferred that the expression profile (data) of the human, particularly human patient, will be determined in the same type of blood sample and/or will be obtained from a human, particularly human patient, of the same gender and/or similar age or stage of life.

The at least one algorithm or mathematical function is preferably comprised, e.g. saved, on at least one data carrier. Said data carrier may be an electronically data carrier such as a floppy disk, a compact disk (CD), or a digital versatile disk (DVD) (e.g. for comparing tested sets of miRNA biomarkers/data with the expression profile data of a human, particularly human patient, to be diagnosed and/or prognosed). The at least one algorithm or mathematical function may further be comprised in a computer program which is saved on an electronically data carrier.

The kit may alternatively comprise an access code, preferably comprised on a data carrier, which allows the access to a database, e.g. an internet database, a centralized, or a decentralized database, where (i) the algorithm or mathematical function is comprised, or (ii) where a computer program comprising the algorithm or mathematical function can be downloaded.

More than one algorithm or mathematical function, e.g. 2, 3, 4, 5 algorithms or mathematical functions, may be comprised on one or more data carrier(s).

As described above, the kit of the present invention may also comprise both afore-mentioned alternatives (ii) at least one reference and algorithm or mathematical function.

It is preferred that said reference and algorithm or mathematical function are comprised on at least one data carrier.

For example, the kit may comprise (i) references (data), preferably (average) reference expression profile(s) (data), which may be comprised on an information leaflet and/or on a compact disk (CD), e.g. two expression profiles (data), for example, one from a subject(s) known to be healthy and one from a subject(s) known to have an acute coronary syndrome, and (ii) algorithms or mathematical functions, which may be comprised on a compact disc (CD) and/or on a digital versatile disk (DVD), e.g. two algorithms or mathematical functions, for example, one obtained from a reference expression profile of a subject(s) known to be healthy and one obtained from a reference expression profile of a subject(s) known to have an acute coronary syndrome.

As to the reference and algorithm or mathematical function, it is also referred to the method of the second aspect of the present invention, particularly to the first and second alternative of step (ii) of the method according to the second aspect of the present invention, respectively (see above).

In a fifth aspect, the above-mentioned kits only comprise (i) the above-mentioned means for determining an expression profile of a miRNA or a set comprising at least two miRNAs representative for an acute coronary syndrome in a blood sample from a human, particularly human patient, wherein the nucleotide sequence of said miRNA or the nucleotide sequences of said miRNAs is (are) selected form the group consisting of SEQ ID NO: 1 to SEQ ID NO: 283, a fragment thereof, and a sequence having at least 80% sequence identity thereto, and only optionally comprise (ii) the above-mentioned at least one reference and/or algorithm or mathematical function, which is (are) preferably comprised on at least one data carrier. As to the preferred miRNA(s) and the preferred embodiments with respect to the means (item (i) of the kit), it is referred to the second to fourth aspect of the present invention.

Cardiac Troponins are currently the best validated biomarkers for the diagnosis of the infract size of AMI. However, measured amounts of Troponin proteins are usually not released from damaged myocardium before 4 to 8 hours after onset of symptoms making an early biomarker based diagnosis of AMI rather difficult. Thus, a plurality of AMI patients will still be Troponin-negative during physical examination although AMI already occurred. The inventors of the present invention surprisingly found that the expression levels of three miRNAs, namely hsa-miR-145 (SEQ ID NO: 181), hsa-miR-223 (SEQ ID NO: 240), and hsa-miR-30c (SEQ ID NO: 241) directly correlate with infract size estimated by Troponin T release. Said miRNAs are significantly up-regulated in AMI and show high correlation to Troponin T levels. Said miRNAs are also earlier detectable in human blood than Troponin. Accordingly, hsa-miR-145 (SEQ ID NO: 181), hsa-miR-223 (SEQ ID NO: 240), and hsa-miR-30c (SEQ ID NO: 241) are biomarkers in order to predict/estimate heart infarct size of a human patient.

Thus, in a sixth aspect, the present invention provides (the use of) a polynucleotide for detecting a miRNA or a set comprising at least two polynucleotides for detecting a set comprising at least two miRNAs for predicting, estimating and/or determining the heart infract size, wherein the nucleotide sequence of said miRNA or the nucleotide sequences of said miRNAs is (are) selected from the group consisting of SEQ ID NO: 181 (hsa-miR-145), SEQ ID NO: 240 (hsa-miR-223), and SEQ ID NO: 241 (hsa-miR-30c).

Said polynucleotide(s) (probe(s)) may also be present as polynucleotide fragments, polynucleotide variants, or polynucleotide fragment variants. As to the definition of said polynucleotide fragments, polynucleotide variants, or polynucleotide fragment variants, it is referred to the first aspect of the present invention.

In a seventh aspect, the present invention relates to a miRNA or a set comprising at least two miRNAs as biomarker(s) for the diagnosis and/or prognosis of an acute coronary syndrome, wherein the nucleotide sequence of said miRNA or the nucleotide sequences of said miRNAs is (are) selected from the group consisting of SEQ ID NO: 1 to 283. In a preferred embodiment, the present invention relates to a miRNA or a set comprising at least two miRNAs as biomarker(s) for the diagnosis and/or prognosis of an acute coronary syndrome, wherein the nucleotide sequence of said miRNA or the nucleotide sequences of said miRNAs is (are) selected from the group consisting of SEQ ID NO: 1 to 153. In a particularly preferred embodiment, said miRNA set comprises at least one further miRNA, wherein the nucleotide sequence of said miRNA is selected from the group consisting of SEQ ID NO: 154 to 241. In another preferred embodiment, the present invention relates to a miRNA as biomarker for the diagnosis and/or prognosis of an acute coronary syndrome, wherein the nucleotide sequence of said miRNA is selected from the list of FIG. 29, or the present invention relates to a set comprising at least two miRNAs as biomarkers for the diagnosis and/or prognosis of an acute coronary syndrome, wherein the nucleotide sequences of said miRNAs are selected from one or more sets listed in FIG. 28 and/or FIG. 30.

In a further aspect, the present invention provides a method for predicting, estimating and/or determining the heart infarct size comprising the steps of:

(i) determining an expression profile of a miRNA or a set comprising, essentially consisting of, or consisting of at least two miRNAs, preferably at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152 or 153 miRNAs, in a blood sample from a human, wherein the nucleotide sequence of said miRNA or the nucleotide sequences of said miRNAs is (are) selected from the group consisting of SEQ ID NO: 1 to SEQ ID NO: 153, particularly of SEQ ID NO: 181 (hsa-miR-145), SEQ ID NO: 240 (hsa-miR-223), and SEQ ID NO: 241 (hsa-miR-30c), a fragment thereof, and a sequence having at least 80% sequence identity thereto, and (ii) comparing said miRNA expression profile to a reference, wherein the comparison of said expression profile to said reference allows for predicting, estimating and/or determining heart infarct size.

As to the definition of the reference, expression profile, the miRNA fragment, miRNA variant, or miRNA fragment variant mentioned above, it is referred to the second aspect of the present invention.

In another further aspect, the present invention relates to a method for diagnosing and/or prognosing of an acute coronary syndrome comprising the steps of:

(i) providing a polynucleotide according to the first aspect of the present invention for detecting a miRNA representative for an acute coronary syndrome in a human blood sample or a set comprising at least two polynucleotides according to the first aspect of the present invention for detecting a set comprising at least two miRNAs representative for an acute coronary syndrome in a human blood sample, wherein the nucleotide sequence of said miRNA or the nucleotide sequences of said miRNAs is (are) selected from the group consisting of SEQ ID NO: 1 to SEQ ID NO: 283, particularly of SEQ ID NO: 1 to SEQ ID NO: 153, a fragment thereof, and a sequence having at least 80% sequence identity thereto, (ii) using the polynucleotide(s) provided in (i) for determining an miRNA expression profile in a blood sample from a human with an unknown clinical condition, comparing said expression profile to a reference, diagnosing or prognosing the clinical condition of the human individual on the basis of said comparison.

In preferred embodiments, the above-mentioned set of miRNAs comprises at least one further miRNA (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88 miRNA(s)), wherein the nucleotide sequence of said miRNA is selected from the group consisting of SEQ ID NO: 154 to 241, a fragment thereof, and a sequence having at least 80% sequence identity thereto, particularly in order to complement a set comprising at least two miRNAs having nucleotide sequences selected from the group consisting of SEQ ID NO: 1 to SEQ ID NO: 153.

The term "human with an unknown clinical condition" refers to a human which may be a healthy or may be diseased, e.g. suffer from an acute coronary syndrome (e.g. myocardial infarction or Unstable angina (UA)) or suffer from another disease not tested/known. It also refers to a human which may suffer from a specific type of myocardial infarction, namely from non-ST segment elevation myocardial infraction (NSTEMI), or from ST segment elevation myocardial infarction (STEMI). It may further refer to a human that will develop the above-mentioned syndrome as the inventors of the present invention surprisingly found that miRNAs representative for an acute coronary syndrome are already present in the blood before an acute coronary syndrome occurs or during the early stage of myocardial injury.

As to the definition of said miRNA fragments, miRNA variants, or miRNA fragment variants, it is referred to the second aspect of the present invention. As to the reference and preferred embodiments of said reference, the preferred embodiments of the blood sample and the definition of an expression profile, it is also referred to the second aspect of the present invention.

In other aspects, the present invention is composed of the following:

In a further aspect of the invention sets of at least two miRNAs for diagnosing and/or prognosing of an acute coronary syndrome in a blood sample from a human are disclosed.

In order to be able to better discriminate, for example, between two or more clinical conditions, e.g. presence of acute coronary syndrome and absence of acute coronary syndrome (e.g. healthy controls), for a defined set (signature) of miRNA biomarkers, the inventors of the present invention applied a machine learning approach (e.g. t-test, AUC, support vector machine, hierarchical clustering, or k-means) which leads to an algorithm or a mathematical function that is trained by reference data (i.e. data of reference miRNA expression profiles from the two or more clinical conditions, e.g. presence of acute coronary syndrome and absence of acute coronary syndrome, for the defined set (signature) of miRNA markers) to discriminate between the two or more statistical classes (i.e. two or more clinical conditions), e.g. presence of acute coronary syndrome and absence of acute coronary syndrome.

The inventors of the present invention surprisingly found that this approach yields miRNA sets (signatures) that can predict or determine with very high diagnostic accuracy, specificity and sensitivity acute coronary syndrome in a human patient Said miRNA sets (Set No 1-1005, FIG. 28) comprise at least two miRNAs.

An exemplarily approach to arrive at miRNA sets (signatures) that correlate with the presence of an acute coronary syndrome is summarized below.

Step 1: Total RNA (or subfractions thereof) is extracted from a blood (including plasma, serum, PBMC or other blood fractions) samples of human subjects with acute coronary syndrome and controls using suitable kits and/or purification methods.

Step 2: From the respective sample, the quantity (expression level) of at least two miRNAs selected from the group of SEQ ID NO: 1 to SEQ ID NO: 279 is measured using experimental techniques. These techniques include, but are not restricted to, array based approaches, amplification methods (PCR, RT-PCR, or qPCR), sequencing, next generation sequencing, and/or mass spectroscopy.

Step 3: In order to gather information on the diagnostic/prognostic value and the redundancy of each of the single miRNA biomarkers, mathematical methods are applied. These methods include, but are not restricted to, basic mathematic approaches (e.g. Fold Quotients, Signal-to-Noise ratios, Correlation), statistical methods as hypothesis tests (e.g. t-test, Wilcoxon-Mann-Whitney test), the Area under the Receiver operator Characteristics Curve, information theory approaches, (e.g. the Mutual Information, Cross-entropy), probability theory (e.g. joint and conditional probabilities) or combinations and modifications of the previously mentioned methods.

Step 4: The information gathered in step 3) is used to estimate for each miRNA biomarker the diagnostic content or value. Usually, however, this diagnostic value is too small to get a highly accurate diagnosis with accuracy rates, specificities and sensitivities beyond the 80% barrier. The diagnostic content of the miRNAs suitable for diagnosing/prognosing an acute coronary syndrome is listed in FIG. 29

Step 5: In order to increase the performance for diagnosing/prognosing of individuals suffering from acute coronary syndrome, more than one miRNA biomarker needs to be employed. Thus statistical learning/machine learning/bioinformatics/computational approaches are applied for set selection in order to select/define sets of miRNA biomarkers that are tailored for the detection of an acute coronary syndrome. These techniques include, but are not restricted to, Wrapper subset selection techniques (e.g. forward step-wise, backward step-wise, combinatorial approaches, optimization approaches), filter subset selection methods (e.g. the methods mentioned in Step 3), principal component analysis, or combinations and modifications of such methods (e.g. hybrid approaches).

Step 6: The subsets, selected/defined in Step 5, which may range from only a small number (at least two for the set) to all measured biomarkers, are then used to carry out a diagnosis/prognosis of an acute coronary syndrome. To this end, statistical learning/machine learning/bioinformatics/computational approaches are applied that include but are not restricted to any type of supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

Step 7: By combination of subset selection (Step 5) and machine learning approaches (Step 6) an algorithm or a mathematical function for diagnosing/prognosing acute coronary syndrome is obtained. This algorithm or mathematical function is applied to a miRNA expression profile (miRNA expression profile data) of an individual (patient) to be diagnosed for an acute coronary syndrome.

Polynucleotides are disclosed for detecting a set comprising at least two miRNAs for diagnosing and/or prognosing of an acute coronary syndrome in a blood sample from a human. The said sets of at least two miRNAs are selected from the sets (Set No. 1-1005) listed in FIG. 28.

It is understood that the said sets of polynucleotides are complementary to the sets of miRNAs (Set No. 1-1005) for diagnosing and/or prognosing of an acute coronary syndrome in a blood sample from a human and/or are fragments of these and/or have at least 80% sequence identity to these sequences.

The individual sets of polynucleotides for detecting a set comprising at least two miRNAs may also be combined with each other, e.g. polynucleotides for detecting Set No. 1 with polynucleotides for detecting Set No. 2, polynucleotides for detecting Set No. 2 with polynucleotides for detecting Set No. 3, polynucleotides for detecting Set No. 1 with polynucleotides for detecting Set No. 2 and Set No. 3, polynucleotides for detecting Set No. 3 with polynucleotides for detecting Set No. 5 and Set No. 8, etc.

In further embodiment, sets of 2, 3, 4, 5, 6, 7, 8, 9, 10, 11, 12, 13, 14, 15, 16, 17, 18, 19, 20, 21, 22, 23, 24, or 25 polynucleotides are disclosed for detecting sets comprising at least two miRNAs for diagnosing and/or prognosing of an acute coronary syndrome in a blood sample from a human, which are selected from one or more sets (Set No. 1-1005) listed in FIG. 28.

In a further embodiment, a method for diagnosing and/or prognosing of an acute coronary syndrome is disclosed, comprising the steps of:

(i) determining an expression profile of a set comprising at least two miRNAs representative for an acute coronary syndrome in a blood sample from a human, wherein the nucleotide sequences of said miRNAs are selected from one or more sets (Set No. 1-1005) listed in FIG. 28

(ii) comparing said expression profile to a reference, wherein the comparison of said expression profile to said reference allows for the diagnosis and/or prognosis of an acute coronary syndrome, and/or applying an algorithm or a mathematical function to said expression profile, wherein the application of said algorithm or mathematical function to said expression profile allows for the diagnosis and/or prognosis of an acute coronary syndrome.

In a further embodiment, a method for diagnosing and/or prognosing of an acute coronary syndrome is disclosed, comprising the steps of:

(i) determining an expression profile of a set comprising 4, 5, 6, 7, 8, 9, 10, 11, 12, 13, 14, 15, 16, 17, 18, 19, 20, 21, 22, 23, 24, 25, or more miRNAs representative for an acute coronary syndrome in a blood sample from a human, wherein the nucleotide sequences of said miRNAs comprise at least one set (Set No. 1-1005) listed in FIG. 28

(ii) comparing said expression profile to a reference, wherein the comparison of said expression profile to said reference allows for the diagnosis and/or prognosis of an acute coronary syndrome, and/or applying an algorithm or a mathematical function to said expression profile, wherein the application of said algorithm or mathematical function to said expression profile allows for the diagnosis and/or prognosis of an acute coronary syndrome.

In a further embodiment, a kit for diagnosing and/or prognosing of an acute coronary syndrome is disclosed comprising:

(i) means for determining an expression profile of a set comprising at 4, 5, 6, 7, 8, 9, 10, 11, 12, 13, 14, 15, 16, 17, 18, 19, 20, 21, 22, 23, 24, 25, or more miRNAs representative for an acute coronary syndrome in a blood sample from a human, wherein the nucleotide sequences of said miRNAs comprise at least one set (Set No. 1-1005) listed FIG. 28 and a sequences having at least 80% sequence identity thereto; and (ii) at least one reference.

In a further embodiment, a kit for diagnosing and/or prognosing of an acute coronary syndrome is disclosed comprising:

(i) means for determining an expression profile of a set comprising at least two miRNAs representative for an acute coronary syndrome in a blood sample from a human, wherein the nucleotide sequences of said miRNAs are selected from the sets (Set No. 1-1005) listed FIG. 28 and a sequences having at least 80% sequence identity thereto; and (ii) at least one reference.

In summary, this aspect of the present invention is composed of the following:

A set of polynucleotides for detecting a set comprising at least two miRNAs for diagnosing and/or prognosing of an acute coronary syndrome in a blood sample from a human, wherein the nucleotide sequences of said miRNAs are selected from the group of sets (Set No. 1-1005) listed in FIG. 28.

The set comprising polynucleotides of item 1, wherein
(i) the polynucleotides comprised in the set are complementary to the miRNAs comprised in the set according to claim 1,
(ii) the polynucleotides comprised in the set are fragments of the polynucleotides comprised in the set according to (i), or
polynucleotide fragments according to (ii), or the polynucleotides comprised in the set have at least 80% sequence identity to the polynucleotide sequences of the polynucleotides comprised in the set according to (i) or polynucleotide fragments comprised in the set according to (ii).

A method for diagnosing and/or prognosing of an acute coronary syndrome comprising the steps of:

(i) determining an expression profile of a set comprising at least two miRNAs representative for an acute coronary syndrome in a blood sample from a human, wherein the nucleotide sequences of said miRNAs are selected from the sets (Set No. 1-1005) listed in FIG. 28, fragments thereof, and sequences having at least 80% sequence identity thereto, and (ii) comparing said expression profile to a reference, wherein the comparison of said expression profile to said reference allows for the diagnosis and/or prognosis of an acute coronary syndrome.

4. The method of item 3, wherein the reference is obtained from reference expression profiles of at least two humans with at least two known clinical conditions from which at least one is an acute coronary syndrome, wherein the reference expression profiles are the profiles of a set comprising at least two miRNAs that have nucleotide sequences that correspond to the nucleotide sequences selected in step (i).

5. The method of items 3 or 4, wherein the comparison to the reference comprises the application of an algorithm or mathematical function, preferably obtained using a machine learning approach.

6. A method of items 3 to 5, wherein in step (i) the set comprising at least two polynucleotides according to claims 1 to 2 is used for determining expression profiles of a set comprising at least two miRNAs representative for an acute coronary syndrome in a blood sample from a human.

7. Means for diagnosing and/or prognosing of an acute coronary syndrome comprising set comprising at least two polynucleotides according to item 1 to 2.

8. The means of item 7, wherein said means comprise a biochip comprising a set comprising at least two polynucleotides according to item 1 to 2.

9. A kit for diagnosing and/or prognosing of an acute coronary syndrome comprising means for determining expression profiles of a set comprising at least two miRNAs representative for an acute coronary syndrome in a blood sample from a human, wherein the nucleotide sequence of said miRNAs are selected from the sets (Set No. 1-1005) listed FIG. 28 and a sequences having at least 80% sequence identity thereto; and (ii) at least one reference.

10. The kit of item 9, wherein said kit comprises the means of items 7 or 8.

11. A set of polynucleotides for detecting a set comprising at least two miRNAs for predicting, estimating and/or determining the heart infarct size, wherein the nucleotide sequences of said miRNAs are selected from the group consisting of SEQ ID NO: 181 (hsa-miR-145) and SEQ ID NO: 241 (hsa-miR-30c).

EXAMPLES

The Examples are designed in order to further illustrate the present invention and serve a better understanding. They are not to be construed as limiting the scope of the invention in any way.

Example: 1

Materials and Methods

Patients and Controls

In the present study, 20 patients with acute ST Elevation Myocardial Infarction (STEMI) were included. Acute myocardial infarction (AMI) was diagnosed according to the ESC/AHA redefined guidelines using Troponin-T as key biomarker. Vessel occlusion by an underlying thrombotic event as cause of AMI was confirmed in all patients by early coronary angiography. As control served miRNA profiles from 22 control subjects, which were recruited in the "Biomarker Discovery Center Heidelberg—Pilot Study". To exclude bias due to sample origin or treatment, 7 controls undergoing routine coronary angiography were additionally recruited. The analysis of blood from patients and healthy subjects has been approved by local ethics committees and participants have given written informed consent. Blood from patients with AMI was obtained briefly before coronary angiography. Serial Troponin T levels were assessed using the Elecsys highly sensitive Troponin T assay (Roche, Germany) [17].

MiRNA Expression Profiling from Peripheral Blood Samples

MiRNA expression profiling was performed by personnel blinded to patient characteristics. 5 ml blood was collected from study subjects in PAXgene Blood RNA tubes (BD, USA) and stored at 4° C. until RNA was extracted. Total RNA was isolated from blood cells using the miRNeasy Mini Kit (Qiagen, Germany) and stored at −80° C. Samples were analyzed with the Geniom Real-time Analyzer (febit group, Germany) using the Geniom Biochip miRNA *homo sapiens*. Each array contains 7 replicates of 866 miRNAs and miRNA star sequences as annotated in the Sanger miRBase 12.0 [18]. Sample labelling with biotin was carried out by microfluidic-based enzymatic on-chip labelling of miRNAs (MPEA) as described before [19].

Following hybridization for 16 hours at 42° C. the biochip was washed and signals were measured. The resulting images were evaluated using the Geniom Wizard Software (febit group, Germany). For each array, the median signal intensity of all features was extracted from the raw data file such that for each miRNA seven intensity values were calculated corresponding to each replicate on the array. Following background correction, the seven replicate intensity values of each miRNA were summarized by their median value. To normalize the data across different arrays, quantile normalization was applied and all further analyses were carried out using the normalized and background subtracted intensity values [19]. To this end, we removed those miRNAs having an overall median signal intensity of less than 10. The final data set contained expression levels of 708 miRNAs.

Statistical Analysis

After ensuring approximate normal distribution of the measured intensity values using Shapiro-Wilk test, we carried out parametric t-test (unpaired, two-tailed) for each miRNA separately to detect miRNAs with different expression levels between study groups. The resulting p-values were adjusted for multiple testing by Benjamini-Hochberg equation [20].

In addition to the single biomarker analysis, classification of samples using miRNA patterns was carried out using Support Vector Machines (SVM) as implemented in the R e1071 package. In particular, different kernel SVMs (linear, polynomial, sigmoid, radial basis function) were evaluated, where the cost parameter was sampled from 0.01 to 10 in decimal powers. The measured miRNA profiles were classified using 20 repetitions of standard 10-fold cross-validation. The classification has been carried out using equal class sizes. Since we analyzed 29 controls and 20 patients, in each cross-validation run 20 of 29 control samples were selected randomly. To detect the most suitable set of miRNAs that achieves the best discriminatory performance, a feature extraction (subset selection) method relying on t-test p-values was used. In detail, the following filter technique was applied: The s miRNAs with lowest p-values in the t-test were computed on the training set in each fold of the cross validation, where s was sampled from 1 to 866 in regular intervals. The respective subset was used to train the SVM and to carry out the prediction of the test samples. The mean accuracy, specificity, and sensitivity were calculated for each subset size. To check for overtraining we applied permutation tests. Here, we sampled the class labels randomly and carried out classifications using the applied permuted class labels. All statistical analyzes were performed using R.

Results

Acute ST Elevation Myocardial Infarction Leads to Dysregulation of Specific miRNAs We analyzed the expression of 866 miRNAs and miRNA star sequences in blood cells of the 20 patients with acute myocardial infarction (AMI) and 29 healthy control subjects. Mean age in AMI patients was 59.3±14 years and in controls 44.4±20.4 years (p<0.01). 20% of the AMI and 59% of the control population were female, respectively. According to ECG criteria 15 patients showed signs of inferior/posterior wall infarction and 5 of anterior wall infarction. The mean hsTnT on admission was 363.5±572.5 pg/ml. 9 patients (45%) with AMI had Troponin T levels of <50 pg/ml, and 2 of them were below 14 pg/ml on admission. Because both, gender and age distribution significantly differed between AMI patients and controls, we first analyzed if gender or age impacts on miRNA profiles. However, neither gender nor age had a statistically significant impact on miRNA expression.

Figure 1B:
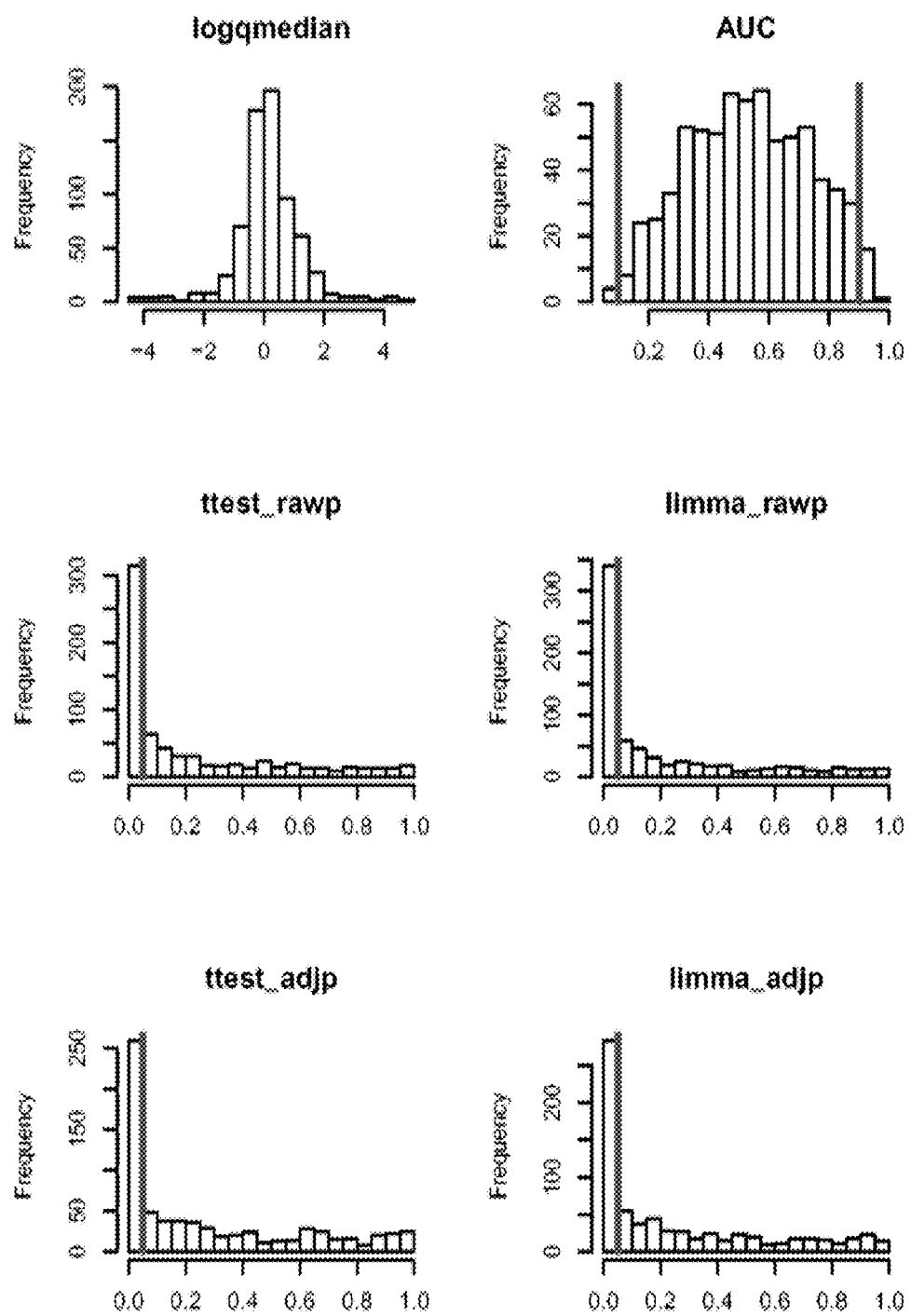
Figure 2:
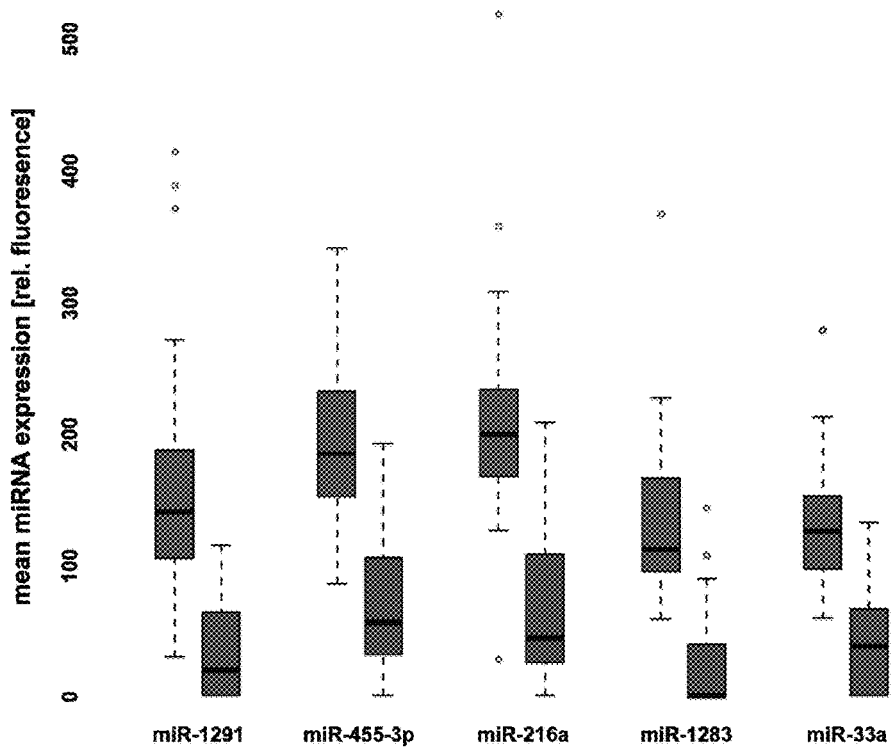
FIG. 2: Specific miRNAs are dysregulated in acute myocardial infarction. Whisker-plots showing median expression values of the five most significantly dysregulated miRNAs (miR-1291, -455-3p, -216a, -1283, and -33a) in patients with myocardial infarction (right bars) in comparison to controls (left bars).

To test for the overall correlation of miRNA expression between cases and controls, we computed the median expression of all miRNAs in both groups on a logarithmic scale. As shown in the scatter plot in FIG. 1A, both groups had a high correlation coefficient of 0.847 and data variance as low as 0.002. After ensuring an approximate normal distribution using Shapiro-Wilk test, we performed two-tailed unpaired t-tests for each miRNA. The respective p-values were adjusted for multiple testing by the Benjamini-Hochberg approach. In total, we detected 67 miRNAs to be significantly dysregulated in blood cells from AMI patients in comparison to controls at an adjusted significance (alpha) level of p<0.001. Histogram plots of the logarithm of fold ratios, the raw t-test p-values and the adjusted p-values are presented in FIG. 1B. A complete list of 241 dysregulated miRNAs is given in FIG. 7. Notably, from the 67 significantly dysregulated miRNAs only 8 (12%) were up-regulated while 59 (88%) were down-regulated in AMI patients. The five most significantly dysregulated miRNAs were miR-1291, miR-455-3p, miR-216a, miR-1283, and miR-33a, which were all down-regulated in comparison to controls (FIG. 2 and Table 1). Two cardiac miRNAs, namely miR-21 and miR-1 were both up-regulated in myocardial infarction (1.6 fold up-regulation of miR-21, p=0.02 and 4.4 fold up-regulation of miR-1, p=0.067).

TABLE 1

Most significantly dysregulated miRNAs in AMI patients.

| miRNA | Mean expression in AMI patients | Mean expression in controls | Fold change | Adjusted p-value |
|---|---|---|---|---|
| miR-1283 | 1.00 | 112.38 | 0.01 | 2.27E−06 |
| miR-455-3p | 56.93 | 184.95 | 0.31 | 3.12E−06 |

TABLE 1-continued

Most significantly dysregulated miRNAs in AMI patients.

| miRNA | Mean expression in AMI patients | Mean expression in controls | Fold change | Adjusted p-value |
|---|---|---|---|---|
| miR-33a | 39.07 | 126.26 | 0.31 | 3.12E-06 |
| miR-216a | 45.15 | 199.40 | 0.23 | 3.23E-06 |
| miR-1291 | 20.21 | 141.03 | 0.14 | 3.30E-06 |
| miR-20b* | 19.07 | 70.09 | 0.27 | 4.51E-06 |
| miR-380* | 32.79 | 86.91 | 0.38 | 5.60E-06 |
| miR-491-3p | 1.00 | 92.62 | 0.01 | 7.39E-06 |
| miR-192* | 54.77 | 112.38 | 0.49 | 1.01E-05 |
| miR-767-5p | 52.74 | 219.15 | 0.24 | 1.08E-05 |

To evaluate the predictive value of miRNA dysregulation on AMI, we calculated Receiver Operator Characteristic curves (ROC) for each of the best miRNAs together with the area under the curve value (AUC). For the most predictive single miRNA, miR-1291, we obtained an AUC value of 0.957. Using miR-1291 we classified 17 of the 20 disease samples and 26 of 29 controls correctly resulting in a specificity of 92.9% and a sensitivity of 85% with a test accuracy of 89.8% (see FIG. 3).

Figure 4A:
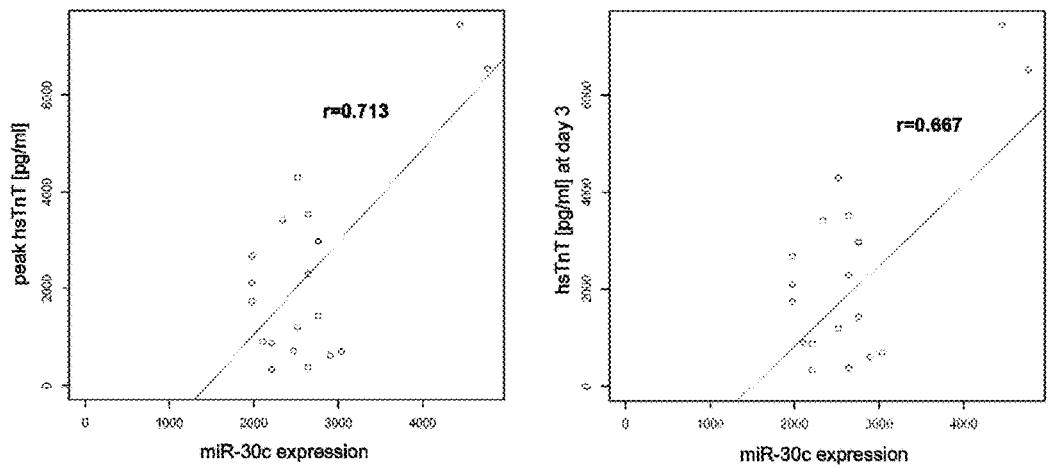
FIGS. 4A-C: MiR-30c and miR-145 levels highly correlate with Troponin T.
Figure 4B:
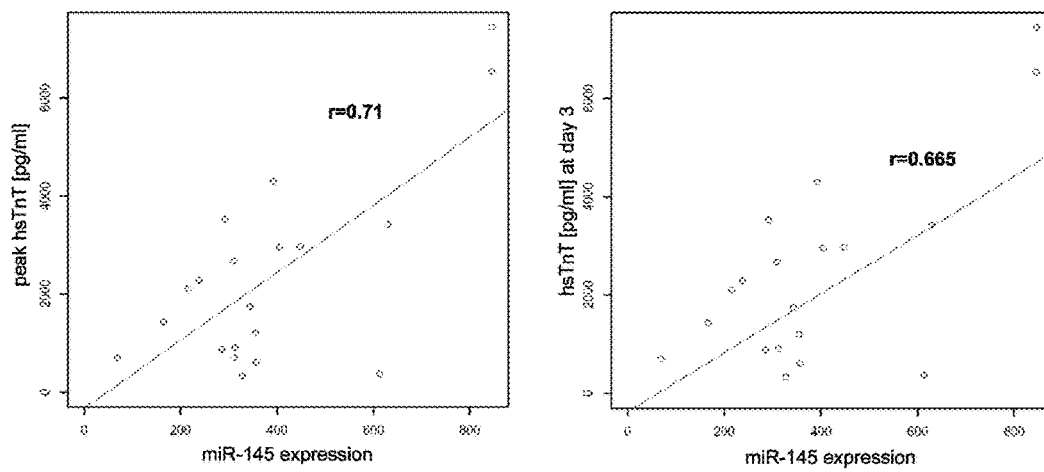
Figure 4C:
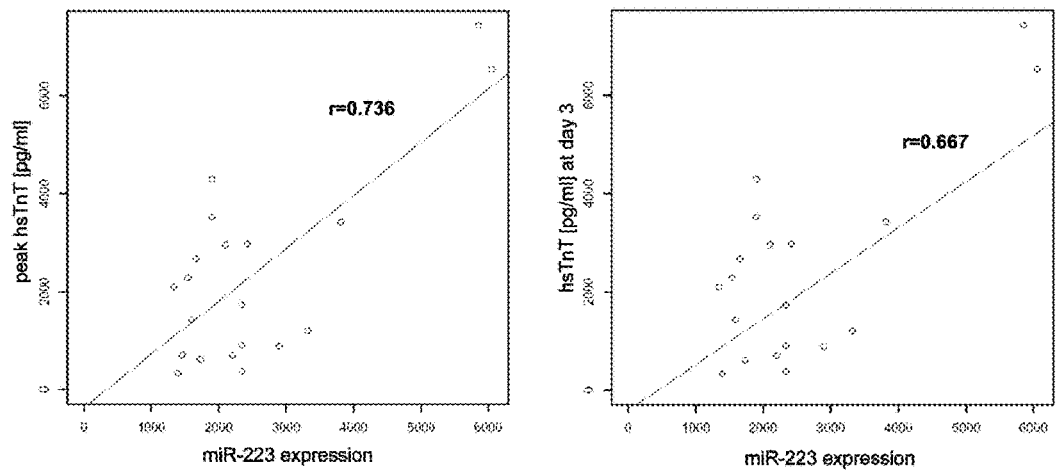

MiR-30c, miR-145, and miR-223 Levels Significantly Correlate with Troponin T Levels With the ability of single miRNAs to predict the presence of AMI, we next wondered if the magnitude of miRNA dysregulation correlates with infarct sizes estimated by Troponin T release (hsTnT). To this end, we computed for all significantly dysregulated miRNAs the correlation between miRNA expression and hsTnT at day 3 and 4. Furthermore, we calculated correlations to peak hsTnT levels. We identified in AMI three significantly upregulated miRNAs that show high correlation to Troponin T levels, with correlation coefficients up to 0.74. FIG. 4 represents the three miRNAs with highest correlation (linear) to Troponin T, miR-30c (A), miR-145 (B), and miR-223 (C) (see also Table 2).

TABLE 2

Correlation of miRNA levels and Troponin T release.

| | Day 3 | | | Peak | | |
|---|---|---|---|---|---|---|
| miRNA | Correlation coefficient to hsTNT | Confidence intervall | p-value | Correlation coefficient to hsTnT | Confidence intervall | p-value |
| miR-30c | 0.667 | 0.31-0.86 | 0.0018 | 0.713 | 0.39-0.88 | 0.0004 |
| miR-145 | 0.665 | 0.30-0.86 | 0.0019 | 0.710 | 0.39-0.88 | 0.0005 |
| miR-223 | 0.667 | 0.32-0.87 | 0.0015 | 0.736 | 0.43-0.89 | 0.0002 |

Complex miRNA Signatures Discriminate AMI Patients from Controls

Although single miRNAs may predict the presence of AMI with good sensitivity and specificity, we tested whether complex miRNA signatures derived from unsupervised hierarchical clustering and supervised classification may improve the sensitivity and specificity.

Figure 5:
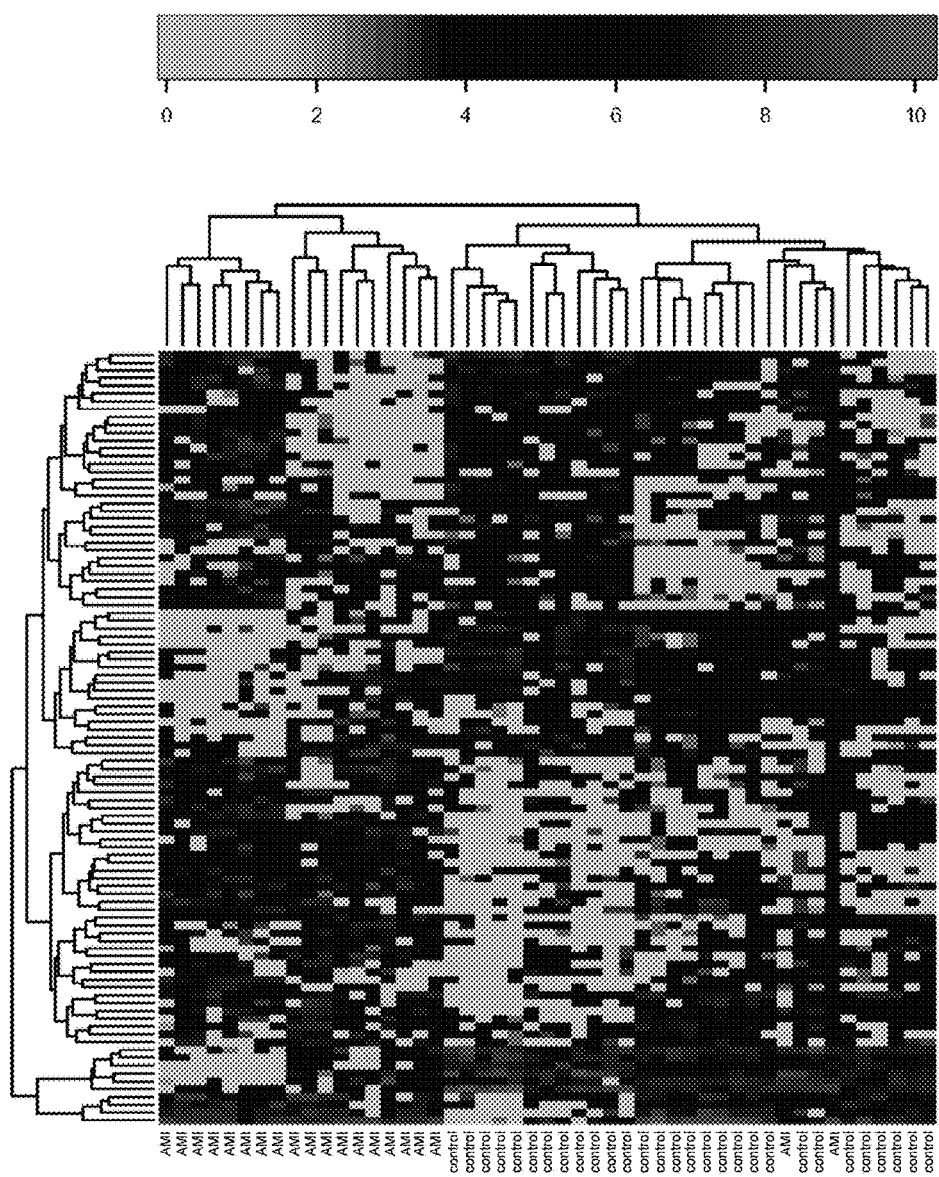
FIG. 5: Hierarchical clustering of miRNA expression levels. Unsupervised hierarchical clustering of expression levels of the 100 most significantly dysregulated miRNAs using the Euclidian distance measure. All AMI patients cluster separately from the controls with only two outliers.
Figure 6A:
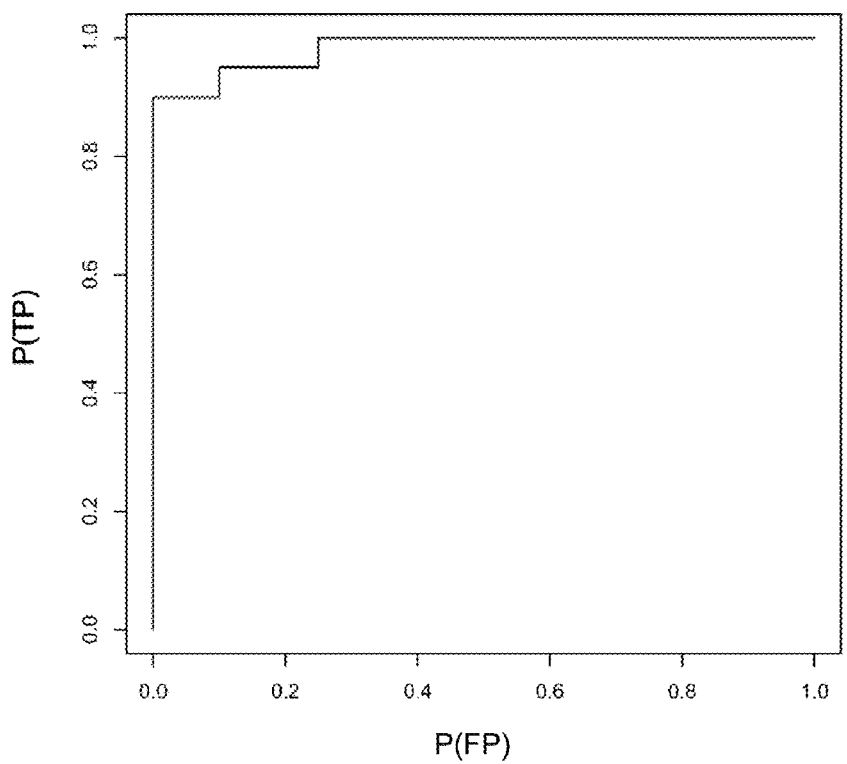
FIGS. 6A-6B: Complex miRNA signatures predict AMI.
Figure 6B:
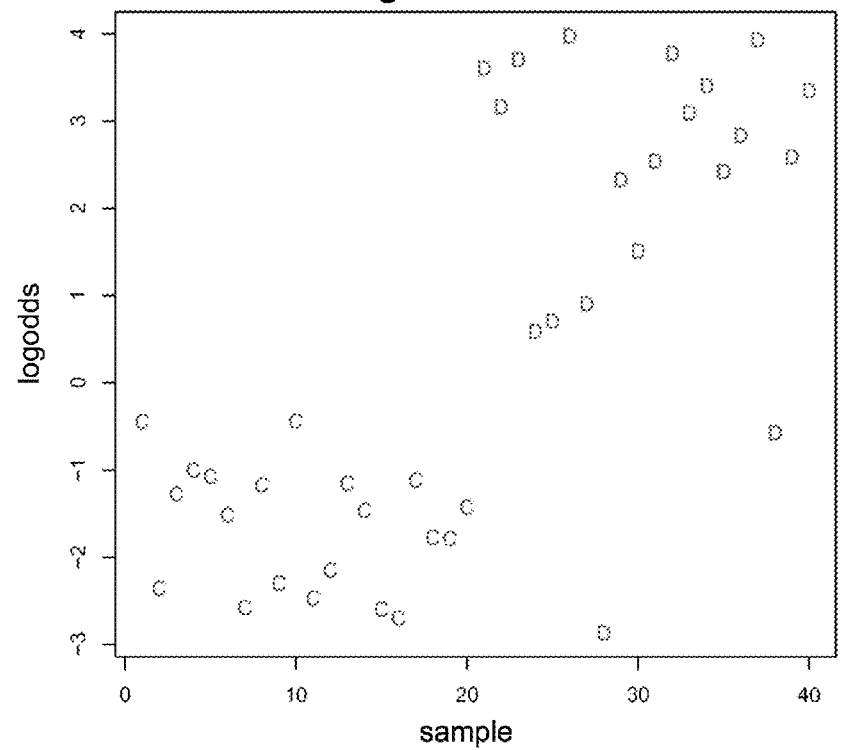

To test for common signatures in AMI patients and controls, we applied hierarchical clustering of expression levels of the 100 most significantly dysregulated miRNAs using the Euclidian distance measure. As shown in FIG. 5, the algorithm correctly clusters all patients and controls separately, with only two outliers. Based on the ability to differentially cluster miRNA patterns in controls and AMI subjects and in order to improve the predictive power of a miRNA-based biomarker screening, we combined the information content of multiple miRNAs by using machine learning techniques. In detail, we applied Support Vector Machines (SVM) with different kernels as described in Materials and Methods. The best results were obtained using radial basis function SVM and a subset of 120 miRNAs. The cross validation procedure has been carried out 20 times to gain additional statistical significance. On average, the selected miRNAs allowed discrimination between blood samples of AMI patients and blood samples of controls with an accuracy of 95%, a specificity of 100%, and a sensitivity of 90% (FIG. 6A). The AUC value for this signature is 0.983. In permutation tests significantly decreased accuracy, specificity, and sensitivity rates were computed, resembling random guessing. As shown in one randomly selected example of the classification algorithm, patients and controls can well be discriminated except for two outliers, leading to a specificity of 100%, a sensitivity of 90%, and a test accuracy of 95% (FIG. 6B).

CONCLUSIONS

Today, biomarkers play a crucial role in the diagnosis of cardiovascular diseases such as acute myocardial infarction and heart failure. However, many of these markers have shortcomings such as reduced sensitivity, not sufficient specificity or do not allow timely diagnosis. A multiple biomarker strategy may circumvent these limitations by adding accuracy and predictive power. To evaluate for first time, if miRNA profiles could potentially serve as a new class of biomarkers, we assessed here whole-genome miRNA expression levels in peripheral blood from patients with acute myocardial infarction (AMI). We find that a unique miRNA signature predicts with high specificity, sensitivity, and accuracy AMI even at a stage where some patients are still Troponin T negative.

In recent studies miRNAs were identified as novel regulators and modifiers of cardiac development, function, and disease [21]. For instance, miRNA-21 controls cardiac fibrosis in response to cardiac overload via ERK-MAP-Kinase signaling [22]. Furthermore, miRNAs were found to be differentially regulated in various cardiac diseases such as ischemic heart disease, arrhythmias, and maladaptive hypertrophy, implicating that specific miRNA signatures might predict distinct disease states and serve as novel biomarkers [8, 9]. We find here that most miRNAs that are dysregulated in AMI patients are not heart-specific. However, this is not surprising, since our miRNA profiles are derived from peripheral blood cells and not myocardial tissue. Hence, miRNAs found to be dysregulated in AMI might equally be derived from other cellular population that play a role in AMI pathophysiology, such as endothelial cells involved in plaque rupture, thrombocytes in aggregation, but also inflammatory cells that are recruited to the ischemic area. Furthermore, miRNAs released from damaged tissue can be taken up by other cells, resulting in convergence of serum and cellular miRNAs [23]. Accordingly, next to the non-cardiac miRNAs we also found cardiac miRNAs such as miR-21, miR-30c, and miR-1 to be up-regulated in blood from AMI patients, implicating that these miRNAs may have been released from ischemic myocardium. Interestingly, in a candidate approach miRNA-1 levels were also found to be elevated in serum of AMI patients [24]. However, with this single biomarker approach, AMI patients could be distinguished from controls only with a moderate sensitivity and specificity (AUC=0.774) [24]. By contrast, to increase the predictive power of miRNA-based diagnosis, we combined here whole-genome miRNA profiling with pattern-recognition algorithms leading to much higher sensitivity and specificity (AUC=0.983) in the diagnosis of AMI.

Cardiac Troponins are currently the best validated biomarkers for the diagnosis of AMI. However, measurable amounts of Troponin proteins are usually not released from damaged myocardium before 4-8 hours after onset of symptoms, making an early biomarker-based diagnosis of AMI rather difficult. Accordingly, 45% of AMI patients included in this study were still Troponin-negative (TnT <50 pg/ml) when entering the catheter laboratory and blood was drawn for miRNA analyses. However, miRNA profiles of these patients also showed the AMI characteristic signature, implicating that miRNA signatures might improve biomarker-based early diagnosis of AMI.

Next to their diagnostic potential, cardiac biomarkers can provide information on disease severity and prognosis [25, 26]. For instance, cardiac Troponin T levels directly correlate with the size of myocardial infarction [27, 28]. Accordingly, we found here that expression levels of three miRNAs, miR-30c, miR-145, and miR-223, significantly correlate with Troponin T levels in AMI patients. Interestingly, miR-30c and miR-233 are highly expressed in the heart and hence might be directly derived from damaged myocardium [29].

Example: 2

Abstract

MicroRNAs (miRNAs) are important regulators of adaptive and maladaptive responses in cardiovascular diseases and hence are considered to be potential therapeutical targets. However, their role as novel biomarkers for the diagnosis of cardiovascular diseases still needs to be systematically evaluated. We assessed here for the first time whole-genome miRNA expression in peripheral total blood samples of patients with acute myocardial infarction (AMI). We identified 121 miRNAs, which are significantly dysregulated in AMI patients in comparison to healthy controls. Amongst these, miR-1291 and miR-663b show the highest sensitivity and specificity for the discrimination of cases from controls. Using a novel self-learning pattern recognition algorithm, we identified a unique signature of 20 miRNAs that predicts AMI with even higher power (specificity=96%, sensitivity=90%, and accuracy=93%). In addition, we show that miR-30c and miR-145 levels correlate with infarct sizes estimated by Troponin T release. The here presented study shows that both, single miRNAs and especially miRNA signatures derived from peripheral blood could be valuable novel biomarkers for cardiovascular diseases.

Introduction

MicroRNAs (miRNAs) represent a group of regulatory elements that enable cells to fine-tune complex gene expression cascades in a wide range of biological processes, such as proliferation, differentiation, apoptosis, and stress-response [38, 41, 55, 71, 72]. In the cardiovascular system, miRNAs are not only important for heart and vascular development, but also play an essential role in cardiac pathophysiology, such as hypertrophy, arrhythmia, and ischemia [36, 40]. However, their potential role as biomarkers for the diagnosis of cardiovascular diseases has not been systematically evaluated yet.

Today, biomarkers play a key role in early diagnosis, risk stratification, and therapeutic management of cardiac diseases such as acute myocardial infarction (AMI) and heart failure [51, 54, 57, 61]. Established biomarkers such as the cardiac troponins and b-type natriuretic peptides were mainly discovered by candidate approach [51, 60]. By contrast, the recent development of high-throughput molecular technologies that allow with a reasonable effort the analysis of whole transcriptomes, proteomes, and metabolomes of individuals at risk, may lead to the discovery of novel biomarkers in an unbiased approach [44, 45].

In the present study we aimed to identify a miRNA signature for the diagnosis of AMI, which is not solely based on the release of miRNAs from necrotic myocardium, but also on active processes involved in the pathogenesis of AMI, like inflammation, plaque rupture, and vascular injury. Therefore, we assessed for the first time the expression of miRNAs on a whole-genome level in total peripheral blood of patients with AMI and identified a unique miRNA signature that predicts myocardial infarction with high specificity and sensitivity, implicating that both, single miRNAs and complex miRNA signatures could be used as novel biomarkers for the diagnosis of cardiovascular diseases.

Materials and Methods

Study Population

According to a priori power analyses (power of 0.95), we included 20 patients with acute ST Elevation Myocardial Infarction (STEMI) and 20 controls in the present study. Acute myocardial infarction (AMI) was diagnosed according to the ESC/AHA redefined guidelines. Vessel occlusion by an underlying thrombotic event as cause of AMI was confirmed in all patients by early coronary angiography. As control served miRNA profiles from 20 control subjects without acute coronary syndrome, who underwent routine coronary angiography (see Table 3 for detailed clinical characteristics). MiRNA profiles from 20 healthy volunteers recruited during the "Biomarker Discovery Center" pilot study served as an internal control. The analysis of blood from patients and controls has been approved by local ethics committees and participants have given written informed consent. Serial Troponin T levels were assessed using the Elecsys highly sensitive Troponin T assay (Roche, Germany) [46].

miRNA Expression Profiling from Whole Peripheral Blood Samples 5 ml blood was collected from study subjects in PAXgene Blood RNA tubes (BD, USA) and stored at 4° C. until total RNA was extracted from blood cells using the miRNeasy Mini Kit (Qiagen, Germany) [56]. MiRNA expression profiling was performed by personnel blinded to patient characteristics. Samples were analyzed with the Geniom Real-time Analyzer (febit, Germany) using the Geniom Biochip miRNA *homo sapiens*. Each array contains 7 replicates of 866 miRNAs and miRNA star sequences as annotated in the Sanger miRBase 12.0 [47]. Sample labelling with biotin was carried out by microfluidic-based enzymatic on-chip labelling of miRNAs (MPEA) as described before [68].

Following hybridization for 16 hours at 42° C. the biochip was washed and signals were measured. The resulting images were evaluated using the Geniom Wizard Software (febit, Germany). For each array, the median signal intensity of all features was extracted from the raw data file such that for each miRNA seven intensity values were calculated corresponding to each replicate on the array. Following background correction, the seven replicate intensity values of each miRNA were summarized by their median value. To normalize the data across different arrays, quantile normalization was applied and all further analyses were carried out using the normalized and background subtracted intensity values. To this end, we removed those miRNAs having an overall median signal intensity of less than 10. The final data set contained expression levels of 697 miRNAs.

To verify the accuracy of the microarray based miRNA measurements, expression levels of miR-145, -30c, -455-3p, -10b*, -216a, -1291, and -223 were assessed using quantitative real-time PCR (measured in triplets) according to manufacture's instructions (ABI, USA). As reference served the small nuclear RNA RNU6B-2.

Statistical Analysis

After ensuring approximate normal distribution of the measured intensity values using Shapiro-Wilk test, we carried out parametric t-test and limma test (unpaired, two-tailed) for each miRNA separately to detect miRNAs with differential expression between the patient and control groups. The resulting p-values were adjusted for multiple testing by Benjamini-Hochberg equation [34]. Correlation coefficients between Troponin T and miRNA levels were calculated using Pearson's product-moment coefficient. Outlier testing was performed using the tests of Grubbs and Dixon. Clustering of miRNAs has been carried out using complete linkage hierarchical clustering. As distance measure, the Euclidian distance has been applied and miRNAs and samples have been clustered independently of each other. To assess significance of the clustering, Fishers exact test on the contingency table has been applied.

In addition to the single biomarker analysis, classification of samples using miRNA patterns was carried out using Support Vector Machines (SVM) as implemented in the R e1 071 package. In particular, different kernel SVMs (linear, polynomial, sigmoid, radial basis function) were evaluated, where the cost parameter was sampled from 0.01 to 10 in decimal powers. The measured miRNA profiles were classified using 20 repetitions of standard 10-fold cross-validation. The classification has been carried out using equal class sizes. To detect the most suitable set of miRNAs that achieves the best discriminatory performance, a feature extraction (subset selection) method relying on t-test p-values was used. In detail, the following filter technique was applied: The s miRNAs with lowest p-values in the t-test were computed on the training set in each fold of the cross validation, where s was sampled from 1 to 697 in regular intervals. The respective subset was used to train the SVM and to carry out the prediction of the test samples. The mean accuracy, specificity, and sensitivity were calculated for each subset size. We additionally computed the area under the curve value (AUC), which is more discriminative than calculating the accuracy alone [33]. To check for overtraining we applied permutation tests. Here, we sampled the class labels randomly and carried out classifications using the permuted class labels. All statistical analyzes were performed using R.

Results

Acute ST Elevation Myocardial Infarction Leads to Dysregulation of Specific miRNAs In the present pilot study, we analyzed the expression of 866 miRNAs and miRNA star sequences in blood cells of 20 patients with acute myocardial infarction (AMI) and 20 control subjects. Mean age in AMI patients was 59.25±14 years and in controls 63.30±14.8 years (p=0.38). In the AMI group 4/20 and in the controls 6/20 patients were female (p=0.72). According to ECG criteria, 15 patients showed signs of inferior/posterior wall infarction and 5 of anterior wall infarction. The blood for miRNA and Troponin T measurements was drawn in the mean 3.0±2.3 hours after the reported onset of symptoms. The mean hsTnT on admission was 345.8±562.8 pg/ml. 10 patients (50%) with AMI had Troponin T levels of <50 pg/ml, and 3 of them were below 14 pg/ml (15%). White blood cell counts showed no significant differences between both groups.

Figure 22A:
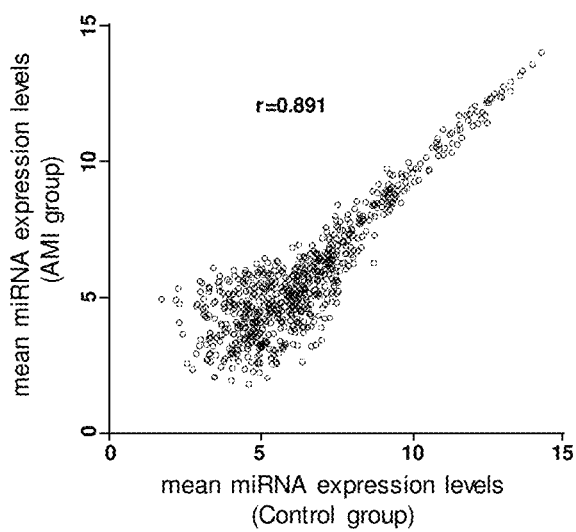
FIGS. 22A-22B: MiRNA expression profiling in peripheral blood cells of AMI patients and controls.
Figure 22B:
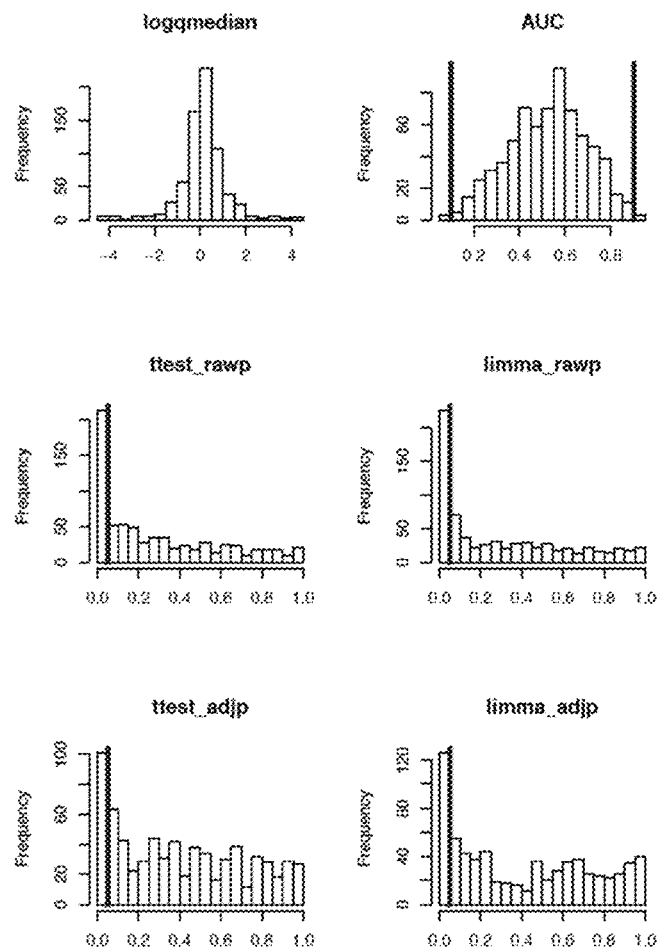
Figure 23A:
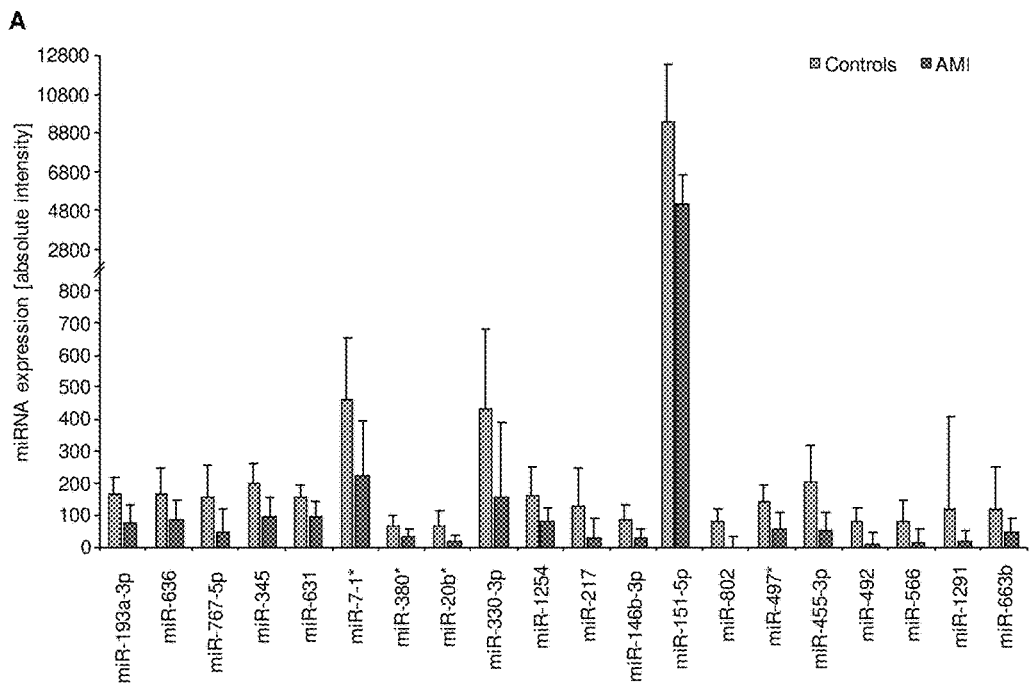
FIGS. 23A-23B: Specific miRNAs are dysregulated in acute myocardial infarction. Bar graphs showing mean expression values of (FIG. 23A) the 20 most significantly downregulated and (FIG. 23B) upregulated miRNAs in patients with acute myocardial infarction (n=20; dark grey bars) in comparison to controls (n=20; light grey bars).
Figure 23B:
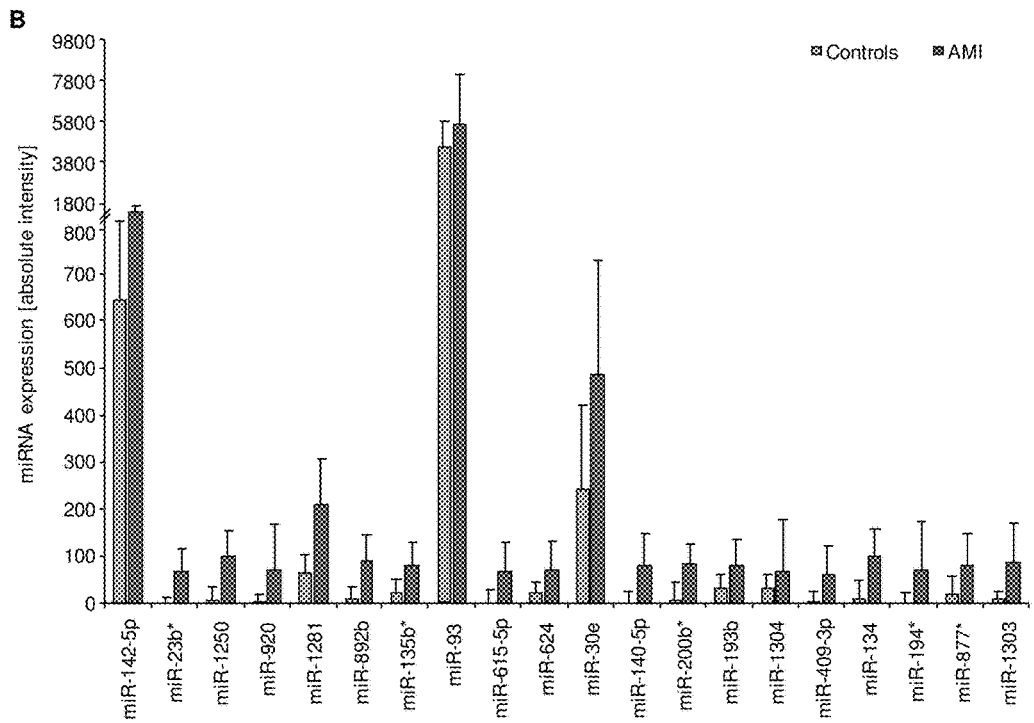

To test for the overall correlation of miRNA expression between cases and controls, we computed the median expression of all miRNAs in both groups on a logarithmic scale. As shown in the scatter plot in FIG. 22A, both groups had high correlation of 0.891 and data variance as low as 0.002. To cross-validate the whole-genome miRNA microarray, we exemplarily measured the expression levels of up- and downregulated miRNAs by real-time PCR. We find a high reproducibility between both methods. Ensuring an approximate normal distribution using Shapiro-Wilk test, we performed two-tailed unpaired t-tests and limma test for each miRNA. The respective p-values were adjusted for multiple testing by the Benjamini-Hochberg approach [48]. In total, we detected 121 miRNAs to be significantly dysregulated in blood cells from AMI patients in comparison to controls at an adjusted significance level of p<0.05. Histogram plots of the logarithm of fold ratios, the raw t-test and limma p-values, and the adjusted p-values are presented in FIG. 22B. Notably, from 121 dysregulated miRNAs only 45 (37%) were upregulated, while 76 (63%) were downregulated in AMI patients. The expression values of the 20 most significantly down- and upregulated miRNAs are shown in FIGS. 23A and B. Interestingly, miR-21, which is known to be upregulated in cardiomyocytes after myocardial infarction and heart failure, was significantly upregulated in blood of AMI patients in comparison to healthy volunteers, however was not significantly dysregulated in comparison to the control group.

Figure 24A:
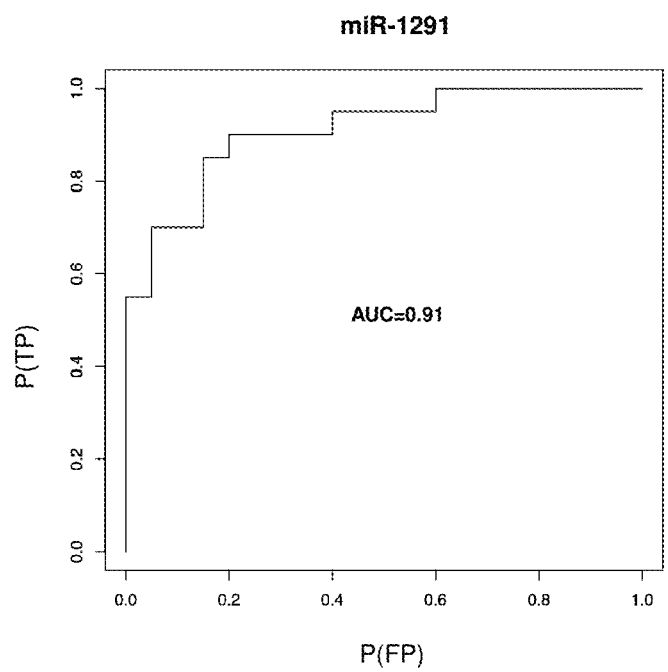
FIG. 24A: Single miRNAs predict myocardial infarction. Receiver Operating Characteristic (ROC) analysis of miRNA-1291 and miRNA-663b to predict AMI in the study population.
Figure 24B:
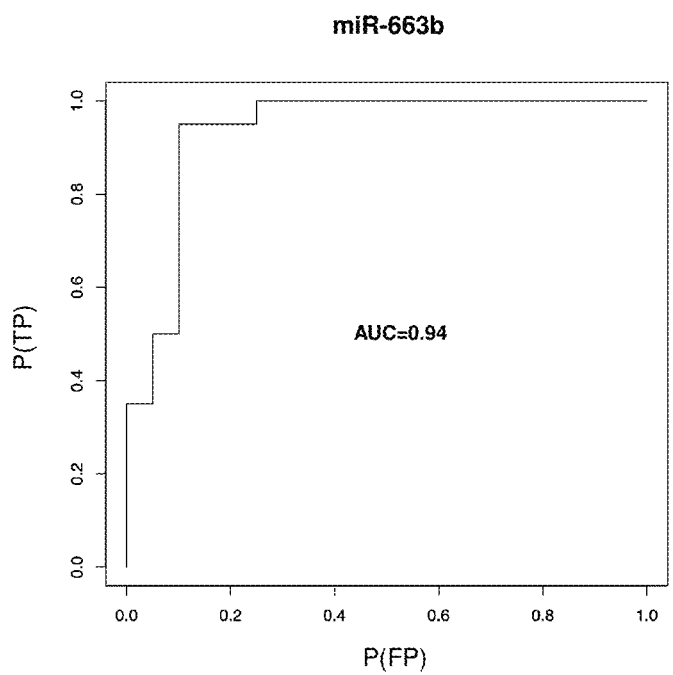

To now evaluate the predictive value of dysregulated miRNA for AMI, we calculated Receiver Operator Characteristic curves (ROC) for each of the best miRNAs together with the area under the curve value (AUC). For the most predictive miRNAs, miR-1291 and miR-663b, we obtained AUC values of up to 0.94 (FIGS. 24A and B). Using miR-1291, we classified 17 of the 20 disease samples and 17 of 20 controls correctly resulting in a specificity of 85% and a sensitivity of 85% with according test accuracy of 85%. miR-663b shows even better predictive values, allowing us to classify 19 of 20 cases and 18 of 20 controls correctly, resulting in specificity, sensitivity, and accuracy of 95%, 90%, and 92.5%, respectively.

MiR-145 and MiR-30c Levels Significantly Correlate with Troponin T Levels

Figure 25A:
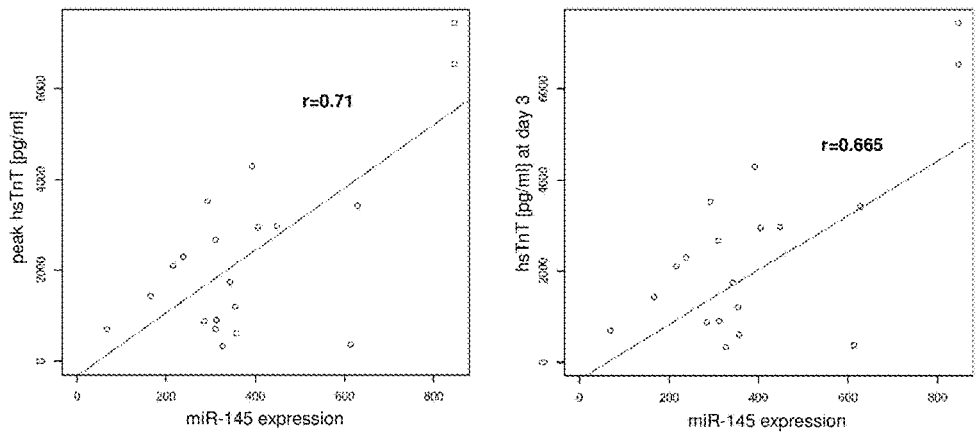
FIGS. 25A-25C: MiR-145 and miR-30c levels correlate with Troponin T release. Matrix-plots showing correlation of miR-145 (FIG. 25A) and miR-30c (FIG. 25B) with peak Troponin T serum levels (left column) and Troponin T levels at day 3 (right column).
Figure 25B:
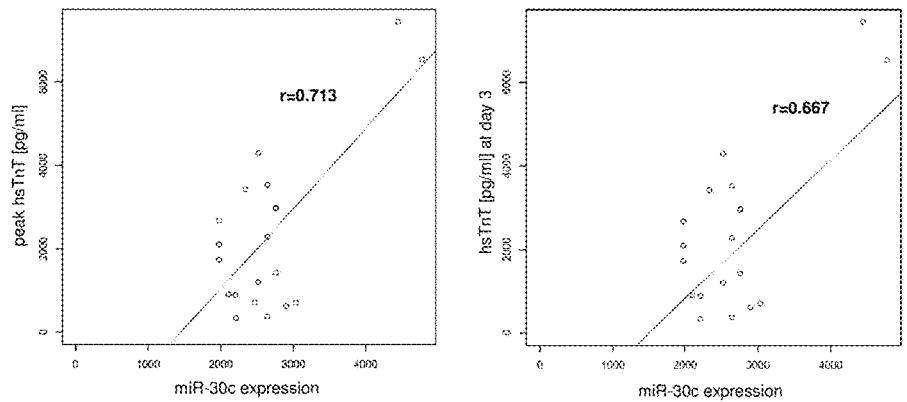
Figure 25C:
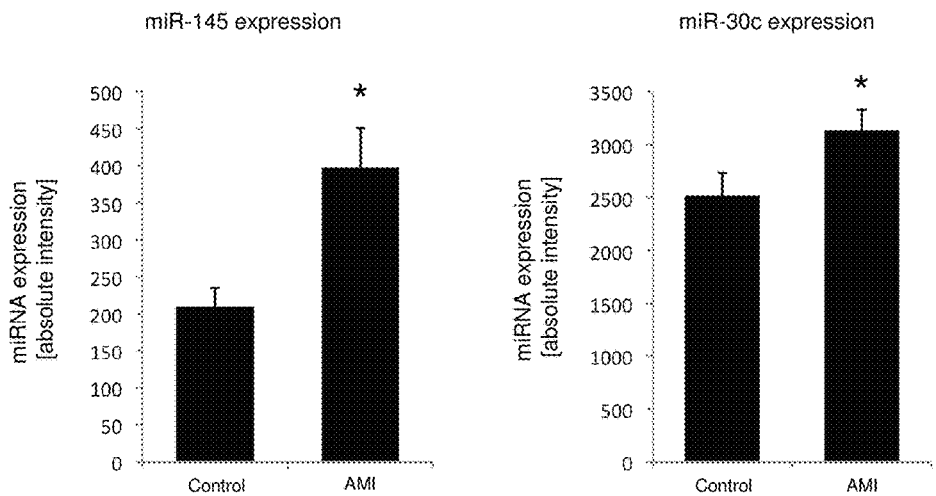

With the ability of single miRNAs to predict AMI, we next wondered if the magnitude of miRNA dysregulation correlates with infarct sizes estimated by Troponin T release (hsTnT). To this end, we computed for all dysregulated miRNAs the correlation between miRNA expression and hsTnT at day 3 and 4. Furthermore, we calculated correlations to peak hsTnT levels. We identified two upregulated miRNAs in AMI patients that show high correlation to Troponin T levels, with correlation coefficients up to 0.71. FIG. 25 represents the two miRNAs with highest linear correlation to Troponin T, miR-145 (A, C) and miR-30c (B, C) (see also Table 4).

TABLE 3

Patient characteristics.

| Characteristics | Patients with AMI (n = 20) | Patients without AMI | P |
|---|---|---|---|
| Age (years) | 59.3 ± 14 | 63.3 ± 14.8 | 0.38 |
| Male/female (n/n) | 16/4 | 14/6 | 0.72 |
| Current smoking, n (%) | 6 (30) | 4 (20) | 0.72 |
| DM, n (%) | 3 (15) | 4 (20) | 1.00 |
| Hypertension, n (%) | 11 (55) | 13 (65) | 0.75 |
| Hyperlipidaemia, n | 9 (45) | 6 (30) | 0.52 |
| SBP (mmHg) | 134 ± 27 | 128 + 13 | 0.45 |
| DBP (mmHg) | 80 ± 15 | 73 ± 9 | 0.08 |
| TG (mg/dL) | 170.4 ± 49.9 | 139.4 ± 77.5 | 0.44 |
| HDL (mg/dL) | 38.1 ± 12.6 | 44.4 ± 28.3 | 0.65 |
| LDL (mg/dL) | 103.5 ± 38.9 | 104.2 ± 34.7 | 0.97 |
| WBC (/nl) | 10.28 ± 3.6 | 9.39 ± 3.2 | 0.47 |
| Creatinine (mg/dL) | 1.12 ± 0.68 | 0.98 ± 0.24 | 0.43 |
| Urea (mg/dL) | 39.2 ± 21.4 | 36.4 ± 10.1 | 0.62 |

DM = Diabetes mellitus, SBP = systolic blood pressure, DBP = diastolic blood pressure, TG = triglycerides, HDL = high-density lipoprotein, LDL = low-density lipoprotein, WBC = white blood cell count.

TABLE 4

Correlation of miRNA levels and Troponin T release.

| | Day 3 | | | Peak | | |
|---|---|---|---|---|---|---|
| miRNA | Correlation coefficient to hsTnT | Confidence intervall | p-value | Correlation coefficient to hsTnT | Confidence intervall | p-value |
| miR-30c | 0.667 | 0.31-0.86 | 0.0018 | 0.713 | 0.39-0.88 | 0.0004 |
| miR-145 | 0.665 | 0.30-0.86 | 0.0019 | 0.710 | 0.39-0.88 | 0.0005 | hsTnT = high sensitive Troponin T.

MiRNA Signatures Enhance Diagnostic Discrimination of AMI Patients from Controls Although single miRNAs may predict the presence of AMI with good sensitivity and specificity, we tested whether complex miRNA signatures derived from unsupervised hierarchical clustering and supervised classification may improve the sensitivity and specificity.

Figure 26:
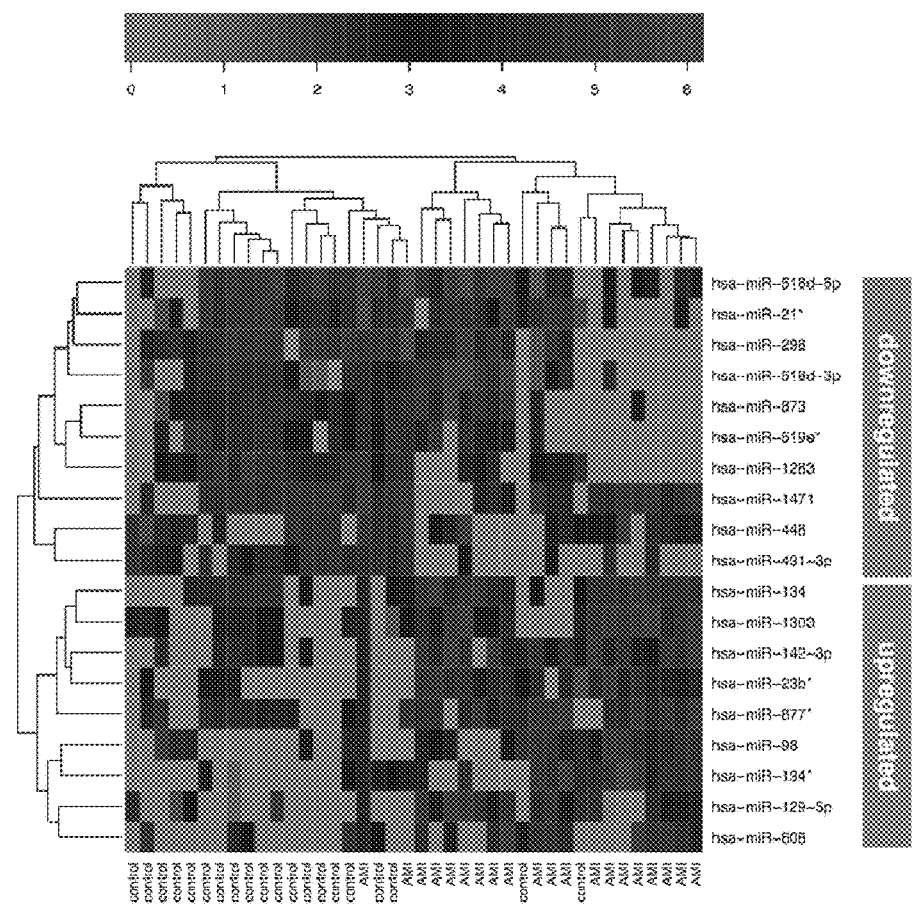
FIG. 26: Clusters of circulating miRNAs in patients with AMI versus controls. Unsupervised hierarchical clustering of expression levels of the 20 most dysregulated miRNAs using the Euclidian distance measure. AMI patients (n=20) and control subjects (n=20) cluster separately with only three outliers, showing that distinct miRNA patterns are unique for cases and controls, respectively.

First, to test for common patterns in AMI patients and controls, we applied hierarchical clustering using the expression levels of the 20 miRNAs with highest data variance and applied the Euclidian distance measure. As shown in FIG. 26, the algorithm clusters all patients and controls separately, with only three outliers. The significance of the clustering has been computed by Fishers test with a p-value of <0.001. Based on the ability to differentially cluster miRNA patterns in controls and AMI subjects and in order to improve the predictive power of a miRNA-based biomarker, we next combined the information content of multiple miRNAs by using statistical learning techniques. In detail, we applied Support Vector Machines (SVM) with different kernels as described in Materials and Methods. The best results were obtained using radial basis function SVM and a subset of 20 miRNAs. The cross validation procedure has been carried out 20 times to gain additional statistical significance. As shown in FIG. 27A, the values for sensitivity, specificity, and accuracy increased with the number of selected miRNAs in the diagnostic signature. 20 miRNAs allowed discrimination of AMI patients and controls with an accuracy of 93%, a specificity of 96%, and a sensitivity of 90%. The AUC for the AMI signature comprising 20 miR-NAs (miR-142-5p, -498, -492, -1281, -497*, -151-5p, -802, -23b*, -455-3p, -1250, -380*, -135b*, -345, -566, -631, -1254, -139-5p, -892b, 20b*, and -146b-3p) is 0.99, representing a significant improvement to single miRNA markers FIG. 27B). As shown in the classification result, this signature allows discrimination of patients and controls except for three outliers (FIG. 27C). In permutation tests significantly decreased accuracy, specificity, and sensitivity rates were computed, resembling random guessing.

Discussion

Today, biomarkers play a fundamental role in the diagnosis of cardiovascular diseases such as acute myocardial infarction and heart failure. However, many of these markers have shortcomings such as reduced sensitivity, not sufficient specificity or do not allow timely diagnosis. A multiple biomarker strategy may circumvent these limitations by adding accuracy and predictive power. To evaluate for the first time if complex miRNA signatures could potentially serve as a new class of biomarkers, we assessed here whole-genome miRNA expression levels in total peripheral blood from patients with acute myocardial infarction (AMI). We find that a unique miRNA signature predicts AMI even at a stage where some patients are still Troponin T negative.

In recent studies, miRNAs were identified as novel regulators and modifiers of cardiac development, function, and disease [58]. For instance, miRNA-21 not only controls cardiac fibrosis in response to cardiac overload, but also is upregulated in the myocardium during the early phase of infarction [40, 65]. We measured increased levels of miR-21 in AMI patients in comparison to healthy individuals, but not in comparison to our control cohort, which includes a high number of patients with stable coronary artery disease (CAD). Hence, the high levels of miR-21 in AMI patients might be due to the underlying CAD, which goes along with elevated miR-21 levels in circulating angiogenic progenitor cells [43]. Likewise, most miRNAs found to be dysregulated in AMI patients are not heart-specific. However, this is not surprising, since our miRNA profiles are derived from whole peripheral blood and not myocardial tissue. Hence, dysregulated miRNAs in AMI might equally be derived from other cellular population that play an active role in AMI pathophysiology, such as endothelial and smooth muscle cells involved in plaque rupture and vessel injury, thrombocytes in aggregation, and inflammatory cells that are recruited to the ischemic area. For instance, the vascular smooth muscle-enriched miR-145 is involved in neointima repair in response to vascular injury, regulating cytoskeletal components and migratory activity of smooth muscle cells (SMC) [70]. Thus, elevated miR-145 levels in the AMI group might be a result of vessel injury during plaque rupture. Similarly, miR-27b, which directly targets and destabilizes peroxisome proliferator activated receptor-gamma (PPARγ) mRNA [50], is also upregulated in the AMI group (24.8 fold; p<0.05). Consequently, elevated miR-27b might result in decreased PPARγ expression in SMCs, enhancing their ability to proliferate, migrate and participate vascular remodeling processes [59]. Peripheral blood monocytes (PBMC) are critically involved in plaque destabilization and rupture as well as early inflammatory responses during myocardial infarction [35, 52]. MiR-134, which is strongly upregulated in our AMI cohort, was very recently identified as PBMC-based biomarker that is able to identify CAD patients at risk for acute coronary syndromes (ACS) [49]. Thus, studying the time-course of miR-134 in PBMCs might reveal its potential as a very early marker for ACS and AMI. In addition to miRNAs transcribed in peripheral blood cells, miRNAs released from damaged tissue can be taken up by leukocytes, resulting in the so-called convergence of serum and cellular miRNAs [37]. A recent study identified miR-NAs specifically modulated in peripheral blood cells of heart failure patients. Intriguingly, many of the identified miRNAs were previously reported to be misexpressed in failing hearts of humans and mice [67]. Accordingly, next to the non-cardiac miRNAs, which significantly contribute to the AMI specific signature, we also found important, cardiac-enriched miRNAs such as miR-30c to be upregulated in blood from AMI patients, implicating that those might have been released from ischemic myocardium.

Cardiac Troponins are currently the best validated biomarkers for the diagnosis of AMI. However, measurable amounts of Troponin proteins are usually not released from damaged myocardium before 4 to 8 hours after onset of symptoms, making an early biomarker-based diagnosis of AMI rather difficult. Accordingly, 50% of AMI patients included in this study were still Troponin-negative (TnT <50 pg/ml) when entering the catheter laboratory and blood was drawn for miRNA analyses. However, miRNA profiles of these patients also showed the AMI characteristic signature, implicating that miRNA signatures might improve biomarker-based early diagnosis of myocardial infarction.

Next to their diagnostic potential, cardiac biomarkers can provide information on disease severity and prognosis [30, 62, 63]. For instance, cardiac Troponin T levels directly correlate with the size of myocardial infarction [53, 66]. Accordingly, we find that early expression levels of miR-30c and miR-145 significantly correlate with Troponin T levels. Interestingly, miR-30c is highly expressed in the heart and hence might be directly derived from damaged myocardium [42].

In a recently published candidate approach, miRNA-1 levels were found to be elevated in serum of AMI patients [32]. However, with this single biomarker approach, AMI patients could be distinguished from controls with only a moderate sensitivity and specificity (AUC=0.774), indicating that miRNA-1 might not be the optimal marker. In subsequent candidate studies using different cardiac miR-NAs, such as miR-208a, -133b, and -499-5p, the predictive values were already considerably better [31, 39, 69]. To further increase the predictive power of miRNA-based markers, we combined here whole-genome miRNA profiling with pattern-recognition algorithms. As shown, our multimarker approach might further increase sensitivity, specificity, and accuracy. However, the number of samples used in our analysis is too small to definitely proof the diagnostic power of microRNA signatures and their value for clinical testing of AMI patients. Hence, future prospective trials on large patient cohorts are needed to establish miRNAs as a novel biomarker class for acute myocardial infarction.

REFERENCES

1. Zhao Y, Samal E, Srivastava D. Serum response factor regulates a muscle-specific microRNA that targets Hand2 during cardiogenesis. Nature. 2005; 436:214-20.
2. Dresios J, Aschrafi A, Owens G C, Vanderklish P W, Edelman G M, Mauro V P. Cold stress-induced protein Rbm3 binds 60S ribosomal subunits, alters microRNA levels, and enhances global protein synthesis. Proc Natl Acad Sci USA. 2005; 102:1865-70.
3. Xu P, Vernooy S Y, Guo M, Hay B A. The *Drosophila* microRNA Mir-14 suppresses cell death and is required for normal fat metabolism. Curr Biol. 2003; 13:790-5.
4. Cimmino A, Calin G A, Fabbri M, Iorio M V, Ferracin M, Shimizu M, Wojcik S E, Aqeilan R L Zupo S, Dono M, Rassenti L, Alder H, Volinia S, Liu C G, Kipps T J, Negrini M, Croce C M. miR-15 and miR-16 induce apoptosis by targeting BCL2. Proc Natl Acad Sci USA. 2005; 102:13944-9.
5. Calin G A, Garzon R, Cimmino A, Fabbri M, Croce C M. MicroRNAs and leukemias: how strong is the connection? Leuk Res. 2006; 30:653-5.
6. Calin G A, Ferracin M, Cimmino A, Di Leva G, Shimizu M, Wojcik S E, Iorio M V, Visone R, Sever N I, Fabbri M, Iuliano R, Palumbo T, Pichiorri F, Roldo C, Garzon R, Sevignani C, Rassenti L, Alder H, Volinia S, Liu C G, Kipps T J, Negrini M, Croce C M. A MicroRNA signature associated with prognosis and progression in chronic lymphocytic leukemia. N Engl J Med. 2005; 353:1793-801.
7. Lee R C, Feinbaum R L, Ambros V. The *C. elegans* heterochronic gene lin-4 encodes small RNAs with antisense complementarity to lin-14. Cell. 1993; 75:843-54.
8. Dong S, Cheng Y, Yang J, Li J, Liu X, Wang X, Wang D, Krall T J, Delphin E S, Zhang C. MicroRNA expression signature and the role of microRNA-21 in the early phase of acute myocardial infarction. J Biol Chem. 2009; 284: 29514-25.
9. Cai B, Pan Z, Lu Y. The Roles of MicroRNAs in Heart Diseases: A Novel Important Regulator. Curr Med Chem. 2009.
10. Newton P J, Betihavas V, Macdonald P. The role of b-type natriuretic peptide in heart failure management. Aust Crit Care. 2009; 22:117-23.
11. Lainscak M, Anker M S, von Haehling S, Anker S D. Biomarkers for chronic heart failure: diagnostic, prognostic, and therapeutic challenges. Herz. 2009; 34:589-93.
12. Manzano-Fernandez S, Boronat-Garcia M, Albaladejo-Oton M D, Pastor P, Garrido I P, Pastor-Perez F J, Martinez-Hernandez P, Valdes M, Pascual-Figal D A. Complementary prognostic value of cystatin C, N-terminal pro-B-type natriuretic Peptide and cardiac troponin T in patients with acute heart failure. Am J Cardiol. 2009; 103:1753-9.
13. Katus H A, Remppis A, Looser S, Hallermeier K, Scheffold T, Kubler W. Enzyme linked immuno assay of cardiac troponin T for the detection of acute myocardial infarction in patients. J Mol Cell Cardiol. 1989; 21:1349-53.
14. Mukoyama M, Nakao K, Saito Y, Ogawa Y, Hosoda K, Suga S, Shirakami G, Jougasaki M, Imura H. Increased human brain natriuretic peptide in congestive heart failure. N Engl J Med. 1990; 323:757-8.
15. Gerszten R E, Wang T J. The search for new cardiovascular biomarkers. Nature. 2008; 451:949-52.
16. Gallego-Delgado J, Lazaro A, Osende J I, Barderas M G, Blanco-Colio L M, Duran M C, Martin-Ventura J L, Vivanco F, Egido J. Proteomic approach in the search of new cardiovascular biomarkers. Kidney Int Suppl. 2005: S103-7.
17. Giannitsis E, Roth H J, Leithauser R M, Scherhag J, Beneke R, Katus H A. New highly sensitivity assay used to measure cardiac troponin T concentration changes during a continuous 216-km marathon. Clin Chem. 2009; 55:590-2.
18. Griffiths-Jones S. miRBase: the microRNA sequence database. Methods Mol Biol. 2006; 342:129-38.
19. Vorwerk S, Ganter K, Cheng Y, Hoheisel J, Stahler P F, Beier M. Microfluidic-based enzymatic on-chip labeling of miRNAs. N Biotechnol. 2008; 25:142-9.
20. Benjamini Y, Hochberg Y. Controlling the false discovery rate: A practical and powerful approach to multiple testing. J R Statist Soc B. 1995; 57:289-300.
21. Meder B, Katus H A, Rottbauer W. Right into the heart of microRNA-133a. Genes Dev. 2008; 22:3227-31.
22. Thum T, Gross C, Fiedler J, Fischer T, Kissler S, Bussen M, Galuppo P, Just S, Rottbauer W, Frantz S, Castoldi M, Soutschek J, Koteliansky V, Rosenwald A, Basson M A, Licht J D, Pena J T, Rouhanifard S H, Muckenthaler M U, Tuschl T, Martin G R, Bauersachs J, Engelhardt S. MicroRNA-21 contributes to myocardial disease by stimulating MAP kinase signalling in fibroblasts. Nature. 2008; 456: 980-4.
23. Chen X, Ba Y, Ma L, Cai X, Yin Y, Wang K, Guo J, Zhang Y, Chen J, Guo X, Li Q, Li X, Wang W, Wang J, Jiang X, Xiang Y, Xu C, Zheng P, hang J, Li R, Zhang H, Shang X, Gong T, Ning G, Zen K, Zhang C Y. Characterization of microRNAs in serum: a novel class of biomarkers for diagnosis of cancer and other diseases. Cell Res. 2008; 18:997-1006.
24. Ai J, Zhang R, Li Y, Pu J, Lu Y, Jiao J, Li K, Yu B, Li Z, Wang R, Wang L, Li Q, Wang N, Shan H, Yang B. Circulating microRNA-1 as a potential novel biomarker for acute myocardial infarction. Biochem Biophys Res Commun. 2009.
25. Risk stratification and survival after myocardial infarction. N Engl J Med. 1983; 309:331-6.
26. Rottbauer W, Greten T, Muller-Bardorff M, Remppis A, Zehelein J, Grunig E, Katus H A. Troponin T: a diagnostic marker for myocardial infarction and minor cardiac cell damage. Eur Heart J. 1996; 17 Suppl F:3-8.
27. Kurz K, Schild C, Isfort P, Katus H A, Giannitsis E. Serial and single time-point measurements of cardiac troponin T for prediction of clinical outcomes in patients with acute ST-segment elevation myocardial infarction. Clin Res Cardiol. 2009; 98:94-100.
28. Tzivoni D, Koukoui D, Guetta V, Novack L, Cowing G. Comparison of Troponin T to creatine kinase and to radionuclide cardiac imaging infarct size in patients with ST-elevation myocardial infarction undergoing primary angioplasty. Am J Cardiol. 2008; 101:753-7.
29. Duisters R F, Tijsen A J, Schroen B, Leenders J J, Lentink V, van der Made I, Herias V, van Leeuwen R E, Schellings M W, Barenbrug P, Maessen J G, Heymans S, Pinto Y M, Creemers E E. miR-133 and miR-30 regulate connective tissue growth factor: implications for a role of microRNAs in myocardial matrix remodeling. Circ Res. 2009; 104:170-8, 6 p following 178.
30. (1983) Risk stratification and survival after myocardial infarction. N Engl J Med 309.331-336
31. Adachi T, Nakanishi M, Otsuka Y, Nishimura K, Hirokawa G, Goto Y, Nonogi H, Iwai N (2010) Plasma microRNA 499 as a biomarker of acute myocardial infarction. Clin Chem 56:1183-1185
32. Ai J, Zhang R, Li Y, Pu J, Lu Y, Jiao J, Li K, Yu B, Li Z, Wang R, Wang L, Li Q, Wang N, Shan H, Yang B (2010) Circulating microRNA-1 as a potential novel biomarker for acute myocardial infarction. Biochem Biophys Res Commun 391:73-77
33. Aliferis C F, Statnikov A. Tsamardinos I, Schildcrout J S, Shepherd B E, Harrell F E, Jr. (2009) Factors influencing the statistical power of complex data analysis protocols for molecular signature development from microarray data. PLoS ONE 4:e4922
34. Benjamini Y, Hochberg Y (1995) Controlling the false discovery rate: A practical and powerful approach to multiple testing. J R Statist Soc B 57:289-300
35. Bose D, von Birgelen C, Zhou X Y, Schmermund A, Philipp S, Sack S, Konorza T, Mohlenkamp S, Leineweber K, Kleinbongard P, Wijns W, Heusch G, Erbel R (2008) Impact of atherosclerotic plaque composition on coronary microembolization during percutaneous coronary interventions. Basic Res Cardiol 103:587-597
36. Cai B, Pan Z, Lu Y (2010) The roles of microRNAs in heart diseases: a novel important regulator. Curr Med Chem 17:407-411
37. Chen X, Ba Y, Ma L, Cai X, Yin Y, Wang K, Guo J, Zhang Y, Chen J, Guo X, Li Q, Li X, Wang W, Wang J, Jiang X, Xiang Y, Xu C, Zheng P, Zhang J, Li R, Zhang H, Shang X, Gong T, Ning G, Zen K, Zhang C Y (2008) Characterization of microRNAs in serum: a novel class of biomarkers for diagnosis of cancer and other diseases. Cell Res 18:997-1006
38. Cimmino A, Calin G A, Fabbri M, Iorio M V, Ferracin M, Shimizu M, Wojcik S E, Aqeilan R I, Zupo S, Dono M, Rassenti L, Alder H, Volinia S, Liu C G, Kipps T J, Negrini M, Croce C M (2005) miR-15 and miR-16 induce apoptosis by targeting BCL2. Proc Natl Acad Sci USA 102:13944-13949
39. D'Alessandra Y, Devanna P, Limana F, Straino S, Di Carlo A, Brambilla P G, Rubino M, Carena M C, Spazzafumo L, De Simone M, Micheli B, Biglioli P, Achilli F, Martelli F, Maggiolini S, Marenzi G, Pompilio G, Capogrossi M C (2010) Circulating microRNAs are new and sensitive biomarkers of myocardial infarction. Eur Heart J published online Jun. 9, 2010 doi:10.1093/eurheartj/ehq167
40. Dong S, Cheng Y, Yang J, Li J, Liu X, Wang X, Wang D, Krall T J, Delphin E S, Zhang C (2009) MicroRNA expression signature and the role of microRNA-21 in the early phase of acute myocardial infarction. J Biol Chem 284:29514-29525
41. Dresios J, Aschrafi A, Owens G C, Vanderklish P W, Edelman G M, Mauro V P (2005) Cold stress-induced protein Rbm3 binds 60S ribosomal subunits, alters microRNA levels, and enhances global protein synthesis. Proc Natl Acad Sci USA 102:1865-1870
42. Duisters R F, Tijsen A J, Schroen B, Leenders J J, Lentink V, van der Made I, Herias V, van Leeuwen R E, Schellings M W, Barenbrug P, Maessen J G, Heymans S, Pinto Y M, Creemers E E (2009) miR-133 and miR-30 regulate connective tissue growth factor: implications for a role of microRNAs in myocardial matrix remodeling. Circ Res 104:170-178, 176 p following 178
43. Fleissner F, Jazbutyte V, Fiedler J, Gupta S K, Yin X, Xu Q, Galuppo P, Kneitz S, Mayr M, Ertl G, Bauersachs J, Thum T (2010) Short communication: asymmetric dimethylarginine impairs angiogenic progenitor cell function in patients with coronary artery disease through a microRNA-21-dependent mechanism. Circ Res 107:138-143
44. Gallego-Delgado J, Lazaro A, Osende J I, Barderas M G, Blanco-Colio L M, Duran M C, Martin-Ventura J L, Vivanco F, Egido J (2005) Proteomic approach in the search of new cardiovascular biomarkers. Kidney Int Suppl:S103-107

45. Gerszten R E, Wang T J (2008) The search for new cardiovascular biomarkers. Nature 451:949-952
46. Giannitsis E, Roth H J, Leithauser R M, Scherhag J, Beneke R, Katus H A (2009) New highly sensitivity assay used to measure cardiac troponin T concentration changes during a continuous 216-km marathon. Clin Chem 55:590-592
47. Griffiths-Jones S (2006) miRBase: the microRNA sequence database. Methods Mol Biol 342:129-138
48. Hochberg Y (1988) A sharper bonferroni procedure for multiple tests of significance. Biometrica 75:185-193
49. Hoekstra M, van der Lans C A, Halvorsen B, Gullestad L, Kuiper J, Aukrust P, van Berkel T J, Biessen E A (2010) The peripheral blood mononuclear cell microRNA signature of coronary artery disease. Biochem Biophys Res Commun 394:792-797
50. Jennewein C, von Knethen A, Schmid T, Brune B (2010) MicroRNA-27b contributes to lipopolysaccharide-mediated peroxisome proliferator-activated receptor gamma (PPARgamma) mRNA destabilization. J Biol Chem 285: 11846-11853
51. Katus H A, Remppis A, Looser S, Hallermeier K, Scheffold T, Kubler W (1989) Enzyme linked immuno assay of cardiac troponin T for the detection of acute myocardial infarction in patients. J Mol Cell Cardiol 21:1349-1353
52. Konstandin M H, Aksoy H, Wabnitz G H, Volz C, Erbel C, Kirchgessner H, Giannitsis E, Katus H A, Samstag Y, Dengler T J (2009) Beta2-integrin activation on T cell subsets is an independent prognostic factor in unstable angina pectoris. Basic Res Cardiol 104:341-351
53. Kurz K, Schild C, Isfort P, Katus H A, Giannitsis E (2009) Serial and single time-point measurements of cardiac troponin T for prediction of clinical outcomes in patients with acute ST-segment elevation myocardial infarction. Clin Res Cardiol 98:94-100
54. Lainscak M, Anker M S, von Haehling S, Anker S D (2009) Biomarkers for chronic heart failure: diagnostic, prognostic, and therapeutic challenges. Herz 34:589-593
55. Lee R C, Feinbaum R L, Ambros V (1993) The *C. elegans* heterochronic gene lin-4 encodes small RNAs with antisense complementarity to lin-14. Cell 75:843-854
56. Leidinger P, Keller A, Borries A, Reichrath J, Rass K, Jager S U, Lenhof H P, Meese E (2010) High-throughput miRNA profiling of human melanoma blood samples. BMC Cancer 10:262
57. Manzano-Fernandez S, Boronat-Garcia M, Albaladejo-Oton M D, Pastor P, Garrido I P, Pastor-Perez F J, Martincz-Hernandez P, Valdes M, Pascual-Figal D A (2009) Complementary prognostic value of cystatin C, N-terminal pro-B-type natriuretic Peptide and cardiac troponin T in patients with acute heart failure. Am J Cardiol 103:1753-1759
58. Meder B, Katus H A, Rottbauer W (2008) Right into the heart of microRNA-133a. Genes Dev 22:3227-3231
59. Meredith D, Panchatcharam M, Miriyala S, Tsai Y S, Morris A J, Maeda N, Stouffer G A, Smyth S S (2009) Dominant-negative loss of PPARgamma function enhances smooth muscle cell proliferation, migration, and vascular remodeling. Arterioscler Thromb Vase Biol 29:465-471
60. Mukoyama M, Nakao K, Saito Y, Ogawa Y, Hosoda K, Suga S, Shirakami G, Jougasaki M, Imura H (1990) Increased human brain natriuretic peptide in congestive heart failure. N Engl J Med 323:757-758
61. Newton P J, Betihavas V, Macdonald P (2009) The role of b-type natriuretic peptide in heart failure management. Aust Crit Care 22:117-123
62. Porela P, Pulkki K, Voipio-Pulkki L M, Pettersson K, Leppanen V, Nevalainen T J (2000) Level of circulating phospholipase A2 in prediction of the prognosis of patients with suspected myocardial infarction. Basic Res Cardiol 95:413-417
63. Rottbauer W, Greten T, Muller-Bardorff M, Remppis A, Zehelein J, Grunig E, Katus H A (1996) Troponin T: a diagnostic marker for myocardial infarction and minor cardiac cell damage. Eur Heart J 17 Suppl F:3-8
64. Team-RDC (2008) R: A Language and Environment for Statistical Computing. R Foundation for Statistical Computing, Vienna, Austria
65. Thum T, Gross C, Fiedler J, Fischer T, Kissler S, Bussen M, Galuppo P, Just S, Rottbauer W, Frantz S, Castoldi M, Soutschek J, Koteliansky V, Rosenwald A, Basson M A, Licht J D, Pena J T, Rouhanifard S H, Muckenthaler M U, Tuschl T, Martin G R, Bauersachs J, Engelhardt S (2008) MicroRNA-21 contributes to myocardial disease by stimulating MAP kinase signalling in fibroblasts. Nature 456:980-984
66. Tzivoni D, Koukoui D, Guetta V, Novack L, Cowing G (2008) Comparison of Troponin T to creatine kinase and to radionuclide cardiac imaging infarct size in patients with ST-elevation myocardial infarction undergoing primary angioplasty. Am J Cardiol 101:753-757
67. Voellenkle C, van Rooij J, Cappuzzello C, Greco S, Arcelli D, Di Vito L, Melillo G, Rigolini R, Costa E, Crea F, Capogrossi M C, Napolitano M, Martelli F (2010) MicroRNA signatures in peripheral blood mononuclear cells of chronic heart failure patients. Physiol Genomics 42:420-426
68. Vorwerk S, Ganter K, Cheng Y, Hoheisel J, Stahler P F, Beier M (2008) Microfluidic-based enzymatic on-chip labeling of miRNAs. N Biotechnol 25:142-149
69. Wang G K, Zhu J Q, Zhang J T, Li Q, Li Y, He J, Qin Y W, Jing Q (2010) Circulating microRNA: a novel potential biomarker for early diagnosis of acute myocardial infarction in humans. Eur Heart J 31:659-666
70. Xin M, Small E M, Sutherland L B, Qi X, McAnally J, Plato C F, Richardson J A, Bassel-Duby R, Olson E N (2009) MicroRNAs miR-143 and miR-145 modulate cytoskeletal dynamics and responsiveness of smooth muscle cells to injury. Genes Dev 23:2166-2178
71. Xu P, Vernooy S Y, Guo M, Hay B A (2003) The *Drosophila* microRNA Mir-14 suppresses cell death and is required for normal fat metabolism. Curr Biol 13:790-795
72. Zhao Y, Samal E, Srivastava D (2005) Serum response factor regulates a muscle-specific microRNA that targets Hand2 during cardiogenesis. Nature 436:214-220

The invention claimed is:

1. A method for detecting a decreased level of at least one miRNA in a human patient having, or suspected of having, an acute coronary syndrome comprising the steps of:
   (i) providing a blood cell sample from a human, wherein the blood cell sample is a blood cellular fraction consisting of a mixture of erythrocytes, leukocytes and thrombocytes, and
   (ii) detecting whether there is a decreased level of the at least one miRNA in the blood cell sample as compared to a control level of a healthy human subject, or a human subject not having or not being suspected of having an acute coronary syndrome, by contacting the sample with at least one probe for at least one down-regulated miRNA and detecting binding between the probe and the down-regulated miRNA;

wherein the nucleotide sequence of said at least one down-regulated miRNA is miR-455-3p having SEQ ID NO: 16, or sequence having at least 95% sequence identity thereto.

2. The method of claim 1, wherein at least one additional nucleotide sequence of at least one additional down-regulated miRNA is detected, wherein the at least one additional down-regulated miRNA is selected from:
   miR-193a-3p having SEQ ID NO: 255;
   miR-636 having SEQ ID NO: 174;
   miR-767-5p having SEQ ID NO: 19;
   miR-345 having SEQ ID NO: 283;
   miR-631 having SEQ ID NO: 259;
   miR-7-1* having SEQ ID NO: 135;
   miR-380* having SEQ ID NO: 32;
   miR-20b* having SEQ ID NO: 22;
   miR-330-3p having SEQ ID NO: 24;

miR-1254 having SEQ ID NO: 150;
miR-217 having SEQ ID NO: 157;
miR-146b-3p having SEQ ID NO: 123;
miR-151-5p having SEQ ID NO: 243;
miR-802 having SEQ ID NO: 52;
miR-497* having SEQ ID NO: 252;
miR-492 having SEQ ID NO: 184;
miR-566 having SEQ ID NO: 157;
miR1291 having SEQ ID NO: 1;
miR663b having SEQ ID NO:257; and,
miRNA sequences having at least 95% sequence identity thereto.

3. The method of claim 1, wherein the method further comprises detecting whether there is an increased level of at least one up-regulated miRNA in the blood cell sample as compared to a control level by contacting the sample with at least one probe for at least one up-regulated miRNA and detecting binding between the probe and the up-regulated miRNA, wherein the at least one up-regulated miRNA is selected from:
miR-142-5p having SEQ ID NO: 162,
miR-23b* having SEQ ID NO:68,
miR-1250 having SEQ ID NO:70,
miR-920 having SEQ ID NO:137,
miR-1281 having SEQ ID NO:62,
miR-892b having SEQ ID NO: 15,
miR-135* having SEQ ID NO:95,
miR-93 having SEQ ID NO:20,
miR-615-5p having SEQ ID NO:266,
miR-624 having SEQ ID NO:232,
miR-30e having SEQ ID NO:55,
miR-140-5p having SEQ ID NO:85,
miR-200b* having SEQ ID NO:261,
miR-193b having SEQ ID NO:267,
miR-1304 having SEQ ID NO:148,
miR-409-3p having SEQ ID NO:215,
miR-134 having SEQ ID NO:256,
miR-194* having SEQ ID NO:272,
miR-877* having SEQ ID NO:268,
miR-1303 having SEQ ID NO:84, and,
miRNA sequences having at least 95% sequence identity thereto.

4. The method of claim 1, wherein step (ii) is determined using reverse-transcribed miRNA.

5. The method of claim 1, wherein step (ii) is determined using a quantitative real-time PCR machine by reverse-transcribing the total RNA into cDNA, and amplifying the cDNA and thereby quantifying said miRNA(s).

6. The method of claim 1, wherein the acute coronary syndrome is acute myocardial infarction (AMI).

7. The method of claim 1, further comprising detecting a deregulated level of at least one additional miRNA, wherein the deregulation comprises an up-regulation or a down-regulation of said at least one additional miRNA, and wherein the at least one additional miRNAs are selected from the following sets:

| Set No. | SEQ ID NO: | miRNAs |
|---|---|---|
| 327 | SEQ ID NO: 16, 253, 174 | hsa-miR-455-3p, hsa-miR-345, hsa-miR-636 |
| 328 | SEQ ID NO: 162, 16, 150 | hsa-miR-142-5p, hsa-miR-455-3p, hsa-miR-1254 |
| 1 | SEQ ID NO: 162, 16 | hsa-miR-142-5p, hsa-miR-455-3p |
| 338 | SEQ ID NO: 243, 16, 32 | hsa-miR-151-5p, hsa-miR-455-3p, hsa-miR-380* |
| 348 | SEQ ID NO: 184, 243, 16 | hsa-miR-492, hsa-miR-151-5p, hsa-miR-455-3p |
| 6 | SEQ ID NO: 243, 16 | hsa-miR-151-5p, hsa-miR-455-3p |
| 357 | SEQ ID NO: 243, 16, 70 | hsa-miR-151-5p, hsa-miR-455-3p, hsa-miR-1250 |
| 361 | SEQ ID NO: 162, 252, 16 | hsa-miR-142-5p, hsa-miR-497*, hsa-miR-455-3p |
| 1005 | SEQ ID NO: 162, 157, 234, 184, 68, 16, 70, 252, 52, 15, 243, 62, 123, 95, 150, 22, 32, 259, 253, 31 | hsa-miR-142-5p, hsa-miR-566, hsa-miR-498, hsa-miR-492, hsa-miR-23b*, hsa-miR-455-3p, hsa-miR-1250, hsa-miR-497*, hsa-miR-802, hsa-miR-8926, hsa-miR-151-5p, hsa-miR-1281, hsa-miR-1466-3p, hsa-miR-135b*, hsa-miR-1254, hsa-miR-20b*, hsa-miR-380*, hsa-miR-631, hsa-miR-345, hsa-miR-139-5p |
| 383 | SEQ ID NO: 62, 16, 253 | hsa-miR-1281, hsa-miR-455-3p, hsa-miR-345 |
| 381 | SEQ ID NO: 184, 52, 16 | hsa-miR-492, hsa-miR-802, hsa-miR-455-3p |
| 389 | SEQ ID NO: 243, 68, 16 | hsa-miR-151-5p, hsa-miR-23b*, hsa-miR-455-3p |
| 397 | SEQ ID NO: 16, 150, 174 | hsa-miR-455-3p, hsa-miR-1254, hsa-miR-636 |
| 402 | SEQ ID NO: 68, 16, 137 | hsa-miR-23b*, hsa-miR-455-3p, hsa-miR-920 |
| 404 | SEQ ID NO: 234, 184, 16 | hsa-miR-498, hsa-miR-492, hsa-miR-455-3p |
| 406 | SEQ ID NO: 234, 68, 16 | hsa-miR-498, hsa-miR-23b*, hsa-miR-455-3p |
| 421 | SEQ ID NO: 162, 62, 16 | hsa-miR-142-5p, hsa-miR-1281, hsa-miR-455-3p |
| 424 | SEQ ID NO: 217, 62, 16 | hsa-miR-148b, hsa-miR-1281, hsa-miR-455-3p |
| 429 | SEQ ID NO: 157, 68, 16 | hsa-miR-566, hsa-miR-23b*, hsa-miR-455-3p |
| 439 | SEQ ID NO: 68, 16, 252 | hsa-miR-23b*, hsa-miR-455-3p, hsa-miR-497* |
| 441 | SEQ ID NO: 16, 137, 52 | hsa-miR-455-3p, hsa-miR-920, hsa-miR-802 |
| 451 | SEQ ID NO: 157, 234, 16 | hsa-miR-566, hsa-miR-498, hsa-miR-455-3p |
| 454 | SEQ ID NO: 52, 243, 16 | hsa-miR-802, hsa-miR-151-5p, hsa-miR-455-3p |
| 463 | SEQ ID NO: 22, 135, 16 | hsa-miR-20b*, hsa-miR-7-1*, hsa-miR-455-3p |
| 464 | SEQ ID NO: 68, 16, 259 | hsa-miR-23b*, hsa-miR-455-3p, hsa-miR-631 |
| 41 | SEQ ID NO: 52, 16 | hsa-miR-802, hsa-miR-455-3p |
| 474 | SEQ ID NO: 157, 184, 16 | hsa-miR-566, hsa-miR-492, hsa-miR-455-3p |
| 487 | SEQ ID NO: 252, 16, 253 | hsa-miR-497*, hsa-miR-455-3p, hsa-miR-345 |
| 499 | SEQ ID NO: 62, 16, 174 | hsa-miR-1281, hsa-miR-455-3p, hsa-miR-636 |
| 515 | SEQ ID NO: 62, 16, 150 | hsa-miR-1281, hsa-miR-455-3p, hsa-miR-1254 |
| 514 | SEQ ID NO: 52, 68, 16 | hsa-miR-802, hsa-miR-23b*, hsa-miR-455-3p |
| 533 | SEQ ID NO: 22, 19, 16 | hsa-miR-20b*, hsa-miR-767-5p, hsa-miR-455-3p |
| 539 | SEQ ID NO: 52, 16, 70 | hsa-miR-802, hsa-miR-455-3p, hsa-miR-1250 |
| 543 | SEQ ID NO: 116, 62, 16 | hsa-miR-339-3p, hsa-miR-1281, hsa-miR-455-3p |
| 60 | SEQ ID NO: 68, 16 | hsa-miR-23b*, hsa-miR-455-3p |
| 554 | SEQ ID NO: 135, 31, 16 | hsa-miR-7-1*, hsa-miR-139-5p, hsa-miR-455-3p |
| 551 | SEQ ID NO: 68, 16, 70 | hsa-miR-23b*, hsa-miR-455-3p, hsa-miR-1250 |
| 61 | SEQ ID NO: 62, 16 | hsa-miR-1281, hsa-miR-455-3p |

-continued

| Set No. | SEQ ID NO: | miRNAs |
|---|---|---|
| 556 | SEQ ID NO: 16, 150, 135 | hsa-miR-455-3p, hsa-miR-1254, hsa-miR-7-1* |
| 567 | SEQ ID NO: 184, 16, 252 | hsa-miR-492, hsa-miR-455-3p, hsa-miR-497* |
| 566 | SEQ ID NO: 184, 16, 70 | hsa-miR-492, hsa-miR-455-3p, hsa-miR-1250 |
| 563 | SEQ ID NO: 184, 68, 16 | hsa-miR-492, hsa-miR-23b*, hsa-miR-455-3p |
| 586 | SEQ ID NO: 252, 62, 16 | hsa-miR-497*, hsa-miR-1281, hsa-miR-455-3p |
| 595 | SEQ ID NO: 135, 19, 16 | hsa-miR-7-1*, hsa-miR-767-5p, hsa-miR-455-3p |
| 602 | SEQ ID NO: 16, 252, 52 | hsa-miR-455-3p, hsa-miR-497*, hsa-miR-802 |
| 603 | SEQ ID NO: 234, 16, 70 | hsa-miR-498, hsa-miR-455-3p, hsa-miR-1250 |
| 607 | SEQ ID NO: 22, 31, 16 | hsa-miR-20b*, hsa-miR-139-5p, hsa-miR-455-3p |
| 612 | SEQ ID NO: 135, 16, 32 | hsa-miR-7-1*, hsa-miR-455-3p, hsa-miR-380* |
| 84 | SEQ ID NO: 16, 253 | hsa-miR-455-3p, hsa-miR-345 |
| 94 | SEQ ID NO: 184, 16 | hsa-miR-492, hsa-miR-455-3p |
| 661 | SEQ ID NO: 16, 174, 135 | hsa-miR-455-3p, hsa-miR-636, hsa-miR-7-1* |
| 664 | SEQ ID NO: 16, 32, 252 | hsa-miR-455-3p, hsa-miR-380*, hsa-miR-497* |
| 100 | SEQ ID NO: 234, 16 | hsa-miR-498, hsa-miR-455-3p |
| 675 | SEQ ID NO: 252, 16, 150 | hsa-miR-497*, hsa-miR-455-3p, hsa-miR-1254 |
| 677 | SEQ ID NO: 16, 252, 137 | hsa-miR-455-3p, hsa-miR-497*, hsa-miR-920 |
| 681 | SEQ ID NO: 217, 116, 16 | hsa-miR-148b, hsa-miR-339-3p, hsa-miR-455-3p |
| 103 | SEQ ID NO: 16, 32 | hsa-miR-455-3p, hsa-miR-380* |
| 693 | SEQ ID NO: 16, 70, 137 | hsa-miR-455-3p, hsa-miR-1250, hsa-miR-920 |
| 725 | SEQ ID NO: 16, 32, 150 | hsa-miR-455-3p, hsa-miR-380*, hsa-miR-1254 |
| 731 | SEQ ID NO: 31, 16, 252 | hsa-miR-139-5p, hsa-miR-455-3p, hsa-miR-497* |
| 750 | SEQ ID NO: 16, 70, 32 | hsa-miR-455-3p, hsa-miR-1250, hsa-miR-380* |
| 758 | SEQ ID NO: 16, 150, 253 | hsa-miR-455-3p, hsa-miR-1254, hsa-miR-345 |
| 760 | SEQ ID NO: 68, 16, 32 | hsa-miR-23b*, hsa-miR-455-3p, hsa-miR-380* |
| 135 | SEQ ID NO: 31, 16 | hsa-miR-139-5p, hsa-miR-455-3p |
| 145 | SEQ ID NO: 16, 150 | hsa-miR-455-3p, hsa-miR-1254 |
| 789 | SEQ ID NO: 16, 253, 135 | hsa-miR-455-3p, hsa-miR-345, hsa-miR-7-1* |
| 793 | SEQ ID NO: 16, 70, 252 | hsa-miR-455-3p, hsa-miR-1250, hsa-miR-497* |
| 802 | SEQ ID NO: 19, 16, 32 | hsa-miR-767-5p, hsa-miR-455-3p, hsa-miR-380* |
| 800 | SEQ ID NO: 19, 31, 16 | hsa-miR-767-5p, hsa-miR-139-5p, hsa-miR-455-3p |
| 804 | SEQ ID NO: 116, 252, 16 | hsa-miR-339-3p, hsa-miR-497*, hsa-miR-455-3p |
| 803 | SEQ ID NO: 16, 32, 259 | hsa-miR-455-3p, hsa-miR-380*, hsa-miR-631 |
| 806 | SEQ ID NO: 16, 259, 150 | hsa-miR-455-3p, hsa-miR-631, hsa-miR-1254 |
| 159 | SEQ ID NO: 16, 70 | hsa-miR-455-3p, hsa-miR-1250 |
| 815 | SEQ ID NO: 16, 70, 150 | hsa-miR-455-3p, hsa-miR-1250, hsa-miR-1254 |
| 164 | SEQ ID NO: 16, 174 | hsa-miR-455-3p, hsa-miR-636 |
| 828 | SEQ ID NO: 16, 32, 273 | hsa-miR-455-3p, hsa-miR-380*, hsa-miR-194* |
| 833 | SEQ ID NO: 16,70, 259 | hsa-miR-455-3p, hsa-miR-1250, hsa-miR-631 |
| 847 | SEQ ID NO: 31, 16, 32 | hsa-miR-139-5p, hsa-miR-455-3p, hsa-miR-380* |
| 850 | SEQ ID NO: 16, 32, 23 | hsa-miR-455-3p, hsa-miR-380*, hsa-miR-491-3p |
| 194 | SEQ ID NO: 16, 252 | hsa-miR-455-3p, hsa-miR-497* |
| 875 | SEQ ID NO: 31, 16, 273 | hsa-miR-139-5p, hsa-miR-455-3p, hsa-miR-194* |
| 881 | SEQ ID NO: 16, 252, 23 | hsa-miR-455-3p, hsa-miR-497*, hsa-miR-491-3p |
| 202 | SEQ ID NO: 135, 16 | hsa-miR-7-1*, hsa-miR-455-3p |
| 232 | SEQ ID NO: 19, 16 | hsa-miR-767-5p, hsa-miR-455-3p |
| 237 | SEQ ID NO: 16, 137 | hsa-miR-455-3p, hsa-miR-920 |
| 239 | SEQ ID NO: 116, 16 | hsa-miR-339-3p, hsa-miR-455-3p |
| 916 | SEQ ID NO: 16, 273, 252 | hsa-miR-455-3p, hsa-miR-194*, hsa-miR-497* |
| 249 | SEQ ID NO: 16, 273 | hsa-miR-455-3p, hsa-miR-194* |
| 931 | SEQ ID NO: 16, 273, 23 | hsa-miR-455-3p, hsa-miR-194*, hsa-miR-491-3p |
| 263 | SEQ ID NO: 16, 259 | hsa-miR-455-3p, hsa-miR-631 |
| 957 | SEQ ID NO: 19, 16, 273 | hsa-miR-767-5p, hsa-miR-455-3p, hsa-miR-194*. |

\* \* \* \* \*

UNITED STATES PATENT AND TRADEMARK OFFICE
CERTIFICATE OF CORRECTION

PATENT NO. : 9,611,511 B2  
APPLICATION NO. : 13/642321  
DATED : April 4, 2017  
INVENTOR(S) : Andreas Keller et al.

Page 1 of 1

It is certified that error appears in the above-identified patent and that said Letters Patent is hereby corrected as shown below:

In the Claims

In the Sequence Listing, Column 176, Claim 1, Line 52, after "or" insert -- a --.

In the Sequence Listing, Column 178, Claim 7, Sequence Set No. 1005, Line Sequence Id No.: 52, 15, 243, 62, 123, 95, change "8926" to -- 892b --.

In the Sequence Listing, Column 178, Claim 7, Sequence Set No. 1005, Line Sequence Id No.: 150, 22, 32, 259, 253, 31, change "1466" to -- 146b --.

Signed and Sealed this  
Thirtieth Day of May, 2017

Michelle K. Lee  
*Director of the United States Patent and Trademark Office*